US012806264B2

(12) United States Patent
He

(10) Patent No.: US 12,806,264 B2
(45) Date of Patent: Nov. 24, 2026

(54) PIV5-BASED COVID-19 VACCINE

(71) Applicant: UNIVERSITY OF GEORGIA RESEARCH FOUNDATION, INC., Athens, GA (US)

(72) Inventor: Biao He, Bogart, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 737 days.

(21) Appl. No.: 18/026,943

(22) PCT Filed: Sep. 21, 2021

(86) PCT No.: PCT/US2021/051196
§ 371 (c)(1),
(2) Date: Mar. 17, 2023

(87) PCT Pub. No.: WO2022/061264
PCT Pub. Date: Mar. 24, 2022

(65) Prior Publication Data

US 2025/0319176 A1 Oct. 16, 2025
US 2026/0069674 A9 Mar. 12, 2026

Related U.S. Application Data

(60) Provisional application No. 63/217,361, filed on Jul. 1, 2021, provisional application No. 63/080,862, filed on Sep. 21, 2020.

(51) Int. Cl.

| | |
|---|---|
| ***A61K 35/76*** | (2015.01) |
| ***A61K 9/00*** | (2006.01) |
| ***A61K 39/215*** | (2006.01) |
| ***A61P 31/14*** | (2006.01) |
| ***A61P 37/04*** | (2006.01) |
| ***C07K 14/005*** | (2006.01) |
| ***C07K 14/165*** | (2006.01) |
| ***C12N 7/00*** | (2006.01) |
| ***C12N 15/86*** | (2006.01) |
| *A61K 39/00* | (2006.01) |

(52) U.S. Cl.
CPC .......... *A61K 39/215* (2013.01); *A61K 9/0043* (2013.01); *A61P 31/14* (2018.01); *C07K 14/005* (2013.01); *C12N 7/00* (2013.01); *C12N 15/86* (2013.01); *A61K 2039/5256* (2013.01); *A61K 2039/542* (2013.01); *A61K 2039/543* (2013.01); *A61K 2039/572* (2013.01); *A61K 2039/575* (2013.01); *C12N 2760/18722* (2013.01); *C12N 2760/18734* (2013.01); *C12N 2760/18743* (2013.01); *C12N 2770/20022* (2013.01)

(58) Field of Classification Search
CPC ............ A61K 2039/5256; A61K 39/12; A61K 39/215; C07K 14/005; C07K 14/165
See application file for complete search history.

(56) References Cited

U.S. PATENT DOCUMENTS

| | | | |
|---|---|---|---|
| 9,505,807 | B2 | 11/2016 | He |
| 9,732,358 | B2 | 8/2017 | He |
| 10,329,585 | B2 | 6/2019 | He |
| 10,752,916 | B2 | 8/2020 | He |
| 11,542,527 | B2 | 1/2023 | He |

FOREIGN PATENT DOCUMENTS

| | | | |
|---|---|---|---|
| JP | 2014503210 | A | 2/2014 |
| JP | 2016198107 | A | 12/2016 |
| RU | 2685185 | C2 | 4/2019 |
| RU | 2731342 | C1 | 9/2020 |
| WO | WO-2013112690 | A1 | 8/2013 |
| WO | WO-2013112720 | A1 | 8/2013 |
| WO | WO-2019043127 | A1 | 3/2019 |
| WO | WO-2023044505 | A2 | 3/2023 |

OTHER PUBLICATIONS

Li et al. “Single-Dose, Intranasal Immunization with Recombinant Parainfluenza Virus 5 Expressing Middle East Respiratory Syndrome COronavirus (MERS-CoV) SPike Protein Protects Mice from Fatal MERS-CoV Infection”,mBio- American Society for Microbiology, Mar. 2020, vol. 11(2):1-12.*
Walls et al. “Tectonic conformational changes of a coronavirus spike glycoprotein promote membrane fusion”, PNAS, Oct. 2017: vol. 114(42):11157-11162.*
Amanat F., et al., “A Serological Assay to Detect SARS-CoV-2 Seroconversion in Humans”, Nature Medicine, vol. 26, No. 7, Jul. 2020, pp. 1033-1036, 12 Pages.
An D., et al., “Potection of K18-hACE2 Mice and Ferrets Against SARS-CoV-2 Challenge by a Single-Dose Mucosal Immunization With a Parainfluenza Virus 5-Based COVID-19 Vaccine,” Science Advances, Jul. 2, 2021, vol. 7, No. 27, pp. 1-13, DOI:10.1126/sciadv.abi5246, XP093063841.
Anderson R.D., et al., “A Simple Method for the Rapid Generation of Recombinant Adenovirus Vectors”, Gene Therapy, 2000, vol. 7, pp. 1034-1038, doi:10.1038/sj.gt.3301197.
Baumgartner W., et al., “Persistent infection of Vero Cells by Paramyxoviruses. A Morphological and Immunoelectron Microscopic Investigation”, Intervirology, 1987, vol. 27, No. 4, pp. 218-223.
Beavis A.C., et al., “Efficacy of Parainfluenza Virus 5 (PIV5)-Vectored Intranasal COVID-19 Vaccine as a Single Dose Vaccine and as a Booster Against SARS-CoV-2 Variants,” bioRxiv, Jun. 8, 2022, pp. 1-48, DOI:10.1101/2022.06.07.495215, XP093130009.
Binn L.N., et al., “Viruses Recovered from Laboratory Dogs with Respiratory Disease”, The Proceedings of the Society for Experimental Biology and Medicine, Oct. 1967, vol. 126, No. 1, pp. 140-145.
Chatziandreou N., et al., “Relationships and Host Range of Human, Canine, Simian and Porcine Isolates of Simian Virus 5 (parainfluenza virus 5)”, Journal of General Virology, Oct. 2004, vol. 85, (Pt 10), pp. 3007-3016.

(Continued)

*Primary Examiner* — Barry A Chestnut
(74) *Attorney, Agent, or Firm* — Mueting Raasch Group

(57) ABSTRACT

The present invention provides constructs of the parainfluenza virus type-5 (PIV5) virus expressing the SARS-CoV-2 envelope spike (S) protein for use as safe, stable, efficacious, and cost-effective vaccines against COVID-19.

25 Claims, 59 Drawing Sheets

Specification includes a Sequence Listing.

(56) References Cited

OTHER PUBLICATIONS

Chen L., et al., "RNA Based mNGS Approach Identifies a Novel Human Coronavirus from Two Individual Pneumonia Cases in 2019 Wuhan Outbreak", Emerging Microbes & Infections, 2020, vol. 9, No. 1, pp. 313-319, 8 Pages.
Chen Z., et al., "A Novel Rabies Vaccine Based on a Recombinant Parainfluenza Virus 5 Expressing Rabies Virus Glycoprotein", Journal of Virology, vol. 87, No. 6, Mar. 2013, pp. 2986-2993.
Chen Z., et al., "Efficacy of Parainfluenza Virus 5 (PIV5)-Based Tuberculosis Vaccines in Mice", Vaccine, 2015, vol. 33, pp. 7217-7224.
Chen Z., et al., "Evaluating a Parainfluenza Virus 5- Based Vaccine in a Host with Pre-existing Immunity Against Parainfluenza Virus 5", PLOS One, vol. 7, No. 11, e50144, Nov. 2012, pp. 1-8.
Choppin P.W., "Multiplication of a Myxovirus (SV5) with Minimal Cytopathic Effects and Without Interference", Virology, vol. 23, No. 2, Jun. 1964, pp. 224-233.
Corbett K.S., et al., "Evaluation of the mRNA-1273 Vaccine against SARS-CoV-2 in Nonhuman Primates", The New England Journal of Medicine, vol. 383, No. 16, Jul. 28, 2020, pp. 1544-1555.
Cornwell H.J.C., et al., "Isolation of Parainfluenza Virus SV5 from Dogs with Respiratory Disease", The Veterinary Record, vol. 98, Apr. 10, 1976, pp. 300-303.
Evermann J.F., et al., "Isolation of a Paramyxovirus from the Cerebrospinal Fluid of a Dog with Posterior Paresis", Journal of the American Veterinary Medical Association, Dec. 1980, vol. 177, No. 11, pp. 1132-1134.
Evermann J.F., et al., "Properties of an Encephalitogenic Canine Parainfluenza Virus", Archives of Virology, 1981, vol. 68, No. 3-4, pp. 165-172.
Frederiksen L.S.F., et al., "The Long Road Toward COVID-19 Herd Immunity: Vaccine Platform Technologies and Mass Immunization Strategies," Frontiers in Immunology, Lausanne, CH, Jul. 21, 2020, vol. 11, pp. 1-26, DOI:10.3389/fimmu.2020.01817, ISSN 1664-3224, XP093130840.
Fuentes S., et al., "Nonglycosylated G-Protein Vaccine Protects against Homologous and Heterologous Respiratory Syncytial Virus (RSV) Challenge, while Glycosylated G Enhances RSV Lung Pathology and Cytokine Levels", Journal of Virology, Aug. 2015, vol. 89, No. 16, pp. 8193-8205.
Gao Q., et al., "Rapid Development of an Inactivated Vaccine Candidate for SARS-CoV-2", Science, Jul. 3, 2020, vol. 369, No. 6499, pp. 77-81, 10 Pages.
Genbank: "Severe Acute Respiratory Syndrome Coronavirus 2 Isolate 2019-nCOV WHU01, Complete Genome", MN988668.1, Feb. 11, 2020, 11 Pages.
Genbank: "Severe Acute Respiratory Syndrome Coronavirus 2 Isolate Wuhan-Hu-1, Complete Genome", MN908947.3, Mar. 18, 2020, 11 Pages.
Havranek K.E., et al., "SARS-CoV-2 Spike Alterations Enhance Pseudoparticle Titers and Replication-Competent VSV-SARS-CoV-2 Virus", Viruses, Dec. 18, 2020, vol. 12, No. 12, 1465, pp. 1-19.
He B., "A Single Dose Intranasal Immunization with Parainfluenza Virus 5-based COVID-19 Vaccine Generates Sterilizing Immunity in Nasal Cavities of Ferrets and Cats", NIH, Sep. 22, 2020, 41 Pages.
He B., et al., "Rapid Mutagenesis and Purification of Phage RNA Polymerases", Protein Expression and Purification, Feb. 1997, vol. 9, No. 1, pp. 142-151.
He B., et al., "Recovery of Infectious SV5 from Cloned DNA and Expression of a Foreign Gene", Virology, Oct. 27, 1997, vol. 237, No. 2, pp. 249-260.
Heffernan K.S., et al., "Exercise as Medicine for COVID-19: On PPAR with Emerging Pharmacotherapy", Medical Hypotheses, vol. 143, 2020, 110197, 5 Pages.
Huang Y., et al., "Parainfluenza Virus 5 Expressing the G Protein of Rabies Virus Protects Mice after Rabies Virus Infection", Journal of Virology, Mar. 2015, vol. 89, No. 6, pp. 3427-3429.
Huang Y., et al., "Structural and Functional Properties of SARS-CoV-2 Spike Protein: Potential Antivirus Drug Development for COVID-19", Acta Pharmacologica Sinica, Sep. 2020, vol. 41, No. 9, pp. 1141-1149, pp. 1-9.
International Preliminary Report on Patentability for International Application No. PCT/US2021/051196, mailed Mar. 30, 2023, 8 Pages.
International Search Report and Written Opinion for International Application No. PCT/US2021/051196, mailed Feb. 17, 2022, 10 Pages.
Jia H.P., et al., "ACE2 Receptor Expression and Severe Acute Respiratory Syndrome Coronavirus Infection Depend on Differentiation of Human Airway Epithelia", Journal of Virology, Dec. 2005, vol. 79, No. 23, pp. 14614-14621, doi:10.1128/JVI.79.23.14614-14621.2005.
Jiang R-D., et al., "Pathogenesis of SARS-CoV-2 in Transgenic Mice Expressing Human Angiotensin-Converting Enzyme 2", Cell, Jul. 9, 2020, vol. 182, No. 1, pp. 50-58.e58, 18 Pages.
Johnson M.C., et al., "Optimized Pseudotyping Conditions for the SARS-CoV2 Spike Glycoprotein", bioRxiv, May 29, 2020, 1-19DOI 10.1101/2020.05.28.122671, 19 Pages.
Kim Y-I., et al., "Infection and Rapid Transmission of SARS-CoV-2 in Ferrets", Cell Host Microbe, May 13, 2020, vol. 27, No. 5, pp. 704-709, 9 Pages.
Kontor E.J., et al., "Canine Infectious Tracheobronchitis: Effects of an Intranasal Live Canine Parainfluenza-Bordetella Bronchiseptica Vaccine on Viral Shedding and Clinical Tracheobronchitis (Kennel Cough)", American Journal of Veterinary Research, 1981, vol. 42, No. 10, pp. 1694-1698.
Li et al., "Single-Dose, Intranasal Immunization with Recombinant Parainfluenza Virus 5 Expressing Middle East Respiratory Syndrome Coronavirus (MERS-CoV) Spike Protein Protects Mice from Fatal MERS-CoV Infection," Apr. 28, 2020, mBio, American Society for Microbiology, 11(2):1-12, DOI:10.1128/mBio.00554-20, ISSN 2161-2129, XP055927553.
Li et al., "Recombinant Parainfluenza Virus 5 Expressing Hemagglutinin of Influenza A virus H5N1 protected mice against lethal highly pathogenic avian influenza virus H5N1 challenge", Jan. 2013, Journal of Virology, 87(1):354-362, 41 pages, doi: 10.1128/JVI.02321-12. Epub: Oct. 17, 2012, PMID: 23077314, PMCID: PMC3536412.
Li N., et al., "Prolonged SARS-CoV-2 RNA Shedding: Not a Rare Phenomenon", Journal of Medical Virology, Nov. 2020, vol. 92, No. 11, pp. 2286-2287, 12 Pages.
Liu X., et al., "Human Parainfluenza Virus Type 3 Expressing the Respiratory Syncytial Virus Pre-Fusion F Protein Modified for Virion Packaging Yields Protective Intranasal Vaccine Candidates," PLOS One, Feb. 11, 2020, vol. 15, No. 2, p. e0228572, pp. 1-24, DOI:10.1371/journal.pone.0228572, XP055839666.
Lu et al., "Importance of SARS-CoV Spike Protein Trp-Rich Region in Viral Infectivity," Apr. 2008, Biochemical and Biophysical Research Communications, 371(3):356-360, p. 358, Figure 1, p. 359, col. 1, paragraph 2, DOI:10.1016/j.bbrc.2008.04.044, ISSN 0006-291X, XP022670702.
Lu R., et al., "Genomic Characterisation and Epidemiology of 2019 novel Coronavirus: Implications for Virus Origins and Receptor Binding", Lancet, Feb. 22, 2020, vol. 395, No. 10224, pp. 565-574, pp. 1-10.
Mccray P.B., et al., "Lethal Infection of K18-hACE2 Mice Infected with Severe Acute Respiratory Syndrome Coronavirus", Journal of Virology, vol. 81, No. 2, Jan. 2007, pp. 813-821.
Mercado N.B., et al., "Single-Shot Ad26 Vaccine Protects Against SARS-CoV-2 in Rhesus Macaques", Nature, Jul. 30, 2020, vol. 586, pp. 583-588, 22 Pages.
Meyerholz D.K., et al., "Principles and Approaches for Reproducible Scoring of Tissue Stains in Research", Laboratory Investigation, vol. 98, No. 7, Jul. 2018, pp. 844-855, 12 Pages.
Mooney A.J., et al., "Recombinant Parainfluenza Virus 5 Vaccine Encoding the Influenza Virus Hemagglutinin Protects Against H5N1 Highly Pathogenic Avian Influenza Virus Infection Following Intranasal

(56) References Cited

OTHER PUBLICATIONS or Intramuscular Vaccination of BALB/c Mice", Journal of Virology, vol. 87, No. 1, Jan. 2013, pp. 363-371.
Mooney A.J., et al., "Vaccination with Recombinant Parainfluenza Virus 5 Expressing Neuraminidase Protects against Homologous and Heterologous Influenza Virus Challenge", Journal of Virology, Nov. 2017, vol. 91, No. 23, 39 Pages.
Nie J., et al., "Establishment and Validation of a Pseudovirus Neutralization Assay for SARS-CoV-2", Emerging Microbes & Infections, 2020, vol. 9, pp. 680-686, oi:10.1080/22221751.2020.1743767.
Office Action and Search Report for Russian Application No. 2023105519, dated Oct. 28, 2024, 26 Pages.
Paterson R.G., et al., "Fusion Protein of the Paramyxovirus SV5: Destabilizing and Stabilizing Mutants of Fusion Activation", Virology, Apr. 25, 2000, vol. 270, No. 1, pp. 17-30.
Phan et al., "Genetic Stability of Parainfluenza Virus 5-Vectored Human Respiratory Syncytial Virus Vaccine Candidates after In Vitro and In Vivo Passage", Sep. 12, 2017, Journal of Virology, 91(19):e00559-17, 37 pages, doi: 10.1128/JVI.00559-17, PMID: 28747497, PMCID: PMC5599752.
Phan S.I., et al., "A Respiratory Syncytial Virus (RSV) Vaccine Based on Parainfluenza Virus 5 (PIV5)", Vaccine, vol. 32, No. 25, May 23, 2014, pp. 3050-3057, pp. 1-21.
Phan S.I., et al., "Parainfluenza Virus 5 Expressing Wild-Type or Prefusion Respiratory Syncytial Virus (RSV) Fusion Protein Protects Mice and Cotton Rats from RSV Challenge", Journal of Virology, Sep. 12, 2017, vol. 91, No. 19, e00560-17, 51 Pages.
Richard M., et al., "SARS-CoV-2 is Transmitted via Contact and via the Air Between Ferrets", Nature Communications, Jul. 8, 2020, vol. 11, No. 1, 3496, pp. 1-6.
Sah R., et al., "Complete Genome Sequence of a 2019 Novel Coronavirus (SARS-CoV-2) Strain Isolated in Nepal", Microbiology, Mar. 12, 2020, vol. 9, No. 11, e00169-20, pp. 1-3.
Salvatori G., et al., "SARS-CoV-2 Spike Protein: An Optimal Immunological Target for Vaccines", Journal of Translational Medicine, 2020, vol. 18, No. 222, pp. 1-3.
Schmitt A.P., et al., "Requirements for Budding of Paramyxovirus Simian Virus 5 Virus-like Particles", Journal of Virology, Apr. 2002, vol. 76, No. 8, pp. 3952-3964.
Shi J., et al., "Susceptibility of Ferrets, Cats, Dogs, and Other Domesticated Animals to SARS-Coronavirus 2", Science, May 29, 2020, vol. 368, No. 6494, pp. 1016-1020, 10 Pages.
Sun J., et al., "Generation of a Broadly Useful Model for COVID-19 Pathogenesis, Vaccination, and Treatment", Cell, Aug. 6, 2020, vol. 182, pp. 734-743, 15 Pages, doi:10.1016/j.cell.2020.06.010.
Sun M., et al., "Conserved Cysteine-rich Domain of Paramyxovirus Simian Virus 5 V Protein Plays an Important Role in Blocking Apoptosis", Journal of Virology, May 2004, vol. 78, No. 10, pp. 5068-5078.
Supplementary European Search Report for European Application No. 21870396.5, mailed Feb. 28, 2024, 12 Pages.
Tortorici M.A., et al., "Structural Insights into Coronavirus Entry", Advances in Virus Research, 2019, vol. 105, pp. 93-116.
Van Doremalen N., et al., "ChAdOx1 nCOV-19 Vaccination Prevents SARS-CoV-2 Pneumonia in Rhesus Macaques", bioRxiv, Oct. 22, 2020, vol. 586, 18 Pages.
Walls et al., "Tectonic Conformational Changes of a Coronavirus Spike Glycoprotein Promote Membrane Fusion," Oct. 2017, PNAS, Proceedings of the National Academy of Sciences, E-journal, 11157-11162, p. 11157, col. 1, paragraph 3, DOI:10.1073/pnas.1708727114, XP055825682.
Wang D., et al., "A Single-Dose Recombinant Parainfluenza Virus 5-Vectored Vaccine Expressing Respiratory Syncytial Virus (RSV) F or G Protein Protected Cotton Rats and African Green Monkeys from RSV Challenge", Journal of Virology, Jun. 2017, vol. 91, No. 11, pp. 1-15.
Wang H., et al., "Development of an Inactivated Vaccine Candidate, BBIBP-CorV, with Potent Protection against SARS-CoV-2", Cell, Aug. 6, 2020, vol. 182, No. 3, pp. 713-721.e9, 47 Pages.
Waning D.L., et al., "Roles for the Cytoplasmic Tails of the Fusion and Hemagglutinin-neuraminidase Proteins in Budding of the Paramyxovirus Simian Virus 5", Journal of Virology, Sep. 2002, vol. 76, No. 18, pp. 9284-9297.
Wansley E.K., et al., "Naturally Occurring Substitutions in the P/V Gene Convert the Noncytopathic Paramyxovirus Simian Virus 5 into a Virus That Induces Alpha/beta Interferon Synthesis and Cell Death", Journal of Virology, Oct. 2002, vol. 76, No. 20, pp. 10109-10121.
Whelan S.P.J., et al., "Transcription and Replication of Nonsegmented Negative-strand RNA Viruses", Current Topics in Microbiology and Immunology, 2004, vol. 283, pp. 61-119.
Winkler E.S., et al., "SARS-CoV-2 Infection of Human ACE2-transgenic Mice Causes Severe Lung Inflammation and Impaired Function", Nature Immunology, Nov. 2020, vol. 21, No. 11, pp. 1327-1335, 21 Pages.
Wolfel R., et al., "Virological Assessment of Hospitalized Patients with COVID-2019", Nature, May 28, 2020, vol. 581, No. 7809, pp. 465-469, 12 pages.
Wrapp D., et al., "Cryo-EM Structure of the 2019-nCOV Spike in the Prefusion Conformation", Science, Mar. 13, 2020, vol. 367, No. 6483, pp. 1260-1263, 9 Pages.
Wu F., et al., "A New Coronavirus Associated With Human Respiratory Disease in China," Nature, Feb. 3, 2020, vol. 579, No. 7798, 20 pages, DOI: 10.1038/S41586-020-2008-3, XP037060203.
Xia S., et al., "Fusion Mechanism of 2019-nCOV and Fusion Inhibitors Targeting HR1 Domain in Spike Protein", Cellular & Molecular Immunology, Jul. 2020, vol. 17, No. 7, pp. 765-767, 3 pages.
Zheng J., et al., "COVID-19 Treatments and Pathogenesis Including Anosmia in K18-hACE2 Mice", Nature, Jan. 2021, vol. 589, No. 7843, pp. 603-607, 20 Pages.
Zhu N., et al., "A Novel Coronavirus from Patients with Pneumonia in China, 2019", The New England Journal of Medicine, Feb. 20, 2020, vol. 382, No. 8, pp. 727-733, pp. 1-7.

* cited by examiner

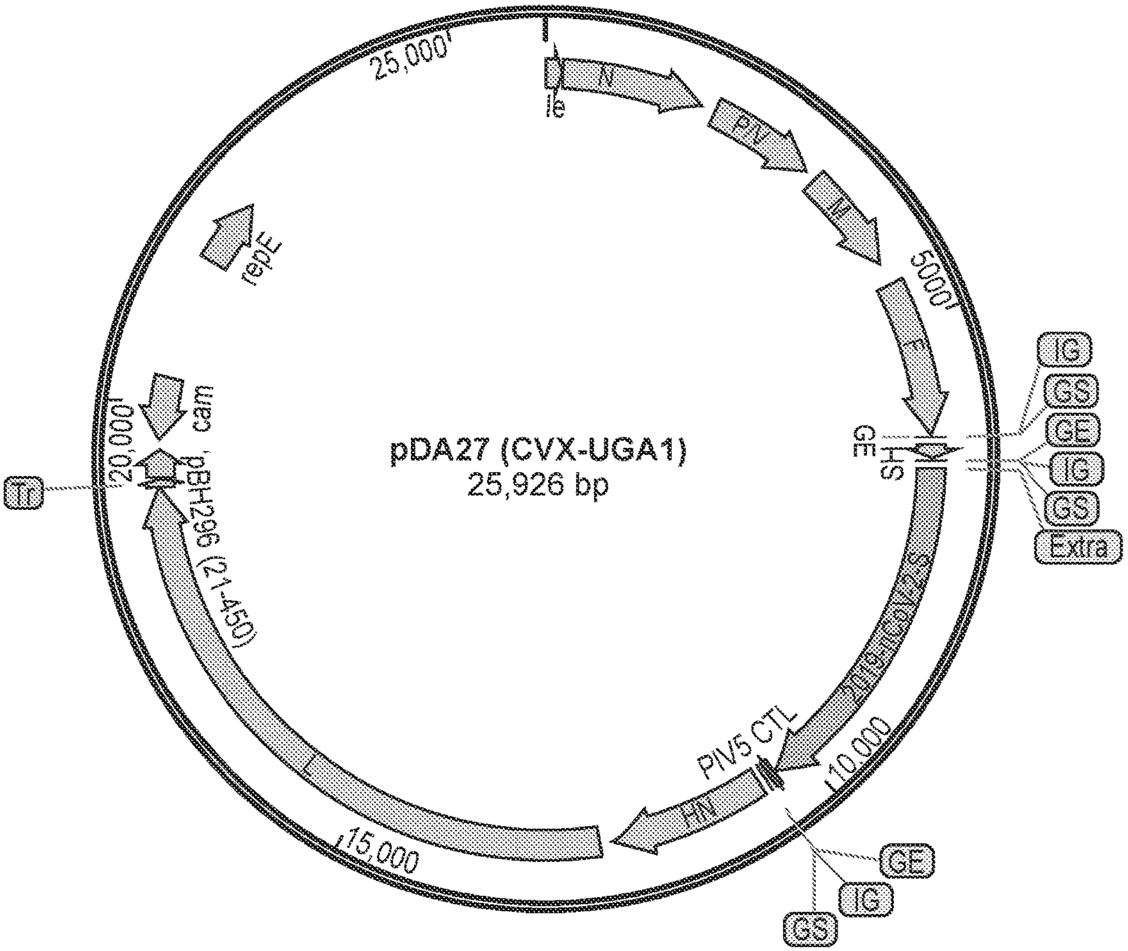

GATCTGACGTCGAATTCTAATACGACTCACTATAGGGACCAGGGGGAAAACGAA
GTGGTGACTCAAATCATCGAAGACCCTCGAGATTACATAGGTCCGGAACCTATG
GCCTTCGTGACCGACCTCGAGTCAGAGTAGTTCAATAAGGACCTATCAAGTTTGG
GCAATTTTTCGTCCCCGACACAAAAATGTCATCCGTGCTTAAAGCATATGAGCGA
TTCACACTCACTCAAGAACTGCAAGATCAGAGTGAGGAAGGTACAATCCCACCT
ACAACACTAAAACCGGTAATCAGGGTATTTATACTAACCTCTAATAACCCAGAG
CTAAGATCCCGGCTTCTTCTATTCTGCCTACGGATTGTTCTCAGTAATGGTGCAAG
GGATTCCCATCGCTTTGGAGCATTACTTACAATGTTTTCGCTACCATCAGCCACA
ATGCTCAATCATGTCAAATTAGCTGACCAGTCACCAGAAGCTGATATCGAAAGG
GTAGAGATCGATGGCTTTGAGGAGGGATCATTCCGCTTAATCCCCAATGCTCGTT
CAGGTATGAGCCGTGGAGAGATCAATGCCTATGCTGCACTTGCAGAAGATCTAC
CTGACACACTAAACCATGCAACACCTTTTGTTGATTCCGAAGTCGAGGGAACTGC
ATGGGATGAGATTGAGACTTTCTTAGATATGTGTTACAGTGTCCTAATGCAGGCA
TGGATAGTGACTTGCAAGTGCATGACTGCGCCAGACCAACCTGCTGCTTCTATTG
AGAAACGCCTGCAAAAATATCGTCAGCAAGGCAGGATCAACCCGAGATATCTCC
TGCAACCGGAGGCTCGAAGAATAATCCAGAATGTAATCCGAAAGGGAATGGTGG
TCAGACATTTCCTCACCTTTGAACTGCAGCTTGCCCGAGCACAAAGCCTTGTATC
AAATAGGTATTATGCTATGGTAGGGGATGTTGGAAAGTATATAGAGAATTGTGG

FIG. 9

AATGGGAGGCTTCTTTTTGACACTAAAATATGCATTAGGAACCAGATGGCCCACA
CTTGCTTTAGCTGCATTTTCAGGAGAGCTAACAAAGCTAAAGTCCCTCATGGCAT
TATACCAGACCCTTGGTGAGCAGGCCCGATATTTGGCCCTATTGGAGTCACCACA
TTTGATGGATTTTGCTGCAGCAAACTACCCACTGCTATATAGCTATGCTATGGGA
ATAGGCTATGTGTTAGATGTCAACATGAGGAACTACGCTTTCTCCAGATCATACA
TGAATAAGACATATTTCCAATTGGGAATGGAAACTGCAAGAAAACAACAGGGTG
CAGTTGACATGAGGATGGCAGAAGATCTCGGTCTAACTCAAGCCGAACGCACCG
AGATGGCAAATACACTTGCCAAATTGACCACAGCAAATCGAGGGGCAGACACCA
GGGGAGGAGTCAACCCGTTCTCATCTATCACTGGGACAACTCAGGTGCCCGCTGC
AGCAACAGGTGACACATTCGAGAGTTACATGGCAGCGGATCGACTGAGGCAGAG
ATATGCTGATGCAGGCACCCACGATGATGAGATGCCACCATTGGAAGAGGAGGA
AGAGGACGACACATCTGCAGGTCCACGCACTGGACTAACTCTTGAACAAGTGGC
CTTGGACATCCAGAACGCAGCAGTTGGAGCTCCCATCCATACAGATGACCTGAAT
GCCGCACTGGGTGATCTTGACATCTAGACAATTCAGATCCCAATCTTAAATCGAC
ACACCTAATTGACCAGTTAGATGGAACTACAGTGGATTCCATAAGGTTCCTGCCT
ACCATCGGCTTTTAAGAAAAAAATAGGCCCGGACGGGTTAGCAACAAGCGACTG
CCGATGCCAATAACACAATCCACAATCTACAATGGATCCCACTGATCTGAGCTTC
TCCCCAGATGAGATCAATAAGCTCATAGAGACAGGCCTGAATACTGTGGAGTATT
TTACTTCCCAACAAGTCACAGGAACATCCTCTCTTGGAAAGAATACAATACCACC
AGGGGTCACAGGACTACTAACCAATGCTGCAGAGGCAAAGATCCAAGAGTCAAC
CAACCATCAGAAGGGTTCAGTTGGTGGGGGCGCAAAACCAAAGAAACCGCGACC
AAAAATTGCCATTGTGCCAGCAGATGACAAAACGGTGCCCGGAAAGCCGATCCC
AAACCCTCTATTAGGTCTGGACTCCACCCCGAGCACCCAAACTGTGCTTGATCTA
AGTGGGAAAACATTACCATCAGGATCCTATAAGGGGGTTAAACTTGCGAAATTTG
GAAAAGAAAATCTGATGACACGGTTCATCGAGGAACCCAGAGAGAATCCTATCG
CAACCAATTCCCCCATCGATTTTAAGAGGGGCAGGGATACCGGCGGGTTCCATAG
AAGGGAGTACTCAATCGGATGGGTGGGAGATGAAGTCAAGGTCACTGAGTGGTG
CAATCCATCCTGTTCTCCAATCACCGCTGCAGCAAGGCGATTTGAATGCACTTGT
CACCAGTGTCCAGTCACTTGCTCTGAATGTGAACGAGATACTTAATACAGTGAGA
AATTTGGACTCTCGGATGAATCAACTGGAGACAAAAGTAGATCGCATTCTCTCAT
CTCAGTCTCTAATCCAGACCATCAAGAATGACATAGTTGGACTTAAAGCAGGGAT
GGCTACTTTAGAAGGAATGATTACAACTGTGAAAATCATGGACCCGGGAGTTCCC
AGTAATGTTACTGTGGAAGATGTACGCAAGAAACTAAGTAACCATGCTGTTGTTG
TGCCAGAATCATTCAATGATAGTTTCTTGACTCAATCTGAAGATGTAATTTCACTT
GATGAGTTGGCTCGACCAACTGCAACAAGTGTTAAGAAGATTGTCAGGAAGGTT
CCTCCTCAGAAGGATCTGACTGGATTGAAGATCACACTAGAGCAATTGGCAAAG
GATTGCATCAGCAAACCGAAGATGAGGGAAGAGTATCTCCTCAAAATCAACCAG
GCTTCCAGTGAGGCTCAGCTAATTGACCTCAAGAAAGCAATCATCCGCAGTGCAA
TTTGATCAAGAAACACCCAATTACACTACACTGGTATGACACTGTACTAACCCTG
AGGGTTTTAGAAAAAACGATTAACGATAAATAAGCCCGAACACTACACACCACC
CGAGGCAGCCATGCCATCCATCAGCATCCCCGCAGACCCCACCAATCCACGTCAA
TCAATAAAAGCGTTCCCAATTGTGATCAACCGTGATGGGGGTGAGAAAGGTCGCT
TGGTTAAACAACTACGCACAACCTACTTGAATGACCTAGATACTCATGAGCCACT
GGTGACATTCGTAAATACTTATGGATTCATCTACGAACAGGATCGGGGAAATACC
ATTGTCGGAGAGGATCAACATGGGAAGAAAAGAGAGGCTGTGACTGCTGCAATG
GTTACCCTTGGATGTGGGCCTAATCTACCATCATTAGGGAATG

FIG. 9 (Cont.)

TCCTGGGACAACTGAGTGAATTCCAGGTCATTGTTAGGAAGACATCCAGCAAAG
CGGAAGAGATGGTCTTTGAAATTGTTAAGTATCCGAGAATATTTCGGGGTCATAC
ATTAATCCAGAAAGGACTAGTCTGTGTCTCCGCAGAAAAATTTGTTAAGTCACCA
GGGAAAGTACAATCTGGAATGGACTATCTCTTCATTCCGACATTTCTGTCAGTGA
CTTACTGTCCAGCTGCAATCAAATTTCAGGTACCTGGCCCCATGTTGAAAATGAG
ATCAAGATACACTCAGAGCTTACAACTTGAACTAATGATAAGAATCCTGTGTAA
GCCCGATTCGCCACTTATGAAGGTCCATATCCCTGACAAGGAAGGAAGAGGATG
TCTTGTATCAGTATGGTTGCATGTATGCAATATCTTCAAATCAGGAAACAAGAAT
GGCAGTGAGTGGCAGGAATACTGGATGAGAAAGTGTGCTAACATGCAACTTGAA
GTGTCGATTGCAGATATGTGGGGACCAACTATCATAATTCATGCCAGAGGTCACA
TTCCCAAAAGTGCTAAGTTGTTTTTGGAAAGGGTGGATGGAGCTGCCATCCACT
TCACGAAGTTGTTCCAAGTGTCACTAAAACACTATGGTCCGTGGGCTGTGAGATT
ACAAAGGCGAAGGCAATAATACAAGAGAGTAGCATCTCTCTTCTCGTGGAGACT
ACTGACATCATAAGTCCAAAAGTCAAAATTTCATCTAAGCATCGCCGCTTTGGGA
AATCAAATTGGGGTCTGTTCAAGAAAACCAAATCACTGCCCAACCTGACGGAGC
TGGAATGACTGACCCCCAATCGAGACTACACCACCTCAAACTATAGGTGGGTGG
TACCTCAGTGATTAATCTCGTAAGCACTGATCGTAGGCTACAACACACTAATATT
ATCCAGATTAGAGAGCTTAATTAGCTCTGTATTAATAATAACACTACTATTCCAA
TAACTGGAATCACCAGCTTGATTTATCTCCAAAATGATTCAAAGAAAACAAATCA
TATTAAGACTATCCTAAGCACGAACCCATATCGTCCTTCAAATCATGGGTACTAT
AATTCAATTTCTGGTGGTCTCCTGTCTATTGGCAGGAGCAGGCAGTCTTGATCCA
GCAGCCCTCATGCAAATCGGTGTCATTCCAACAAATGTCCGGCAACTTATGTATT
ATACTGAGGCCTCATCAGCATTCATTGTTGTGAAGTTAATGCCTACAATTGACTC
GCCGATTAGTGGATGTAATATAACATCAATTTCAAGCTATAATGCAACAGTGACA
AAACTCCTACAGCCGATCGGTGAGAATTTGGAGACGATTAGGAACCAGTTGATT
CCAACTCGGAGGAGACGCCGGTTTGCAGGGGTGGTGATTGGATTAGCTGCATTA
GGAGTAGCTACTGCCGCACAGGTCACTGCCGCAGTAGCACTAGTAAAGGCAAAT
GAAAATGCTGCGGCTATACTCAATCTCAAAAATGCAATCCAAAAAACAAATGCA
GCAGTTGCAGATGTGGTCCAGGCCACACAATCACTAGGAACAGCAGTTCAAGCA
GTTCAAGATCACATAAACAGTGTGGTAAGTCCAGCAATTACAGCAGCCAATTGT
AAAGCCCAAGATGCTATCATTGGCTCAATCCTCAATCTCTATTTGACCGAGTTGA
CAACTATCTTCCACAATCAAATTACAAACCCTGCATTGAGTCCTATTACAATTCA
AGCTTTAAGGATCCTACTAGGGAGTACCTTGCCGACTGTGGTCGAAAAATCTTTC
AATACCCAGATAAGTGCGGCTGAGCTTCTCTCATCAGGGTTATTGACAGGCCAGA
TTGTGGGATTAGATTTGACCTATATGCAGATGGTCATAAAAATTGAGCTGCCAAC
TTTAACTGTACAACCTGCAACCCAGATCATAGATCTGGCCACCATTTCTGCATTC
ATTAACAATCAAGAAGTCATGGCCCAATTACCAACACGTGTTATTGTGACTGGCA
GCTTGATCCAAGCCTATCCCGCATCGCAATGCACTATTACACCCAACACTGTGTA
CTGTAGGTATAATGATGCCCAAGTACTCTCAGATGATACGATGGCTTGCCTCCAA
GGTAACTTGACAAGATGCACCTTCTCTCCAGTGGTTGGGAGCTTTCTCACTCGAT
TCGTGCTGTTCGATGGAATAGTTTATGCAAATTGCAGGTCGATGTTGTGCAAGTG
CATGCAGCCTGCTGCTGTGATCCTACAGCCGAGTTCATCCCCTGTAACTGTCATT
GACATGTACAAATGTGTGAGTCTGCAGCTTGACAATCTCAGATTCACCATCACTC
AATTGGCCAATGTAACCTACAATAGCACCATCAAGCTTGAAACATCCCAGATCTT
GCCTATTGATCCGTTGGATATATCCCAGAATCTAGCTGCGGTGAATAAGAGTCTA
AGTGATGCACTACAACACTTAGCACAAAGTGACACATACCTTTCTGCAATCACAT

FIG. 9 (Cont.)

CAGCTACGACTACAAGTGTATTATCCATAATAGCAATCTGTCTTGGATCGTTAGG
TTTAATATTAATAATCTTGCTCAGTGTAGTTGTGGAAGTTATTGACCATTGTCG
CTGCTAATCGAAATAGAATGGAGAATTTTGTTTATCATAATTCAGCATTCCACCA
CTCACGATCTGATCTCAGTGAGAAAAATCAACCTGCAACTCTTGGAACAAGATA
AGACAGTCATCCATTAGTAATTTTTAAGAAAAAAACGATAGGACCGAAACTAGT
ATTGAAAGAACCGTCTCGGTCAATCTAGGTAATCGAGCTGCTACCGTCTCGGAAA
GCTCAAATCATGCTGCCTGATCCGGAAGATCCGGAAAGCAAAAAAGCTACAAGG
AGAACAGGAAACCTAATTATCTGCTTCCTATTCATCTTCTTTCCGTTTGTAAACTT
CATTGTTCCAACTCTAAGACACTTGCTGTCCTAACACCTGCTATAGGCTATCCACT
GCATCATCTCTTTTTAAGAAAAAAATAGGCCCGGACGGGTTAGCAACAAGCGAC
TGCCGGTGCCAACAACACAATCCACAATCTACAGTCGACGCGGCCGCCatgttcgtcttc
ctggtcctgctgcctctggtctcctcacagtgcgtcaatctgacaactcggactcagctgccacctgcttatactaatagcttcaccagag
gcgtgtactatcctgacaaggtgtttagaagctccgtgctgcactctacacaggatctgtttctgccattctttagcaacgtgacctggttc
cacgccatccacgtgagcggcaccaatggcacaaagcggttcgacaatcccgtgctgccttttaacgatggcgtgtacttcgcctctac
cgagaagagcaacatcatcagaggctggatctttggcaccacactggactccaagacacagtctctgctgatcgtgaacaatgccacc
aacgtggtcatcaaggtgtgcgagttccagttttgtaatgatcccttcctgggcgtgtactatcacaagaacaataagagctggatggag
tccgagtttagagtgtattctagcgccaacaactgcacatttgagtacgtgagccagcctttcctgatggacctggagggcaagcaggg
caatttcaagaacctgagggagttcgtgtttaagaatatcgacggctacttcaaaatctactctaagcacaccccccatcaacctggtgcg
cgacctgcctcagggcttcagcgccctggagcccctggtggatctgcctatcggcatcaacatcacccggtttcagacactgctggcc
ctgcacagaagctacctgacacccggcgactcctctagcggatggaccgccggcgctgccgcctactatgtgggctacctccagccc
cggaccttcctgctgaagtacaacgagaatggcaccatcacagacgcagtggattgcgccctggacccccctgagcgagacaaagtg
tacactgaagtcctttaccgtggagaagggcatctatcagacatccaatttcagggtgcagccaaccgagtctatcgtgcgctttcctaat
atcacaaacctgtgcccatttggcgaggtgttcaacgcaacccgcttcgccagcgtgtacgcctggaataggaagcggatcagcaact
gcgtggccgactatagcgtgctgtacaactccgcctctttcagcacctttaagtgctatggcgtgtcccccacaaagctgaatgacctgt
gctttaccaacgtctacgccgattctttcgtgatcaggggcgacgaggtgcgccagatcgcccccggccagacaggcaagatcgcag
actacaattataagctgccagacgatttcaccggctgcgtgatcgcctggaacagcaacaatctggattccaaagtgggcggcaacta
caattatctgtaccggctgtttagaaagagcaatctgaagcccttcgagagggacatctctacagaaatctaccaggccggcagcacc
ccttgcaatggcgtggagggctttaactgttatttcccactccagtcctacggcttccagcccacaaacggcgtgggctatcagccttac
cgcgtggtggtgctgagctttgagctgctgcacgccccagcaacagtgtgcggccccaagaagtccaccaatctggtgaagaacaa
gtgcgtgaacttcaacttcaacggcctgaccggcacaggcgtgctgaccgagtccaacaagaagttcctgccatttcagcagttcggc
agggacatcgcagataccacagacgccgtgcgcgacccacagaccctggagatcctggacatcacaccctgctctttcggcggcgt
gagcgtgatcacacccggcaccaatacaagcaaccaggtggccgtgctgtatcaggacgtgaattgtaccgaggtgcccgtggctat
ccacgccgatcagctgaccccaacatggcgggtgtacagcaccggctccaacgtcttccagacaagagccggatgcctgatcggag
cagagcacgtgaacaattcctatgagtgcgacatcccaatcggcgccggcatctgtgcctcttaccagacccagacaaactctcccag
aagagcccggagcgtggcctcccagtctatcatcgcctataccatgtccctgggcgccgagaacagcgtggcctactctaacaatag
catcgccatcccaaccaacttcacaatctctgtgaccacagagatcctgcccgtgtccatgaccaagacatctgtggactgcacaatgt
atatctgtggcgattctaccgagtgcagcaacctgctgctccagtacggcagcttttgtacccagctgaatagagccctgacaggcatc
gccgtggagcaggataagaacacacaggaggtgttcgcccaggtgaagcaaatctacaagaccccccctatcaaggactttggcgg
cttcaatttttcccagatcctgcctgatccatccaagccttctaagcggagctttatcgaggacctgctgttcaacaaggtgaccctggcc
gatgccggcttcatcaagcagtatggcgattgcctgggcgacatcgcagccagggacctgatctgcgcccagaagtttaatggcctga
ccgtgctgccacccctgctgacagatgagatgatcgcacagtacacaagcgccctgctggccggcaccatcacatccggatggacct
tcggcgcaggagccgccctccagatcccctttgccatgcagatggcctataggttcaacggcatcggcgtgacccagaatgtgctgta
cgagaaccagaagctgatcgccaatcagtttaactccgccatcggcaagatccaggacagcctgtcctctacagccagcgccctggg
caagctccaggatgtggtgaatcagaacgcccaggccctgaataccctggtgaagcagctgagcagcaacttcggcgccatctctag
cgtgctgaatgacatcctgagccggctggacaaggtggaggcagaggtgcagatcgaccggctgatcaccggccggctccagagc
ctccagacctatgtgacacagcagctgatcagggccgccgagatcagggccagcgccaatctggcagcaaccaagatgtccgagtg

FIG. 9 (Cont.)

cgtgctgggccagtctaagagagtggacttttgtggcaagggctatcacctgatgtccttccctcagtctgccccacacggcgtggtgtt
tctgcacgtgacctacgtgcccgcccaggagaagaacttcaccacagcccctgccatctgccacgatggcaaggcccactttccaag
ggagggcgtgttcgtgtccaacggcacccactggtttgtgacacagcgcaatttctacgagccccagatcatcaccacagacaacacc
ttcgtgagcggcaactgtgacgtggtcatcggcatcgtgaacaataccgtgtatgatccactccagcccgagctggacagctttaagga
ggagctggataagtatttcaagaatcacacctcccctgacgtggatctgggcgacatcagcggcatcaatgcctccgtggtgaacatc
cagaaggagatcgaccgcctgaacgaggtggctaagaatctgaacgagagcctgatcgacctccaggagctgggcaagtatgagc
agtacatcaagtggccctggtacatctggctgggcttcatcgccggcctgatcgccatcgtgatggtgaccatcatgctgtgctgtatga
catcctgctgttcttgcctgaagggctgctgtagctgtggctcctgctgtAAGTTATTGACCATTGTCGTTGCTA
ATCGAAATAGAATGGAGAATTTTGTTTATCATAAATGAACGCGTGCTAGCCTCCT
GCCATACTTCCTACTCACATCATATCTATTTTAAAGAAAAAATAGGCCCGAACAC
TAATCGTGCCGGCAGTGCCACTGCACACACAACACTACACATACAATACACTAC
AATGGTTGCAGAAGATGCCCCTGTTAGGGGCACTTGCCGAGTATTATTTCGAACA
ACAACTTTAATTTTTCTATGCACACTATTAGCATTAAGCATCTCTATCCTTTATGA
GAGTTTAATAACCCAAAAGCAAATCATGAGCCAAGCAGGCTCAACTGGATCTAA
TTCTAGATTAGGAAGTATCACTGATCTTCTTAATAATATTCTCTCTGTCGCAAATC
AGATTATATATAACTCTGCAGTCGCTCTACCTCTACAATTGGACACTCTTGAATC
AACACTCCTTACAGCCATTAAGTCTCTTCAAACAAGTGACAAGCTAGAACAGAA
CTGCTCGTGGGGTGCTGCACTGATTAATGATAATAGATACATTAATGGCATCAAT
CAGTTCTATTTCTCAATTGCTGAGGGTCGCAAGCTGACACTTGGCCCACTTCTTA
ATATACCTAGTTTCATTCCAACTGCCACGACACCAGAGGGCTGCACCAGGATCCC
ATCATTCTCGCTCACCAAGACACACTGGTGTTATACACACAATGTTATCCTGAAT
GGATGCCAGGATCATGTATCCTCAAATCAATTTGTTTCCATGGGAATCATTGAAC
CCACTTCTGCCGGGTTTCCATCCTTTCGAACCCTAAAGACTCTATATCTCAGCGAT
GGGGTCAATCGTAAGAGCTGCTCTATCAGTACAGTTCCGGGGGGTTGTATGATGT
ACTGTTTCGTCTCTACTCAACCAGAGAGGGATGACTACTTTTCTACCGCTCCTCCA
GAACAACGAATTATTATAATGTACTATAATGATACAATCGTGGAGCGCATAATTA
ATCCACCCGGGGTACTAGATGTATGGGCAACATTGAACCCAGGAACAGGAAGCG
GGGTATATTATTTAGGTTGGGTACTCTTTCCAATATATGGCGGCGTGATTAAAGA
TACGAGTTTATGGAATAATCAAGCAAATAAATACTTTATCCCCCAGATGGTTGCT
GCTCTCTGCTCACAAAACCAGGCAACTCAAGTCCAAAATGCTAAGTCATCATACT
ATAGCAGCTGGTTTGGCAATCGAATGATTCAGTCTGGGATCCTGGCATGTCCTCT
TCAACAGGATCTAACCAATGAGTGTTTAGTTCTGCCCTTTTCTAATGATCAGGTG
CTTATGGGTGCTGAAGGGAGATTATACATGTATGGTGACTCGGTGTATTACTACC
AAAGAAGCAATAGTTGGTGGCCTATGACCATGCTGTATAAGGTAACCATAACAT
TCACTAATGGTCAGCCATCTGCTATATCAGCTCAGAATGTGCCCACACAGCAGGT
CCCTAGACCTGGGACAGGAAGCTGCTCTGCAACAAATAGATGTCCCGGTTTTTGC
TTGAAAGGAGTGTATGCTGATGCCTGGTTACTGACCAACCCTTCGTCTACCAGTA
CATTTGGATCAGAAGCAACCTTCACTGGTTCTTATCTCAACGCAGCAACTCAGCG
TATCAATCCGACGATGTATATCGCGAACAACACACAGATCATAAGCTCACAGCA
ATTTGGATCAAGCGGTCAAGAAGCAGCATATGGCCACACAACTTGTTTTAGGGA
CACAGGCTCTGTTATGGTATACTGTATCTATATTATTGAATTGTCCTCATCTCTCT
TAGGACAATTTCAGATTGTCCCATTTATCCGTCAGGTGACACTATCCTAAAGGCA
GAAGCCTCCAGGTCTGACCCAGCCAATCAAAGCATTATACCAGACCATGGAATG
CATACCAAACATTATTGACACTAATGACACACAAAATTGGTTTAAGAAAAACC
AAGAGAACAATAGGCCAGAATGGCTGGGTCTCGGGAGATATTACTCCCTGAAGT
CCATCTCAATTCACCAATTGTAAAGCATAAGCTATACTATTACATTCTACTTGGA

FIG. 9 (Cont.)

AACCTCCCAAATGAGATCGACATTGACGATTTAGGTCCATTACATAATCAAAATT
GGAATCAAATAGCACATGAAGAGTCTAACTTAGCCCAACGCTTGGTAAATGTAA
GAAATTTTCTAATTACCCACATCCCTGATCTTAGAAAGGGCCATTGGCAAGAGTA
TGTCAATGTAATACTGTGGCCGCGAATTCTTCCCTTGATCCCGGATTTTAAAATC
AATGACCAATTGCCTCTACTCAAAAATTGGGACAAGTTAGTTAAAGAATCATGTT
CAGTAATCAATGCGGGTACTTCCCAGTGCATTCAGAATCTCAGCTATGGACTGAC
AGGTCGTGGGAACCTCTTTACACGATCACGTGAACTCTCTGGTGACCGCAGGGAT
ATTGATCTTAAGACGGTTGTGGCAGCATGGCATGACTCAGACTGGAAAAGAATA
AGTGATTTTTGGATTATGATCAAATTCCAGATGAGACAATTAATTGTTAGGCAAA
CAGATCATAATGATCCTGATTTAATCACGTATATCGAAAATAGAGAAGGCATAAT
CATCATAACCCCTGAACTGGTAGCATTATTTAACACTGAGAATCATACACTAACA
TACATGACCTTTGAAATTGTACTGATGGTTTCAGATATGTACGAAGGTCGTCACA
ACATTTTATCACTATGCACAGTTAGCACTTACCTGAATCCTCTGAAGAAAAGAAT
AACATATTTATTGAGCCTTGTAGATAACTTAGCTTTTCAGATAGGTGATGCTGTAT
ATAACATAATTGCTTTGCTAGAATCCTTTGTATATGCACAGTTGCAAATGTCAGA
TCCCATCCCAGAACTCAGAGGACAATTCCATGCATTCGTATGTTCTGAGATTCTT
GATGCACTAAGGGGAACTAATAGTTTCACCCAGGATGAATCAAGAACTGTGACA
ACCAATTTGATATCCCCATTCCAAGATCTGACCCCAGATCTTACGGCTGAATTGC
TCTGTATAATGAGGCTTTGGGGACACCCCATGCTCACCGCCAGTCAAGCTGCGGG
AAAGGTACGCGAGTCCATGTGTGCTGGAAAAGTATTAGACTTTCCCACCATTATG
AAAACACTAGCCTTTTTCCATACTATTCTGATCAATGGATACAGGAGGAAGCATC
ATGGAGTATGGCCACCCTTAAACTTACCGGGTAATGCTTCAAAGGGTCTCACGGA
ACTTATGAATGACAATACTGAGATAAGCTATGAATTCACACTTAAGCATTGGAAG
GAAATCTCTCTTATAAAATTCAAGAAATGTTTTGATGCAGACGCAGGTGAGGAAC
TCAGTATATTTATGAAAGATAAAGCAATTAGTGCCCCAAAACAAGATTGGATGA
GTGTGTTTAGAAGAAGCCTAATCAAACAGCGCCATCAGCATCATCAGGTCCCCCT
ACCAAATCCATTCAATCGACGGCTATTGCTAAACTTTCTCGGAGATGACAAATTC
GACCCGAATGTGGAGCTACAGTATGTAACATCAGGTGAGTATCTACATGATGAC
ACGTTTTGTGCATCATATTCACTAAAAGAGAAGGAAATTAAACCTGATGGTCGAA
TTTTTGCAAAGTTGACTAAGAGAATGAGATCATGTCAAGTTATAGCAGAATCTCT
TTTAGCGAACCATGCTGGGAAGTTAATGAAAGAGAATGGTGTTGTGATGAATCA
GCTATCATTAACAAAATCACTATTAACAATGAGTCAGATTGGAATAATATCCGAG
AAAGCTAGAAAATCGACTCGAGATAACATAAATCAACCTGGTTTCCAGAATATC
CAGAGAAATAAATCACATCACTCCAAGCAAGTCAATCAGCGAGATCCAAGTGAT
GACTTTGAATTGGCAGCATCTTTTTTAACTACTGATCTCAAAAAATATTGTTTACA
ATGGAGGTACCAGACAATTATCCCATTTGCTCAATCATTAAACAGAATGTATGGT
TATCCTCATCTCTTTGAGTGGATTCACTTACGGCTAATGCGTAGTACACTTTACGT
GGGGGATCCCTTCAACCCACCAGCAGATACCAGTCAATTTGATCTAGATAAAGT
AATTAATGGAGATATCTTCATTGTATCACCCAGAGGTGGAATTGAAGGGCTATGT
CAAAAGGCTTGGACAATGATATCTATCTCTGTGATAATTCTATCTGCCACAGAGT
CTGGCACACGAGTAATGAGTATGGTGCAGGGAGATAATCAAGCAATTGCTGTCA
CCACACGAGTACCAAGGAGCCTGCCGACTCTTGAGAAAAAGACTATTGCTTTTA
GATCTTGTAATCTATTCTTTGAGAGGTTAAAATGTAATAATTTTGGATTAGGTCAC
CATTTGAAAGAACAAGAGACTATCATTAGTTCTCACTTCTTTGTTTATAGCAAGA
GAATATTCTATCAGGGGAGGATTCTAACGCAAGCCTTAAAAAATGCTAGTAAGC
TCTGCTTGACAGCTGATGTCCTAGGAGAATGTACCCAATCATCATGTTCTAATCT

FIG. 9 (Cont.)

TGCAACTACTGTCATGAGGTTAACTGAGAATGGTGTTGAAAAAGATATCTGTTTC
TACTTGAATATCTATATGACCATCAAACAGCTCTCCTATGATATCATCTTCCCTCA
AGTGTCAATTCCTGGAGATCAGATCACATTAGAATACATAAATAATCCACACCTG
GTATCACGATTGGCTCTTCTGCCATCCCAGCTAGGAGGTCTAAACTACCTGTCAT
GCAGTAGGCTGTTCAATCGAAACATAGGCGACCCGGTGGTTTCCGCAGTTGCAG
ATCTTAAGAGATTAATTAAATCAGGATGTATGGATTACTGGATCCTTTATAACTT
ATTAGGGAGAAAACCGGGAAACGGCTCATGGGCTACTTTAGCAGCTGACCCGTA
CTCAATCAATATAGAGTATCAATACCCCCCAACTACAGCTCTTAAGAGGCACACC
CAACAAGCTCTGATGGAACTCAGTACGAATCCAATGTTACGTGGCATATTCTCTG
ACAATGCACAGGCAGAAGAAAATAATCTTGCTAGATTTCTCCTGGATAGGGAGG
TGATCTTTCCGCGTGTAGCTCACATCATCATTGAGCAAACCAGTGTCGGGAGGAG
AAAACAGATTCAAGGATATTTGGATTCAACTAGATCGATAATGAGTAAATCACT
AGAAATTAAGCCCTTGTCCAATAGGAAGCTTAATGAAATACTGGATTACAACAT
CAATTACCTAGCTTACAATTTGGCATTACTCAAGAATGCTATTGAACCTCCGACT
TATTTGAAAGCAATGACTCTTGAAACATGTAGCATCGACATTGCAAGGAGCCTCC
GGAAGCTCTCCTGGGCCCCACTCTTGGGTGGGAGAAATCTTGAAGGATTAGAGA
CGCCAGATCCCATTGAAATTACTGCAGGAGCATTAATTGTTGGATCGGGCTACTG
TGAACAGTGTGCTGCAGGAGACAATCGATTCACATGGTTTTTCTTGCCATCTGGT
ATCGAGATAGGAGGGGATCCCCGTGATAATCCTCCTATCCGTGTACCGTACATTG
GCTCCAGGACTGATGAGAGGAGGGTAGCCTCAATGGCATACATCAGGGGTGCCT
CGAGTAGCCTAAAAGCAGTTCTTAGACTGGCGGGAGTGTACATCTGGGCATTCG
GAGATACTCTGGAGAATTGGATAGATGCACTGGATTTGTCTCACACTAGAGTTAA
CATCACACTTGAACAGCTGCAATCCCTCACCCCACTTCCAACCTCTGCCAATCTA
ACCCATCGGTTGGATGATGGCACAACTACCCTAAAGTTTACTCCTGCGAGCTCTT
ACACCTTTTCAAGTTTCACTCATATATCAAATGATGAGCAATACCTGACAATTAA
TGACAAAACTGCAGATTCAAATATAATCTACCAACAGTTAATGATCACTGGACTC
GGAATTTTAGAAACATGGAATAATCCCCCAATCAATAGAACATTCGAAGAATCT
ACCCTACATTTGCACACTGGTGCATCATGTTGTGTCCGACCTGTGGACTCCTGCA
TCATCTCAGAAGCATTAACAGTCAAGCCACATATTACAGTACCGTACAGCAATA
AATTTGTATTTGATGAAGACCCGCTATCTGAATATGAGACTGCAAAACTGGAATC
GTTATCATTTCAAGCCCAATTAGGCAACATTGATGCTGTAGATATGACAGGTAAA
TTAACATTATTGTCCCAATTCACTGCAAGGCAGATTATTAATGCAATCACTGGAC
TCGATGAGTCTGTCTCTCTTACTAATGATGCCATTGTTGCATCAGACTATGTCTCC
AATTGGATTAGTGAATGCATGTATACCAAATTAGATGAATTATTTATGTATTGTG
GGTGGGAACTACTATTGGAACTATCCTATCAAATGTATTATCTGAGGGTAGTTGG
GTGGAGTAATATAGTGGATTATTCTTACATGATCTTGAGAAGAATCCCGGGTGCA
GCATTAAACAATCTGGCATCTACATTAAGTCATCCAAAACTTTTCCGACGAGCTA
TCAACCTAGATATAGTTGCCCCCTTAAATGCTCCTCATTTTGCATCTCTGGACTAC
ATCAAGATGAGTGTGGATGCAATACTCTGGGGCTGTAAAAGAGTCATCAATGTG
CTCTCCAATGGAGGGGACTTAGAATTAGTTGTGACATCTGAAGATAGCCTTATTC
TCAGTGACCGATCCATGAATCTCATTGCAAGGAAATTAACTTTATTATCACTGAT
TCACCATAATGGTTTGGAACTACCAAAGATTAAGGGGTTCTCTCCTGATGAGAAG
TGTTTCGCTTTGACAGAATTTTTGAGGAAAGTGGTGAACTCAGGGTTGAGTTCAA
TAGAGAACCTATCAAATTTTATGTACAATGTGGAGAACCCACGGCTTGCAGCATT
CGCCAGCAACAATTACTACCTGACCAGAAAATTATTGAATTCAATACGAGATACT
GAGTCGGGTCAAGTAGCAGTCACCTCATATTATGAATCATTAGAATATATTGATA

FIG. 9 (Cont.)

GTCTTAAGCTAACCCCACATGTGCCTGGTACCTCATGCATTGAGGATGATAGTCT
ATGTACAAATGATTACATAATCTGGATCATAGAGTCTAATGCAAACTTGGAGAA
GTATCCAATTCCAAATAGCCCTGAGGATGATTCCAATTTCCATAACTTTAAGTTG
AATGCTCCATCGCACCATACCTTACGCCCATTAGGGTTGTCATCAACTGCTTGGT
ATAAGGGTATAAGCTGTTGCAGGTACCTTGAGCGATTAAAGCTACCACAAGGTG
ATCATTTATATATTGCAGAAGGTAGTGGTGCCAGTATGACAATCATAGAATACCT
ATTCCCAGGAAGAAAGATATATTACAATTCTTTATTTAGTAGTGGTGACAATCCC
CCACAAAGAAATTATGCACCAATGCCTACTCAGTTCATTGAGAGTGTCCCATACA
AGCTCTGGCAAGCACACACAGATCAATATCCCGAGATTTTTGAGGACTTCATCCC
TCTATGGAACGGAAATGCCGCCATGACTGACATAGGAATGACAGCTTGTGTAGA
ATTCATCATCAATCGAGTCGGCCCAAGGACTTGCAGTTTAGTACATGTAGATTTG
GAATCAAGTGCAAGCTTAAATCAACAATGCCTGTCAAAGCCGATAATTAATGCT
ATCATCACTGCTACAACTGTTTTGTGCCCTCATGGGGTGCTTATTCTGAAATATAG
TTGGTTGCCATTTACTAGATTTAGTACTTTGATCACTTTCTTATGGTGCTACTTTG
AGAGAATCACTGTTCTTAGGAGCACATATTCTGGTCCAGCTAATCATGAGGTTTA
TTTAATTTGTATCCTTGCCAACAACTTTGCATTCCAGACTGTCTCGCAGGCAACA
GGAATGGCGATGACTTTAACCGATCAAGGGTTTACTTTGATATCACCTGAAAGAA
TAAATCAGTATTGGGATGGTCACTTGAAGCAAGAACGTATCGTAGCAGAAGCAA
TTGATAAGGTGGTTCTAGGAGAAGATGCTCTATTCAATTCGAGTGATAATGAATT
AATTCTCAAATGTGGAGGGACACCAAATGCACGGAATCTTATCGATATCGAGCC
AGTCGCAACTTTCATAGAATTTGAACAACTGATCTGCACAATGTTGACAACCCAC
TTGAAGGAAATAATTGATATAACAAGGTCTGGAACCCAGGATTATGAAAGTTTA
TTACTCACTCCTTACAATTTAGGTCTTCTTGGTAAAATCAGTACGATAGTGAGATT
ATTAACAGAAAGGATTCTAAATCATACTATCAGGAATTGGTTGATCCTCCCACCT
TCGCTCCGGATGATCGTGAAGCAGGACTTGGAATTCGGCATATTCAGGATTACTT
CCATCCTCAATTCTGATCGGTTCCTGAAGCTTTCTCCAAATAGGAAATACTTGATT
ACACAATTAACTGCAGGCTACATTAGGAAATTGATTGAGGGGGATTGTAATATC
GATCTAACCAGACCTATCCAAAAACAAATCTGGAAAGCATTAGGTTGTGTAGTCT
ATTGTCACGATCCAGTAGATCAAAGGGAATCAACAGAGTTTATTGATATAAATAT
TAATGAAGAAATAGACCGCGGGATCGATGGCGAGGAAATCTAAATATATCAAGA
ATCAGAATTAGTTTAAGAAAAAAGAAGAGGATTAATCTTGGTTTTCCCCTTGGTG
GGTCGGCATGGCATCTCCACCTCCTCGCGGTCCGACCTGGGCATCCGAAGGAGG
ACGCACGTCCACTCGGATGGCTAAGGGAGCGGCCGGGGATCCGGCTGCTAACAA
AGCCCGAAAGGAAGCTGAGTTGGCTGCTGCCACCGCTGAGCAATAACTAGCATA
ACCCCTTGGGGCCTCTAAACGGGTCTTGAGGGGTTTTTTGCTGAAAGGAGGAACT
ATATCCGGATCATGTGAGCAAAAGGCCAGCAAAAGGCCAGGAACCGTAAAAAG
GCCGCGTTGCTGGCGTTTTTCCATAGGCTCCGCCCCCCTGACGAGCAAAGCTTCT
CGACCAATTCTCATGTTTGACAGCTTATCATCGAATTTCTGCCATTCATCCGCTTA
TTATCACTTATTCAGGCGTAGCAACCAGGCGTTTAAGGGCACCAATAACTGCCTT
AAAAAAATTACGCCCCGCCCTGCCACTCATCGCAGTACTGTTGTAATTCATTAAG
CATTCTGCCGACATGGAAGCCATCACAAACGGCATGATGAACCTGAATCGCCAG
CGGCATCAGCACCTTGTCGCCTTGCGTATAATATTTGCCCATGGTGAAAACGGGG
GCGAAGAAGTTGTCCATATTGGCCACGTTTAAATCAAAACTGGTGAAACTCACCC
AGGGATTGGCTGAGACGAAAAACATATTCTCAATAAACCCTTTAGGGAAATAGG
CCAGGTTTTCACCGTAACACGCCACATCTTGCGAATATATGTGTAGAAACTGCCG
GAAATCGTCGTGGTATTCACTCCAGAGCGATGAAAACGTTTCAGTTTGCTCATGG

FIG. 9 (Cont.)

AAAACGGTGTAACAAGGGTGAACACTATCCCATATCACCAGCTCACCGTCTTTCA
TTGCCATACGGAATTCCGGATGAGCATTCATCAGGCGGGCAAGAATGTGAATAA
AGGCCGGATAAAACTTGTGCTTATTTTTCTTTACGGTCTTTAAAAAGGCCGTAAT
ATCCAGCTGAACGGTCTGGTTATAGGTACATTGAGCAACTGACTGAAATGCCTCA
AAATGTTCTTTACGATGCCATTGGGATATATCAACGGTGGTATATCCAGTGATTT
TTTTCTCCATTTTAGCTTCCTTAGCTCCTGAAAATCTCGATAACTCAAAAAATACG
CCCGGTAGTGATCTTATTTCATTATGGTGAAAGTTGGAACCTCTTACGTGCCGAT
CAACGTCTCATTTTCGCCAAAAGTTGGCCCAGGGCTTCCCGGTATCAACAGGGAC
ACCAGGATTTATTTATTCTGCGAAGTGATCTTCCGTCACAGGTATTTATTCGCGAT
AAGCTCATGGAGCGGCGTAACCGTCGCACAGGAAGGACAGAGAAAGCGCGGAT
CTGGGAAGTGACGGACAGAACGGTCAGGACCTGGATTGGGGAGGCGGTTGCCGC
CGCTGCTGCTGACGGTGTGACGTTCTCTGTTCCGGTCACACCACATACGTTCCGC
CATTCCTATGCGATGCACATGCTGTATGCCGGTATACCGCTGAAAGTTCTGCAAA
GCCTGATGGGACATAAGTCCATCAGTTCAACGGAAGTCTACACGAAGGTTTTTGC
GCTGGATGTGGCTGCCCGGCACCGGGTGCAGTTTGCGATGCCGGAGTCTGATGC
GGTTGCGATGCTGAAACAATTATCCTGAGAATAAATGCCTTGGCCTTTATATGGA
AATGTGGAACTGAGTGGATATGCTGTTTTTGTCTGTTAAACAGAGAAGCTGGCTG
TTATCCACTGAGAAGCGAACGAAACAGTCGGGAAAATCTCCCATTATCGTAGAG
ATCCGCATTATTAATCTCAGGAGCCTGTGTAGCGTTTATAGGAAGTAGTGTTCTG
TCATGATGCCTGCAAGCGGTAACGAAAACGATTTGAATATGCCTTCAGGAACAA
TAGAAATCTTCGTGCGGTGTTACGTTGAAGTGGAGCGGATTATGTCAGCAATGGA
CAGAACAACCTAATGAACACAGAACCATGATGTGGTCTGTCCTTTTACAGCCAGT
AGTGCTCGCCGCAGTCGAGCGACAGGGCGAAGCCCTCGAGTGAGCGAGGAAGC
ACCAGGGAACAGCACTTATATATTCTGCTTACACACGATGCCTGAAAAAACTTCC
CTTGGGGTTATCCACTTATCCACGGGGATATTTTTATAATTATTTTTTTTATAGTTT
TTAGATCTTCTTTTTTAGAGCGCCTTGTAGGCCTTTATCCATGCTGGTTCTAGAGA
AGGTGTTGTGACAAATTGCCCTTTCAGTGTGACAAATCACCCTCAAATGACAGTC
CTGTCTGTGACAAATTGCCCTTAACCCTGTGACAAATTGCCCTCAGAAGAAGCTG
TTTTTTCACAAAGTTATCCCTGCTTATTGACTCTTTTTTATTTAGTGTGACAATCTA
AAAACTTGTCACACTTCACATGGATCTGTCATGGCGGAAACAGCGGTTATCAATC
ACAAGAAACGTAAAAATAGCCCGCGAATCGTCCAGTCAAACGACCTCACTGAGG
CGGCATATAGTCTCTCCCGGGATCAAAAACGTATGCTGTATCTGTTCGTTGACCA
GATCAGAAAATCTGATGGCACCCTACAGGAACATGACGGTATCTGCGAGATCCA
TGTTGCTAAATATGCTGAAATATTCGGATTGACCTCTGCGGAAGCCAGTAAGGAT
ATACGGCAGGCATTGAAGAGTTTCGCGGGGAAGGAAGTGGTTTTTTATCGCCCTG
AAGAGGATGCCGGCGATGAAAAAGGCTATGAATCTTTTCCTTGGTTTATCAAACG
TGCGCACAGTCCATCCAGAGGGCTTTACAGTGTACATATCAACCCATATCTCATT
CCCTTCTTTATCGGGTTACAGAACCGGTTTACGCAGTTTCGGCTTAGTGAAACAA
AAGAAATCACCAATCCGTATGCCATGCGTTTATACGAATCCCTGTGTCAGTATCG
TAAGCCGGATGGCTCAGGCATCGTCTCTCTGAAAATCGACTGGATCATAGAGCGT
TACCAGCTGCCTCAAAGTTACCAGCGTATGCCTGACTTCCGCCGCCGCTTCCTGC
AGGTCTGTGTTAATGAGATCAACAGCAGAACTCCAATGCGCCTCTCATACATTGA
GAAAAAGAAAGGCCGCCAGACGACTCATATCGTATTTTCCTTCCGCGATATCACT
TCCATGACGACAGGATAGTCTGAGGGTTATCTGTCACAGATTTGAGGGTGGTTCG
TCACATTTGTTCTGACCTACTGAGGGTAATTTGTCACAGTTTTGCTGTTTCCTTCA
GCCTGCATGGATTTCTCATACTTTTTGAACTGTAATTTTTAAGGAAGCCAAATTT

FIG. 9 (Cont.)

GAGGGCAGTTTGTCACAGTTGATTTCCTTCTCTTTCCCTTCGTCATGTGACCTGAT
ATCGGGGGTTAGTTCGTCATCATTGATGAGGGTTGATTATCACAGTTTATTACTCT
GAATTGGCTATCCGCGTGTGTACCTCTACCTGGAGTTTTTCCCACGGTGGATATTT
CTTCTTGCGCTGAGCGTAAGAGCTATCTGACAGAACAGTTCTTCTTTGCTTCCTCG
CCAGTTCGCTCGCTATGCTCGGTTACACGGCTGCGGCGAGCGCTAGTGATAATAA
GTGACTGAGGTATGTGCTCTTCTTATCTCCTTTTGTAGTGTTGCTCTTATTTTAAAC
AACTTTGCGGTTTTTTGATGACTTTGCGATTTTGTTGTTGCTTTGCAGTAAATTGC
AAGATTTAATAAAAAAACGCAAAGCAATGATTAAAGGATGTTCAGAATGAAACT
CATGGAAACACTTAACCAGTGCATAAACGCTGGTCATGAAATGACGAAGGCTAT
CGCCATTGCACAGTTTAATGATGACAGCCCGGAAGCGAGGAAAATAACCCGGCG
CTGGAGAATAGGTGAAGCAGCGGATTTAGTTGGGGTTTCTTCTCAGGCTATCAGA
GATGCCGAGAAAGCAGGGCGACTACCGCACCCGGATATGGAAATTCGAGGACG
GGTTGAGCAACGTGTTGGTTATACAATTGAACAAATTAATCATATGCGTGATGTG
TTTGGTACGCGATTGCGACGTGCTGAAGACGTATTTCCACCGGTGATCGGGGTTG
CTGCCCATAAAGGTGGCGTTTACAAAACCTCAGTTTCTGTTCATCTTGCTCAGGA
TCTGGCTCTGAAGGGGCTACGTGTTTTGCTCGTGGAAGGTAACGACCCCCAGGGA
ACAGCCTCAATGTATCACGGATGGGTACCAGATCTTCATATTCATGCAGAAGACA
CTCTCCTGCCTTTCTATCTTGGGGAAAAGGACGATGTCACTTATGCAATAAAGCC
CACTTGCTGGCCGGGGCTTGACATTATTCCTTCCTGTCTGGCTCTGCACCGTATTG
AAACTGAGTTAATGGGCAAATTTGATGAAGGTAAACTGCCCACCGATCCACACC
TGATGCTCCGACTGGCCATTGAAACTGTTGCTCATGACTATGATGTCATAGTTATT
GACAGCGCGCCTAACCTGGGTATCGGCACGATTAATGTCGTATGTGCTGCTGATG
TGCTGATTGTTCCCACGCCTGCTGAGTTGTTTGACTACACCTCCGCACTGCAGTTT
TTCGATATGCTTCGTGATCTGCTCAAGAACGTTGATCTTAAAGGGTTCGAGCCTG
ATGTACGTATTTTGCTTACCAAATACAGCAATAGTAATGGCTCTCAGTCCCCGTG
GATGGAGGAGCAAATTCGGGATGCCTGGGGAAGCATGGTTCTAAAAAATGTTGT
ACGTGAAACGGATGAAGTTGGTAAAGGTCAGATCCGGATGAGAACTGTTTTTGA
ACAGGCCATTGATCAACGCTCTTCAACTGGTGCCTGGAGAAATGCTCTTTCTATT
TGGGAACCTGTCTGCAATGAAATTTTCGATCGTCTGATTAAACCACGCTGGGAGA
TTAGATAATGAAGCGTGCGCCTGTTATTCCAAAACATACGCTCAATACTCAACCG
GTTGAAGATACTTCGTTATCGACACCAGCTGCCCCGATGGTGGATTCGTTAATTG
CGCGCGTAGGAGTAATGGCTCGCGGTAATGCCATTACTTTGCCTGTATGTGGTCG
GGATGTGAAGTTTACTCTTGAAGTGCTCCGGGGTGATAGTGTTGAGAAGACCTCT
CGGGTATGGTCAGGTAATGAACGTGACCAGGAGCTGCTTACTGAGGACGCACTG
GATGATCTCATCCCTTCTTTTCTACTGACTGGTCAACAGACACCGGCGTTCGGTC
GAAGAGTATCTGGTGTCATAGAAATTGCCGATGGGAGTCGCCGTCGTAAAGCTG
CTGCACTTACCGAAAGTGATTATCGTGTTCTGGTTGGCGAGCTGGATGATGAGCA
GATGGCTGCATTATCCAGATTGGGTAACGATTATCGCCCAACAAGTGCTTATGAA
CGTGGTCAGCGTTATGCAAGCCGATTGCAGAATGAATTTGCTGGAAATATTTCTG
CGCTGGCTGATGCGGAAAATATTTCACGTAAGATTATTACCCGCTGTATCAACAC
CGCCAAATTGCCTAAATCAGTTGTTGCTCTTTTTTCTCACCCCGGTGAACTATCTG
CCCGGTCAGGTGATGCACTTCAAAAAGCCTTTACAGATAAAGAGGAATTACTTA
AGCAGCAGGCATCTAACCTTCATGAGCAGAAAAAAGCTGGGGTGATATTTGAAG
CTGAAGAAGTTATCACTCTTTTAACTTCTGTGCTTAAAACGTCATCTGCATCAAG
AACTAGTTTAAGCTCACGACATCAGTTTGCTCCTGGAGCGACAGTATTGTATAAG
GGCGATAAAATGGTGCTTAACCTGGACAGGTCTCGTGTTCCAACTGAGTGTATAG

FIG. 9 (Cont.)

AGAAAATTGAGGCCATTCTTAAGGAACTTGAAAAGCCAGCACCCTGATGCGACC
ACGTTTTAGTCTACGTTTATCTGTCTTTACTTAATGTCCTTTGTTACAGGCCAGAA
AGCATAACTGGCCTGAATATTCTCTCTGGGCCCACTGTTCCACTTGTATCGTCGGT
CTGATAATCAGACTGGGACCACGGTCCCACTCGTATCGTCGGTCTGATTATTAGT
CTGGGACCACGGTCCCACTCGTATCGTCGGTCTGATTATTAGTCTGGGACCACGG
TCCCACTCGTATCGTCGGTCTGATAATCAGACTGGGACCACGGTCCCACTCGTAT
CGTCGGTCTGATTATTAGTCTGGGACCATGGTCCCACTCGTATCGTCGGTCTGATT
ATTAGTCTGGGACCACGGTCCCACTCGTATCGTCGGTCTGATTATTAGTCTGGAA
CCACGGTCCCACTCGTATCGTCGGTCTGATTATTAGTCTGGGACCACGGTCCCAC
TCGTATCGTCGGTCTGATTATTAGTCTGGGACCACGATCCCACTCGTGTTGTCGGT
CTGATTATCGGTCTGGGACCACGGTCCCACTTGTATTGTCGATCAGACTATCAGC
GTGAGACTACGATTCCATCAATGCCTGTCAAGGGCAAGTATTGACATGTCGTCGT
AACCTGTAGAACGGAGTAACCTCGGTGTGCGGTTGTATGCCTGCTGTGGATTGCT
GCTGTGTCCTGCTTATCCACAACATTTTGCGCACGGTTATGTGGACAAAATACCT
GGTTACCCAGGCCGTGCCGGCACGTTAACCGGGCTGCATCCGATGCAAGTGTGTC
GCTGTCGAGTTTAAACG

FIG. 9 (Cont.)

PIV5-BASED COVID-19 VACCINE

CONTINUING APPLICATION DATA

This application is the § 371 U.S. National Stage of International Application No. PCT/US2021/051196, filed 21 Sep. 2021, which claims the benefit of U.S. Provisional Application No. 63/080,862, filed Sep. 21, 2020, and U.S. Provisional Application Ser. No. 63/217,361, filed Jul. 1, 2021, each of which is incorporated by reference herein.

SEQUENCE LISTING

This application contains a Sequence Listing electronically submitted via EFS-Web to the United States Patent and Trademark Office as an ASCII text file entitled "0235-000294WO01__ST25" having a size of 37 kilobytes and created on Dec. 16, 2021. The information contained in the Sequence Listing is incorporated by reference herein.

BACKGROUND

SARS-CoV-2 is a novel coronavirus that was first identified in Wuhan, China in December 2019 as a cause of pneumonia and has subsequently spread globally to cause the COVID-19 pandemic. The virus has infected more than 221 million persons world-wide, caused more than 4,574,000 deaths as of Sep. 8, 2021, and is poised to continue to spread in the absence of herd immunity (see who.int/emergencies/diseases/novel-coronavirus-2019 on the worldwide web). Social distancing, use of PPE, and widespread testing with contact tracing, quarantine procedures and limited supplies of the single FDA approved vaccine and FDA approved vaccines under the Emergency Use Authorization (EUA) are currently the only measures available to limit virus spread. Vaccines that prevent mortality and reduce transmission are urgently needed.

SUMMARY OF THE INVENTION

The present invention includes a viral expression vector having a parainfluenza virus 5 (PIV5) genome having a heterologous nucleotide sequence expressing a heterologous polypeptide, wherein the heterologous polypeptide includes a coronavirus spike (S) protein.

In some aspects of the viral expression vector, the coronavirus S protein includes the coronavirus S protein of the severe acute respiratory syndrome coronavirus 2 (SARS-CoV-2).

In some aspects of the viral expression vector, the cytoplasmic tail of the coronavirus S protein has been replaced with the cytoplasmic tail of the fusion (F) protein of PIV5.

In some aspects of the viral expression vector, the coronavirus S protein includes the coronavirus S protein of the severe acute respiratory syndrome coronavirus 2 (SARS-CoV-2) and wherein the cytoplasmic tail of the coronavirus S protein has been replaced with the cytoplasmic tail of the fusion (F) protein of PIV5.

In some aspects of the viral expression vector, the heterologous polypeptide comprises a coronavirus spike (S) protein that contains mutations at amino acid residue W886 and/or F888.

In some aspects, the amino acid substitution at amino acid residue W886 comprises a substitution of tryptophan (W) to arginine (R) and/or the amino acid substitution at amino acid residue W888 comprises a substitution of phenylalanine (F) to arginine (R).

In some aspects of a viral expression vector of the present invention, the heterologous nucleotide sequence is inserted between the small hydrophobic protein (SH) gene and the hemagglutinin-neuraminidase (HN) gene of the PIV5 genome.

In some aspects of a viral expression vector of the present invention, the heterologous nucleotide sequence replaces the SH gene nucleotide sequence.

In some aspects of a viral expression vector of the present invention, the heterologous nucleotide sequence is inserted between the hemagglutinin-neuraminidase (HN) gene and the large RNA polymerase protein (L) gene of the PIV5 genome.

In some aspects of a viral expression vector of the present invention, the heterologous nucleotide sequence is inserted closer to the leader than between the hemagglutinin-neuraminidase (HN) gene and the large RNA polymerase protein (L) gene of the PIV5 genome; is inserted upstream of the nucleocapsid protein (NP) gene of the PIV5 genome; is inserted immediately downstream of the leader sequence of the PIV5 genome; is inserted between the fusion (F) protein gene and the SH gene of the PIV5 genome; is inserted between the VP gene and the matrix protein (M) gene of the PIV5 genome; is inserted between the M gene and the F gene of the PIV5 genome; is inserted between the nucleocapsid protein (NP) gene and the V/P gene of the PIV5 genome; is inserted between the leader sequence and the nucleocapsid protein (NP) gene of the PIV5 genome; is inserted wherein a portion of the F or HN gene of PIV5 has been replaced with the heterologous nucleotide sequence; is inserted within the SH gene nucleotide sequence, is inserted within the NP gene nucleotide sequence, is inserted within the V/P gene nucleotide sequence, is inserted within the M gene nucleotide sequence, is inserted within the F gene nucleotide sequence, is inserted within the HN gene nucleotide sequence, and/or is inserted within the L gene nucleotide sequence.

In some aspects of a viral expression vector of the present invention, the PIV5 genome further comprises one or more mutations. In some aspects, the one or more mutations includes a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof. In some aspects, the one or more mutations includes PIV5 VAC, PIV5ASH, PIV5-P-S308G, or a combination thereof.

The present invention includes a viral particle having a viral expression vector as described herein.

The present invention includes a composition of a viral expression vector as described herein or a viral particle as described herein.

The present invention includes a method of expressing a heterologous coronavirus spike (S) glycoprotein in a cell, the method including contacting the cell with a viral expression vector, viral particle, or composition as described herein.

The present invention includes a method of inducing an immune response in a subject to a coronavirus spike (S) glycoprotein, the method including administering the viral expression a viral expression vector, viral particle, or composition as described herein to the subject. In some aspects, the immune response includes a humoral immune response and/or a cellular immune response. In some aspects, the viral expression vector, viral particle, or composition is administered intranasally, intramuscularly, topically, or orally.

The present invention includes a method of vaccinating a subject against coronavirus disease 2019 (COVID-19), the method including administering a viral expression vector, viral particle, or composition as described herein to the subject. In some aspects, the viral expression vector, viral particle, or composition is administered intranasally, intramuscularly, topically, or orally.

BRIEF DESCRIPTION OF THE FIGURES

FIG. 9 shows the map and sequence of the pDA27 (CVX-UGA1) plasmid (SEQ ID NO:1).

FIG. 18A shows schematics of CVXGA1. PIV5 has seven genes and encodes 8 proteins, NP, V, P, M, F, SH, HN and L. Leader and trailer sequences are important for viral RNA synthesis. S of SARS-CoV-2 contains signal peptide (SP), receptor binding domain (RBD), fusion peptide (FP), transmembrane domain (TM) and cytoplasmic tail (CT). CVXGA1 contains S whose CT was replaced with that of F of PIV5 and which was inserted between SH and HN of PIV5. FIG. 18B shows detection of S expression. To detect SARS-CoV-2-S expression, immunofluorescence assays were performed. MDBK cells were mock infected or infected at 1 multiplicity of infection (MOI) with PIV5 or CVXGA1. Two days post-infection, the cells were fixed, permeabilized, and stained with antibodies specific for PIV5-V/P (anti-vector) and SARS-CoV-2 S. To detect expression using immunoblotting, Vero cells were infected with PIV5, CVXGA1 at 1 MOI and lysed at 24 hours post infection (hpi). The lysates were resolved on an SDS-PAGE gel and immunoblotted with anti-SARS-CoV-2 S and anti-PIV5-V/P. FIG. 18C shows syncytial formation by CVXGA1. Vero cells were infected with PIV5 or CVXGA1 at an MOI of 0.1. At 48 hpi, the cells were photographed. FIG. 18D show anti-S titers in BALB/c mice immunized with CVXGA1. BALB/c mice (n=5 per group) were immunized via intranasal (IN) route with CVXGA1 at a dose of $10^4$, $10^5$ and $10^6$ plaque forming unit (PFU). At 28 days after immunization (dpi), mice were bled and anti-S titers were measured using ELISA. FIG. 18E shows anti-receptor binding domain (RBD) titers in BALB/c mice immunized with CVXGA1. Titers of RBD of samples in FIG. 18D were determined using ELISA. FIG. 18F shows neutralization titers in BALB/c mice immunized with CVXGA1. Neutralization titers of samples in FIG. 18D were determined as described in Materials and Methods of Example 2.

FIG. 19A shows schematic of experimental protocol for CVXGA1 vaccine study in BALB/c mice. Treatment groups (Gp) include: Gp 1: DMEM immunization via intramuscular (IM) route; Gp 2: CVXGA1 immunization via intranasal (IN) route; Gp 3: UV inactivated SARS-CoV-2 administered via IM route with Alum adjuvant. All animals were then sensitized to SARS-CoV-2 infection with Ad-hACE2, and 5 days later were inoculated with $1\times10^5$ PFU of SARS-CoV-2. Other measurements and the number of animals per group are indicated. Days post immunization denoted by dpi. FIG. 19B shows outcomes in mouse model of SARS-CoV-2 infection. Ad5-hACE2 transduced BALB/c mice were intranasally infected with $1\times10^5$ PFU of SARS-CoV-2 in 50 μl of DMEM. Weight changes in 6- to 8-week-old mice were monitored daily (DMEM: n=6, CVXGA1: n=14, UV-inactivated SARS-CoV-2: n=6 mice per group). Mice immunized with CVXGA1 showed significantly less weight loss. *P value <0.05; P value <0.005; Mann-Whitney test. FIG. 19C shows CVXGA1 vaccine reduces lung disease severity. Results of histopathological scoring for lung disease. Mononuclear cell infiltrates were present in all groups, while granulocytic infiltration increased in mice immunized IM with UV inactivated SARS-CoV-2 followed by a second boost dose. n=4. FIG. 19**D shows CVXGA1 vaccine reduces lung disease. Five days post SARS-CoV-2 infection, lungs were harvested, fixed in zinc formalin, and embedded in paraffin. Representative H&E staining of lungs are presented. Eosinophilic infiltrates were noted in the UV inactivated SARS-CoV-2 group at day 5 post SARS-CoV-2 infection (indicated by arrows in lower panel and inset). Eosinophilic infiltrates are enumerated in graph on right. Bar=255 and 51 μm, top and bottom panels, respectively.

FIG. 20A shows a schematic of ferret immunization and viral challenge. Groups of six ferrets were immunized CVXGA1) or mock immunized (PBS) at a dose of $10^6$ PFU Intranasally. Nasal washes were performed for vaccine shedding and weekly blood collections obtained following immunization. Ferrets were challenge 39 days post challenge (dpc) with $4\times10^5$ PFU SARS-CoV-2 intranasally. Nasal washes and rectal swabs were performed 1, 3, 5, and 7 dpc. One-half (n=6) ferrets were humanely euthanized four days post infection. The study ended at 7 dpc. FIG. 20B shows anti-RBD serum IgG in ferrets after IN immunization. Serum anti-RBD IgG titers were evaluated via ELISA. Titers of 28 dpi are shown. FIG. 20C shows neutralization titers after immunization. Anti-SARS-CoV-2 neutralization titers at 28 dpi were determined using a VSV-CoV-SARS2-S pseudo-particle. The +RHS (positive recovered human serum) was used as a positive control, and media alone was used as a negative control. FIG. 20D shows viral RNA in nasal washes after challenge. Amount of viral RNAs in nasal washes at 1, 3, 5 and 7 dpc were determined using qRT-PCR as described in Materials and Methods. FIG.

20E shows viral RNA in lung after challenge. Amount of viral RNAs in lungs at 4 dpc and 7 dpc were determined using qRT-PCR. FIG. 20F shows viral RNA in trachea after challenge. Amount of viral RNAs in trachea at 4 dpc and 7 dpc were determined using qRT-PCR.

FIG. 21A is a schematic of immunization and challenge. Cats in a group of 4 were immunized with PBS, CVXGA1 at a dose of $10^6$ PFU via IN or subcutaneous (subQ) route. For the subQ group, the cats were boosted with the same dose at 21 dpi. At 42 days after initial immunization, the cats were challenged with $4\times10^5$ PFU of SARS-CoV-2 via IN route. Nasal washes and rectal swaps were collected every other day until termination of the experiment at 14 dpc. FIG. 21B shows anti-S titer in cats after immunization. Titers of anti-S serum IgG were determined by ELISA. Titers of sera at 28 dpi are shown. FIG. 21C shows anti-RBD titer in cats after immunization. Titers of anti-RBD in sera were determined using ELISA. Titers of sera at 28 dpi were shown. FIG. 21D shows anti-S IgA titer in nasal washes after immunization. Titers of anti-S IgA in nasal washes were determined using ELISA. Titers at 28 dpi were shown. FIG. 21E shows virus titers in nasal washes after challenge. SARS-CoV-2 infectious particles recovered in feline nasal washes quantified as focus forming units (FFU) and presented as to $\log_{10}$ FFU/mL after viral challenge.

FIG. 22A is a schematic of immunization. C57B16 mice (n=5 per group) were immunized intranasal (IN) route with PBS, PIV5 at a dose $10^6$ plaque forming unit (PFU) or of CVXGA1 at a dose of $6\times10^3$ PFU. At 28 days after immunization, mice were sacrificed. Terminal bleed and splenocytes were collected. FIG. 22B shows anti-S titers in mice. Anti-S titers were measured using ELISA. FIG. 22C shows cellular immune response. Cellular immune response was determined using Elispot. Splenocytes were stimulated with SARS-CoV-2 S protein peptide library. Results were presented as the number of IFN-γ secreting cells per 106 splenocytes. Error bars are standard error of the mean. * ($P<0.05$) significance between PIV5 and vaccine group.

FIG. 23A is a schematic of experimental protocol for PIV5-based SARS-CoV-2 vaccine study in BALB/c mice. Treatment groups included: Group (Gp) 1: DMEM immunization IN; Gp 2: CVXGA1 immunization $5\times10^3$ PFU IN; Gp 3: CVXGA1 immunization $5\times10^4$ PFU IN. All animals were then sensitized to SARS-CoV-2 infection with Ad-hACE2, and 5 days later were inoculated with $1\times10^5$ PFU of SARS-CoV-2. Other measurements and the number of animals per group are indicated. Days post immunization denoted by dpi. FIG. 23B shows outcomes in mice immunized with CVXGA1, followed by SARS-CoV-2 infection. Ad5-hACE2 transduced BALB/c mice were infected intranasally with $1\times10^5$ PFU of SARS-CoV-2 in 50 μl of DMEM. Weight changes in 6 to 8 week old mice were monitored daily (n=5 mice per group). Mice immunized with $5\times10^4$ PFU CVXGA1 showed less weight loss than those receiving $5\times10^3$ PFU (*P value <0.05; **P value <0.005; Mann-Whitney test). FIG. 23C shows CVXGA1 intranasal immunization reduces lung tissue SARS-CoV-2 titers. To obtain virus kinetics, lungs were harvested and homogenized at 1 dpi, and virus titered by plaque assay. Titers are expressed as PFU per lung tissue (n=3 mice per group). Mice immunized with $5\times10^4$ PFU CVXGA1 showed a greater reduction in lung tissue titers (*P value <0.05; **P value <0.005; Mann-Whitney test).

FIG. 24A shows anti-S levels in mice after prime-boost immunization with inactivated SARS-CoV-2. Anti-S levels in sera from mice immunized with inactivated SARS-CoV-2 as described in FIG. 19A were determined using ELISA. FIG. 24B shows anti-RBD levels in mice after prime-boost immunization with inactivated SARS-CoV-2. Anti-RBD levels in sera from mice immunized with inactivated SARS-CoV-2 as described in FIG. 19A were determined using ELISA.

FIG. 25A shows anti-S IgG titer in sera after immunization. Anti-S levels in sera at 7, 28 dpi and 7 dpc were determined using ELISA and graphed. FIG. 25B shows anti-S IgA in nasal washes. IgA levels in nasal washes collected at 28 dpi were measured using ELISA. FIG. 25 shows detection of virus and viral RNA in nasal wash at 5 dpc. Titers of SARS-CoV-2 in nasal washes at 5 dpc were determined using immunofluorescence assay after plaque assay and graphed as FFU (fluorescence foci forming unit) per milliliter. qRT-PCR results for nasal washes at 5 dpc were the same as in FIG. 20D. FIG. 25D shows detection of SARS-CoV-2 antigen in lungs at 4 dpc. Sections of lungs from ferrets sampled at 4 days post challenge were fixed in formalin and processed for immunohistochemistry for SARS-CoV2 antigen N. FIG. 25E is a comparison of anti-S before and after challenge. Levels of anti-S in ferrets at 28 dpi (dashed line) and 7 dpc (solid line) were determined using ELISA.

FIG. 26A shows neutralizing antibody titers. Serum collected at 28 dpi was assayed using a VSV—CoV-SARS2-S pseudo-particle. The +RHS (positive recovered human serum) was used as a positive control. FIG. 26B shows detection of viral RNA in nasal washes. Amount of viral RNAs in nasal washes at 1, 3, 5, 7, 9, 11, 13, and 14 dpc were determined using qRT-PCR. FIG. 26C is a comparison of anti-S before and after challenge. Levels of anti-S in ferrets at 41 dpi and 14 dpc were determined using ELISA. FIG. 26D is a comparison of anti-N before and after challenge. Levels of anti-N in ferrets at 41 dpi and 14 dpc were determined using ELISA.

FIG. 28A shows the weight loss and FIG. 26B shows the survival outcomes in K18-hACE2 transgenic mice. Weight changes in 6- to 8-week-old mice were monitored daily (DMEM: n=9, CVXGA1: n=8, UV inactivated SARS-CoV-2: n=10 mice per group, PIV5: n=10). CVXGA1 immunized mice lost no weight and survived. All DMEM and PIV5 treated mice succumbed. One UV inactivated SARS-CoV-2 treated mouse survived. Days post infection with SARS-CoV-2 denoted by days p.i. FIG. 28A and FIG. 28B show that the CVXGA1 vaccine reduces lung tissue titer and prevents viral spread to the brain. Five days post SARS-CoV-2 infection, lung (n=4) and brain (n=4) tissues were obtained from groups in A and B, and titrated. See Materials and Methods for details. Limit of detection (LOD): Error bars represent the standard error of the mean. **P value <0.01; One-way ANOVA with Dunnet's post test.

FIG. 29A-FIG. 29C show the histology of fixed lung tissues, five days post SARS-CoV-2 infection. Representative images of SARS-CoV-2 infected mice that received DMEM, CVXGA1, UV-SARS2, or PIV5. FIG. 29A shows representative distribution of virus antigen (N protein, brown stain) in lung tissues from indicated groups (n=4 per group). Note the rare focal immunostaining in CVXGA1 group compared to diffuse immunostaining in other groups. Bar=220 μm. FIG. 29B shows the hematoxylin and eosin-stained tissues (n=4 per group). Eosinophilic infiltrates were only noted in the UV-SARS2 group (arrows in inset, Bar=45 μm). FIG. 29C shows the hematoxylin and eosin-stained tissues (n=4 per group). Interstitial lung disease was in reduced in the CVXGA1. Bar=90 μm. FIG. 29D shows the histopathologic scoring of lung tissues (see Methods for details, n=4 per group). Tissues from all 4 groups were ordinally scored for eosinophilic infiltrates, perivascular infiltrates, and interstitial lung disease. Error bars represent the standard error of the mean. * P<0.05, ** P<0.01, One-way ANOVA with Dunnet's post test.

FIG. 30 A shows the schematic of ferret immunization and viral challenge. Groups of six ferrets were immunized CVXGA1) or mock immunized (PBS) at a dose of $10^6$ PFU intranasally. Ferrets were challenge 39 days post immunization (dpi) with $4\times10^5$ PFU SARS-CoV-2 intranasally. Nasal washes and rectal swabs were performed at 1, 3, 5, and 7 day post challenge (dpc). One-half (n=6) ferrets were humanely euthanized four days after challenge. The study ended at 7 dpc. FIG. 30B shows the anti-RBD serum IgG in ferrets after immunization. Serum anti-RBD IgG titers were evaluated via ELISA. Titers of 28 dpi are shown. Error bars represent the standard error of the mean. FIG. 30C shows the neutralization titers after immunization. Anti-SARS-CoV-2 neutralization titers at 28 dpi were determined using a VSV-CoV-SARS2-S virus. The +RHS (positive recovered human serum) was used as a positive control, and media alone was used as a negative control. Error bars represent the standard error of the mean, and P-values were calculated with one-way ANOVA. ****P value <0.0001.

FIG. 31A shows the detection of viral RNA in 1, 3, 5, and 7 post-challenge nasal wash via qRT-PCR. Viral RNA was quantified as genome copies per ml and presented as $\log_{10}$ Genome/ml as described in the Materials and Methods. Each symbol represents a different animal (6 PBS and 6 CVXGA1). PBS animals are black symbols, and CVXGA1-vaccinated animals are red symbols. 1 pfu/PCR reaction (rxn) is marked to differentiate between infectious viral particles and un-infectious genomic remnants. The limit of detection (LOD) is indicated by the lowest dashed line. FIG. 31B shows the detection of viral RNA in lung tissues collected at 4, 7 dpc via qRT-PCR. Viral RNA was quantified and presented as genome copies per reaction (rxn). FIG. 31C shows the detection of viral RNA in trachea tissues collected at 4, 7 dpc via qRT-PCR. Viral RNA was quantified and presented as genome copies per reaction (rxn).

FIG. 32A shows the schematic of ferret immunization, viral challenge, and transmission. Groups of six ferrets were immunized CVXGA1), empty viral vector or mock immunized (PBS) at a dose of $10^6$ PFU Intranasally. Ferrets were challenged at 42 dpi with $4\times10^5$ PFU SARS-CoV-2 intranasally. Nasal washes were collected at 1, 3, 5, 7, 9, and 11 dpc. One-half ferrets were humanely euthanized four days after challenge. The study ended at 11 dpc. At 2 dpc, one challenged ferret was mixed with one naïve ferret, nasal washes were collected from naïve ferrets at 1, 3, 5, 7, and 9 days post mixing (3, 5, 7, 9, and 11 dpc respectively). FIG. 32B shows the detection of SARS-CoV 2 in 1, 3, 5, 7, 9 and 11 dpc in nasal washes. Live virus was detected using focus-forming unit assay (FFA, FFU/ml) as described in the Materials and Methods. Each symbol represents a different animal. The limit of detection (LOD) is indicated by the lowest dashed line.

FIG. 33A shows the schematic of immunization. C57BL/6 mice (n=5 per group) were immunized via intranasal (IN) route with PBS, PIV5 at a dose $10^6$ plaque forming unit (PFU), or CVXGA1 at a dose of $6\times10^3$ PFU. At 28 days post immunization, mice were sacrificed. Terminal bleed and splenocytes were collected. FIG. 33B shows the anti-S antibody titers in mice. Anti-S titers were measured using ELISA. Error bars indicate standard error of the mean. FIG. 33C shows the cellular immune response. Cellular immune response was determined using Elispot assay. Splenocytes were stimulated with SARS-CoV-2 S protein peptide library. Results were presented as the number of IFN-γ secreting cells per $10^6$ splenocytes. Error bars indicate standard error of the mean. * (P<0.05) significance between PIV5 and vaccine group. Analysis of variance (ANOVA) followed by Dunnett's multiple comparison test.

FIG. 34A shows the weight loss and FIG. 34B shows the survival outcomes in K18-hACE2 transgenic mice. Weight changes in 6 to 8 week-old mice were monitored daily (DMEM: n=5, CVXGA1: n=6, UV inactivated SARS-CoV-2: n=5 mice per group). While all mice had weight loss only the CVXGA1 immunized mice survived. Days post infection with SARS-CoV-2 denoted by dpi. *P value <0.05; **P value <0.005; Two-way ANOVA. FIGS. 34C and 34D is an analysis that shows CVXGA1 vaccine reduces lung tissue titer and prevents viral spread to the brain. Five days post SARS-CoV-2 infection, lung (n=4) and brain (n=4) tissues were obtained and titrated. (N/D: not detectable) *P value <0.05; P value <0.005; One-way ANOVA. FIG. 34E shows the histology and scoring of lung tissues at five days post SARS-CoV-2 challenge. Left panels: Representative histology of DMEM, CVXGA1, or UV-SARS2 groups. Eosinophilic infiltrates (arrows in inset) were noted in the UV-SARS2 group. Eosinophilic infiltrates are enumerated in graph on right. ** P<0.0001, UV-SARS2 vs. DMEM or CVXGA1, One-way ANOVA. Bar=387 and 78 μm, (top and bottom rows, respectively).

FIG. 35A shows the post-immunization replication of CVXGA1 in ferret upper respiratory tracts. Ferret nasal washes were collected at 3, 7, and 14 days post-immunization. Plaque assays were performed in Vero cells. Nasal wash CVXGA1 was quantified as plaque-forming units per mL (PFU/mL). FIG. 35B shows the anti-S IgG titer in sera after immunization. Anti-S levels in sera at 7, 14, 21, 28 dpi, and 7 dpc were determined using ELISA. Data points represent mean values +/−SD of duplicate values for individual animals (n=6 dpi; n=3 dpc). ** P<0.0001, Two-way ANOVA with Sidak's multiple comparisons test. FIG. 35C shows the anti-S IgA in nasal washes. IgA levels in nasal washes collected at 28 dpi were measured using ELISA. Data points represent pooled samples (n=6) in triplicate+/−SD. FIG. 35D shows the comparison of anti-S serum IgG responses before and after SARS-CoV-2 challenge. Levels of anti-S IgG in ferrets at 28 dpi (dashed line) and 7 dpc (solid line) were determined using ELISA. Data points represent mean values+/−SD of duplicate values for individual animals (n=6 dpi; n=3 dpc). ** P <0.0001, Two-way ANOVA with Sidak's multiple comparisons test.

FIG. 36A shows the room layout for experiment described in FIG. 31. Challenge studies were completed in BSL3-Ag facilities. Rooms are equipped with single HEPA supply air and double HEPA exhaust and maintain negative pressure relative to outside "clean" corridors. Individually ventilated cages (IVCs) complete with solid cage bottoms and a plastic cage (Tecniplast) were supplied with HEPA supply and exhaust. FIG. 36B shows a representative image of Allentown, Inc conventional ferret caging. Each conventional ferret rack has six individual cages complete with plastic cage inserts with perforated floors and removable stainless-steel doors, plastic excreta pans, J-feeders, and automatic water manifold with lixits. FIG. 36C shows group locations within the cage racks. Naïve ferrets were housed in IVCs before mixing with challenged ferrets in conventional (open) cages. Individual cages are labeled with the vaccine treatment group and animal identification with "C" indicative of naïve contact animals. Gp3 represents a vaccine candidate that did not work as well as CVXGA1 did: these ferrets had the challenge virus in nasal cavities at 3 dpc.

FIG. 37A-FIG. 37 B show viral RNA levels of ferrets immunized with CVXGA1 and their direct contacts. FIG. 37A shows the RNA levels in nasal washes. Detection of viral RNA in nasal washes collected at 1, 3, 5, 7, and 9 dpc in via qRT-PCR. Viral RNA was quantified using qRT-PCR. Each point represents a different animal, 1 pfu/PCR reaction (rxn) is marked to differentiate between infectious viral particles and un-infectious genomic remnants. The limit of detection (LOD) is indicated by the lowest dashed line.

DETAILED DESCRIPTION

Figure 1:
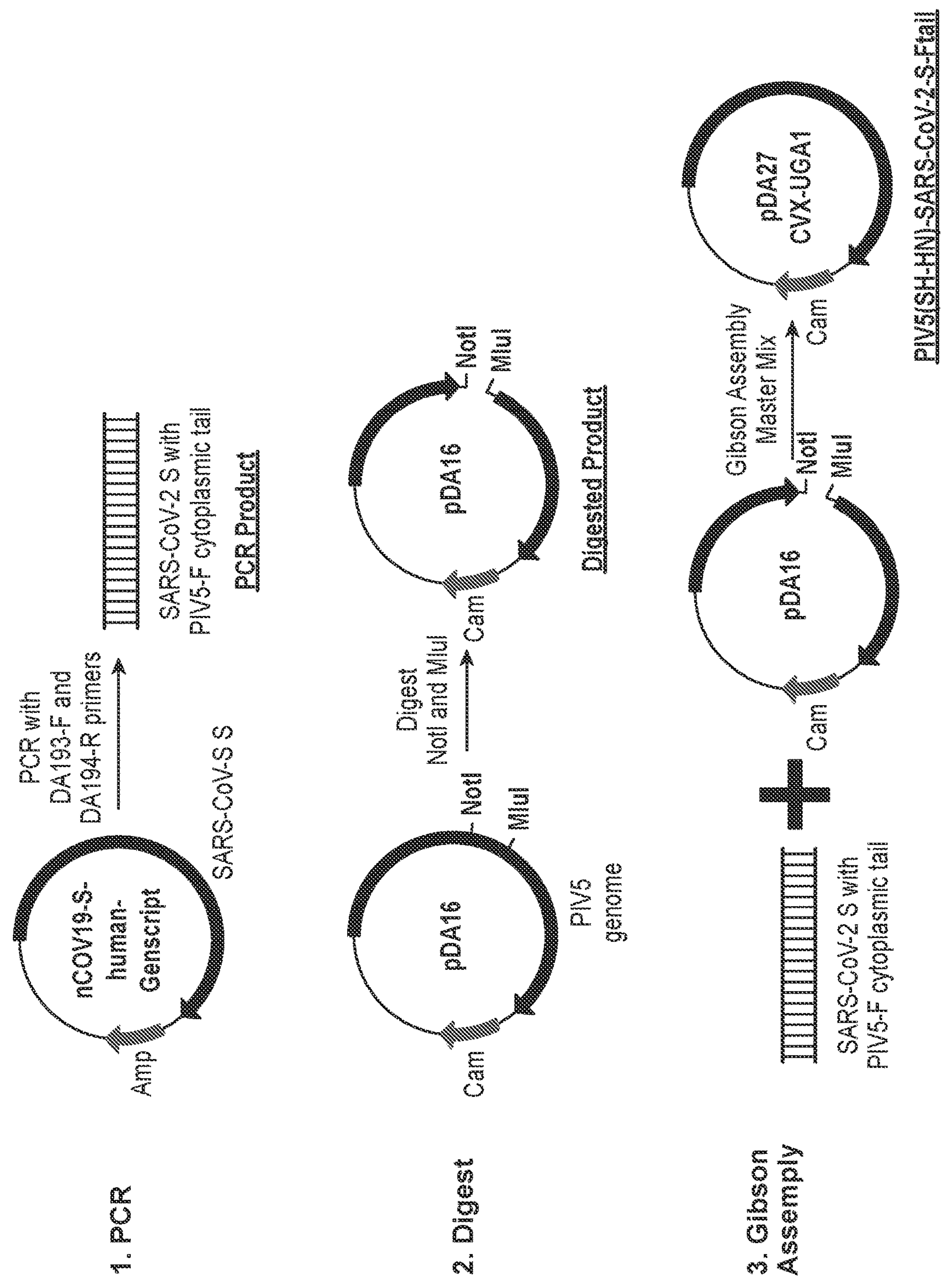
FIG. 1 shows the plasmid cloning outline for pDA27.

With the present invention, constructs of the parainfluenza virus type-5 (PIV5) virus expressing the SARS-CoV-2 envelope spike (S) protein have been generated for use as vaccines against COVID. These constructs demonstrate effectiveness as vaccines, with single dose intranasal immunization inducing sterilizing immunity in ferrets and cats.

Coronavirus disease 2019 (COVID-19) is a newly emerging infectious disease currently spreading across the world. It is caused by a novel coronavirus, severe acute respiratory syndrome coronavirus 2 (SARS-CoV-2) (Zhu et al. *N Engl J Med* 382, 727-733 (2020)). SARS-CoV-2 was first identified in Wuhan, China in December 2019, and has subsequently spread globally to cause the COVID-19 pandemic. The virus has infected more than 221 million persons world-wide, caused more than 4,574,000 deaths as of Sep. 8, 2021, and is poised to continue to spread in the absence of herd immunity (see the worldwide web at who.int/emergencies/diseases/novel-coronavirus-2019). Social distancing and widespread testing with contact tracing and quarantine procedures are currently the only measures available to limit spread of the virus. A vaccine to protect against SARS-CoV-2 is urgently needed to prevent further mortality and reduce transmission.

SARS-CoV-2 is a single-stranded RNA-enveloped virus belonging to the 8 coronavirus family (Lu et al. *Lancet* 395, 565-574 (2020)). An RNA-based metagenomic next-generation sequencing approach has been applied to characterize its entire genome, which is 29,881 nucleotides (nt) in length (GenBank Sequence Accession MN908947) encoding 9860 amino acids (Chen et al. *Emerg Microbes Infect* 9, 313-319 (2020)). Full-genome sequenced genomes available at GenBank include isolate 2019-nCoV WHU01 (GenBank accession number MN988668) and NC_045512 for SARS-CoV-2, both isolates from Wuhan, China, and at least seven additional sequences (MN938384.1, MN975262.1, MN985325.1, MN988713.1, MN994467.1, MN994468.1, and MN997409.1), which are >99.9% identical.

Parainfluenza virus 5 (PIV5), a negative-stranded RNA virus, is a member of the *Rubulavirus* genus of the family Paramyxoviridae which includes many important human and animal pathogens such as mumps virus, human parainfluenza virus type 2 and type 4, Newcastle disease virus, Sendai virus, HPIV3, measles virus, canine distemper virus, rinderpest virus and respiratory syncytial virus. PIV5 was previously known as Simian Virus-5 (SV5). Although PIV5 is a virus that infects many animals and humans, no known symptoms or diseases in humans have been associated with PIV5. Unlike most paramyxoviruses, PIV5 infects normal cells with little cytopathic effect. As a negative stranded RNA virus, the genome of PIV5 is very stable. As PIV5 does not have a DNA phase in its life cycle and it replicates solely in cytoplasm, PIV5 is unable to integrate into the host genome. Therefore, using PIV5 as a vector avoids possible unintended consequences from genetic modifications of host cell DNAs. PIV5 can grow to high titers in cells, including Vero cells which have been approved for vaccine production by WHO and FDA. Thus, PIV5 presents many advantages as a vaccine vector.

A PIV5-based vaccine vector of the present invention may be based on any of a variety of wild type, mutant, or recombinant (rPIV5) strains. Wild type strains include, but are not limited to, the PIV5 strains W3A, WR (ATCC® Number VR-288™), canine parainfluenza virus strain 78-238 (ATCC number VR-1573) (Evermann et al. *Arch Virol* 68, 165-172 (1981); Evermann et al. *J Am Vet Med Assoc* 177, 1132-1134 (1980)), canine parainfluenza virus strain D008 (ATCC number VR-399) (Binn et al. *Proc Soc Exp Biol Med* 126, 140-145 (1967)), MIL, DEN, LN, MEL, cryptovirus, CPI+, CPI−, H221, 78524, T1 and SER. See, for example, (Baumgartner et al. *Intervirology* 27, 218-223 (1987); Chatziandreou et al. *J Gen Virol* 85, 3007-3016 (2004); Choppin *Virology* 23, 224-233 (1964)). Additionally, PIV5 strains used in commercial kennel cough vaccines, such as, for example, BI, FD, Merck, and Merial vaccines, may be used.

A PIV5 vaccine vector of the present invention may be constructed using any of a variety of methods, including, but not limited to, the reverse genetics system described in more detail in He et al. (*Virology;* 237(2):249-60, 1997). PIV5 encodes eight viral proteins. Nucleocapsid protein (NP), phosphoprotein (P) and large RNA polymerase (L) protein are important for transcription and replication of the viral RNA genome. The V protein plays important roles in viral pathogenesis as well as viral RNA synthesis. The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified. The hemagglutinin-neuraminidase (HN) glycoprotein is also involved in virus entry and release from the host cells. The matrix (M) protein plays an important role in virus assembly and budding. The hydrophobic (SH) protein is a 44-residue hydrophobic integral membrane protein and is oriented in membranes with its N terminus in the cytoplasm. For reviews of the molecular biology of paramyxoviruses see, for example, (Lamb *Fields Virology: Sixth Edition* 1, 957-995 (2013); Whelan et al. *Biology of Negative Strand RNA Viruses: The Power of Reverse Genetics,* 61-119 (2004)).

With the PIV5-based vaccine vectors of the present invention, a heterologous nucleotide sequence encoding the spike (S) protein of a coronavirus, including, but not limited to, the S protein of SARS-CoV-2, is inserted in the PIV5 genome. Coronavirus entry into host cells is mediated by the transmembrane S glycoprotein (Tortorici et al. *Adv Virus Res* 105, 93-116 (2019)). As the coronavirus S glycoprotein is surface-exposed and mediates entry into host cells, it is the main target of neutralizing antibodies upon infection and the focus of therapeutic and vaccine design. The spike S protein of SARS-CoV-2 is composed of two subunits, S1 and S2. The S1 subunit contains a receptor-binding domain that recognizes and binds to the host receptor angiotensin-converting enzyme 2, while the S2 subunit mediates viral cell membrane fusion by forming a six-helical bundle via the two-heptad repeat domain (Huang et al. *Acta Pharmacologica Sinica* 41, 1141-1149 (2020)).

The total length of SARS-CoV-2 S is 1273 amino acids (aa) and consists of a signal peptide (amino acids 1-13) located at the N-terminus, the S1 subunit (14-685 residues), and the S2 subunit (686-1273 residues); the last two regions are responsible for receptor binding and membrane fusion, respectively. In the S1 subunit, there is an N-terminal domain (14-305 residues) and a receptor-binding domain (RBD, 319-541 residues); the fusion peptide (FP) (788-806 residues), heptapeptide repeat sequence 1 (HR1) (912-984 residues), HR2 (1163-1213 residues), TM domain (1213-1237 residues), and cytoplasm domain (1237-1273 residues) comprise the S2 subunit (Xia et al. *Cell Mol Immunol* 17, 765-767 (2020)).

Figure 2:
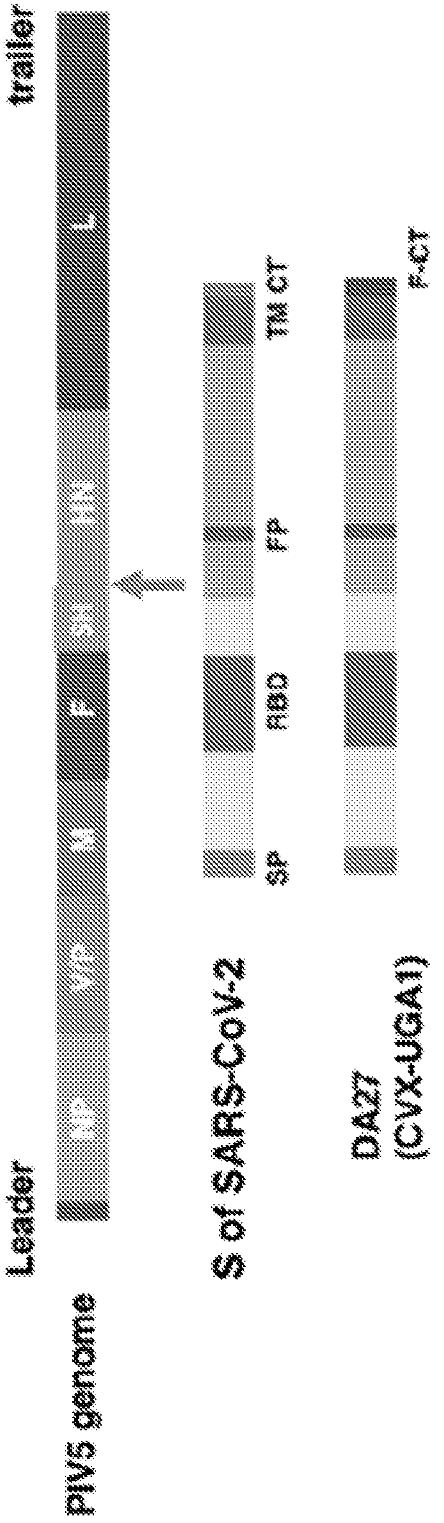
FIG. 2 shows the construct of CVX-UGA1 generated from pDA27.

In some PIV5-based vaccine vectors of the present invention, the heterologous nucleotide sequence encoding the spike (S) protein of a coronavirus, including, but not limited to, the S protein of SARS-CoV-2, has been modified so that the cytoplasmic tail of the coronavirus S protein has been replaced with the cytoplasmic tail of the fusion (F) protein of PIV5. An example of such a PIV5 construct includes the PIV5 construct CVX-GA1, also referred to herein as CVXGA1, CVX-UGA1, pDA27, or DA27. A plasmid map of CVX-GA1 is shown in FIGS. 2 and 9, with the sequence of the construct included in FIG. 9.

In some PIV5-based vaccine vectors of the present invention, the heterologous nucleotide sequence encoding the coronavirus S protein, including but not limited to, the S protein of SARS-CoV-2, has been modified so that the S protein includes an amino acid substitution at amino acid residue W886 and/or F888. In some aspects, the amino acid substitution at amino acid residue W886 includes a substitution of tryptophan (W) to arginine (R) and/or the amino acid substitution at amino acid residue W888 includes a substitution of phenylalanine (F) to arginine (R).

Figure 38:
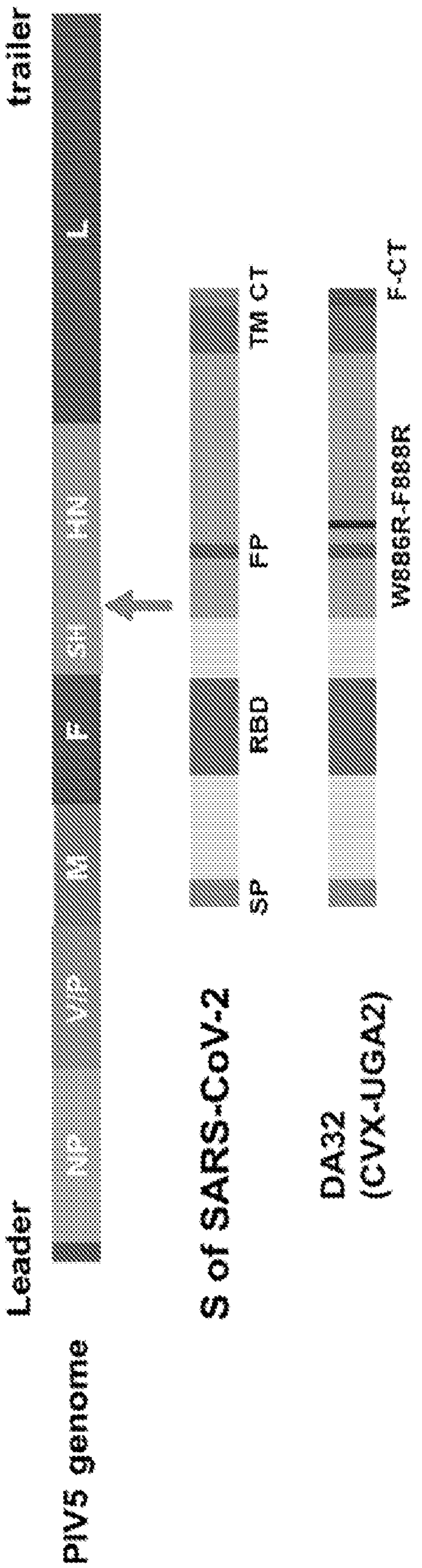
FIG. 38 shows a schematic of the CVX-UGA2 vector construct.

In some PIV5-based vaccine vectors of the present invention, the heterologous nucleotide sequence encoding the spike (S) protein of a coronavirus, including, but not limited to, the S protein of SARS-CoV-2, includes both a modification so that the cytoplasmic tail of the coronavirus S protein has been replaced with the cytoplasmic tail of the fusion (F) protein of PIV5 and includes an amino acid substitution at amino acid residue W886 and/or F888. In some aspects, the amino acid substitution at amino acid residue W886 includes a substitution of tryptophan (W) to arginine (R) and/or the amino acid substitution at amino acid residue W888 includes a substitution of phenylalanine (F) to arginine (R). An example of such a PIV5 construct includes the PIV5 construct CVX-GA2, also referred to herein as CVXGA2 or CVX-UGA2. A plasmid map of CVX-GA1 is shown in FIG. 38.

The heterologous nucleotide sequence encoding the coronavirus S protein, including but not limited to the S protein of SARS-CoV-2, may be inserted in any of a variety of locations in the PIV5 genome.

In some preferred embodiments, the heterologous nucleotide sequence encoding the coronavirus S protein, including but not limited to the S protein of SARS-CoV-2, may be inserted between the small hydrophobic protein (SH) gene and the hemagglutinin-neuraminidase (HN) gene of the PIV5 genome.

The heterologous nucleotide sequence encoding the coronavirus S protein, including but not limited to the S protein of SARS-CoV-2, may be inserted between the hemagglutinin-neuraminidase (HN) and large RNA polymerase protein (L) gene of the PIV5 genome. In some embodiments, the heterologous nucleotide sequence is not inserted at a location between the hemagglutinin-neuraminidase (HN) and large RNA polymerase protein (L) gene of the PIV5 genome. In some embodiments, the heterologous nucleotide sequence is inserted at a location other than between the hemagglutinin-neuraminidase (HN) and large RNA polymerase protein (L) gene of the PIV5 genome.

The heterologous nucleotide sequence encoding the coronavirus S protein, including but not limited to the S protein of SARS-CoV-2, may be inserted between the nucleocapsid protein (NP) gene and the V/P gene of the PIV5 genome.

The heterologous nucleotide sequence encoding the coronavirus S protein, including but not limited to the S protein of SARS-CoV-2, may be inserted between the M gene and the F gene of the PIV5 genome.

The heterologous nucleotide sequence encoding the coronavirus S protein, including but not limited to the S protein of SARS-CoV-2, may be inserted between the F gene and the SH gene of the PIV5 genome.

The heterologous nucleotide sequence encoding the coronavirus S protein, including but not limited to the S protein of SARS-CoV-2, may be inserted between the VP gene and the matrix protein (M) gene of the PIV5 genome.

The heterologous nucleotide sequence encoding the coronavirus S protein, including but not limited to the S protein of SARS-CoV-2, may be inserted between the leader sequence and the nucleocapsid protein (NP) gene of the PIV5 genome.

The heterologous nucleotide sequence encoding the coronavirus S protein, including but not limited to the S protein of SARS-CoV-2, may be inserted immediately downstream of the leader sequence of the PIV5 genome.

The heterologous nucleotide sequence encoding the coronavirus S protein, including but not limited to the S protein of SARS-CoV-2, may be inserted to replace all or part of a PIV5 gene within the PIV5 genome. For example, the heterologous nucleotide sequence may replace the F, HN, or SH gene of the PIV5 genome. A heterologous nucleotide sequence may be inserted within a PIV5 gene, resulting in the expression of a chimeric polypeptide. For example, the heterologous nucleotide sequence may be inserted within the SH gene nucleotide sequence, within the NP gene nucleotide sequence, within the V/P gene nucleotide sequence, within the M gene nucleotide sequence, within the F gene nucleotide sequence, within the HN gene nucleotide sequence, and/or within the L gene nucleotide sequence of a PIV5 genome.

A PIV5 viral vaccine of the present invention may also have a mutation, alteration, or deletion in one or more of these eight proteins of the PIV5 genome. For example, a PIV5 viral expression vector may include one or more mutations, including, but not limited to any of those described herein. In some aspects, a combination of two or more (two, three, four, five, six, seven, or more) mutations may be advantageous and may demonstrated enhanced activity.

A mutation includes, but is not limited to, a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, and/or a mutation that enhances syncytial formation.

A mutation may include, but is not limited to, rPIV5-V/P-CPI−, rPIV5-CPI−, rPIV5-CPI+, rPIV5V ΔC, rPIV-Rev, rPIV5-RL, rPIV5-P-S157A, rPIV5-P-S308A, rPIV5-L-A1981D and rPIV5-F-S443P, rPIV5-MDA7, rPIV5 ASH-CPI−, rPIV5 ASH-Rev, and combinations thereof.

PIV5 can infect cells productively with little cytopathic effect (CPE) in many cell types. In some cell types, PIV5 infection causes formation of syncytia, i.e., fusion of many cells together, leading to cell death. A mutation may include one or more mutations that promote syncytia formation (see, for example (Paterson et al. *Virology* 270, 17-30 (2000))).

The V protein of PIV5 plays a critical role in blocking apoptosis induced by virus. Recombinant PIV5 lacking the conserved cysteine-rich C-terminus (rPIV5V ΔC) of the V protein induces apoptosis in a variety of cells through an intrinsic apoptotic pathway, likely initiated through endoplasmic reticulum (ER)-stress (Sun et al. *Journal of virology* 78, 5068-5078 (2004)). Mutant recombinant PIV5 with mutations in the N-terminus of the V/P gene products, such as rPIV5-CPI−, also induce apoptosis (Wansley et al. *J Virol* 76, 10109-10121 (2002)). A mutation includes, but is not limited to, rPIV5 ASH, rPIV5-CPI−, rPIV5 VAC, and combinations thereof.

Also included in the present invention are virions and infectious viral particles that include a PIV5 genome including a heterologous nucleotide sequence encoding a coronavirus S protein, including but not limited to the S protein of SARS-CoV-2.

Also included in the present invention are compositions including one or more of the PIV5 viral constructs or virions, as described herein. Such a composition may include a pharmaceutically acceptable carrier. As used, a pharmaceutically acceptable carrier refers to one or more compatible solid or liquid fillers, diluents or encapsulating substances which are suitable for administration to a human or other vertebrate animal. Such a carrier may be pyrogen free. The present invention also includes methods of making and using the viral vectors and compositions described herein.

The compositions of the present disclosure may be formulated in pharmaceutical preparations in a variety of forms adapted to the chosen route of administration. One of skill will understand that the composition will vary depending on mode of administration and dosage unit.

The agents of this invention can be administered in a variety of ways, including, but not limited to, intravenous, topical, oral, intranasal, subcutaneous, intraperitoneal, intramuscular, and intratumor deliver. In some aspects, the agents of the present invention may be formulated for controlled or sustained release. One advantage of intranasal immunization is the potential to induce a mucosal immune response.

Also included in the present invention are methods of making and using PIV5 viral expression vectors, including, but not limited to any of those described herein.

For example, the present invention includes methods of expressing a coronavirus S protein, including but not limited to the S protein of SARS-CoV-2, in a cell by contacting or infection the cell with a PIV5 viral expression vector, viral particle, or composition as described herein.

The present invention includes methods of inducing an immune response in a subject to a coronavirus S protein, including but not limited to the S protein of SARS-CoV-2, by administering a viral expression vector, viral particle, or composition as described herein to the subject. The immune response may include a humoral immune response and/or a cellular immune response. The immune response may enhance an innate and/or adaptive immune response.

The present invention includes methods expressing a heterologous coronavirus S protein, including but not limited to the S protein of SARS-CoV-2, in a subject by administering a viral expression vector, viral particle, or composition as described herein to the subject.

The present invention includes methods of vaccinating a subject by administering a viral expression vector, viral particle, or composition as described herein to the subject.

With the methods of the present invention, any of a variety of modes of administration may be used. For example, administration may be intravenous, topical, oral, intranasal, subcutaneous, intraperitoneal, intramuscular, intratumor, in ovo, maternally, and the like. In some aspects, administration is to a mucosal surface. A vaccine may be administered by mass administration techniques such as by placing the vaccine in drinking water or by spraying the animals' environment. When administered by injection, the immunogenic composition or vaccine may be administered parenterally. Parenteral administration includes, for example, administration by intravenous, subcutaneous, intramuscular, or intraperitoneal injection.

An agent of the present disclosure may be administered at once, as a single dose, or may be administered as multiple doses administered at intervals of time. For example, agents of the invention may be administered repeatedly, e.g., at least 2, 3, 4, 5, 6, 7, 8, or more times. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

In some aspects, any of the PIV5-based constructs and methods described in WO 2013/112690 and WO 2013/112720 (which is hereby incorporated by reference herein in its entirety) may be used in the present invention.

As used herein, the term "subject" represents an organism, including, for example, a mammal. A mammal includes, but is not limited to, a human, a non-human primate, and other non-human vertebrates. A subject may be an "individual," "patient," or "host." Non-human vertebrates include livestock animals (such as, but not limited to, a cow, a horse, a goat, and a pig), a domestic pet or companion animal, such as, but not limited to, a dog or a cat, and laboratory animals. Non-human subjects also include non-human primates as well as rodents, such as, but not limited to, a rat or a mouse. Non-human subjects also include, without limitation, poultry, horses, cows, pigs, goats, dogs, cats, guinea pigs, hamsters, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

Exemplary Embodiments of the present invention include, but are not limited to, the following.

1. A viral expression vector comprising a parainfluenza virus 5 (PIV5) genome comprising a heterologous nucleotide sequence expressing a heterologous polypeptide, wherein the heterologous polypeptide comprises a coronavirus spike (S) protein.

2. The viral expression vector of Embodiment 1, wherein the coronavirus S protein comprises the coronavirus S protein of the severe acute respiratory syndrome coronavirus 2 (SARS-CoV-2).

3. The viral expression vector of Embodiment 1, wherein the cytoplasmic tail of the coronavirus S protein has been replaced with the cytoplasmic tail of the fusion (F) protein of PIV5.

4. The viral expression vector of Embodiment 1, wherein the coronavirus S protein comprises the coronavirus S protein of the severe acute respiratory syndrome coronavirus 2 (SARS-CoV-2) and wherein the cytoplasmic tail of the coronavirus S protein has been replaced with the cytoplasmic tail of the fusion (F) protein of PIV5.

5. The viral expression vector of any one of Embodiments 1 to 4, wherein the heterologous polypeptide comprises a coronavirus spike (S) protein that contains mutations at amino acid residue W886 and/or F888.

6. The viral expression vector of Embodiment 5, wherein the amino acid substitution at amino acid residue W886 comprises a substitution of tryptophan (W) to arginine (R) and/or the amino acid substitution at amino acid residue W888 comprises a substitution of phenylalanine (F) to arginine (R).

7. The viral expression vector of any one of Embodiments 1 to 6, wherein the heterologous nucleotide sequence is inserted between the small hydrophobic protein (SH) gene and the hemagglutinin-neuraminidase (HN) gene of the PIV5 genome.

8. The viral expression vector of any one of Embodiments 1 to 6, wherein the heterologous nucleotide sequence replaces the SH gene nucleotide sequence.

9. The viral expression vector of any one of Embodiments 1 to 6, wherein the heterologous nucleotide sequence is inserted between the hemagglutinin-neuraminidase (HN) gene and the large RNA polymerase protein (L) gene of the PIV5 genome.

10. The viral expression vector of any one of Embodiments 1 to 6, wherein the heterologous nucleotide sequence is inserted closer to the leader than between the hemagglutinin-neuraminidase (HN) gene and the large RNA polymerase protein (L) gene of the PIV5 genome; is inserted upstream of the nucleocapsid protein (NP) gene of the PIV5 genome; is inserted immediately downstream of the leader sequence of the PIV5 genome; is inserted between the fusion (F) protein gene and the SH gene of the PIV5 genome; is inserted between the VP gene and the matrix protein (M) gene of the PIV5 genome; is inserted between the M gene and the F gene of the PIV5 genome; is inserted between the nucleocapsid protein (NP) gene and the V/P gene of the PIV5 genome; is inserted between the leader sequence and the nucleocapsid protein (NP) gene of the PIV5 genome; is inserted wherein a portion of the F or HN gene of PIV5 has been replaced with the heterologous nucleotide sequence; is inserted within the SH gene nucleotide sequence, is inserted within the NP gene nucleotide sequence, is inserted within the V/P gene nucleotide sequence, is inserted within the M gene nucleotide sequence, is inserted within the F gene nucleotide sequence, is inserted within the HN gene nucleotide sequence, and/or is inserted within the L gene nucleotide sequence.

11. The viral expression vector of any one of Embodiments 1 to 10, wherein the PIV5 genome further comprises one or more mutations.

12. The viral expression vector of Embodiment 11, wherein the one or more mutations comprise a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof.

13. The viral expression vector of Embodiment 11 or 12, wherein the one or more mutations comprise PIV5 VΔC, PIV5ΔSH, PIV5-P-S308G, or a combination thereof.

14. A viral particle comprising the viral expression vector of any one of Embodiments 1 to 13.

15. A composition comprising the viral expression vector of any one of Embodiments 1 to 13 and/or a viral particle of claim 14.

16. A method of expressing a heterologous coronavirus spike (S) glycoprotein in a cell, the method comprising contacting the cell with the viral expression vector, viral particle, or composition of any one of Embodiments 1 to 15.

17. A method of inducing an immune response in a subject to a coronavirus spike (S) glycoprotein, the method comprising administering the viral expression vector, viral particle, or composition of any one of claims Embodiments 1 to 15 to the subject.

18. The method of Embodiment 17 wherein the immune response comprises a humoral immune response and/or a cellular immune response.

19. A method of vaccinating a subject against coronavirus disease 2019 (COVID-19), the method comprising administering the viral expression vector, viral particle, or composition of any one of Embodiments 1 to 15 to the subject.

20. The method of any one of Embodiments 17 to 19, wherein the viral expression vector, viral particle, or composition is administered intranasally, intramuscularly, topically, or orally.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

For any method disclosed herein that includes discrete steps, the steps may be conducted in any feasible order. And, as appropriate, any combination of two or more steps may be conducted simultaneously.

The description exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of CVX-UGA1

CVX-UGA1 was generated from plasmid pDA27 (pDA27). Plasmid pDA27 has the SARS-CoV-2-S gene from nCOV19-S-human-Genscript plasmid (high-copy plasmid from GenScript), with the cytoplasmic tail replaced with PIV5 F cytoplasmic tail which was inserted into plasmid pDA16 (low-copy plasmid) backbone between genes SH and HN. The S gene sequence was based on MN908947 and codon-optimized for expression in human. Plasmid pDA16 contains the whole PIV5 virus genome and a chloramphenicol resistance gene. The sequence of the low-copy pDA16 plasmid has been fully verified.

Process for obtaining pDA27 is shown in FIG. 1. SARS-CoV-2-S gene with the cytoplasmic tail replaced with PIV5 F tail was obtained through PCR from nCOV19-S-human-Genscript plasmid. The DA193-F and DA194-R primers used for the PCR reaction have overlapping regions with pDA16 plasmid and DA194-R primers contains the PIV5 F tail sequence. pDA16 plasmid was used as the backbone. The plasmid was digested with NotI and MluI restriction enzymes to remove previous gene inserted between PIV5 SH and HN genes. pDA27 plasmid was constructed through Gibson assembly. The SARS-CoV-2-S-Ftail PCR product was combined with digested pDA16 and Gibson assembly master mix and incubated at 50° C. for 1 hour.

Figure 3:
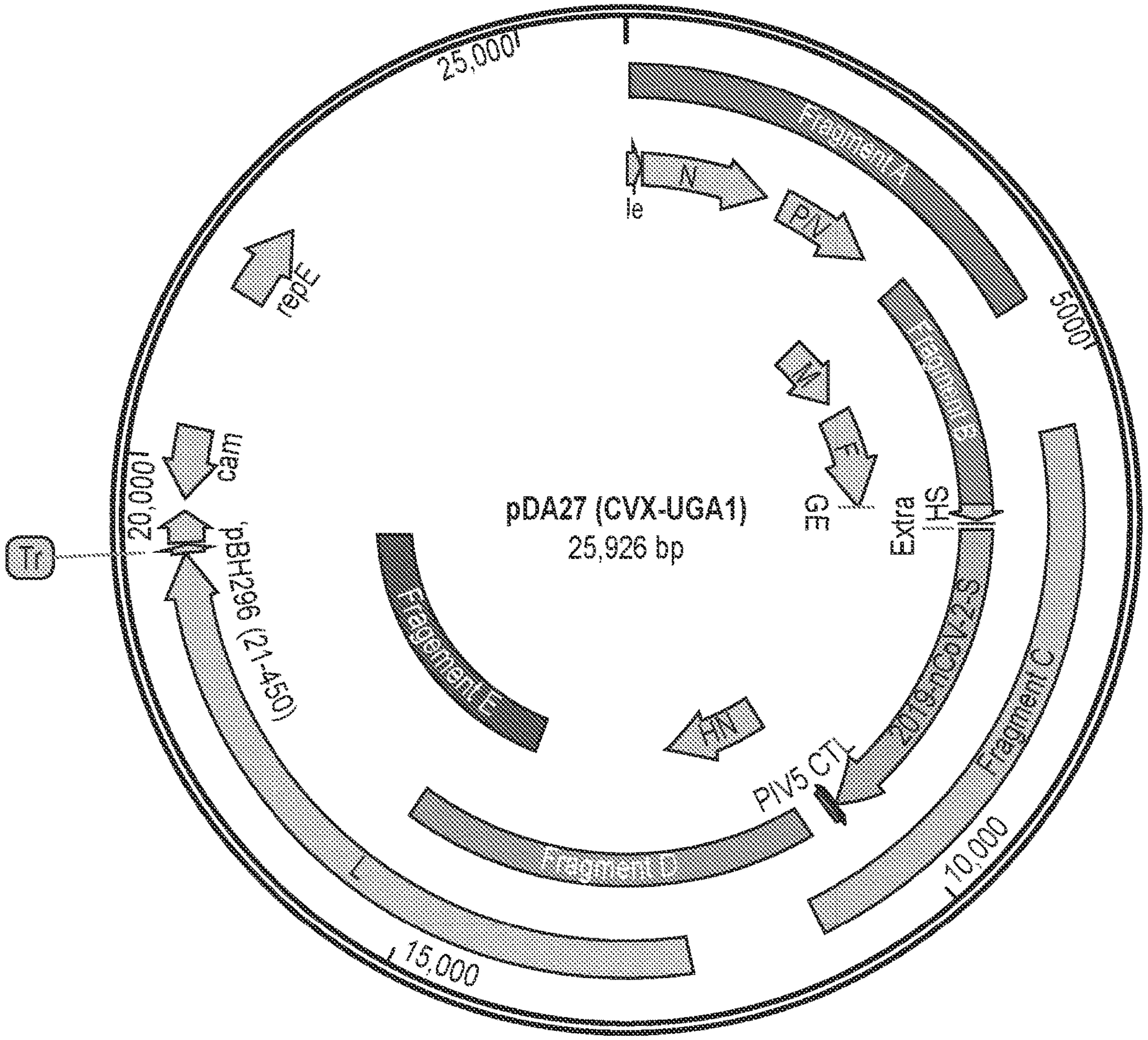
FIG. 3 shows the plasmid map showing sequencing fragments.

FIG. 2 shows where the S of SARS-CoV-2 was inserted into the PIV5 genome in pDA27 (CVX-UGA1). The new pDA27 plasmid was then transformed into TOP10 competent cells obtained from Thermo Fisher Scientific and plated on LB agar plates containing chloramphenicol. A single colony was expanded in LB media containing chloramphenicol and plasmid was purified and sequenced by PCR amplification of 5 fragments shown in FIG. 3 using primers listed in Table 1 and Table 2.

Figure 5:
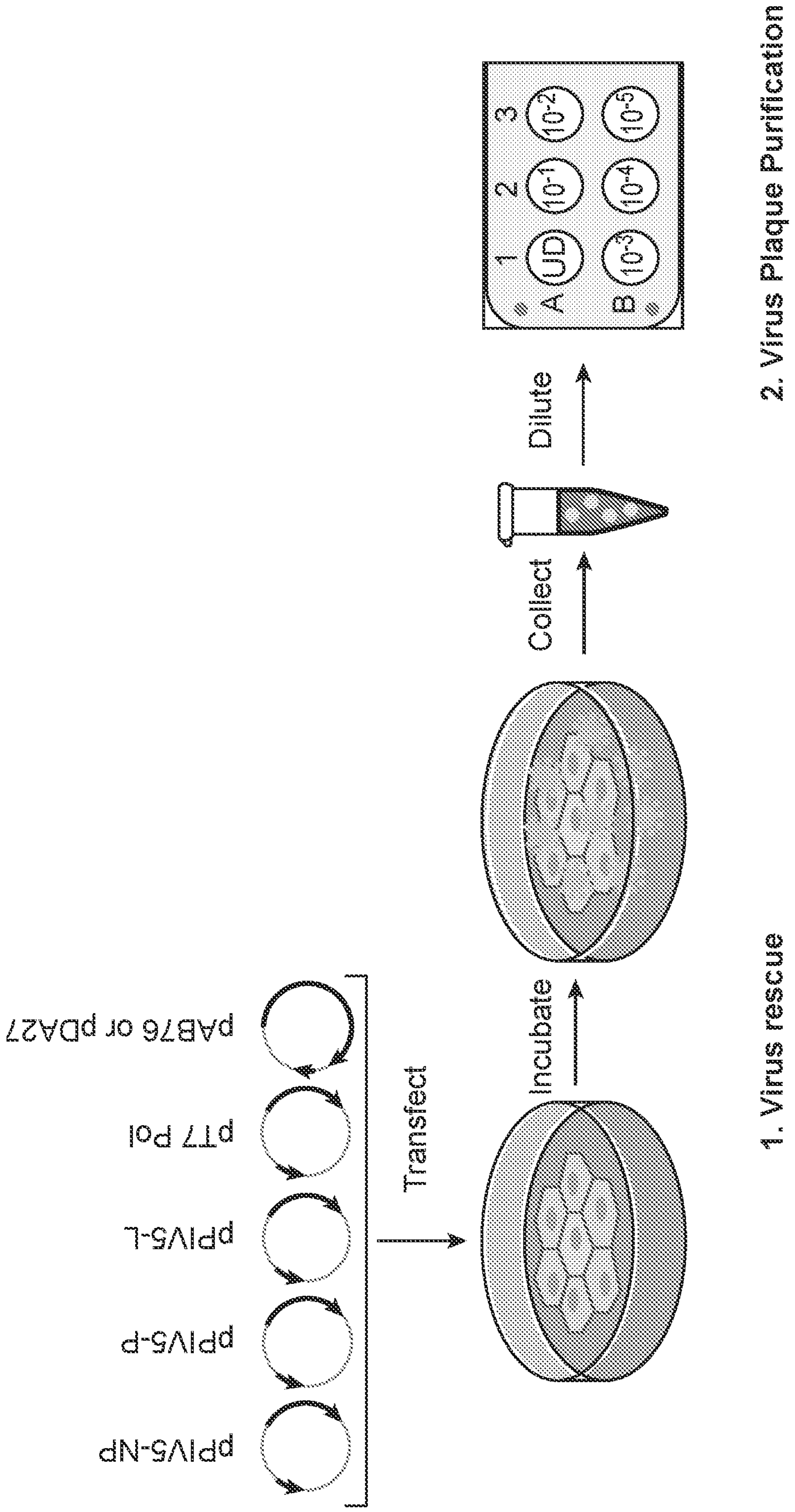
FIG. 5 shows an outline scheme for virus rescue and plaque purification.

The plasmid was sent for deep-sequencing, where the whole plasmid sequence and not just the part with the PIV5(SH-HN)-CoV-2-S-Ftail genome was obtained and the sequence verified. After confirmation of the proper sequence, viral rescue took place. This process shown in FIG. 5.

Figure 4:
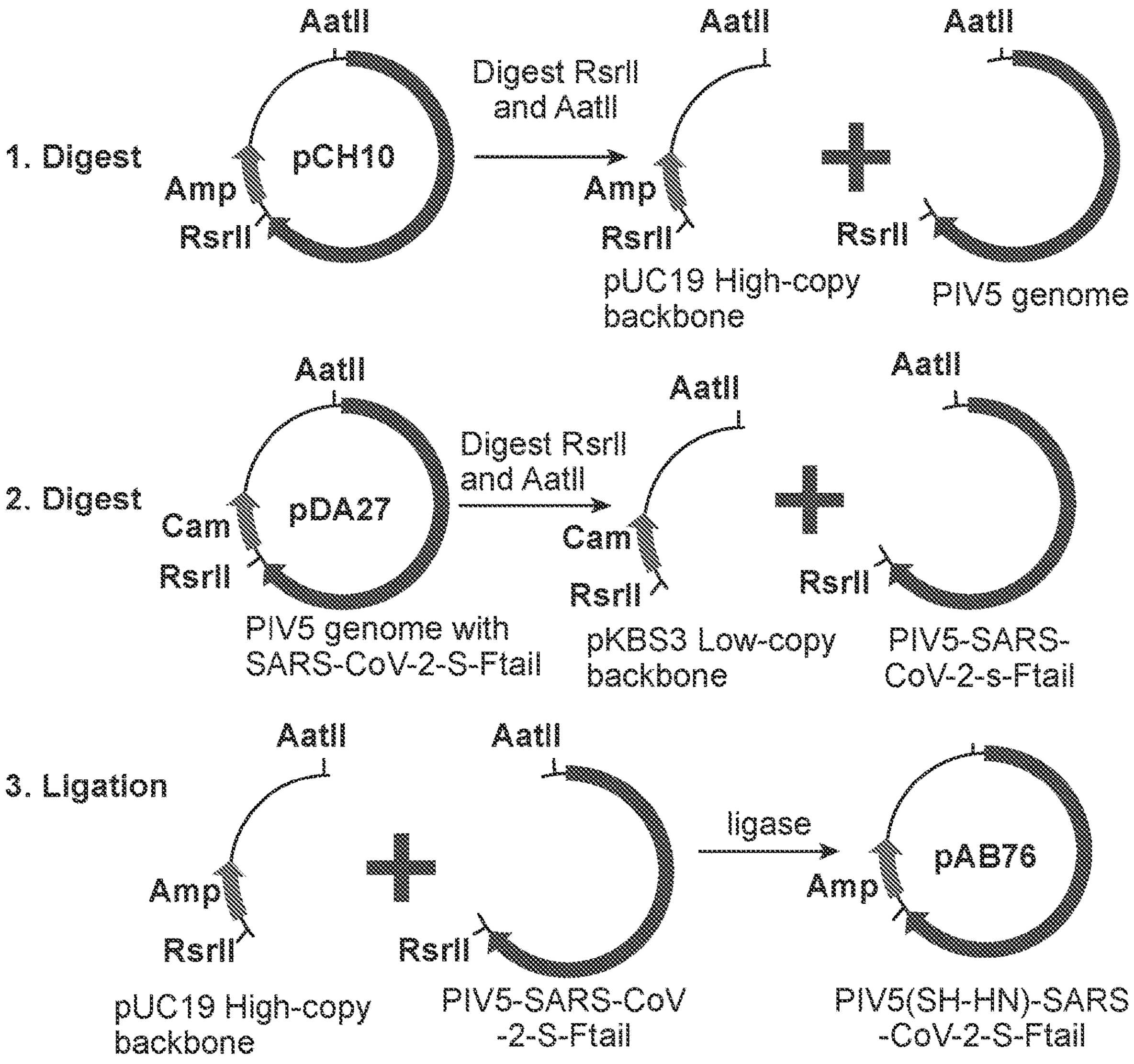
FIG. 4 shows the process for constructing the CVX-UGA1 vaccine using the pAB76 plasmid.

An alternative method for the construction of CVX-UGA1 vaccine is by construction of the pAB76 plasmid. This plasmid contains the exact PIV5(SH-HN)-SARS-CoV-2-S genome as pDA27 but with a high-copy backbone (pUC19) containing an ampicillin resistance gene. The process for pAB76 is shown in FIG. 4.

The pCH10 plasmid was used to obtain the high-copy pUC19 backbone. The plasmid was digested with RsrII and AatII restriction enzymes.

The pDA27 plasmid (low-copy) was used to obtain the PIV5(SH-HN)-SARS-CoV-2-S-Ftail. The plasmid was digested with pDA27 plasmid with RsrII and AatII restriction enzymes.

Digested products (pUC19 high-copy backbone and PIV5 (SH-HN)-SARS-CoV-2-S-Ftail) were ligated following Rapid Ligation protocol to obtain final plasmid.

Either of the processes shown in FIG. 1 or FIG. 2 can be used to produce the final plasmid used for the production of seed CVX-UGA1. The PIV5(SH-HN)-SARS-CoV-2-S-Ftail genomes in pDA27 and pAB76 are identical. The only difference is that pDA27 is a low-copy plasmid (chloramphenicol resistant) and pAB76 is a high-copy plasmid (ampicillin resistant).

For the rescue of the recombinant vector virus, the pDA27 plasmid was transfected into BHK-21 cells(obtained from ATCC) together with plasmids encoding the PIV5 NP, P, L proteins and T7 RNA Polymerase allowing for the rescue of recombinant virus from the supernatant. Rescue plasmids are CAGGS-NP, pCAGGS-P, CAGGS-L, and pBH437-T7. The full sequence of the rescue plasmids was confirmed prior to use in virus rescue. The media used for virus rescue was DMEM media (obtained from Gibco) with TPB (obtained from BD), FBS (obtained from HyClone), and PenStrep (obtained from Lonza).

Following seven days of incubation, 5 mL of supernatant containing the vector virus was obtained and mixed with 10×SPG and stored at −80° C. Aliquots of this frozen stock were serially diluted to perform a plaque assay on Vero cells (obtained from ATCC) in 6-well plates, with the objective of obtaining a 6-well with a single plaque. A 1000 uL pipette tip was used to poke the single plaque and re-suspend in DMEM media containing FBS and PenStrep. The re-suspended plaque was then used to infect naïve Vero cells in a 6 cm dish. After 7 days, the supernatant (5 mL) from the 6 cm dish containing the single plaque purification was mixed with 10×SPG and stored at −80° C. Part of the supernatant (140 uL) was used to do RNA extraction and RT-PCR to verify sequence. The RT-PCR was done with the same primers described in Table 1.

TABLE 1

| Primers | |
|---|---|
| | Primers |
| A | PIV5-1-F, PIV5-4369-R |
| B | PIV5-3469-F, PIV5-6276-R |
| C | PIV5-5590-F, PIV5-7149-R |
| D | PIV5-6814-F, PIV5-11607-R |
| E | PIV5-10545-F, PIV5-15246-R |

TABLE 2

| Artificial Oligonucleotide Primers | | | | |
|---|---|---|---|---|
| Number | SEQ ID NO: | Name | Sequence | Concentration |
| 1 | 2 | PIV5-1-F | ACCAAGGGGAAAATG AAGTGGTGAC | 100 uM |
| 2 | 3 | PIV5-3469-F | TCCAGGTCACTGTTAG GAAGACATC | 100 uM |
| 3 | 4 | PIV5-4369-R | AGTGTGTTGTAGCCTA CGATCAGTG | 100 uM |
| 4 | 5 | PIV5-5590-F | CAAGATGCACCTTCTCT CCAGTG | 100 uM |
| 5 | 6 | PIV5-6276-R | GCTCGATTACCTAGATT GACCGAGAC | 100 uM |
| 6 | 7 | PIV5-6814-F | TAACTCTGCAGTCGCTC TACCTC | 100 uM |
| 7 | 8 | PIV5-7149-R | ACATGATCCTGGCATC CATTCAG | 100 uM |
| 8 | 9 | PIV5-10545-F | TCAACCCACCAGCAGA TACCAG | 100 uM |

TABLE 2-continued

| Artificial Oligonucleotide Primers | | | | |
|---|---|---|---|---|
| Number | SEQ ID NO: | Name | Sequence | Concentration |
| 9 | 10 | PIV5-11607-R | TCAATGATGATGTGAG CTACACGC | 100 uM |
| 10 | 11 | PIV5-15246-R | ACCAAGGGGAAAACCA AGATTAATCC | 100 uM |
| 11 | 12 | DA193-F | ATCCACAATCTACAGTC GACGCGGCCGCCATGT TCGTCTTCCTGGTCCT | 100 uM |
| 12 | 13 | DA194-R | GTATGGCAGGAGGCTA GCACGCGTTCATTTAT GATAAACAAAATTCTC CATTCTATTTCGATTAG | 100 uM |

For the rescue of the CVX-UGA1 to produce master seed, the DA27 or AB76 plasmid is transfected into 293T serum-free cells (obtained from ATCC) together with plasmids encoding the PIV5 NP, P, L proteins and T7 RNA Polymerase allowing for the rescue of recombinant virus from the supernatant. The next day, 293T serum free-transfected cells are trypsinized and co-cultured with Vero-SF (serum free) cells in a 10 cm dish and then incubated for seven days. Following seven days of incubation, 5 mL of supernatant containing the vector virus is obtained and mixed with 10×SPG and stored at −80° C. Aliquots of this frozen stock are serially diluted to perform a plaque assay on Vero-SF cells in 6-well plates, to obtain a 6-well with a single plaque. A 1000 uL pipette tip is used to poke the single plaque and re-suspend in VP-SFM media. The re-suspended plaque is then be used to infect naïve Vero-SF cells in a 6 cm dish. After 7 days, the supernatant (5 mL) from the 6 cm dish containing the single plaque purification was mixed with 10×SPG and stored at −80° C. Aliquots from the initial round of single plaque purification are used as the seed inoculum for manufacture of the pre-master seed vaccine to generate a master seed in a GMP facility using qualified GMP produced Vero-SF cell banks in serum free media (VP-SFM Media).

The CVX-UGA1 virus rescue may be performed with either pDA27 or pAB76 as they have the exact PIV5(SH-HN)-SARS-CoV-2-S-Ftail genome. The only difference is that pDA27 is a low-copy plasmid and pAB76 is a high-copy plasmid.

Plasmids used in future rescue to obtain CVX-UGA1 will be prepared using animal-free products. The goal is to produce CVX-UGA1 free of animal products except cells (293T-serum free and Vero-serum free, and animal-products free).

Figure 6:
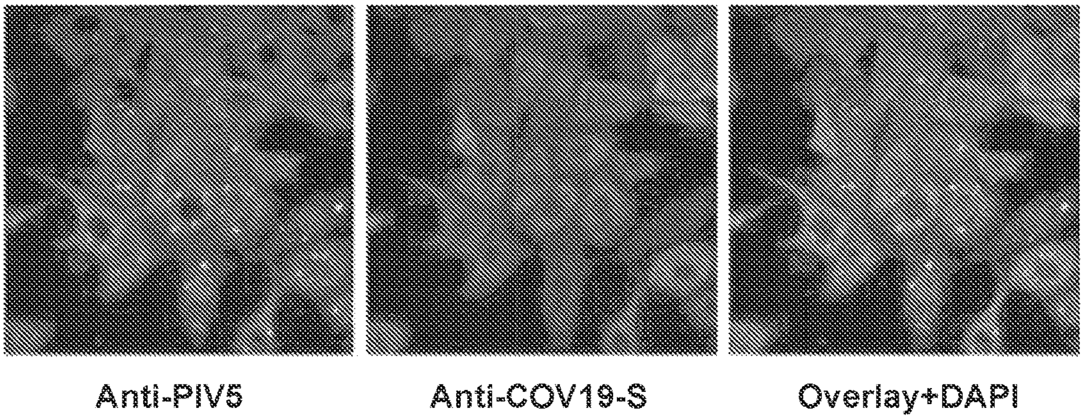
FIG. 6 shows the immunofluorescence assay images of MDBK cells infected with CVX-UGA1 and stained for SARS-CoV-2 S with SARS-CoV-2 Spike S1 monoclonal antibody.

The production of SARS-CoV-2-S-protein by the seed construct was confirmed by immunofluorescence assay. This is shown in FIG. 6. Primary antibody: SARS-CoV-2 Spike S1 rabbit monoclonal antibody from Sino Biological and Secondary Antibody: Cy3 labeled Goat anti-rabbit IgG (H+L) from KPL.

Detection of SARS-CoV-2 S in CVX-UGA1-infected MDBK cells by immunofluorescence assay. SARS-CoV-2 S was detected using SARS-CoV-2 Spike S1 monoclonal antibody followed by Cy3 labeled Goat anti-rabbit IgG as a secondary. Infected cells were also labeled with anti-PIV5-P/V (PK) antibody as a control followed by Goat anti-mouse IgG H&L (FITC) secondary antibody. DAPI (4=,6-diamidino-2-phenylindole; blue) was used as a nuclear stain. For future experiments, Vero-SF cells will be used instead of MDBK cells.

Figure 7:
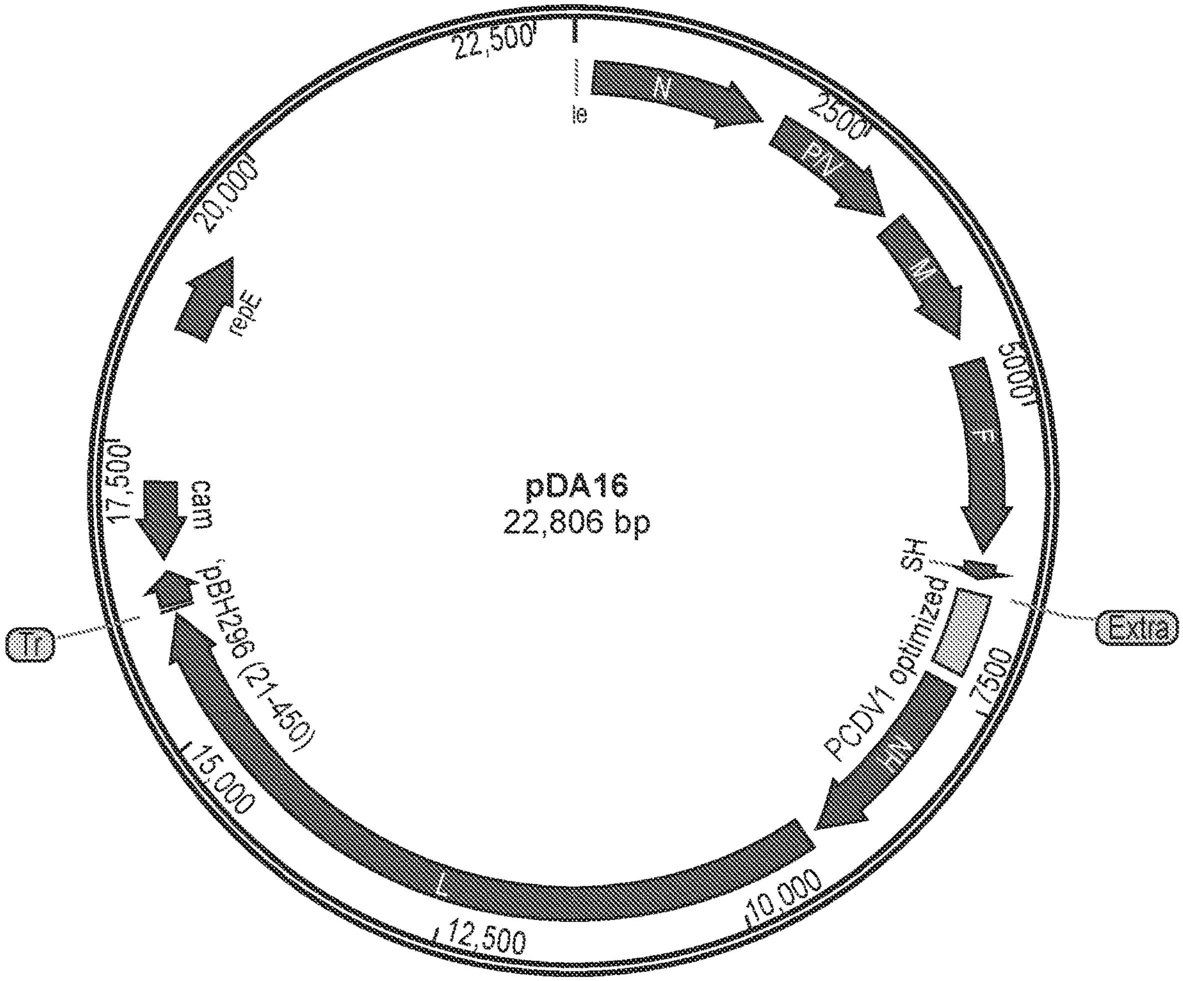
FIG. 7 shows the map of the pDA16 plasmid.

A map of the pDA16 plasmid is shown in FIG. 7. This plasmid contains the PIV5 genome plus the PCDV1 gene. It is a low-copy plasmid with a chloramphenicol resistance gene.

Figure 8:
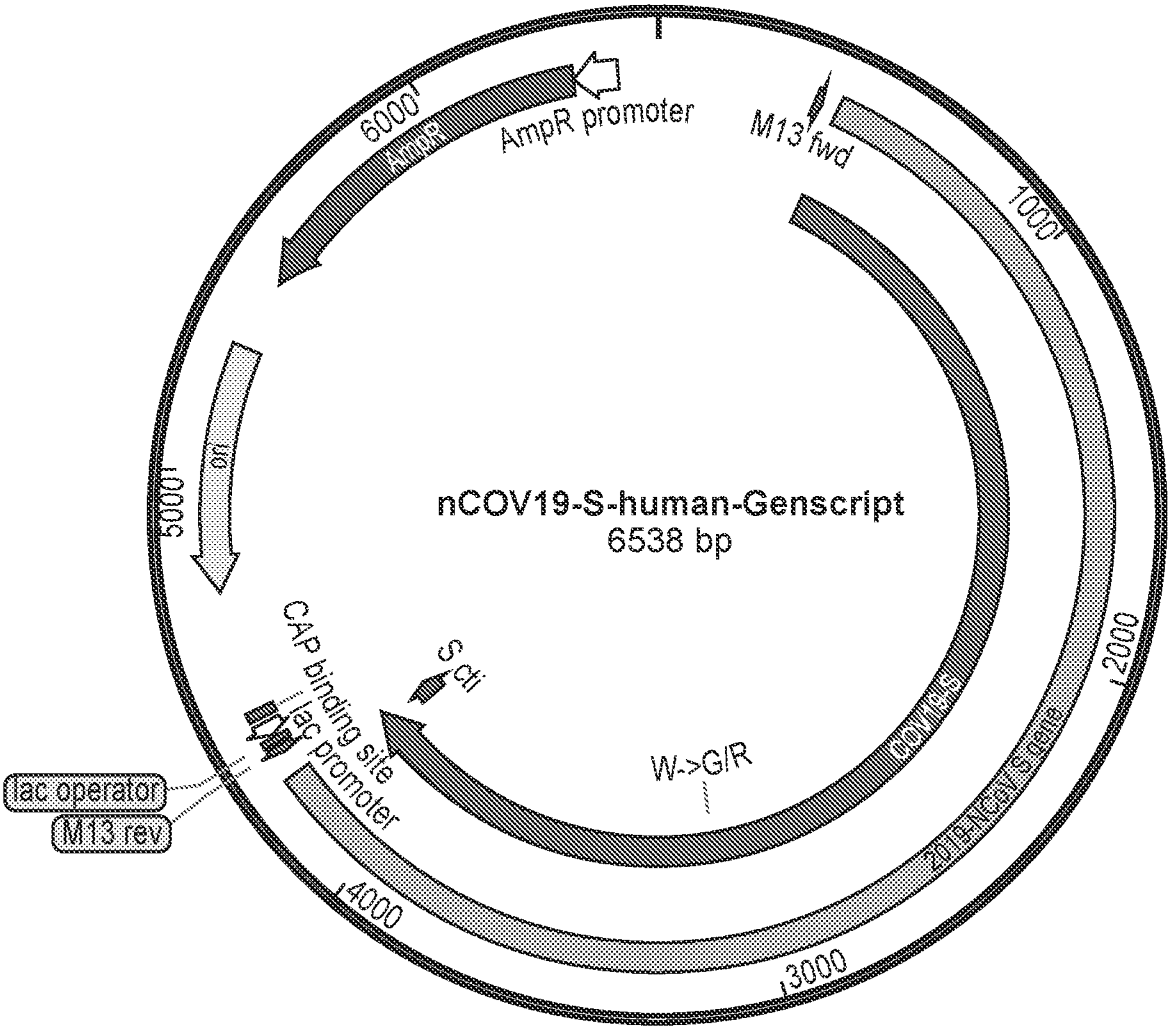
FIG. 8 shows the map of the nCOV19-S-human-Genscript plasmid.

A map of the nCOV19-S-human-Genscript plasmid is shown in FIG. 8. This is a high-copy plasmid and it contains and ampicillin resistance gene. It was obtained from GenScript.

Figure 10:
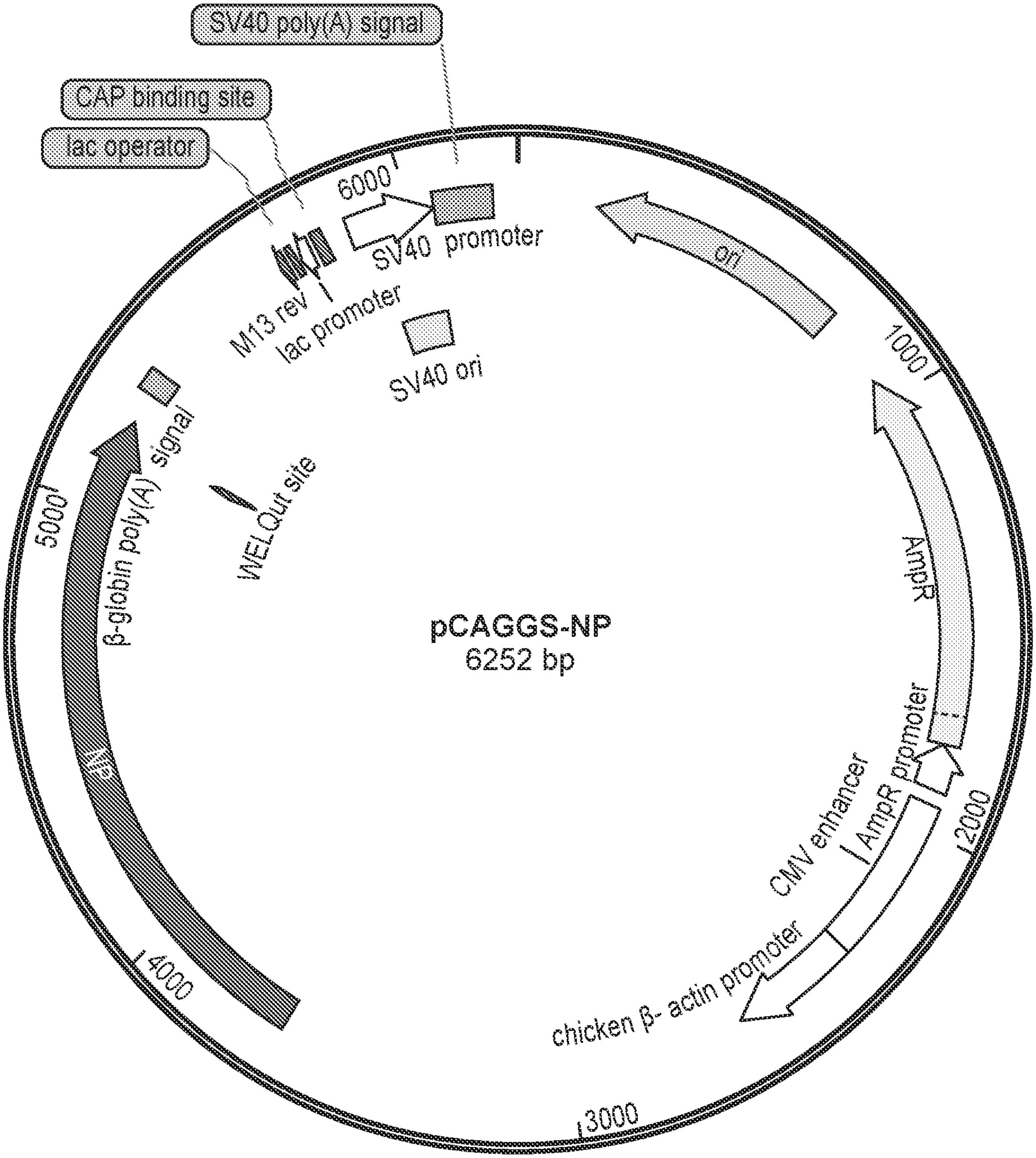
FIG. 10 shows the map of the pCAGGS-NP plasmid.

A map and sequence of the pDA27 (CVX-UGA1) plasmid is shown in FIG. 9. This plasmid is a low-copy plasmid and it contains a chloramphenicol resistance gene. A map of the pCAGGS-NP plasmid is shown in FIG. 10. This plasmid is a high-copy plasmid and it contain an ampicillin resistance gene. PIV5 NP DNA sequence from pBH276 plasmid was subcloned into pCAGGS expression plasmid. For more detail, see Schmitt et al., 2002, *J Virol* 76, 3952-3964, doi:10.1 128/jvi.76.8.3952-3964.2002.

Figure 11:
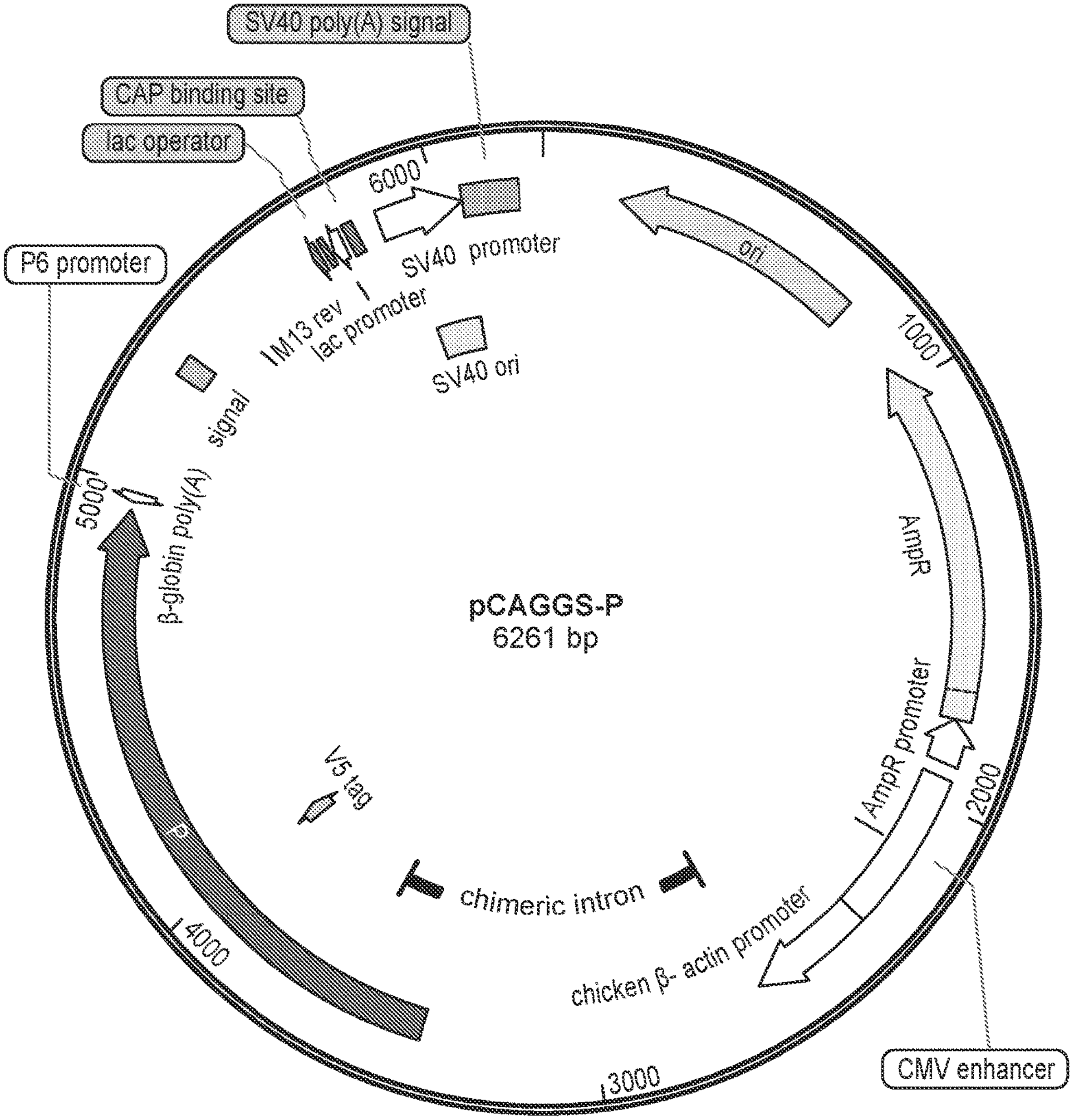
FIG. 11 shows the map of the pCAGGS-P plasmid.

A map of the pCAGGS-P plasmid is shown in FIG. 11. This plasmid is a high-copy plasmid and it contain an ampicillin resistance gene. PIV5 P DNA sequence from pBH276 plasmid was subcloned into pCAGGS expression plasmid. For more detail, see Waning et al., 2002, *J Virol;* 76:9284-9297, doi:10.1 128/jvi.76.18.9284-9297.2002.

Figure 12:
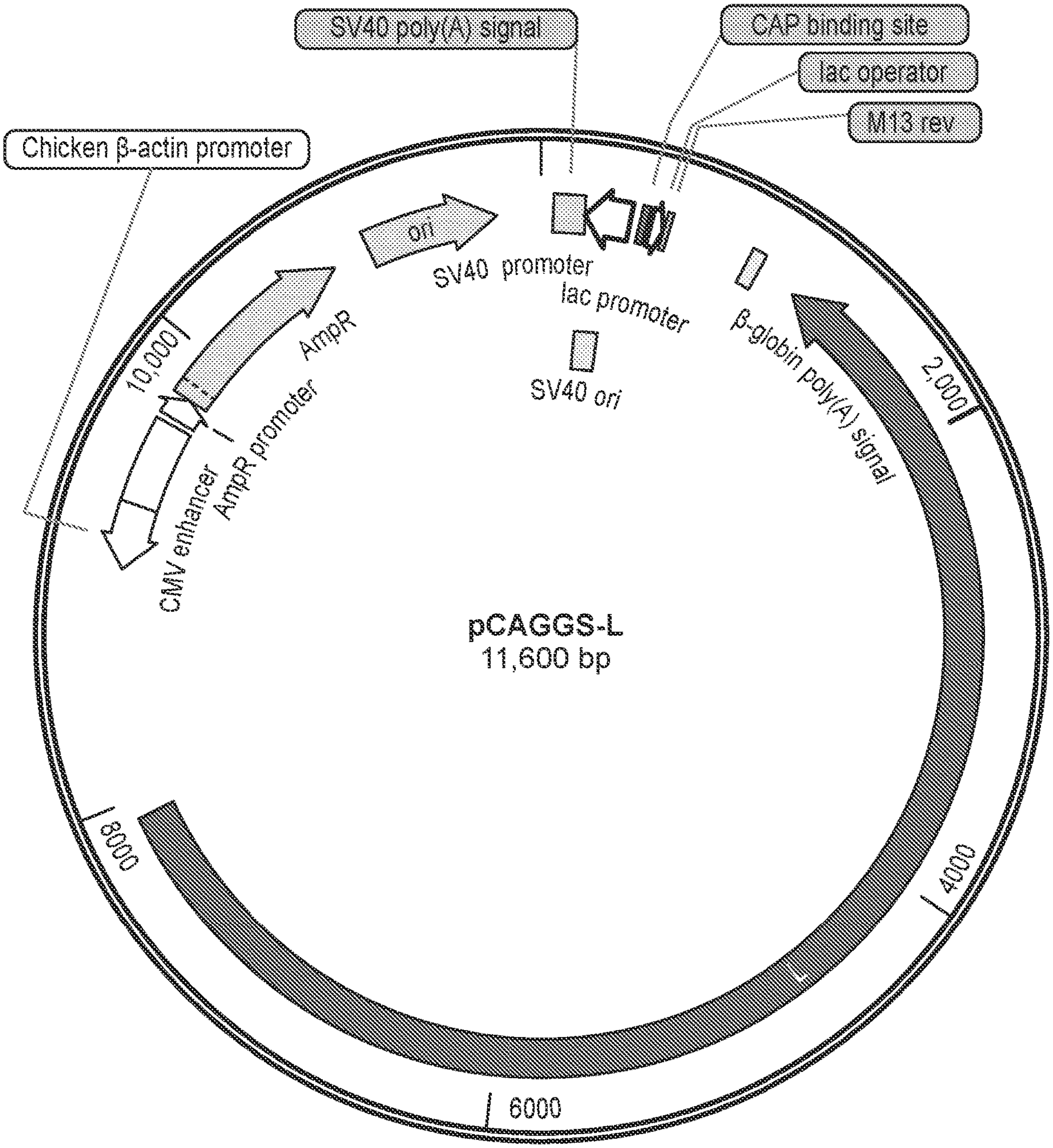
FIG. 12 shows the map of the pCAGGS-L plasmid.

A map of the pCAGGS-L plasmid is shown in FIG. 12. This plasmid is a high-copy plasmid and it contain an ampicillin resistance gene. PIV5 L DNA sequence from pBH276 plasmid was subcloned into pCAGGS expression plasmid. For more detail, see Waning et al., 2002, *J Virol;* 76:9284-9297, doi:10.1 128/jvi.76.18.9284-9297.2002.

Figure 13:
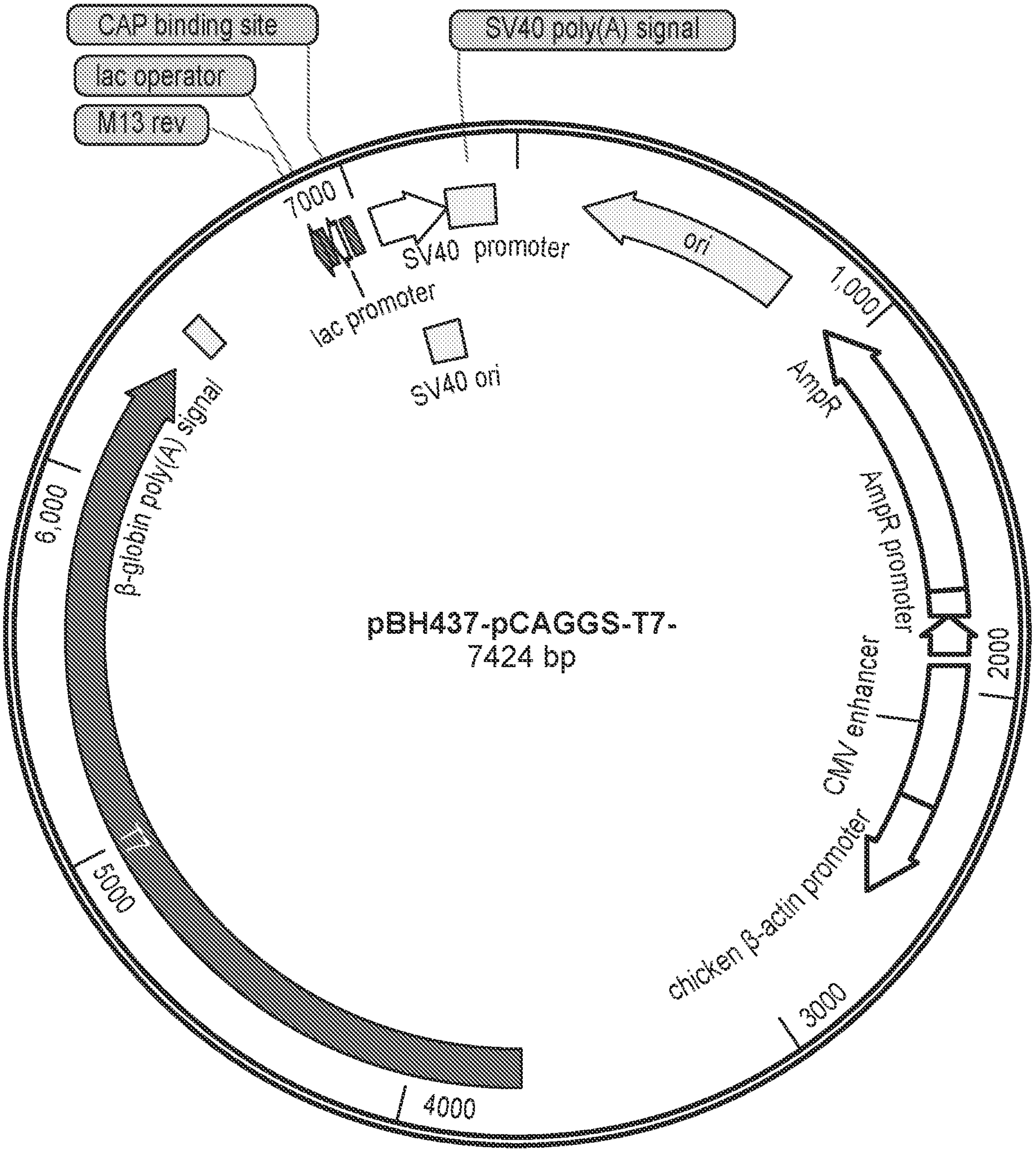
FIG. 13 shows the map of the pBH437-pCAGGS-T7 plasmid.

A map of the pBH437-pCAGGS-T7 plasmid is shown in FIG. 13. This plasmid is a high-copy plasmid and it contain an ampicillin resistance gene. T7 polymerase DNA sequence from pBH161 plasmid was subcloned into pCAGGS expression plasmid.

Figure 14:
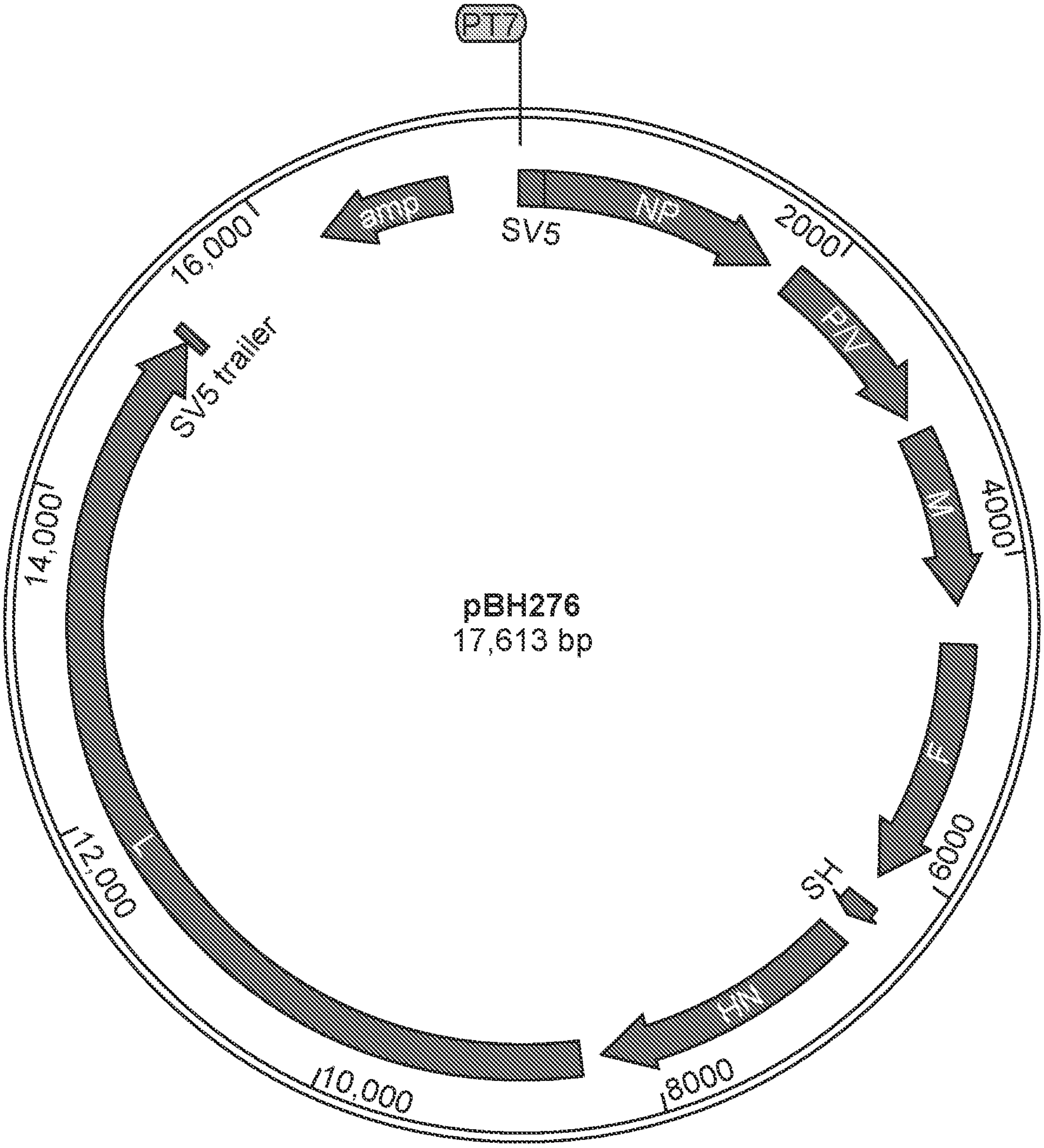
FIG. 14 shows the map of the pBH276 plasmid.

A map of the pBH276 plasmid is shown in FIG. 14. This plasmid contains the PIV5 genome. It is a high-copy plasmid with an ampicillin resistance gene. For more detail, see He et al., 1997, *Virology;* 237:249-260, doi:10.1006/viro.1997.8801.

Figure 15:
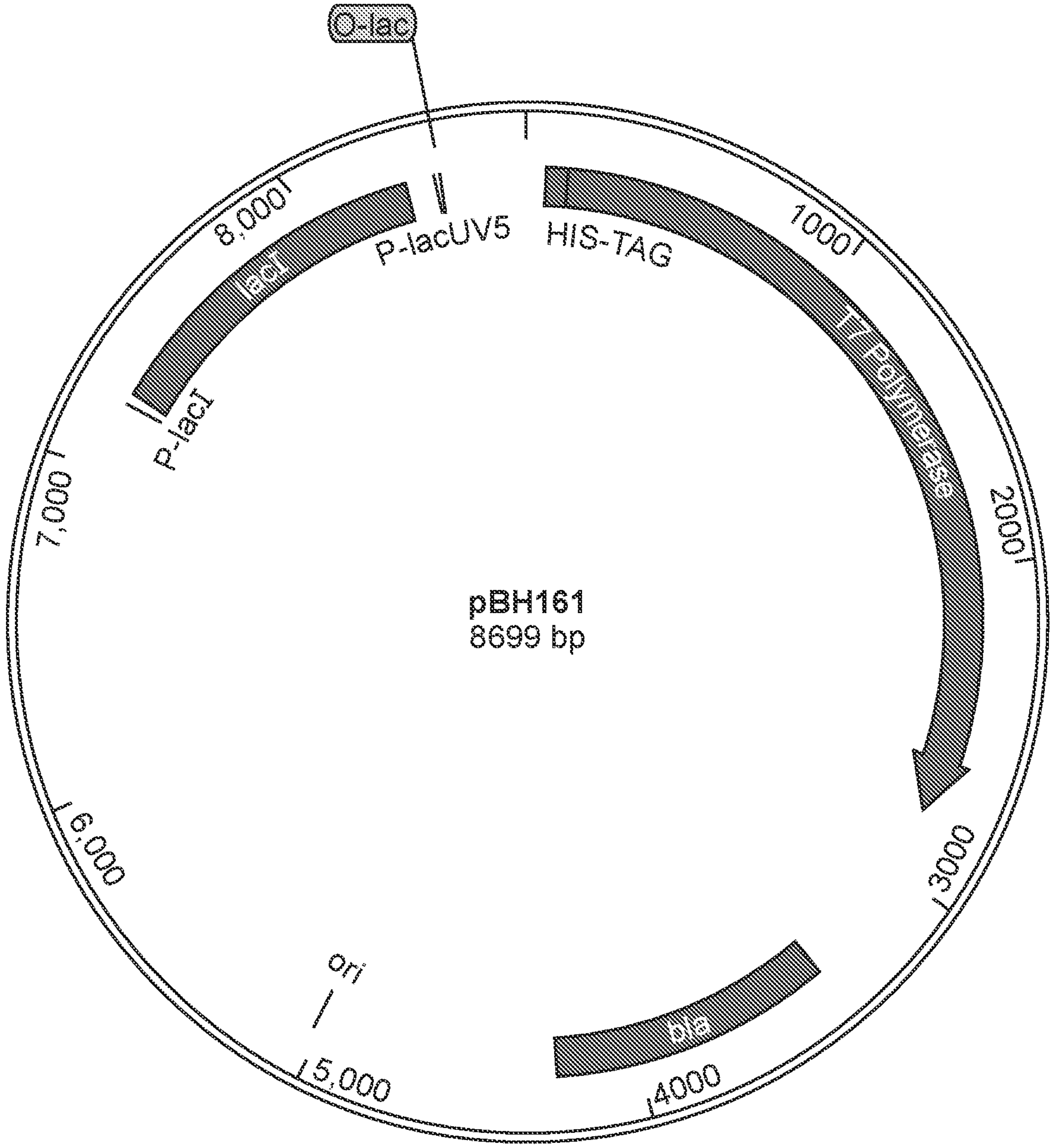
FIG. 15 shows the map of the pBH161 plasmid.

A map of the pBH161 plasmid is shown in FIG. 15. This plasmid is a high-copy plasmid and contain an ampicillin resistance gene. For more detail, see He et al., 1997, *Protein Expression and Purification;* 9:142-151, doi:10.1006/prep.1996.0663.

Figure 16:
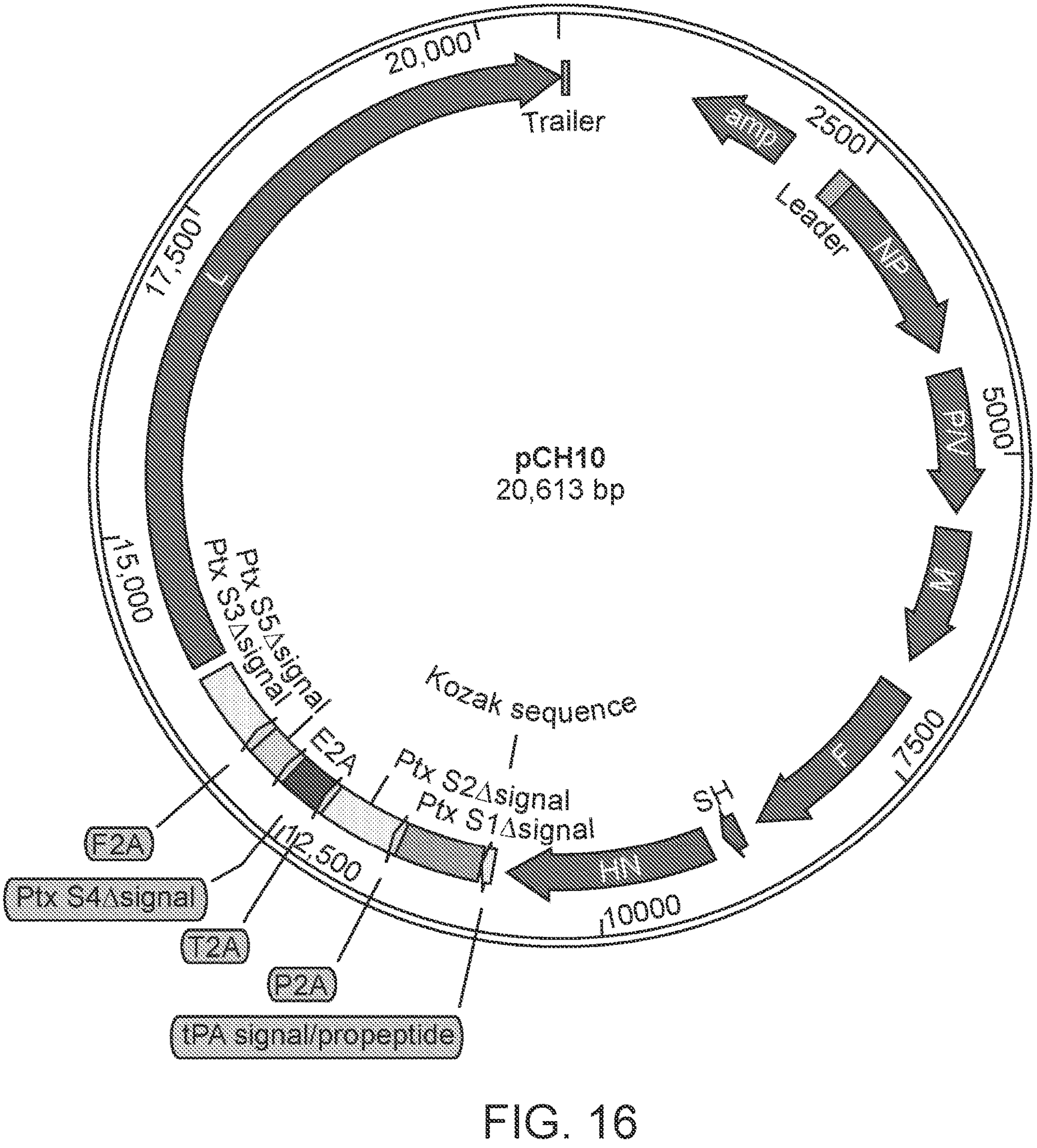
FIG. 16 shows the map of the pCH10 plasmid.

A map of the pCH10 plasmid is shown in FIG. 16. This plasmid contains the PIV5 genome. It is a high-copy plasmid with an ampicillin resistance gene.

Figure 17:
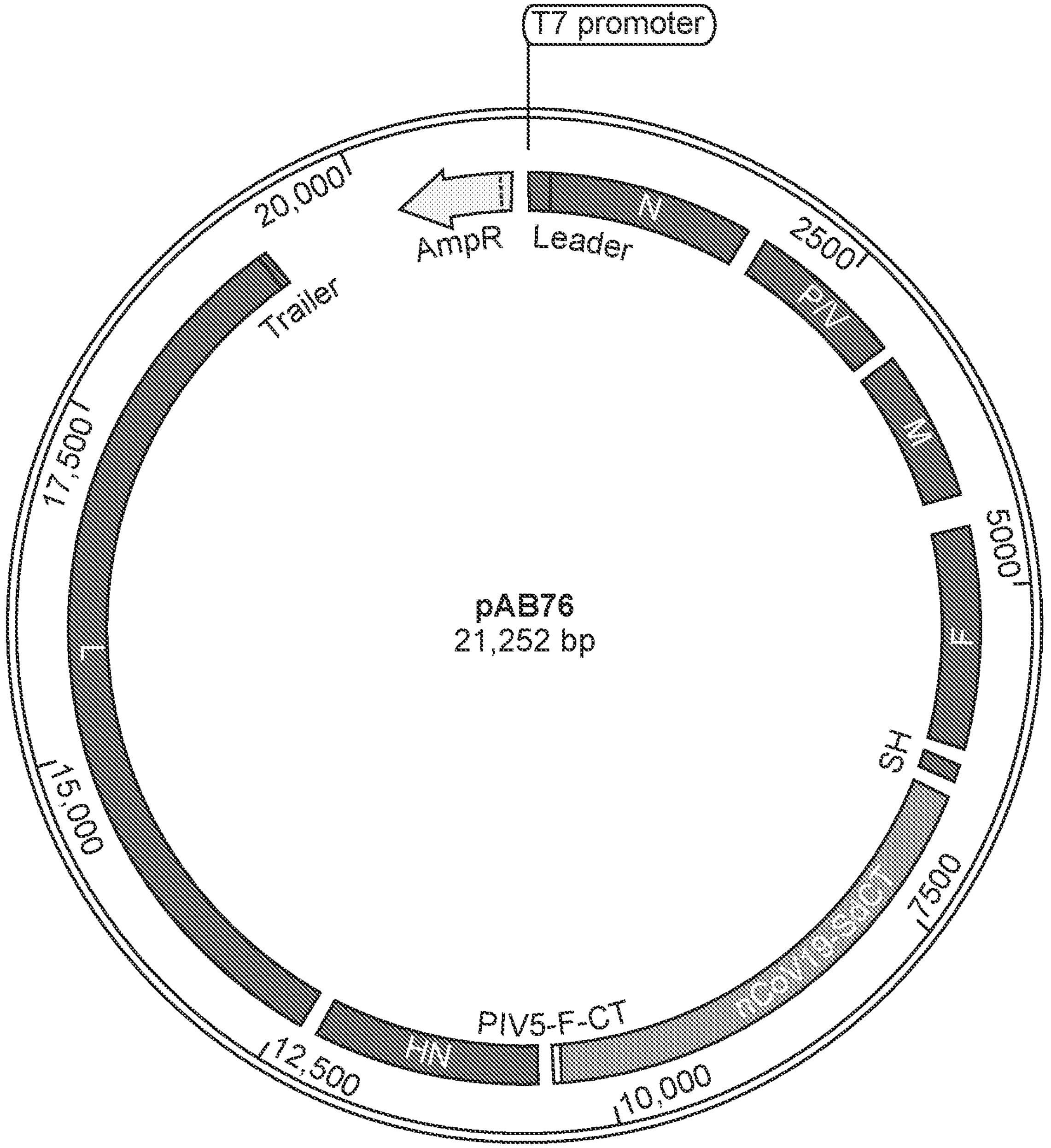
FIG. 17 shows the map of the pAB76 Plasmid.

A map of the pAB76 plasmid is shown in FIG. 17. This plasmid is a high-copy plasmid and it contains an ampicillin resistance gene.

Protocols

Subculturing Procedure for Vero-SF

Volumes used in this protocol are for a 75 $cm^2$ flask.

Remove and discard culture medium using pasteur pipet and vacuum pump.

Briefly rinse the cell layer with 10 mL Ca++/Mg++ free Dulbecco's phosphate buffered saline (DPBS).

Add 5 mL of TrypLE to flask. Incubate at 37° C. until cells have detached. Observe cell monolayer using an inverted microscope to ensure complete cell detachment from the surface of the flask.

To avoid clumping do not agitate the cells by tapping or shaking the flask while waiting for the cells to detach. Cells that are difficult to detach may be placed at 37° C. to facilitate dispersal.

Add 10 mL of pre-warmed VP-SFM medium to flask and aspirate cells by gently pipetting with 10 mL serological pipet. Tilt flask in all directions to thoroughly rinse flask.

Transfer cell suspension to a 15 mL conical tube and spin at 125 g for 10 minutes.

Discard supernatant and re-suspend cells in fresh VP-SFM. Add appropriate aliquots of cell suspension to new culture vessels.

Incubate cultures at 37° C.

Cells grow best after the first subculture.

Subcultivation Ratio: 1:4 dilution.

Medium Renewal: Two times weekly.

Subculturing Procedure for 293T-SF

Volumes used in this protocol are for a 75 $cm^2$ flask.

Remove and discard culture medium using pasteur pipet and vacuum pump.

Briefly rinse the cell layer with 10 mL Ca++/Mg++ free Dulbecco's phosphate buffered saline (DPBS).

Add 10 mL of pre-warmed BalanCD HEK293 medium to flask and re-suspend cells by gently pipetting with 10 mL serological pipet.

Transfer cell suspension to a 15 mL conical tube and spin at 125 g for 10 minutes.

Discard supernatant and re-suspend cells in fresh BalanCD HEK293 medium. Add appropriate aliquots of cell suspension to new culture vessels.

Incubate cultures at 37° C.

Cells grow best after the first subculture.

Subcultivation Ratio: 1:4 dilution.

Medium Renewal: Two times weekly.

Subculturing Procedure for BHK-21 and Vero Cells

Volumes used in this protocol are for a 75 $cm^2$ flask.

Remove and discard culture medium using pasteur pipet and vacuum pump (IV-18).

Briefly rinse the cell layer with 10 mL Ca++/Mg++ free Dulbecco's phosphate buffered saline (DPBS).

Add 5 mL of Trypsin/EDTA to flask. Tilt flask to cover surface and remove excess.

Incubate at 37° C. until cells have detached. Observe cell monolayer using an inverted microscope to ensure complete cell detachment from the surface of the flask.

To avoid clumping do not agitate the cells by tapping or shaking the flask while waiting for the cells to detach. Cells that are difficult to detach may be placed at 37° C. to facilitate dispersal Add 20 mL of pre-warmed respective culture medium to flask and re-suspend cells using 10 mL serological pipet. Tilt flask in all directions to thoroughly rinse flask. Add appropriate aliquots of cell suspension to new culture vessels.

Incubate cultures at 37° C.

Culture medium for BHK is DMEM+TPB+FBS+PenStrep and for Vero is DMEM+FBS+PenStrep.

PIV5 Rescue (Transfection)

1 Day Before:

Plate BHK-21 cells in 60 mm tissue culture dish at a 1:8 dilution (75% confluency the next day)

Day of:

Mix plasmid DNA, pCAGGs-NP, pCAGGs-P, pCAGGs-L, and pBH437 (pCAGGS-T7) in 1.6 mL microcentrifuge tube in the biological safety cabinet.

Mix by pipetting between additions.

Add JetPRIME Buffer and JetPRIME Transfection Reagent.

Incubate at room temperature for 15 minutes.

Add transfection mixture to cells dropwise.

Monitor cells for next 7 days for syncytia using EVOS.

Once syncytia are present, start collecting 1 mL of media in a Cryo Tube and mix with 10×SPG.

Store at −80° C.

Piv5 Rescue Co-Culture (Transfection)

1 Day Before:

Plate 293T-SF cells in 6-well tissue culture dish at a 1:6 (about 75% confluency) dilution.

Plate Vero-SF cells in 10 cm dish at a 1:20 (about 50% confluency) dilution.

Day of:

Mix plasmid DNA, pCAGGs-NP, pCAGGs-P, pCAGGs-L, and pBH437 (pCAGGs-T7) in 1.6 mL microcentrifuge tube containing serum-free Opti-MEM in the biological safety cabinet.

Mix by pipetting between additions.

Add P3000 Reagent.

In a different 1.6 mL microcentrifuge tube containing serum-free Opti-MEM add Lipofectamine3000 Transfection Reagent.

Incubate at room temperature for 20 minutes.

Add transfection mixture to cells dropwise.

Next Day:

Trypsinize 293T-SFs, re-suspend well in 1 mL VP-SFM, move to a separate 15 mL conical tube.

Trypsinize 10 cm Vero-SFs, re-suspend in 3 mL VP-SFM, move to 15 mL conical tube.

Add 6 mL VP-SFM to 15 mL conical tube.

Mix well and add the full 10 mL from 15 mL conical tube to a new 10 cm dish.

Monitor cells for next 7 days for syncytia using EVOS.

Once syncytia are present, start collecting 1 mL of media in a Cryo Tube and mix with 10×SPG.

Store at −80° C.

Virus Plaque Purification

Take 1 mL frozen rescue aliquots and do plaque assay.

After 7 days, poke an individual plaque using a 1000 uL pipette tip and add to 6 cm dish of Vero-SF cells plated at a 90% confluency the day before following protocol on Appendix IV-1. Use VP-SFM media.

At day 7, collect 140 uL media sample and use for RNA extraction using QIAamp Viral RNA Mini Kit.

Collect the rest of the media (4.8 mL) in a Cryo Tube and mix with 10×SPG.

Store at −80° C.

PIV5 Plaque Assay

All steps are done in the biological safety cabinet.

1 Day Before:

Plate Vero-SF cells in 6 well culture plate at a 1:3 dilution (95% confluency the next day).

Day of:

Thaw PIV5 virus at 37° C. in incubator and keep on ice after thawing.

While virus is thawing prepare 10-fold dilutions in 96-well plate starting with undiluted sample and ending with 10-5 dilution using multichannel pipette and label 6 well plates with name of virus, passage number, date collected and dilution factor, as follows:

Add 200 μL of undiluted sample to first well

Add 180 μL of infection media to wells 2-6

Take 20 uL from first well, transfer to second well, and mix thoroughly using pipetting+mixing feature in multichannel pipette. Discard tips.

Repeat previous step 5 more times.

Aspirate media from cells using pasteur pipet and vacuum pump. Add 900 μL of VP-SFM media to each well in the 6 well culture plate.

Infect 6 well culture plate with 100 μL of virus dilution per well. Use same tip going from least concentrated to most and incubate for 1 hour.

Aspirate media after 1 hour of infection.

Add 4 mL of overlay to each well. Overlay: For 1 6 well culture plate, mix 13 mL of 2% LMP agar and 13 mL of 2× VP-SFM media.

Incubate at 37° C. for 7 days.

Growing PIV5 Virus

1 Day Before:

Plate Vero-SF cells in 175 $cm^2$ flask at a 1:3 dilution (95% confluency the next day).

Day of:

Prepare inoculum. Virus at MOI=0.01 in 20 mL of VP-SFM media.

Aspirate maintenance media from cells using pasteur pipet and vacuum pump Infect Vero-SF cells for 2 hours at 37° C. Rock plate every 15 minutes.

Aspirate inoculum and add 40 mL of VP-SFM media.

Incubate at 37° C. for 7 days.

Day 7:

Collected media in 50 mL conical tube and centrifuge at 1500 rpm for 10 minutes at 4° C. to remove cell debris.

Transfer 38 mL supernatant to new 50 mL conical tube.

Add 3.8 mL of 10×SPG and make 1 mL aliquots in Cryo tubes.

Label tubes as follows:

Virus name Plaque #

Cell Passage

Date Initials

Store virus aliquots at −80° C.

Example 2

A Single Dose Intranasal Immunization with Parainfluenza Virus 5-Based COVID-19 Vaccine Generates Sterilizing Immunity in Nasal Cavities of Ferrets and Cats SARS-CoV-2 is a novel betacoronavirus and the cause of COVID-19 pandemic. A vaccine to protect against SARS-CoV-2 infection is urgently needed to reduce spread and limit further mortality. Numerous vaccine candidates are being evaluated to identify an effective means to combat the pandemic. The upper respiratory tract is an initial site of SARS-CoV-2 infection, and for many infected individuals remains the primary site of viral replication. High viral loads and shedding from this region can begin several days before symptom onset and can continue for days after illness onset. Controlling infection at these sites is critical to combat the pandemic. To date, no vaccine has provided sterilizing immunity in the upper respiratory tract, such as nasal cavity of large animal models. This example has optimized a vaccine candidate in mouse models and subsequently demonstrates that a single dose intranasal immunization with a parainfluenza virus 5 (PIV5) expressing the S protein of SARS-CoV-2 induced sterilizing immunity in ferrets and cats. This mucosal vaccine strategy inhibited SARS-CoV-2 replication in upper respiratory tract, thus preventing progression of infection into lower respiratory tract. Most importantly, a vaccine candidate that induces sterilizing immunity in upper respiratory tract will likely limit transmission, thus, reducing SARS-CoV-2 infections in populations.

The sinonasal epithelium of the upper respiratory tract is an initial site of SARS-CoV-2 infection, and for many individuals remains the primary site of virus replication. High levels of viral replication occur in the upper respiratory tract (Wolfel et al. *Nature* 581, 465-469 (2020)), and nasopharyngeal shedding can continue for several days following initial presentation (Li et al. *Journal of Medical Virology* 92, 2286-2287 (2020)). Progressive lower respiratory tract manifestations of pneumonia, acute respiratory distress syndrome (ARDS), and respiratory failure contribute to much of the COVID-19 morbidity and mortality, and there is increasing evidence of involvement of other organ systems beyond the lungs. Because the upper and lower respiratory tracts are critical sites of COVID-19 pathogenesis, stopping viral replication in the upper respiratory tract prior to progression to the lung is an important goal for a protective vaccine. Leading vaccines to date generated robust antibody responses in immunized animals and in human clinical trials, and reduced SARS-CoV-2 replication in the lower respiratory tract in non-human primate models (Corbett et al. *N Engl J Med* 383, 1544-1555 (2020); Gao et al. *Science* 369, 77-81 (2020); Mercado et al. *Nature*, (2020); van Doremalen et al. bioRxiv, (2020); Wang et al. *Cell* 182, 713-721 e719 (2020)). However, complete protection in the upper respiratory tract, which is important to prevent SARS-CoV-2 transmission, has been difficult to achieve. There are currently no reports on whether these vaccine candidates can block transmission.

Parainfluenza virus type-5 (PIV5) is a negative-stranded RNA virus in the family Paramyxoviridae that has been evaluated as a vaccine vector for influenza, respiratory syncytial virus (RSV), rabies, and a variety of other pathogens (Chen et al. *J Virol* 87, 2986-2993 (2013); Li et al. *mBio* 11, (2020); Mooney et al. *J Virol* 87, 363-371 (2013); Phan et al. *Vaccine* 32, 3050-3057 (2014); Phan et al. *J Virol* 91, (2017)). In animal models PIV5 is safe, and is not associated with any disease with the exception of kennel cough in dogs (Cornwell et al. *Vet Rec* 98, 301-302 (1976)). Intranasally administered kennel cough vaccines containing live PIV5 have been used for over four decades with an excellent safety record. Dogs immunized with kennel cough vaccines can shed PIV5 up to for 5 days and it has been safe to humans in close contact with immunized animals (Kontor et al. *American journal of veterinary research* 42, 1694-1698 (1981); Chen et al. *PLoS One* 7, e50144 (2012)). PIV5 is particularly well suited as a vaccine vector for respiratory diseases, as when administered intranasally it elicits locally protective IgA responses in the respiratory tract as well as systemic innate and adaptive immune responses (Wang et al. *J Virol* 91, (2017)). Recently, a single intranasal dose of a PIV5-based MERS vaccine induced neutralizing antibodies and cellular immune responses and was 100% protective against a lethal challenge with MERS-CoV in a murine model of MERS (Li et al. *mBio* 11, (2020)). This example provides a promising vaccine candidate for protection against SARS-CoV-2.

Figure 18A:
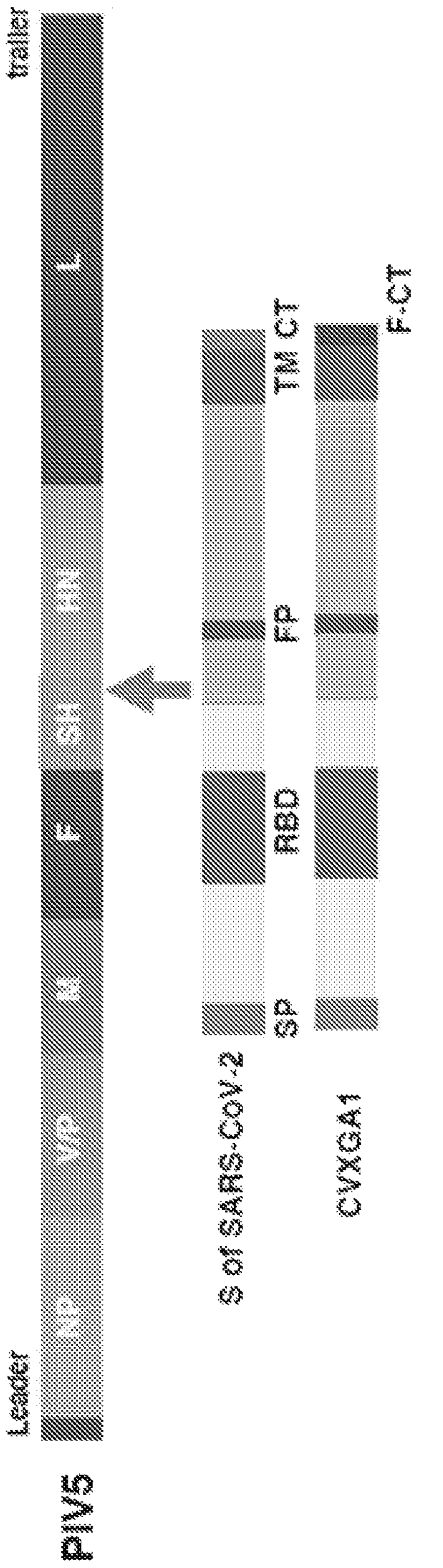
FIG. 18A-FIG. 18F show the generation of CVXGA1 and analysis of CVXGA1 in tissue culture cells and mice.
Figure 18B:
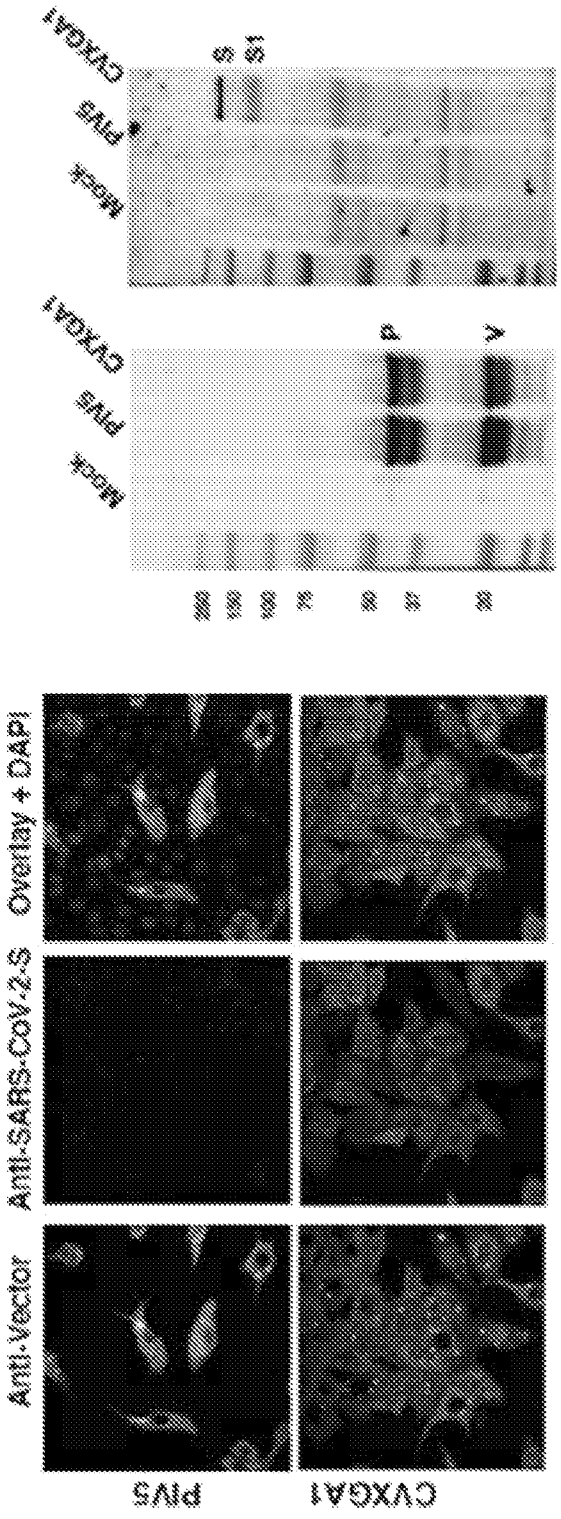
Figure 18C:
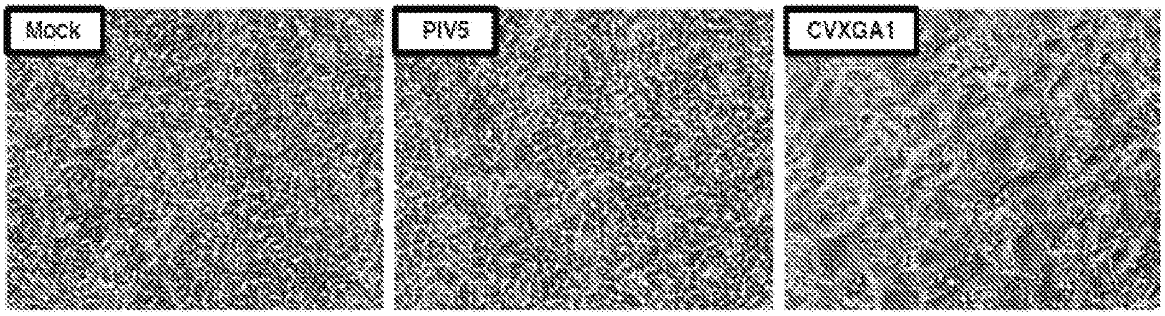
Figure 18D:
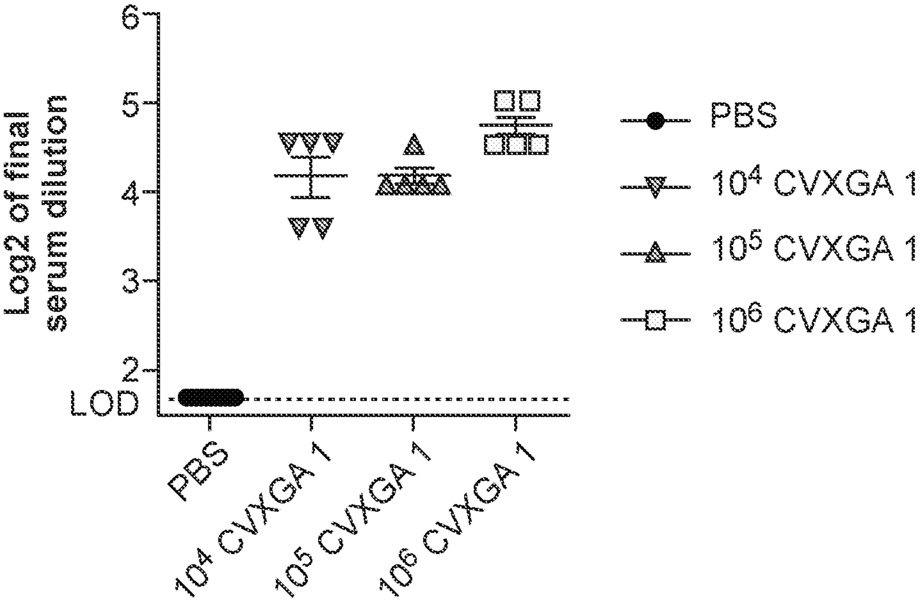
Figure 18E:
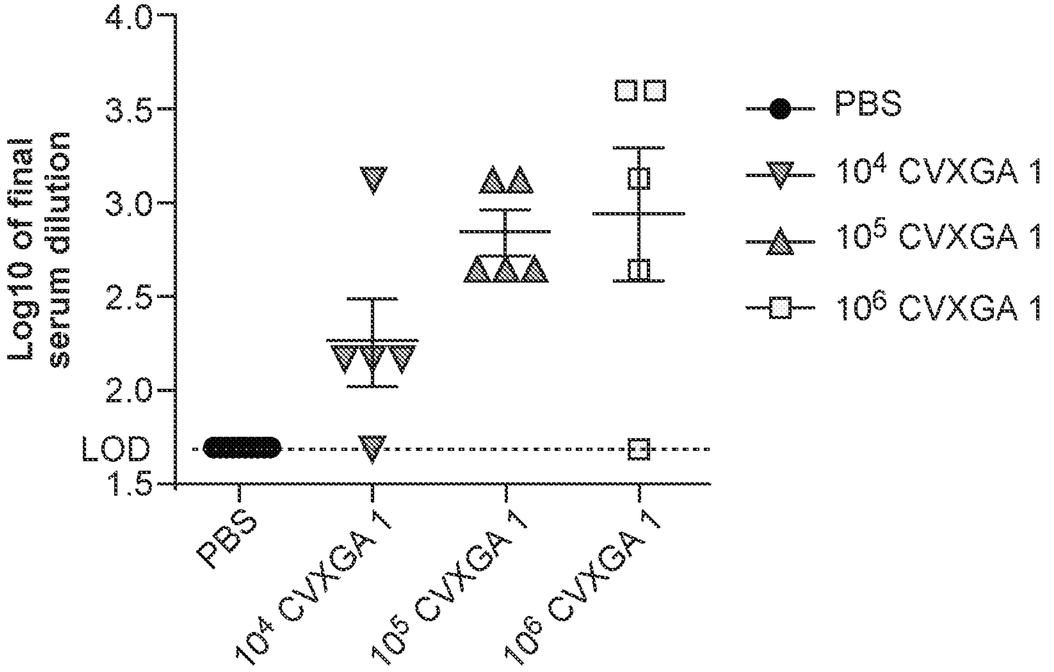
Figure 18F:
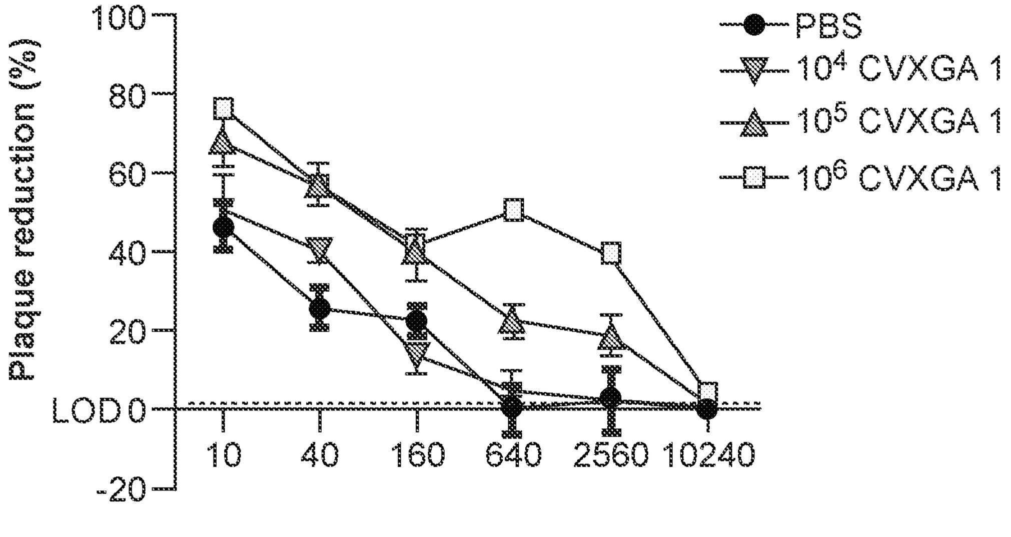
Figure 22A:
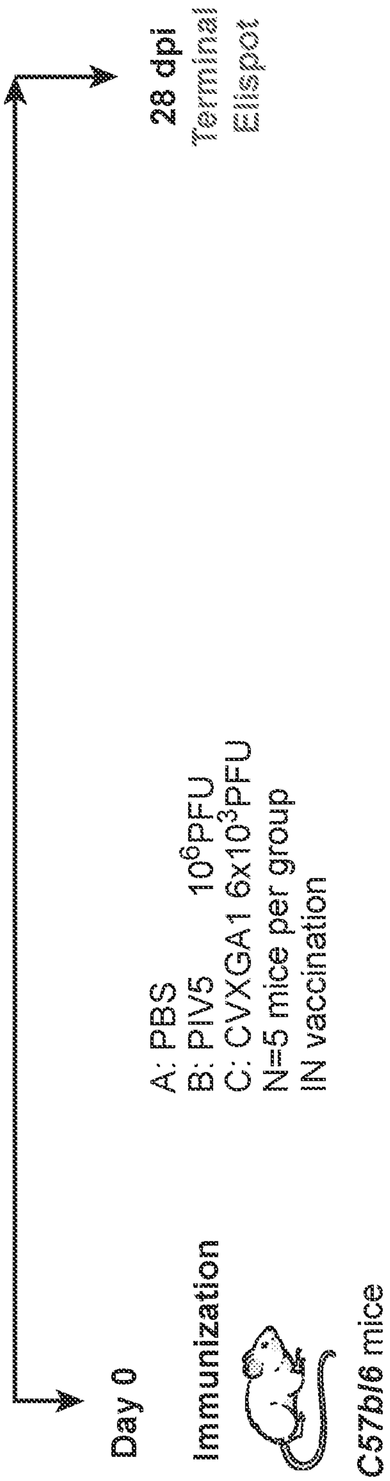
FIG. 22A-FIG. 22C present immunogenicity of CVCGA1 in C57B16 mice.
Figure 22B:
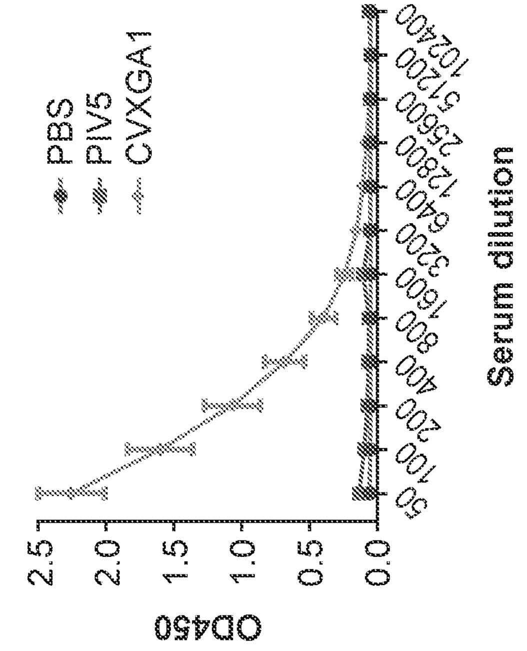
Figure 22C:
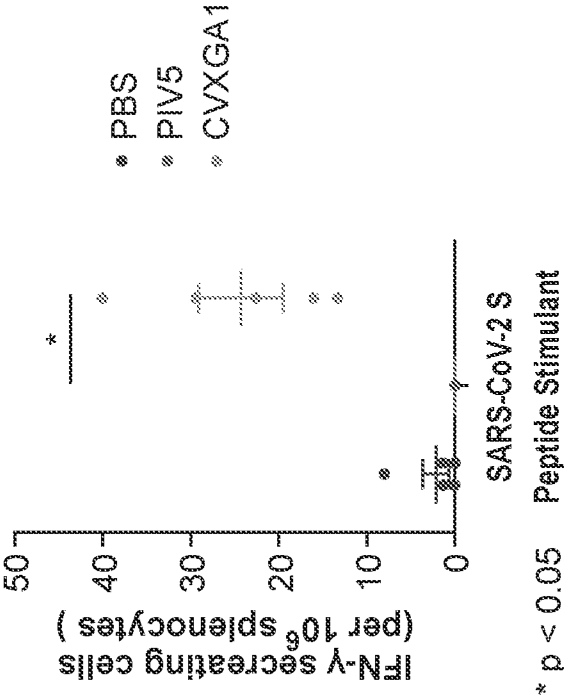

Employing a strategy similar to that used in PIV5-based MERS-CoV vaccine development, a PIV5 expressing the SARS-CoV-2 Spike (S) protein (termed CVXGA1) was generated (FIG. 18A) and confirmed its S glycoprotein expression by immunofluorescence and western blot (FIG. 18B). Besides full-length S, a cleaved product, S1, was also detected in CVXGA1-infected cells, indicating S was processed (FIG. 18B). S promotes cell-to-cell fusion and virus-to cell fusion to facilitate viral entry and immunization with S generates protective immunity against SARS-CoV-2. It is thought that the native (pre-fusion) conformation of S induces desirable immunity for optimal protection. To examine whether S expressed by CVXGA1 is functional, Vero cells, which express the ACE2 receptor, were infected with CVXGA1. Syncytia formation (cell-to-cell fusion) was observed only in CVXGA1-infected cells, indicating the S protein expressed by CVXGA1 is functional (FIG. 18C). To investigate CVXGA1 immunogenicity, immunized mice were intranasally immunized with various doses of CVXGA1. A dose-dependent increase in anti-S antibodies was detected in BALB/c mice after a single intranasal administration (FIG. 18D). Similarly, antibodies recognizing the receptor binding domain (RBD) of S were detected in a dose-dependent manner in BALB/c mice immunized with CVXGA1 (FIG. 18E). Furthermore, neutralizing antibodies against SARS-CoV-2 were detected in BALB/c mice immunized in a dose-dependent manner (FIG. 18F). Significant antibody generation and cellular responses were observed in C57BL/6 mice after a single intranasal (IN) immunization with a dose as low as $6\times10^3$ plaque forming units (PFU) (FIG. 22). These results indicate that a single intranasal dose immunization with CVXGA1 generated robust immune responses in mice.

Figure 19A:
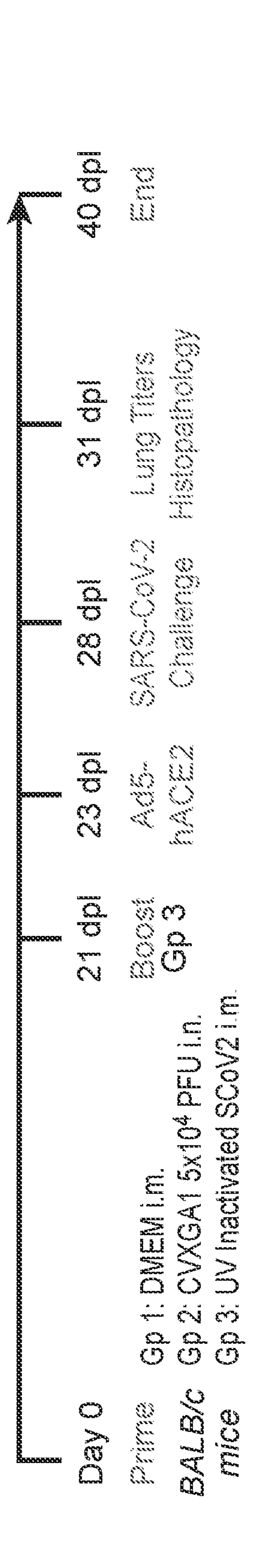
FIG. 19A-FIG. 19D show intranasal vaccination with CVXGA1 reduces clinical and pathological disease in Ad-hACE2 sensitized BALB/c mice following SARS-CoV-2 infection.
Figure 19B:
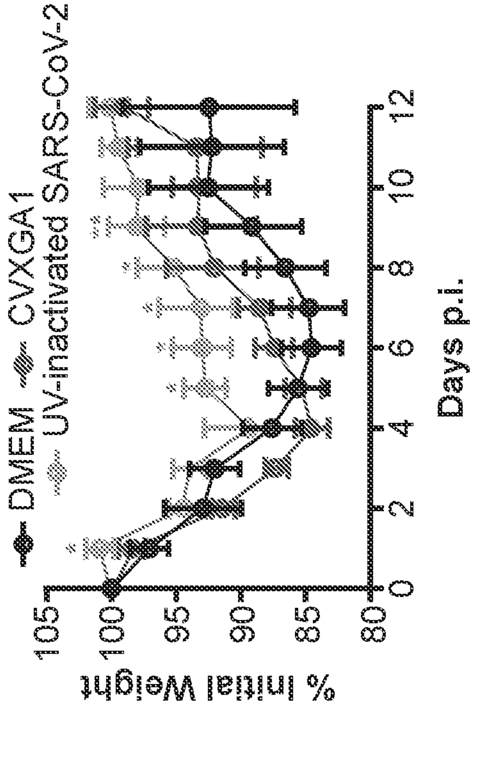
Figure 23A:
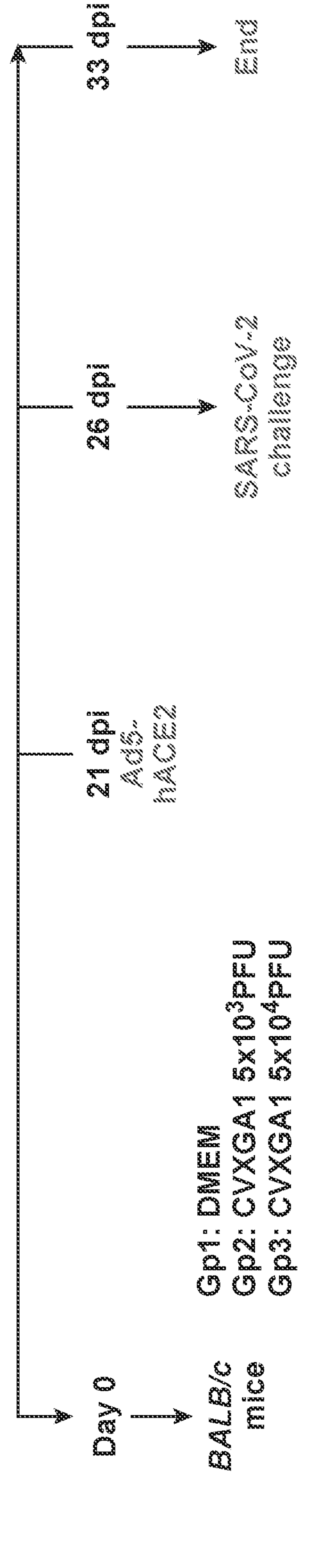
FIG. 23A-FIG. 23C present protection of Ad-hACE2 sensitized mice by CVXGA1.
Figure 23B:
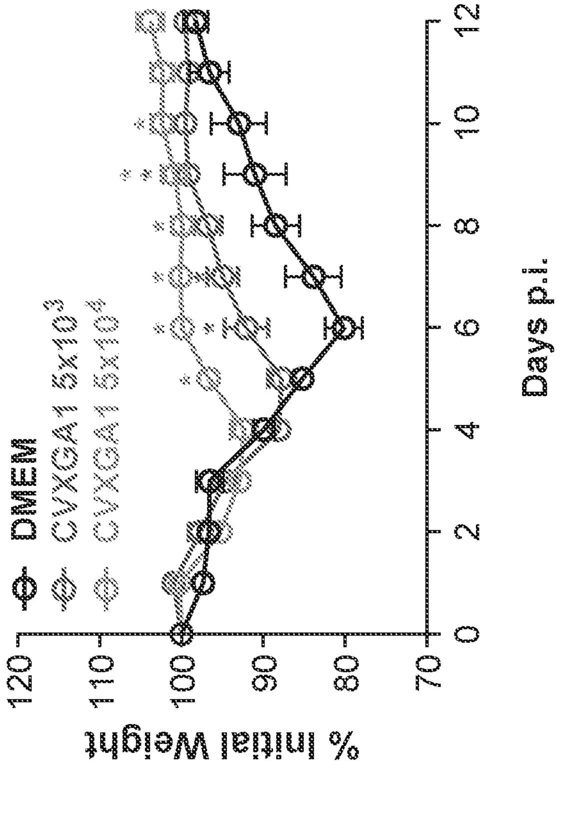
Figure 23C:
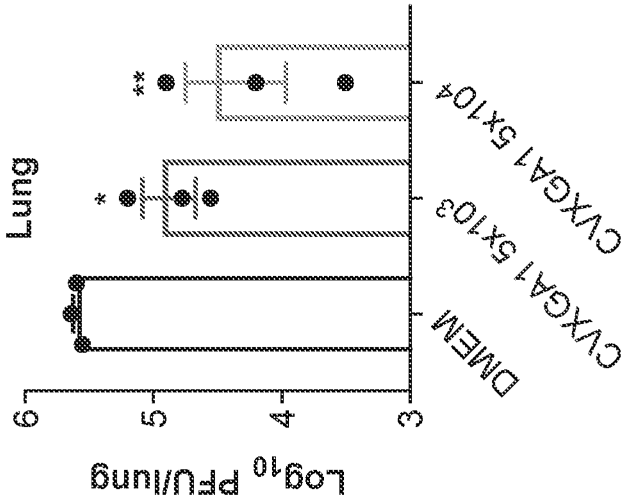
Figure 24A:
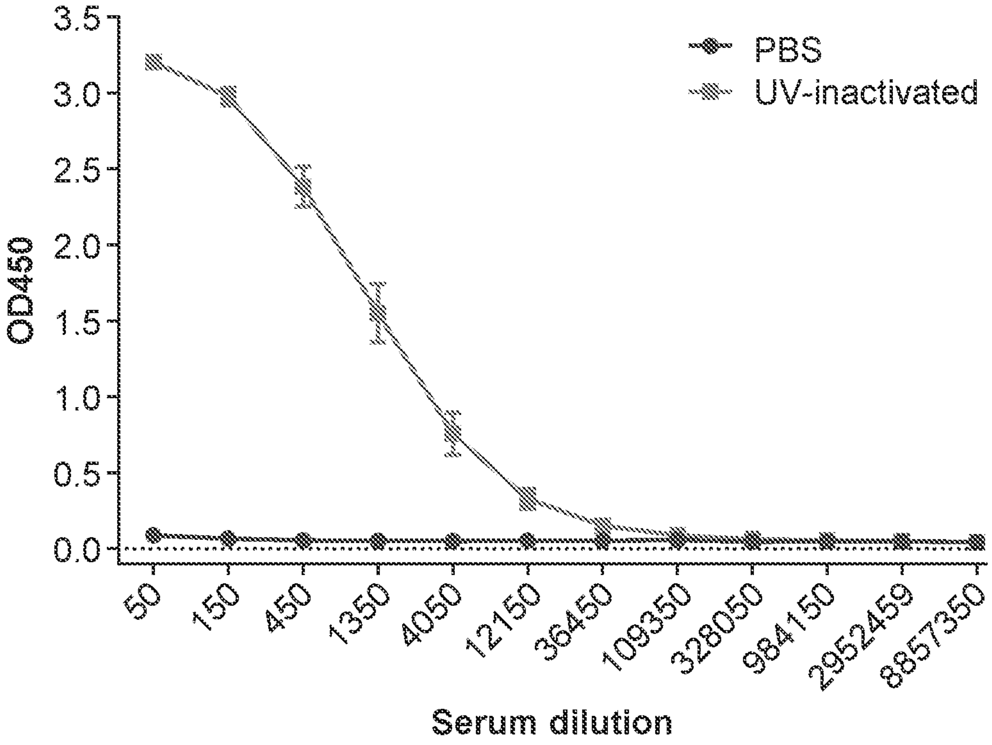
FIG. 24A-FIG. 24B present immunogenicity of inactivated SARS-CoV-2 in mice.
Figure 24B:
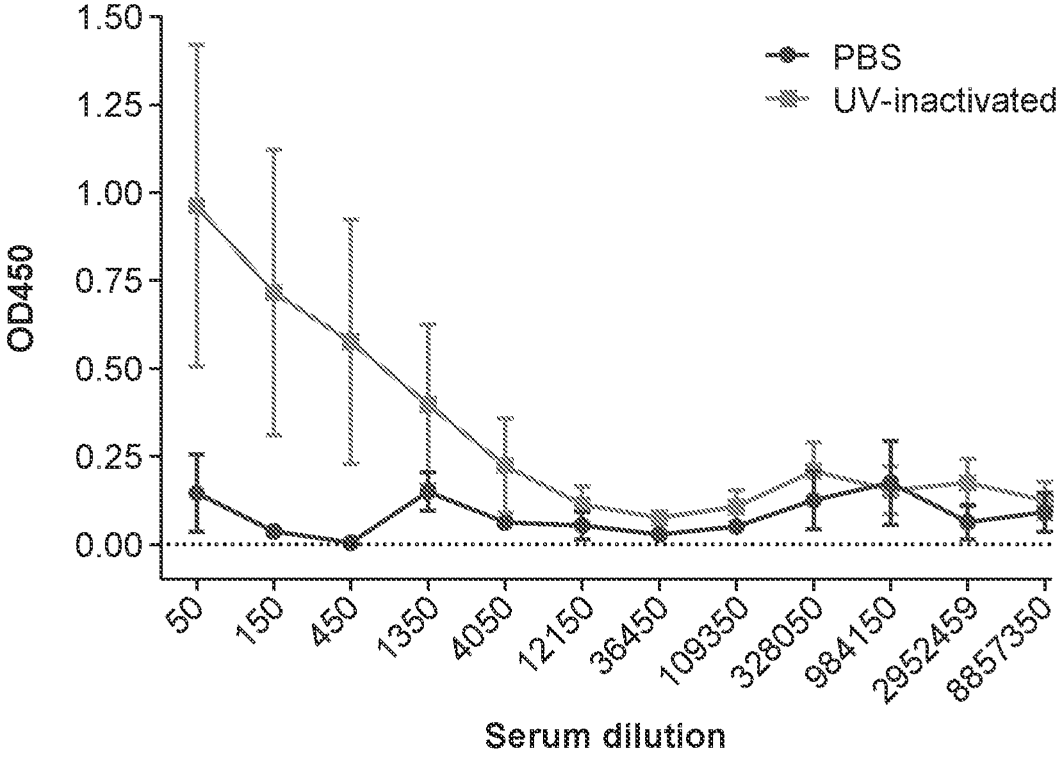

To determine efficacy of CVXGA1, three complementary animal models were used. BALB/c mice lack a functional ACE2 receptor for SARS-CoV-2, and thus are resistant to infection. Introducing human ACE2 by adenoviral vector transduction (Ad5-hACE2) sensitized mice to SARS-CoV-2 infection resulting in a transient pneumonic infection. This mouse model was used to evaluate the efficacy of CVXGA1. Intranasal vaccination with CVXGA1 protected mice from weight loss (FIG. 23) and also reduced lung tissue titers, and tissue histopathological changes. The lack of complete protection of mice may be due to lower doses (highest at $5\times10^4$ PFU per mouse) used in these experiments. Alternatively, it is possible that Ad5-hACE2 transduction may be a contributing factor in the lack of sterilizing immunity in this model. While immunization with UV inactivated SARS-CoV-2 generated higher anti-S antibody titers, no neutralizing antibody was detected (FIG. 24) and inactivated SARS-CoV-2 immunization did not protect mice against SARS-CoV-2 challenge (FIG. 19B). While CVXGA1 generated lower anti-S titers than inactivated SARS-CoV-2, it protected mice better than inactivated SARS-CoV-2, suggesting that cellular immunity generated by CVXGA1 likely played a role this outcome. This is consistent with the lack of sterilizing immunity in lungs of CVXGA1 immunized mice sensitized with Ad5-ACE2 and challenged with SARS-CoV-2.

Figure 19C:
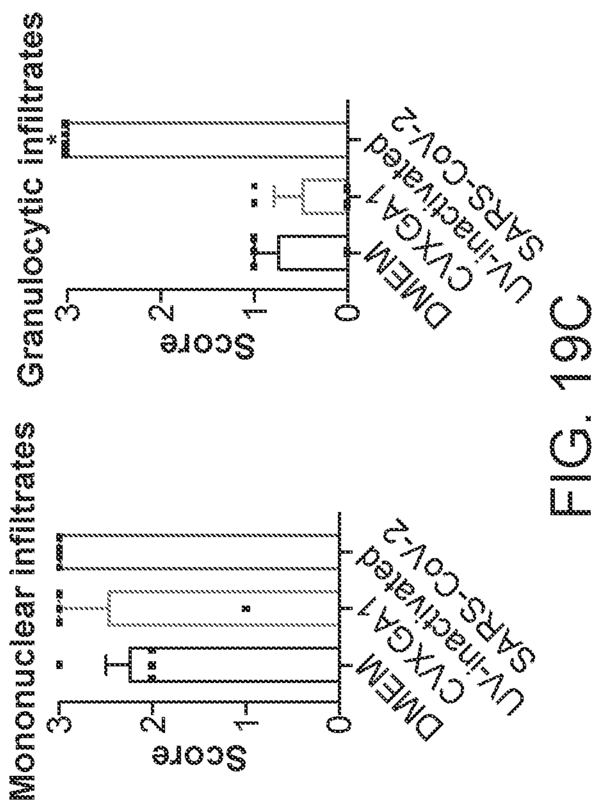
Figure 19D:
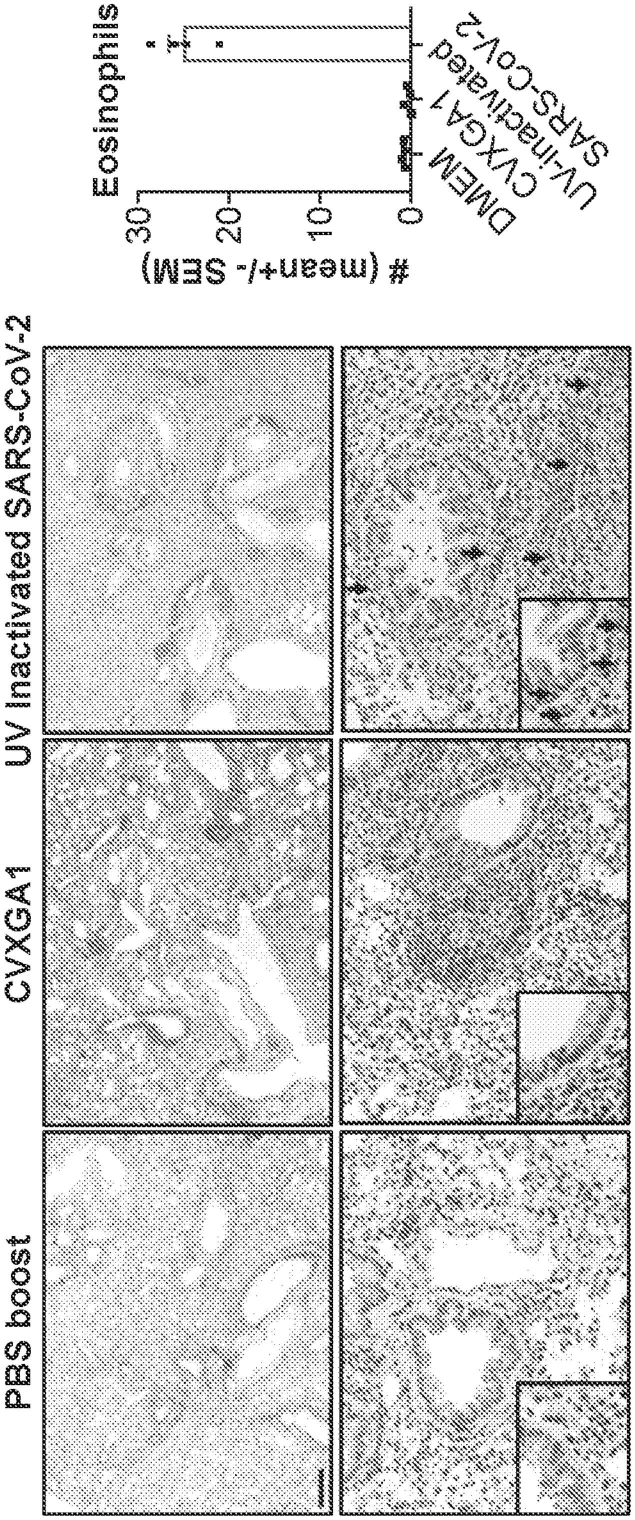

Previously, a PIV5-based MERS vaccine to an inactivated MERS-CoV vaccine were compared in mice and it was found that immunization with inactivated MERS-CoV caused a hypersensitivity-type immune response, indicated by an influx of eosinophils into the lungs after virus challenge. Similar to this observation, immunization with UV inactivated SARS-CoV-2 was associated with eosinophilic infiltrates, while CVXGA1 immunized mice lacked such infiltrates after challenge, suggesting that CVXGA1 did not elicit a hypersensitivity-type response (FIG. 19C, D). In contrast, all treatment groups had similar degrees of mononuclear cell infiltrations (FIG. 19C).

Figure 20A:
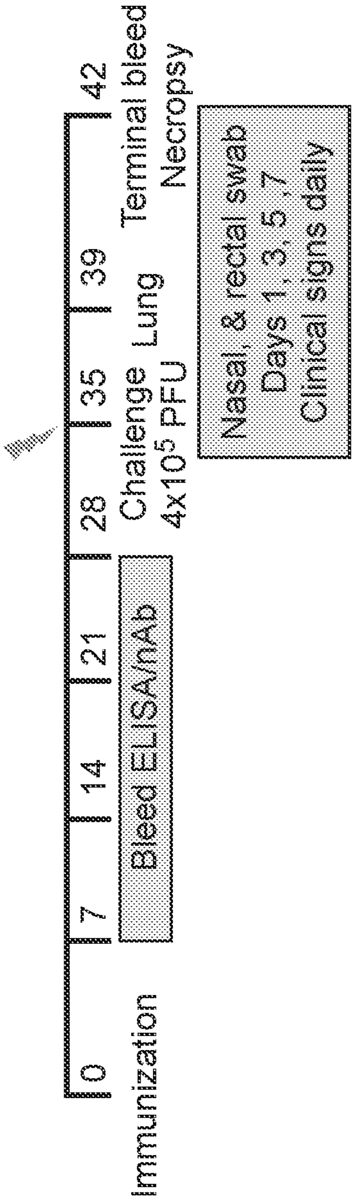
FIG. 20A-FIG. 20F present immunogenicity and efficacy of CVXGA1 in ferrets.
Figure 20B:
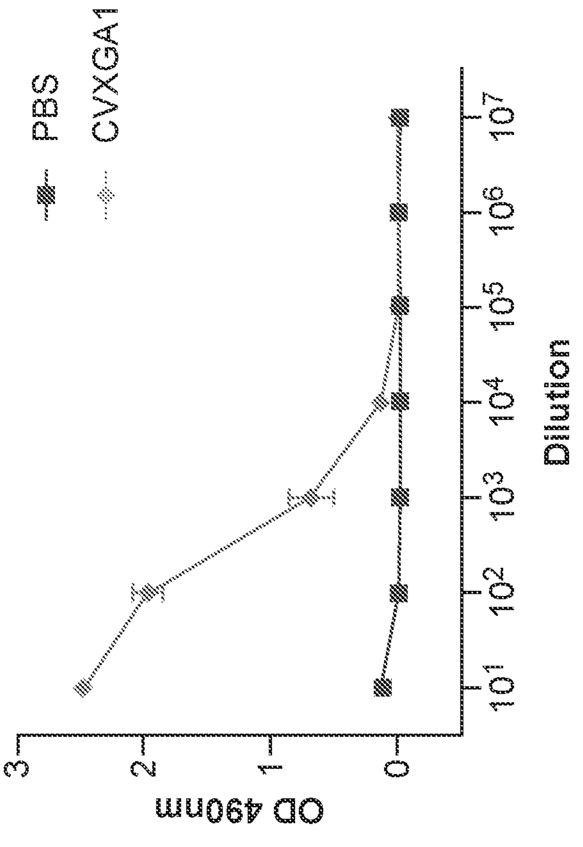
Figure 20C:
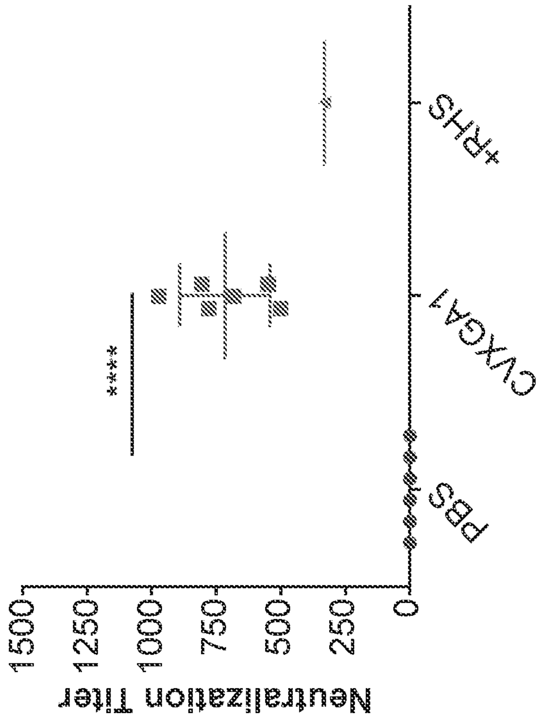
Figure 20E:
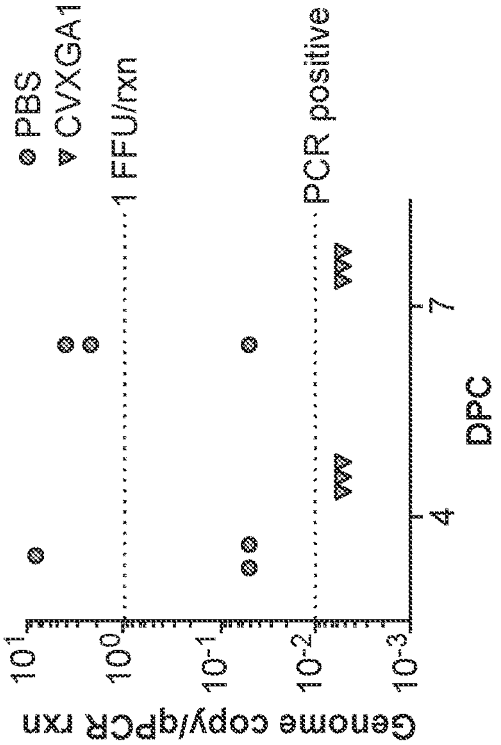
Figure 20D:
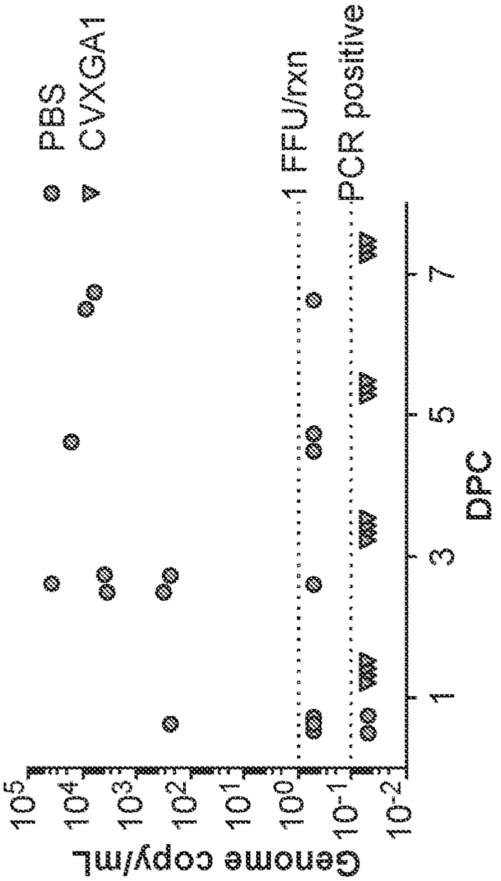
Figure 25A:
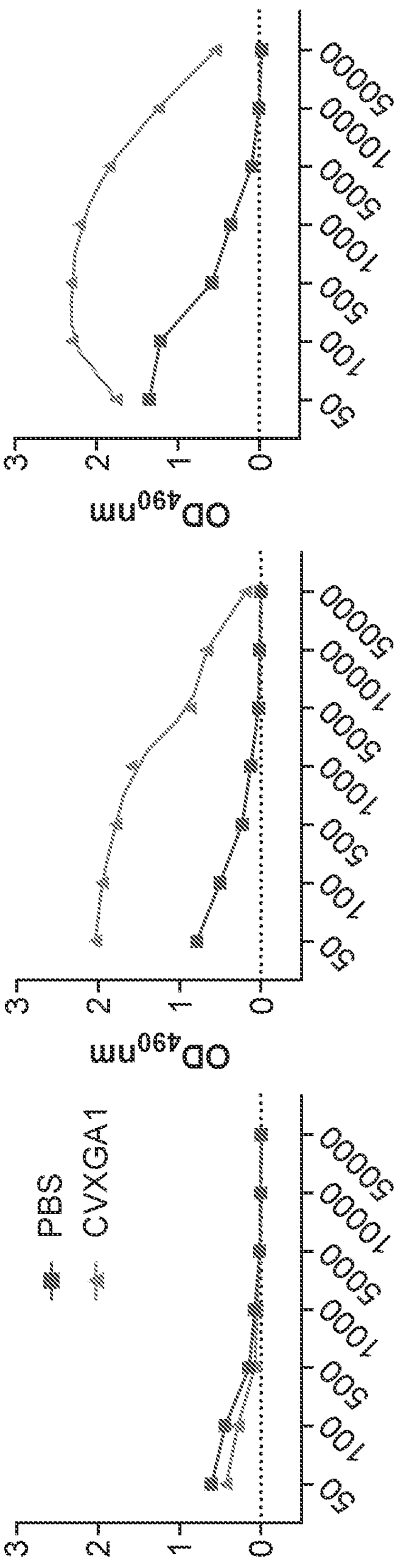
FIG. 25A-FIG. 25E presents immunogenicity and efficacy of CVXGA1 in ferrets.
Figure 25B:
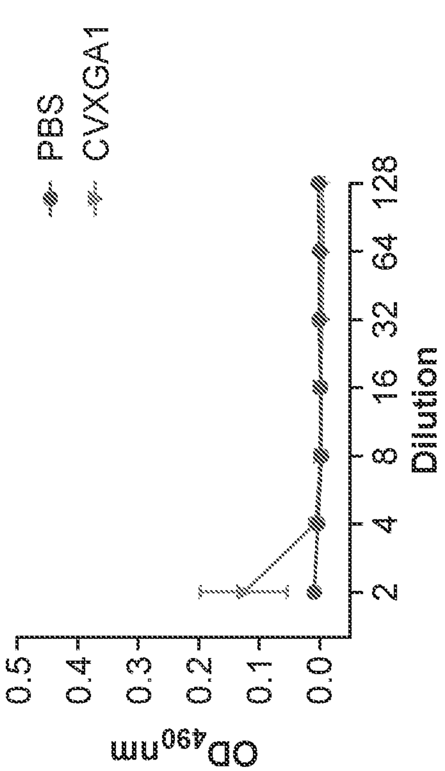

Ferrets are a widely used model of human respiratory infections, are susceptible to SARS-CoV-2 infection, and can transmit the virus to other animals via direct contact and aerosol (Kim et al. *Cell Host Microbe*, (2020); Shi et al. *Science*, (2020); Richard et al. *Nat Commun* 11, 3496 (2020)). To examine CVXGA1 efficacy in ferrets, animals were immunized intranasally with PBS or CVXGA1 (FIG. 20A). CVXGA1 immunization generated robust antibody responses as evident by high titers of anti-S IgG (FIG. 25A), anti-RBD IgG (FIG. 20B) and neutralizing antibodies in FIG. 20C. Low levels of anti-S IgA were detected in nasal washes (FIG. 25B). When challenged with SARS-CoV-2 intranasally, no viral RNA was detected in nasal washes from CVXGA1 immunized ferrets (FIG. 20D). In contrast, viral RNA was detected in all mock-immunized ferrets (FIG. 20D and Table 3). To compare viral RNA detection with an infectious focus forming assay, infectious virus in nasal washes from 5 day post challenge (dpc) was determined using infectious focus forming assay.

TABLE 3

Viral genome numbers determined using qRT-PCR in nasal washes from ferrets.

| | 1 dpc | 3 dpc | 5 dpc | 7 dpc |
|---|---|---|---|---|
| PBS-1 | 58 | 302 | | |
| PBS-2 | 51 | 237 | 41 | 44 |
| PBS-3 | 232 | 35705 | | |
| PBS-4 | 22 | 3489 | 153 | 5819 |
| PBS-5 | 121 | 3838 | | |
| PBS-6 | 97 | 23 | 15744 | 8645 |

Figure 20F:
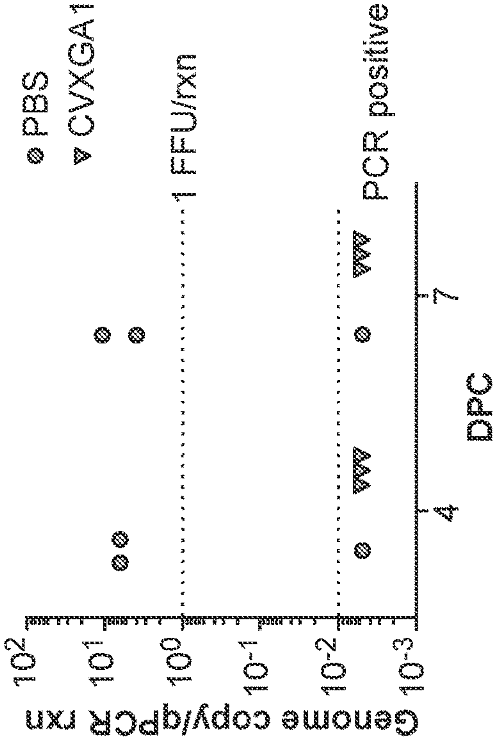
Figure 25C:
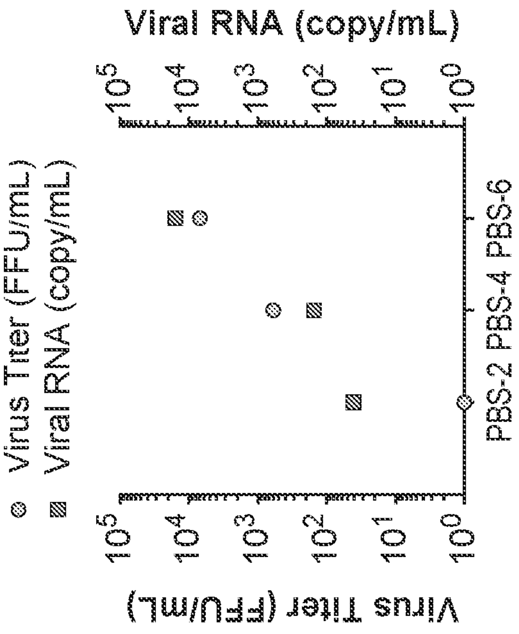
Figure 25D:
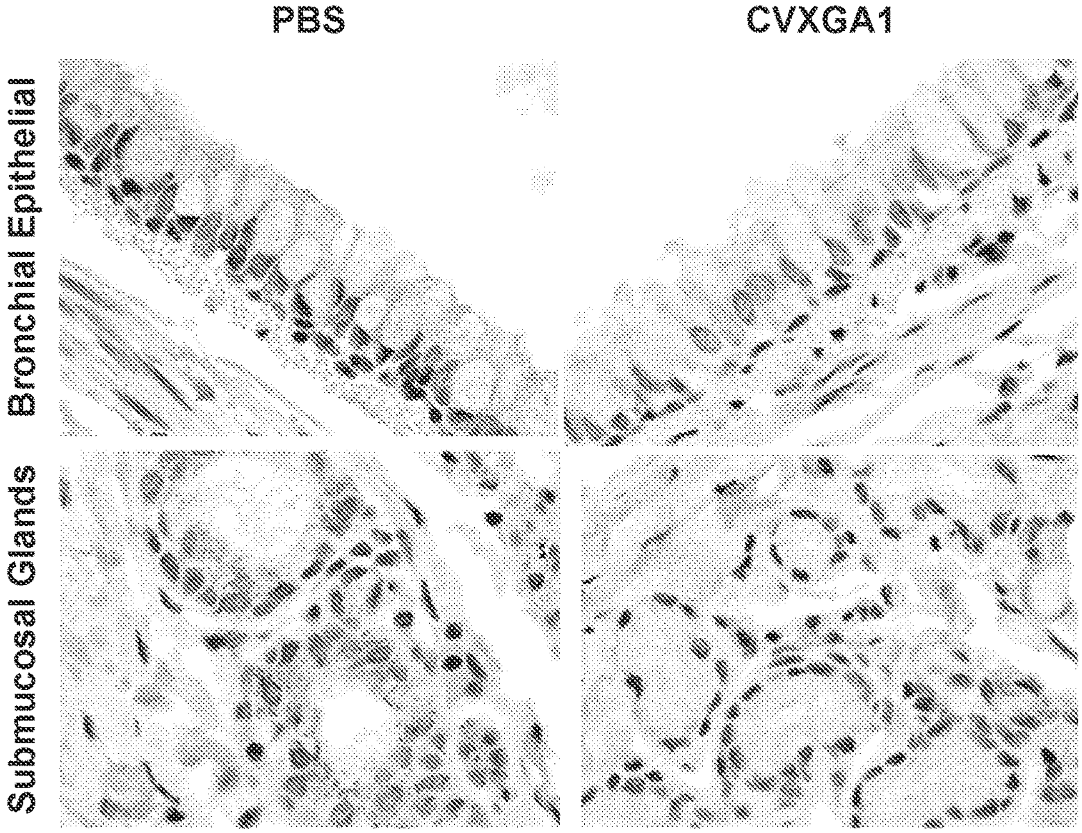
Figure 25E:
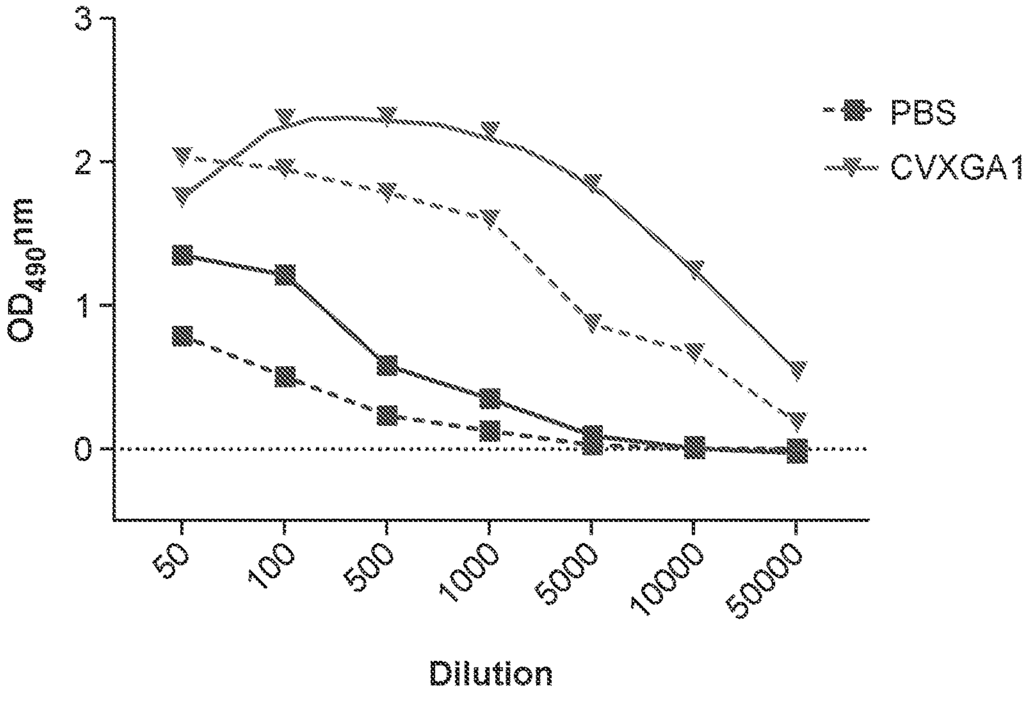

The detection of viral RNA genomes with qRT-PCR was comparable to the infectious focus forming assay (FIG. 25C). SARS-CoV-2 N protein was detected in the airways and parenchyma of PBS-immunized, SARS-COV-2 challenged ferrets at 4 dpc (FIG. 25D). Viral RNA was also detected in the trachea and lungs of mock-immunized ferrets but not in trachea and lungs of CVXGA1 immunized ferrets (FIGS. 20E and 20F). To assess SARS-CoV-2 exposure in ferrets, anti-S antibody levels were quantified at the time of experiment termination (7 dpc). Anti-S levels in CVXGA1 immunized group increased after challenge (FIG. 25E), indicative of a memory response and exposure to the S antigen. These results indicate that CVXGA1 immunization induced sterilizing immunity after challenge with SARS-CoV 2, most importantly in the nasal cavity, a critical site for SARS-CoV 2 replication and transmission.

Figure 21A:
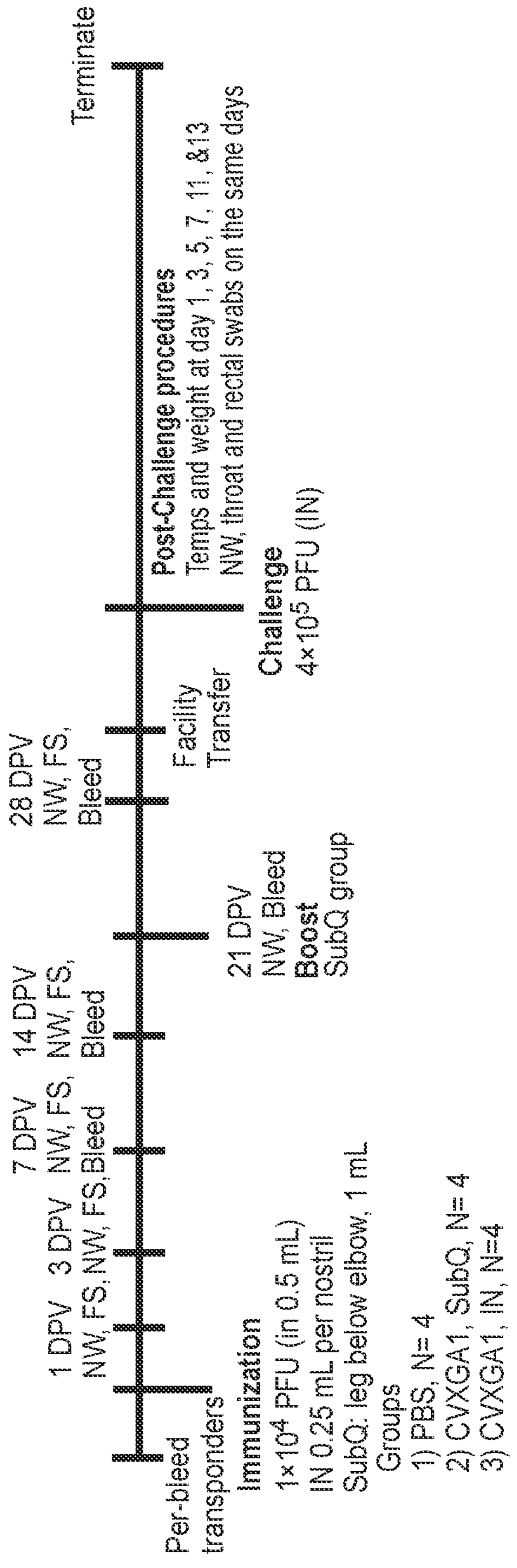
FIG. 21A-FIG. 21E present immunogenicity and efficacy of CVXGA1 in cats.
Figure 21D:
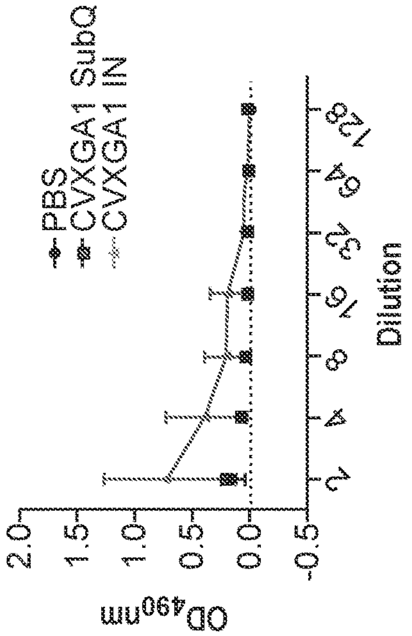
Figure 21C:
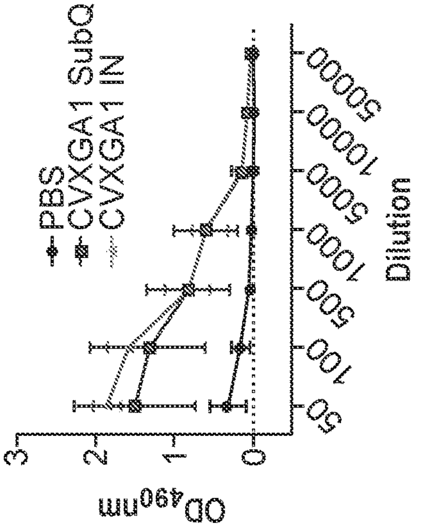
Figure 21B:
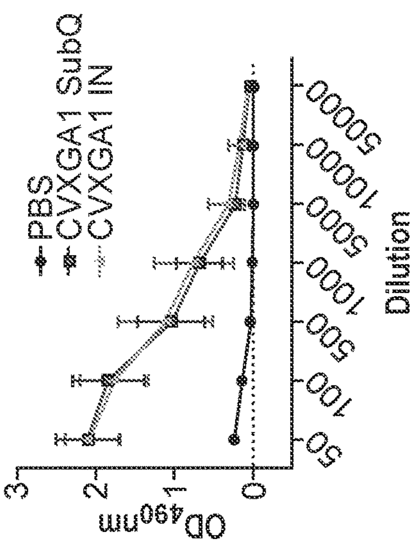
Figure 21E:
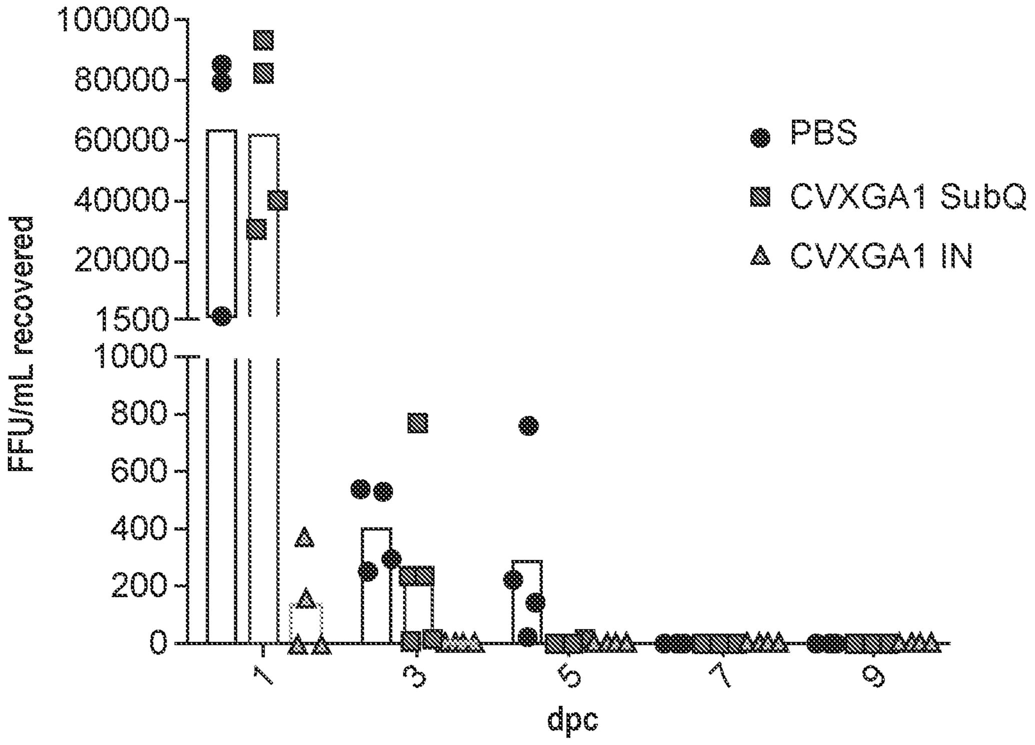
Figure 26A:
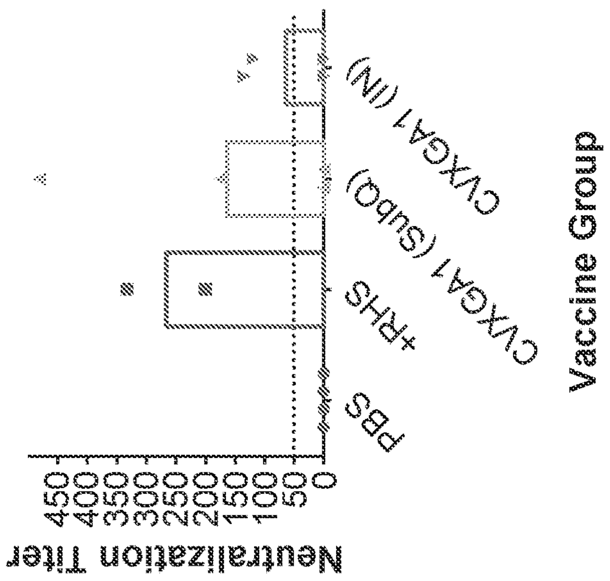
FIG. 26A-FIG. 26D present immunogenicity and efficacy of CVXGA1 in cats.
Figure 26B:
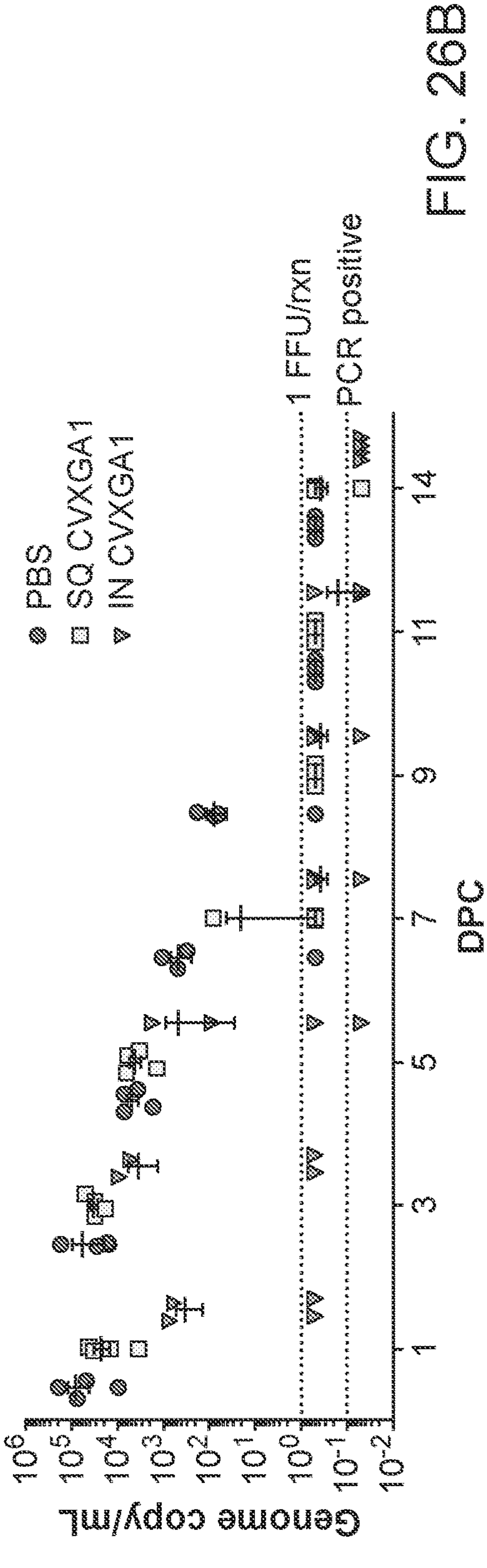

Cats are naturally susceptible to SARS-CoV-2 infection and in the laboratory, setting can transmit the virus. To determine whether CVXGA1 immunization blocks upper respiratory tract infection, cats were immunized with CVXGA1 intranasally (IN) and subcutaneously (subQ) without an adjuvant (FIG. 21A). To enhance immune responses, the group immunized via the subQ route were boosted (FIG. 21A). Both subQ (prime-boost) and IN immunizations generated similar antibody responses (FIGS. 21B and 21C and FIG. 26A). Of note, IN immunization generated detectable anti-S IgA in nasal washes (FIG. 21D). Following challenge, cats in the mock immunization group (PBS) all had high SARS-CoV-2 titers in nasal washes (average over $6.27\times10^4$ FFU/ml) at 1 day post challenge. Excitingly, in the IN immunization group, two of four cats (50%) had no detectable virus, and two of four had a 230-fold reduction in SARS-CoV-2 titers (average $2.7\times10^2$ FFU/ml). Interestingly, while subQ immunization generated serum antibody titers similar to IN immunization, it did not protect against infection of the nasal cavities at 1 dpc ($6.16\times10^4$ FFU/ml). However, subQ immunized cats cleared infection faster than mock-immunized cats: by 5 dpc, 3 out of 4 cats had no virus detected, while all mock immunized animals remained infected (FIG. 21E). By 7 dpc, no virus was detected in nasal washes of all cats. These results were confirmed using qRT-PCR for viral RNA (FIG. 26B). It is noteworthy and consistent with previous reports that while no live virus was detected in nasal washes at 7 dpc, viral genomes were detected up to 11 dpc in the PBS group.

Figure 26C:
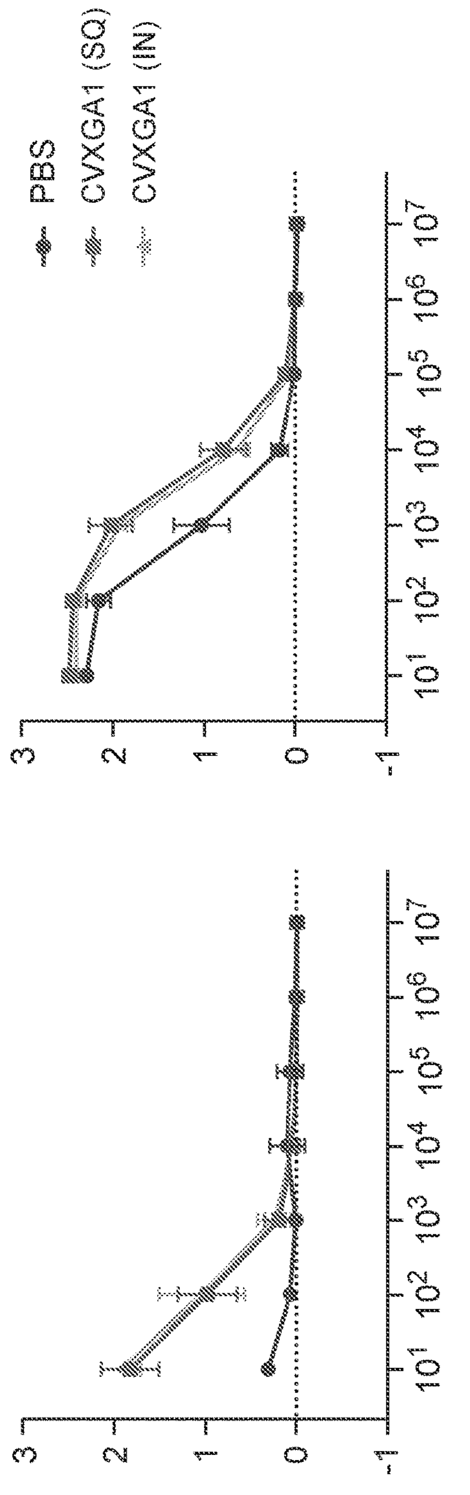
Figure 26D:
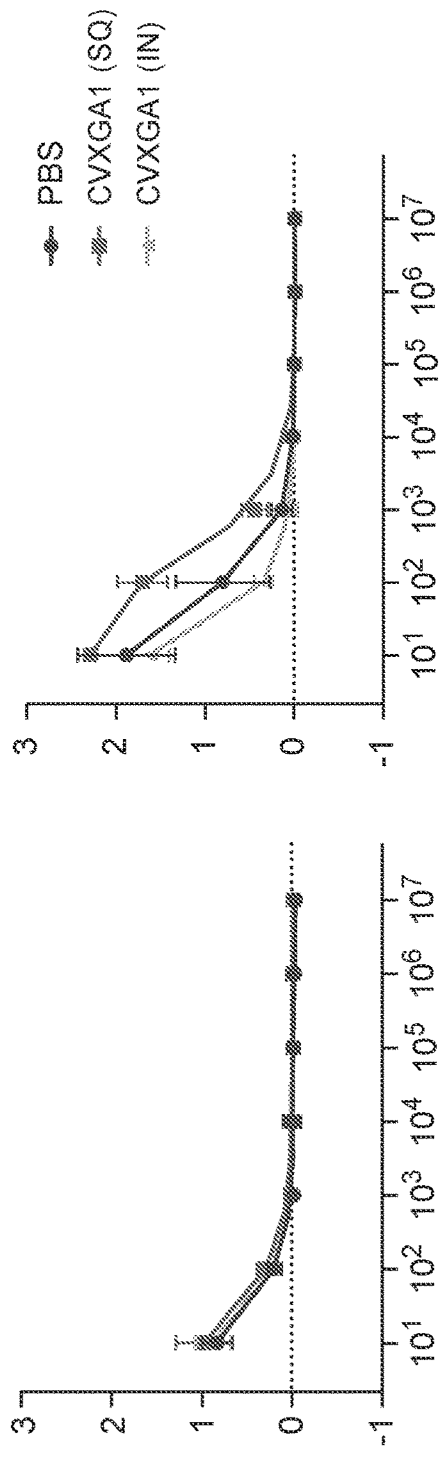

To determine the animal's exposure to SARS-CoV-2 replication, anti-N antibodies levels were measured at the end of the experiment (14 dpc). Anti-N antibodies were detected in all cats at 14 dpc; PBS- and subQ immunized cats had higher anti-N levels than IN immunized animals (FIG. 26C). Consistent with exposure to SARS-CoV-2, IN immunized animals had an increase of anti-S titers after challenge (FIG. 26D). The finding that subQ immunization generated anti-S responses comparable to the IN immunization but did not prevent infection in nasal cavities is consistent with observations that high serum antibody responses do not prevent infection of the nasal cavities. In evaluating the immune responses of individual animals, no correlation between serum antibody titers and protection of nasal cavities was observed, further confirming that anti-S antibody titers are not a predictor of protection in the sinonasal tract (Table 4).

TABLE 4

Summary of Cat Experiment

| Vaccine Group | Animal ID | Anti-S | Anti-RBD | Neutralizing VSV-S (28 dpi endpoint titer) | Anti-S IgA (28 dpi endpoint dilution) | 1 DPC | 3 DPC | 5 DPC | 7 DPC |
|---|---|---|---|---|---|---|---|---|---|
| PBS | 1.1 | 0.21 | 0.34 | 0 | 2 | 85000 | 290 | 140 | 0 |
| PBS | 1.2 | 0.21 | 0.26 | 0 | 0 | 1880 | 530 | 760 | 0 |
| PBS | 1.3 | 0.27 | 0.14 | 0 | 0 | 85000 | 253 | 220 | 0 |
| PBS | 1.4 | 0.25 | 0.23 | 0 | 0 | 79000 | 540 | 20 | 0 |
| CVXGA1 (SubQ) | 2.1 | 2.29 | 1.88 | 479.6 | 0 | 82000 | 0 | 0 | 0 |
| CVXGA1 (SubQ) | 2.2 | 2.45 | 2.14 | 176.2 | 0 | 31000 | 770 | 10 | 0 |
| CVXGA1 (SubQ) | 2.3 | 1.43 | 0.24 | 0 | 2 | 40300 | 235 | 0 | 0 |
| CVXGA1 (SubQ) | 2.4 | 2.25 | 2.02 | 0 | 0 | 93000 | 10 | 0 | 0 |
| CVXGA1 (IN) | 3.1 | 1.78 | 1.73 | 0 | 2 | 160 | 0 | 0 | 0 |
| CVXGA1 (IN) | 3.2 | 2.27 | 1.57 | 0 | 8 | 0 | 0 | 0 | 0 |
| CVXGA1 (IN) | 3.3 | 1.72 | 1.77 | 118.8 | 2 | 0 | 0 | 0 | 0 |
| CVXGA1 (IN) | 3.4 | 2.46 | 1.99 | 135.6 | 8 | 380 | 0 | 0 | 0 |

This work demonstrates that a PIV5-based intranasal COVID-19 vaccine can generate sterilizing immunity in animals. Further development of this vaccine candidate may provide a COVID-19 vaccine that could block SARS-CoV-2 transmission. Kennel cough vaccines have been produced inexpensively for decades. A safe, efficacious, and inexpensive COVID-19 vaccine based on the PIV5 vector may contribute to the control of COVID-19 pandemic.

Materials and Methods

Virus and Cells

The CVXGA1 plasmid, encoding the full-length genome of PIV5 with SARS-CoV-2-S whose cytoplasmic tail was replaced with that of F of PIV5 and which was inserted between SH and HN of PIV5. Virus rescue was performed as described previously (Li et al., 2013, *J Virol;* 87:354-362, doi:10.1128/JVI.02321-12). Briefly, the CVXGA1 plasmid, as well as four helper plasmids, pPIV5-NP, pPIV5-P, pPIV5-L, and pT7-polymerase, encoding NP, P, L proteins and T7 RNA polymerase, respectively, were co-transfected into BHK21 cells at 90% confluence in 6-cm plates with Lipofectamine 3000 (Invitrogen). Virus released into the media was amplified in Vero cells. Recovery of virus is indicated by syncytia formation in Vero cells. The virus was then plaque-purified as a single plaque from Vero cells. The full-length genomes of the plaque-purified single clone of CVXGA1 virus was sequenced as described (Li et al., 2013, *J Virol;* 87:354-362, doi:10.1128/JVI.02321-12). Viruses were grown in Vero cells for 5 to 7 days using DMEM containing 2% FBS. Media were collected and pelleted at 3000 rpm to remove cell debris by using a Sorvall tabletop centrifuge for 10 min. Virus supernatant was supplemented with 10% sucrose-phosphate-glutamate (SPG) buffer, snap-frozen in liquid nitrogen, and stored at −80° C. immediately after collection.

SARS-CoV-2 virus or tissue homogenate supernatants were serially diluted in DMEM. 12 well plates of VeroE6 cells were inoculated at 37° C. in 5% $CO_2$ for 1 hr and gently rocked every 15 min. After removal of the inocula, plates were overlaid with 1.2% agarose containing 4% FBS. Three days later, overlays were removed, and plaques visualized using 0.1% crystal violet staining. Viral titers were quantified as PFU/mL tissue. SARS-CoV-2 was inactivated by exposure to UV light for 1 hr using a wattage of 4,016 $\mu W/cm^2$.

All cell lines were incubated at 37° C. in 5% C02. Vero cells were grown in Dulbecco's modified Eagle medium (DMEM) supplemented with 5% fetal bovine serum (FBS), 100 IU/ml penicillin, and 100 µg/ml streptomycin. BHK21 cells were grown in DMEM containing 10% tryptose phosphate broth (TPB), 5% fetal bovine serum (FBS), 100 IU/ml penicillin, and 100 µg/ml streptomycin.

Immunofluorescence and Immunoblotting

Immunofluorescence of SARS-CoV-2-S expression was carried out in MDBK cells in 24-well plates that were infected with CVXGA1 or PIV5 at an MOI of 1. At 2 days postinfection (dpi), the cells were washed with PBS and then were fixed in 2% formaldehyde. The cells were permeabilized in 0.1% PBS-Saponin solution and incubated for 1 hpi with anti-SARS-CoV-2-S(Sino Biological, catalog no.40150-R007) and anti-PIV5-V/P at 1:200 dilution, and then fluorescein isothiocyanate (FITC)-labeled goat anti-Rabbit (KPL, catalog no. 02-15-16) and Cy3-labeled goat anti-Mouse (KPL, catalog no. 072-01-18-06) secondary antibodies were added to the cells. The cells were incubated for 30 min and were examined and photographed using a fluorescence microscope (Advanced Microscopy Group).

Immunoblotting was performed on Vero cells in 12-well plates that were infected with PIV5 or CVXGA1 at an MOI of 1. At 24 hpi, Laemmli sample buffer (Bio-Rad, catalog no. 1610737) with 5% P-mercaptoethanol was used to lyse cells. The lysates were run on an SDS-PAGE gel and immunoblotted with anti-SARS-CoV-2-S(Sigma, catalog no. ZHU1076) and anti-PIV5-V/P antibody.

Purification of S and RBD of S

The plasmid encoding the cDNA for pre-fusion stabilized SARS-CoV-2 spike ectodomain (Wrapp et al. 2020, *Science;* 367:1260-1263, doi:10.1126/science.abb2507) was synthesized (Twist Bioscience) and cloned into the pTwist CMV Hygro vector. The plasmid encoding the monomeric spike receptor binding domain was obtained from BEI Resources (NR-52309). The plasmids were expanded by transformation into *Escherichia coli* DH5α cells with 100 µg/mL of ampicillin (Thermo Fisher Scientific) used for selection. Plasmids were purified using the EZNA plasmid maxi kit (Omega Biotek), according to the manufacturer's protocol. For each liter of transfection, 1 mg of plasmid DNA was mixed with 4 mg of 25,000-molecular-weight polyethylenimine (PEI; PolySciences Inc.) in 66 ml Opti-MEM cell culture medium (Gibco). After 30 min, the DNA-PEI mixture was added to HEK293F cells (1 million cells/ml) in Freestyle 293 medium (Gibco). After 5 to 7 days, the cultures were centrifuged to pellet the cells, and the supernatants were filtered through a 0.45-µm sterile filter. Recombinant proteins were purified from the filtered culture supernatants using HisTrap Excel columns (GE Healthcare Life Sciences). Each column was stored in 20% ethanol and washed with 5 column volumes (CV) of wash buffer (20 mM Tris pH 7.5, 500 mM NaCl, and 20 mM imidazole) before loading samples onto the column. After sample application, columns were washed with 10 CV of wash buffer. Proteins were eluted from the column with 6 CV of elution buffer (20 mM Tris pH 7.5, 500 mM NaCl, and 250 mM imidazole). Proteins were concentrated and buffer exchanged into phosphate buffered saline (PBS) using Amicon Ultra-15 centrifugal filter units with a 30-kDa cutoff (Millipore Sigma).

ELISA

To quantify the anti-SARS-CoV-2-S humoral response post-prime and post-boost, mouse serum was analyzed via ELISA. IMMULON® 2HB 96-well microtiter plates were coated with 100 uL purified SARS-CoV-2-S at 1 ug/mL. The serum was serial diluted two-fold and incubated on the plates for 2 hrs. Horseradish peroxidase-labelled goat anti-mouse IgG secondary antibody (Southern Biotech, Birmingham, Alabama) was diluted 1:2500 and incubated on the wells for 1 hr. The plates were developed with KPL Sure-Blue Reserve TMB Microwell Peroxidase Substrate (Sera-Care Life Sciences, Inc., Milford, Massachusetts), and OD450 values were detected with a BioTek Epoch Microplate Spectrophotometer (BioTek, Winooski, Vermont). Antibody endpoints were calculated as log 10 of the highest serum dilution at which the OD450 was greater than two standard deviations above the mean OD450 of naïve serum.

To detect Ferret IgG, medium binding 96-well ELISA microplates (Greiner Bio-One 655001) were coated with 20 ug of either the full length SARS-Cov-2 full spike protein or SARS-Cov-2 receptor binding domain (RBD) (Amana et al. 2020, *Nat Med;* 26:1033-1036, doi:10.1038/s41591-020-0913-15) in sterile 1× Phosphate Buffered Saline (Corning, 21-040-CV) overnight at 4° C. Plates were washed 3× with 300 uL 0.05% PBS-T using an automated plate washer (BioTek 405 TS Washer). All washes were performed using the same technique. Wells were blocked with 200 uL Blocking Buffer (0.5% bovine serum albumin+3% non-fat dry milk in 0.05% PBS-T), incubated 2 hours at room temperature, then washed. Heat inactivated serum was diluted in blocking buffer, 100 ul added to the appropriate wells, and incubated 2 hours at room temperature followed by a wash step. Goat anti-ferret IgG HRP conjugated antibody (Bethyl Laboratories, A140-108P) diluted 1:5000-1:10000 in blocking buffer was added at 100 uL per well and incubated for 1 hour at room temperature. Plates were washed and tapped dry to remove residual solutions. SIGMAFAST™ OPD (o-Phenylenediamine dihydrochloride) tablets (Sigma-Aldrich, P9187) for the detection of peroxidase activity was prepared in 20 mL DIH20 and added at 100 uL per well. Following an 8-minute development period, 50 uL 1 N $H_2SO_4$ was added to stop the reaction. Immediately, plates were read at absorbance of 490 nm (BioTek, Cytation7 machine). Background signal was calculated from the average absorbance values obtained from capture protein coated wells that received goat-anti ferret IgG HRP antibody.

To detect feline IgG, 96-well ELISA microplates were coated and blocked as for ferret IgG assays. Heat inactivated serum was diluted in blocking buffer, 100 ul added to the appropriate wells, and incubated 2 hours at room temperature. Plates were washed and goat anti-cat IgG HRP conjugated antibody (Bethyl Laboratories, A20-120P) diluted 1:10000 in blocking buffer was added at 100 uL per well and incubated for 1 hour at room temperature. Plates were washed and tapped dry to remove residual solutions. Plates were developed and read as for ferret IgG ELISAs. Background signal was calculated from the average absorbance values obtained from capture protein coated wells that received goat-anti cat IgG HRP antibody.

To detect feline IgA, ELISA microplates were coated, blocked, and washed as for ferret IgG detection. Two-fold serial dilutions of each nasal wash sample (collected in PBS) was performed in blocking buffer and 100 ul added to the appropriate wells. Nasal wash dilutions were incubated 2 hours at room temperature, washed, and goat anti-cat IgA HRP Conjugated Antibody (Bethyl Laboratories, A20-101P) diluted 1:10000 in blocking buffer was added at 100 uL per well and incubated 1 hour at room temperature. Plates were washed and tapped dry to remove residual solutions. Plates were developed and read as for ferret IgG ELISAs. Background signal was calculated from the average of absorbance values obtained from spike coated goat-anti cat IgA HRP only controls wells.

To detect ferret IgA, ELISA microplates were coated, blocked, and washed as for ferret IgG detection. Two-fold serial dilutions of pooled heat inactivated nasal wash sample (collected in PBS) was performed in blocking buffer and 100 ul added to the appropriate wells. Nasal wash dilutions were incubated 2 hours at room temperature, washed, and goat anti-ferret IgA AP Conjugated Antibody (Rockland, 618-105-006) diluted 1:2000 in blocking buffer was added at 100 uL per well and incubated 1 hour at room temperature. Plates were washed and tapped dry to remove residual solutions. SIGMAFAST™ p-Nitrophenyl phosphate tablets (Sigma-Aldrich, N1891) for the detection of alkaline phosphatase activity was prepared in 5 mL DI $H_20$ and added at 200 uL per well. Plates were wrapped in foil to protect from light and incubated 30-45 minutes at room temperature. Following an 8-minute development period, 50 uL 1 N $H_2SO_4$ was added to stop the reaction. Immediately, plates were read at absorbance of 405 nm (BioTek, Cytation7 machine). Background signal was calculated from the average absorbance values obtained from capture protein coated wells that received goat-anti ferret IgA AP antibody.

Interferon-γ (IFN-γ) ELISPOT Assay

BD™ ELISPOT Mouse IFN-γ Set (BD Biosciences, San Jose, CA) was used for analyzing cellular immune responses. BD™ ELISPOT plates were coated with purified anti-mouse IFN-γ antibody 24 hours prior to performing assay. Mouse spleens (n=5, per group) were collected at 28-days post-immunization and put into 15 mL conical tubes containing 5 mL of HBSS. Splenocytes were prepared by pressing spleens through a 70 μM cell strainer, incubating them with ACK lysis buffer, washing them with HBSS, and re-suspending in complete tumor medium (CTM) to a concentration of $5\times10^6$ cells/mL. The capture antibody solution was removed from the plates and then the plates were washed 5-6 times with PBS. The plates were then blocked with CTM for 90 minutes. The blocking solution was discarded, and 0.1 pg of SARS-CoV-2 S peptides covering the whole protein in 50 μL of CTM were added to the wells. 50 μL of splenocytes were added to plates ($2.5\times10^5$ cells/well) and incubated at 37° C., 5% C02, for 48 hours. The spots were immunostained according to the BD™ ELISPOT Set instruction manual and counted using an IMMUNOSPOT® analyzer (Cellular Technology Limited, CTL). Results were presented as the number of IFN-γ secreting cells per 106 splenocytes.

Immunization and Infection of Mice with SARS-CoV 2

Immunization. Six- to eight-week-old female mice (Envigo) were used in this study. The mice were anesthetized by intraperitoneal injection of 250 uL 2,2,2-tribromoethanol in tert-amyl alcohol (Avertin) and intranasally inoculated with 50 μL of PBS or $10^4$, $10^5$, $10^6$ PFU CVXGA1. 28 days post-immunization, the mice were euthanized, serum was collected via cardiothoracic bleeds, and spleens were harvested. The mice were housed and immunized in enhanced biosafety level 2 facilities in HEPA-filtered isolators. All experiments were performed in accordance with protocols approved by the Institutional Animal Care and Use Committee at the University of Georgia.

$10^6$ PFU UV-inactivated SARS-CoV-2 were 1:1 (vol/vol) mixed with Alum Adjuvant (Thermo, catalog no. 77161) in a volume of 200 μl and delivered to mice intramuscularly. Sensitization of mice with Ad5-ACE2. The Ad5-hACE2 vector was previous described (Jia et al., 2005, *J Virol;* 79:14614-14621, doi:10.1128/JVI.79.23.14614-14621.2005; and Sun et al. 2020, *Cell*, doi:10.1016/j.cell.2020.06.010). Viral vector construction is performed using the RAPAD™ System VVC (Anderson et al., 2000, *Gene Ther;* 7:1034-1038, doi:10.1038/sj.gt.3301197). Mice were anesthetized with ketamine/xylazine (87.5 mg/kg ketamine/12.5 mg/kg xylazine) and transduced intranasally with $2.5\times10^8$ PFU of Ad5-hACE2 in 75 μl DMEM.

Infection of mice. Mice were lightly anesthetized with ketamine/xylazine and intranasally inoculated with the indicated amount of SARS-CoV-2 in a total volume of 50 μl DMEM. Animal weight and health were monitored daily. All experiments with SARS-CoV-2 were performed in a Biosafety Level 3 (BSL3) Laboratory. Five days post transduction, mice were anesthetized with ketamine/xylazine (87.5 mg/kg ketamine/12.5 mg/kg xylazine) and infected intranasally with 105 PFU SARS-CoV-2 (isolate USA-WA1/2020 BEI #NR-52281) in 50 μl DMEM. Mice were monitored and weighted daily.

Immunization and Infection of Ferrets with SARS-CoV 2

Twelve, eight to nine-month-old male and female (700-2000 g) fitch ferrets were received from Triple F Farms and acclimated in UGA animal facilities. Prior to arrival, ferrets underwent sterilization and scent gland removal. Following an acclimation period of at least seven days, ferrets were anesthetized for subcutaneous placement of thermal transponders between the shoulder blades. Implantable Programmable Temperature Transponders (Bio Medic Data Systems, USA) are anchored securely to the tissue at the implantation site and allow temperature readouts ranging from 90-110 degrees Fahrenheit. Simultaneously, whole blood was collected for baseline serology and fecal swab performed for analysis of viral shedding.

All experimental procedures were performed at the University of Georgia Biosciences Animal Facility. Animals were housed in pairs, with ad libitum access to food and water. All experiments were approved by the IACUC of the University of Georgia College of Veterinary Medicine. All procedures including nasal wash and blood collections were performed under short term isoflurane gas anesthesia.

For infectious Sars-CoV-2 challenge, animals were transferred to the University of Georgia Animal Health Research Center Animal Biosafety Level-3 (ABSL3) facility. All experiments were approved by the IACUC of the University of Georgia College of Veterinary Medicine.

Groups of six ferrets were vaccinated intranasally (IN) with $5\times10^6$ PFU CVXGA1 in 1.0 mL sterile Phosphate Buffered Saline (PBS) distributed as 500 uL per nostril. Following vaccination, animals were monitored daily for clinical signs including nasal discharge, sneezing, diarrhea, lethargy, increased respiratory rate and effort (congestion), cyanosis, neurological changes, and response to external stimuli. Body temperature was tracked using the implanted temperature probes. Nasal washes and fecal swabs were collected 3, 7, 14, 21, and 28-days post immunization (dpi) to assess vaccine shedding. Whole blood was obtained weekly following immunization. Peripheral blood mononuclear cells (PBMCs) were isolated and cryopreserved for future analysis. For infectious challenge with SARS-Cov-2, $4\times10^5$ PFU was delivered via the IN route. Again, physical observations, weights and temperatures were carried out daily. A subset of six animals were humanely euthanized and necropsied on day 4 post-challenge and remaining animals (n=6) were humanely euthanized on day 7 post-challenge. All necropsies were performed under the guidance of a board-certified veterinary pathologist. Tissue samples (trachea and lung) were collected for pathology and viral load. Terminal blood collection was carried out for serum and PBMC isolation.

Immunization and Infection of Cats With SARS-CoV 2

Twelve, sub adult (seven to nine-months old), intact male domestic shorthair (DSH) cats were received from MBR Wavery LLC. Following a period of acclimation, male cats were surgically castrated by a board-certified veterinary surgeon. All sterilized males were solo housed pending complete surgical recovery as determined by a boarded-certified lab animal veterinarian. Prior to immunization, cats were anesthetized using injectable anesthetics for subcutaneous placement of Implantable Programmable Temperature Transponders, IPTT 300 (Bio Medic Data Systems, USA) between the shoulder blades. Simultaneously, whole blood and fecal samples were collected. Individual serum was screened for the presence of SARS-CoV-2 protein reactive IgG antibodies by ELISA. Fecal swabs were evaluated via qRT-PCR for the presence of feline enteric coronavirus.

All cat procedures performed prior to infectious challenge were performed at the University of Georgia Lifesciences Animal Facility. Animals were housed in groups or in pairs based on sex and temperament. Cats were fed a diet of commercially available dry food and given ad-libitum access water.

Groups of cats (n=4/group) were vaccinated either intranasally (IN) or Subcutaneously (SQ) with $1\times10^6$ PFU CVXGA1 suspended in sterile Phosphate Buffered Saline (PBS). Intranasal vaccination was completed with a 0.5 mL volume distributed as 250 uL per nostril. Subcutaneous delivery was carried out using 1.0 mL total volume. Subcutaneously vaccinated animals were boosted twenty-one days after primary injection. Following vaccination, animals were monitored daily for clinical signs including nasal discharge, sneezing, diarrhea, lethargy, increased respiratory rate and effort (congestion), cyanosis, neurological change, and response to external stimuli. Body temperature was tracked using the implanted temperature probes. Nasal washes and fecal swabs were collected 1, 3, 7, 14, 21, and 28-days post-vaccination (dpv) to assess vaccine shedding. Whole blood was obtained weekly following immunization. Peripheral blood mononuclear cells (PBMCs) were isolated and cryopreserved for future analysis. For infectious challenge SARS-Cov-2 was delivered via the IN route at a dose of $4\times10^5$ PFU in 1.0 mL volume. All animals (n=12) were humanely euthanized fourteen days post-challenge. Necropsies were performed under the guidance of a board-certified veterinary pathologist. In addition to tissues, terminal blood collection was carried out for serum and PBMC isolation.

Histology and Immunohistochemistry.

Animals were anesthetized and perfused transcardially with PBS. Lung tissues were harvested, fixed (10% neutral buffered formalin), dehydrated through a series of alcohol and xylene baths, paraffin-embedded, sectioned (~4 μm) and stained with hematoxylin and eosin (HE) stains. Tissues were examined by a boarded pathologist in masked manner and following principles for reproducible tissues scores (Meyerholz and Beck, 2018, *Invest;* 98:844-855, doi: 10.1038/s41374-018-0057-0). Perivascular eosinophil infiltration was assessed as previously described (Fuentes et al., 2015, *J Virol;* 89:8193-8205, doi:10.1128/JVI.00133-15). Briefly, perivascular regions with cellular infiltration were randomly selected (n=20/lung) by a masked pathologist, and the number of eosinophils was enumerated and averaged for a final score for each lung. Lungs were scored for mononuclear infiltrates, with scores of 0 representing values within normal parameters, 1 representing small aggregates in peribronchial and perivascular areas, 2 representing perivascular and periairway aggregates filling perivascular space, and 3 representing a score of 2 plus expanding sheets of infiltrates into septa and consolidation lesions in regions of the lung, respectively. Lungs were scored for granulocytic infiltrates, with scores as follows: 0, within normal parameters; 1, scattered PMNs sequestered in septa; 2, a score of 1 plus solitary PMNs extravasated in airspaces; 3, a score of 2 plus small aggregates in vessels and airspaces, respectively.

SARS-COV2-S Neutralization

VSV pseudotyped with SARS-CoV 2 (VSV-S) described before (Nie et al., 2020, *Emerg Microbes Infect;* 9:680-686, oi:10.1080/22221751.2020.1743767) was used for neutralization assay. VSV-S particles were titered by TCID50 in a 96 well plate in Vero cells to determine the optimal number of particles for neutralization. They were diluted in 2% FBS, 1% P/S in DMEM media. Titer was determined using Firefly luciferase detected Bio-Glo Luciferase Assay System by Promega. A particle control was used on each plate that consisted of a 1:1 ratio of diluted particles and sterile PBS (no serum). A negative control was also used on each plate consisting of sterile PBS and 2% FBS, 1% P/S in DMEM media to account for background.

Serum was heat inactivated at 56° C. for 45 minutes prior to neutralization assay. It was then serial diluted in sterile PBS using 1:2 dilutions starting at 1:50 (felines) or 1:100 (ferrets) in a 96 well untreated plate containing no cells. A recovered human serum sample (+RHS) was used as a positive control in each assay and was serial diluted 1:2 starting at 1:100. Samples and controls were done in quadruplicate.

50 ul of diluted VSV-S particles were added to the 96 well plate containing 50 ul of diluted serum and incubated for 1 hour at 5% $CO_2$ in 37° C. After 1 hr, the media was aspirated from a white 96 well plate contained Vero cells at 90-100% confluency and the particle-serum mixture (100 ul) was added to the cells. The plate was incubated at 5% $CO_2$ in 37° C. for 18-24 hrs. The next day, samples were equilibrated to room temperate for 10-20 minutes and 50 ul of the Bio-Glo reagent was added to each well. Plates were read immediately using the Bio-Glo Protocol on a GloMax Luminometer by Promega.

For neutralization with SARS-CoV-2, serum samples were heat inactivated at 56° C. for 30 minutes prior to neutralization assay. They were then serially diluted in sterile DMEM and mixed with equal volume of DMEM containing ~20 PFU SARS-CoV-2. After incubation at 37° C. for 1 hr, the aliquots were added into Vero E6 cells in 12-well plates and incubated at 37° C. in 5% $CO_2$ for 1 hr. After removal of inocula, plates were overlaid with 1.2% agarose containing 4% FBS. After further incubation at 37° C. in 5% C02 for 2 days, overlays were removed, and plaques were visualized by staining with 0.1% crystal violet.

Sars-CoV-2 Nasal Shedding qPCR

Generation of a standard curve. To propagate the virus used for the standard curve, Vero E6 cells were infected at approximately MOI 0.001 with SARS-CoV-2 USA-WA01/2020 (BEI Resources, cat #NR52281) passage 1 and incubated at 37° C.+5% $CO_2$. 48 hours post-infection, the virus was collected and titered via plaque assay on Vero E6 cells with an avicel overlay of 1.2% Avicel+0.5×DMEM+1% FBS+0.5× antibiotic/antimycotic. Virus, at a concentration of $1.1\times10^6$ PFU/mL or $1.44\times10^7$ PFU/mL for the ferret and feline sample respectively, was mixed 1:1 with TRIzol Reagent (ThermoFisher Scientific) in order to inactivate and preserve the genetic material. Using a Quick RNA Viral Kit (Zymo Research), RNA was extracted from 600 μL and eluted in 50 uL TRIzol. The RNA was serially diluted 1:10. 10 μL of each virus dilution was used in a 40 uL qPCR reaction with 10 uL TaqPath 1-Step RT-qPCR Master Mix (ThermoFisher Scientific) and 3 uL nCov N1 primer/probe from EUA CDC SARS-2 kit (Integrated DNA Technologies). All qPCR reactions were analyzed using an Agilent Mx3000P.

Ferret nasal wash qPCR. 500 uL retrieved nasal wash sample was mixed 1:1 with DNA/RNA Shield (Zymo Research). Using a Quick RNA Viral Kit (Zymo Research), RNA was extracted from 600 μL and eluted in 15 uL DNA/RNA Shield. 2 ng of each nasal wash sample was used in a 40 uL qPCR reaction with 10 uL TaqPath 1-Step RT-qPCR Master Mix (ThermoFisher Scientific) and 3 uL nCov N1 primer/probe from EUA CDC SARS-2 kit (Integrated DNA Technologies). Genome copy per qPCR reaction was calculated using the standard curve. The ratio of RNA used in the qPCR reaction was calculated by dividing 2 ng by the total RNA ng per sample. To calculate the genome copy for each sample, genome copy per qPCR reaction was multiplied by the ratio of RNA used in the reaction, and genome copy per mL was back-calculated using the dilution and extraction volumes described. Samples with CT values over 37 were considered PCR-negative. For each qPCR experiment, the 1 FFU/reaction (rxn) CT value cutoff was established using the standard curve, and samples with a CT value under 37, but over the 1 FFU/rxn cutoff, were assigned a genome copy/mL value of 0.5 for graphing purpose. The 1 FFU/mL and PCR-positive cutoff lines were plotted at y=1 and y=0.1, respectively.

Feline Nasal Wash qPCR.

500 uL retrieved nasal wash sample was mixed 1:1 with DNA/RNA Shield (Zymo Research). Using a Quick RNA Viral Kit (Zymo Research), RNA was extracted from 600 μL and eluted in 15 uL DNA/RNA Shield. 1 μL of each nasal wash sample was used in a 40 uL qPCR reaction with 10 uL TaqPath 1-Step RT-qPCR Master Mix (ThermoFisher Scientific) and 3 uL nCov N1 primer/probe from EUA CDC SARS-2 kit (Integrated DNA Technologies).

Genome copy per qPCR reaction was calculated using the standard curve. Genome copy per mL was back-calculated using the dilution and extraction volumes described. Samples with CT values over 37 were considered PCR-negative. For each qPCR experiment, the 1 FFU/rxn CT value cutoff was established using the standard curve, and samples with a CT value under 37, but over the 1 FFU/rxn cutoff, were assigned a genome copy/mL value of 0.5 for the purpose of graphing. The 1 FFU/mL and PCR-positive cutoff lines were plotted at y=1 and y=0.1, respectively.

Focus Forming Units Assay

Quantification of infectious SARS-Cov-2 was carried completed by focus forming units (FFU) on Vero E6 cells. Briefly, 96-well cell culture plates were seeded at $3.2\times10^5$ cells/well and incubated overnight. Confluent monolayers were incubated with 10-fold serial dilutions of inoculum in culture media of DMEM containing 2% FBS and 1× antibiotic/antimycotic media. Growth media from culture plates, 50 uL inoculum was incubated for 1 hour, 37° C., 5% $CO_2$ with humidity. Overlay media, 0.8% methylcellulose in culture media, was applied at 150 uL/well and plates returned to 37° C., 5% $CO_2$ with humidity for 20-24 hours. For colorimetric development of focus forming units (FFU), methylcellulose overlay was decanted, and plates washed three times with 1×PBS. Fixative solution (80% methanol, 20% acetone), was added at 100 μL and allowed to incubate for a minimum of 10 minutes at room temperature before submersion in fixative solution and removal from BSL3 facilities. Primary antibody (HRP-conjugated $1CO_2$, 1.4 μg/ml) was diluted to a 1:1000 in blocking buffer (0.1% Tween 20, 5% NFDM, 5% BSA) at 75 uL/well and incubated at room temperature for 45 minutes. Next, primary solution was decanted, and plates washed twice with 0.1% PBS-T. An additional wash step was completed with $dH_20$, 75 uL/well TMB development solution and incubated at room temperature for 1 hour. A final $dH_20$ wash step was completed, plates air dried and images obtained with BioTek Cytation7 machine for manual FFU quantification.

Example 3

Protection of K18-hACE2 Mice and Ferrets Against SARS-CoV-2 Challenge by a Single Dose Mucosal Immunization with a Parainfluenza Virus 5-Based COVID-19 Vaccine In this example, a recombinant PIV5 containing the full-length spike of SARS-CoV-2 with its cytoplasmic tail replaced with that of PIV5 F protein (CVXGA1) was generated and tested its efficacy as a vaccine in mice and ferrets.

Generation and analysis of PIV5 expressing the S protein of SARS-CoV 2 (CVXGA1) Employing a strategy similar to that used in PIV5-based MERS-CoV vaccine development, a PIV5 expressing the SARS-CoV-2 Spike (S) protein (termed CVXGA1) was generated (FIG. 18A). The viral genome sequence by RT-PCR sequencing and also confirmed expression of the S glycoprotein in CVXGA1-infected cells using immunofluorescence and western blot (FIG. 18B). Besides full-length S, a cleaved product, S1, was also detected in CVXGA1-infected cells, indicating S was processed (FIG. 18B). The S protein mediates cell-to-cell fusion and virus-to cell fusion to facilitate viral entry and immunization with S generates protective immunity against SARS-CoV-2 (Corbett et al. *N Engl J Med*, (2020)). It is thought that the native (containing pre-fusion) conformation of S induces desirable immunity for optimal protection (Corbett et al. *N Engl J Med*, (2020)). To examine whether the S protein expressed by the PIV5 vector is functional, Vero cells, which express the ACE2 receptor, were infected with CVXGA1. Syncytia formation (cell-to-cell fusion) was observed only in CVXGA1-infected cells, indicating functional expression of the S protein (FIG. 18C).

CVXGA1 Generated Humoral and Cellular Immune Responses in Mice

Figure 27:
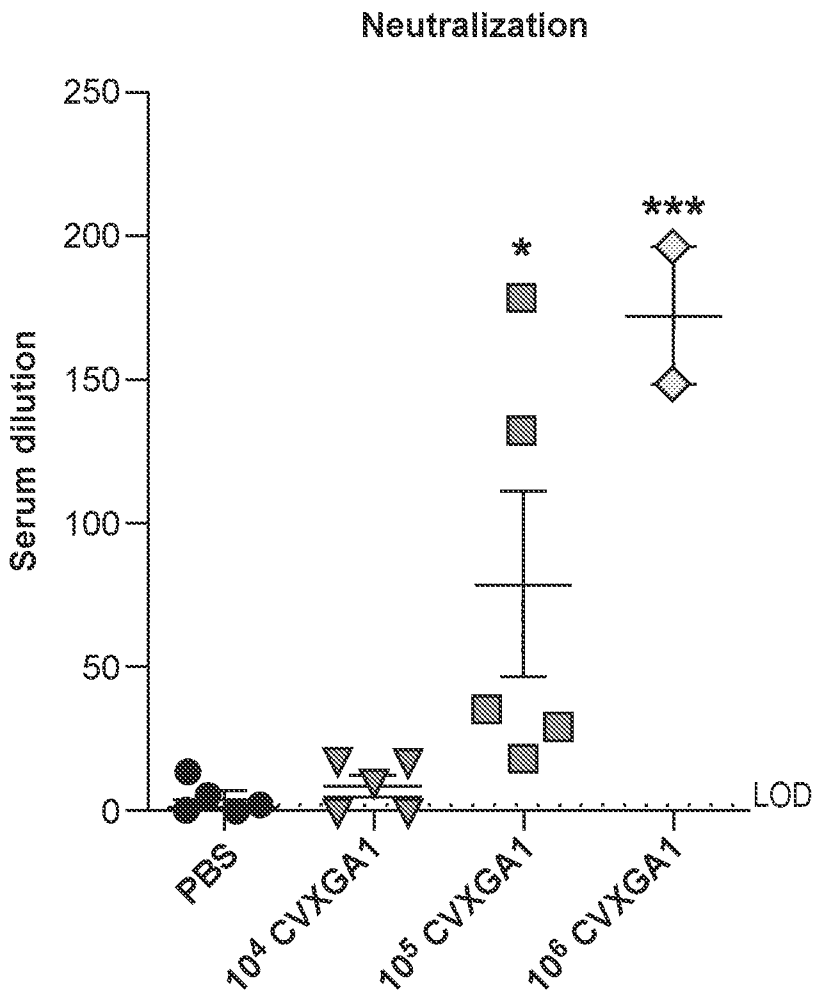
FIG. 27 shows the neutralization titers in BALB/c mice immunized with CVXGA1. Neutralization titers of samples were determined as described in Materials and Methods. Error bars represent the standard error of the mean, and P-values were calculated with one-way ANOVA. *P value<0.05, ***P value <0.001.
Figure 33A:
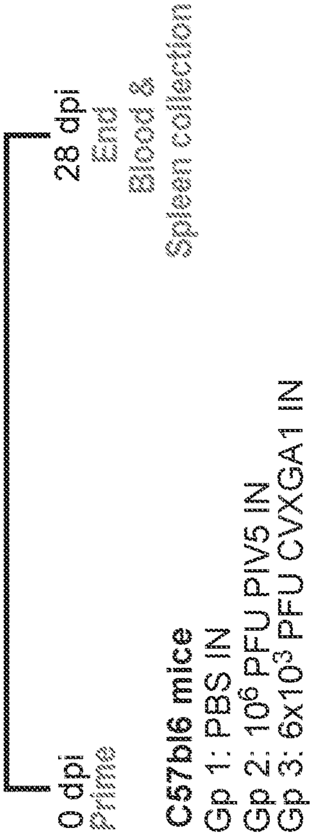
FIG. 33A-FIG. 33C show immunogenicity of CVXGA1 in C57BL/6 mice.
Figure 33B:
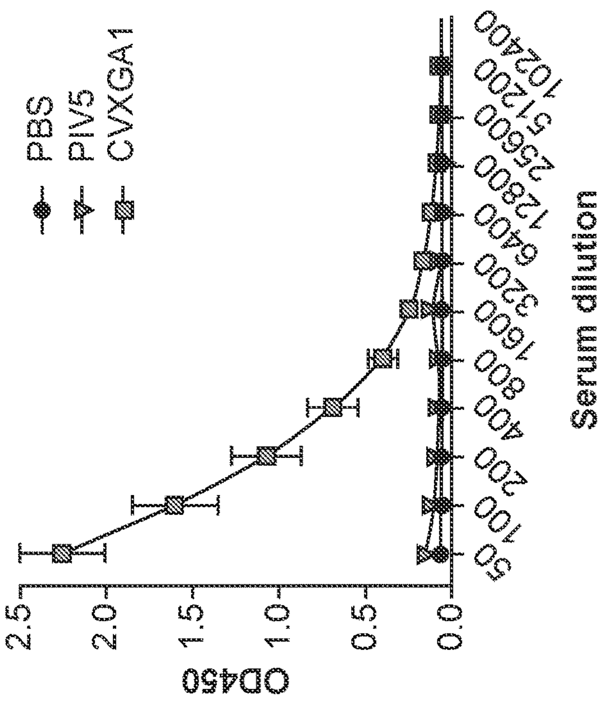
Figure 33C:
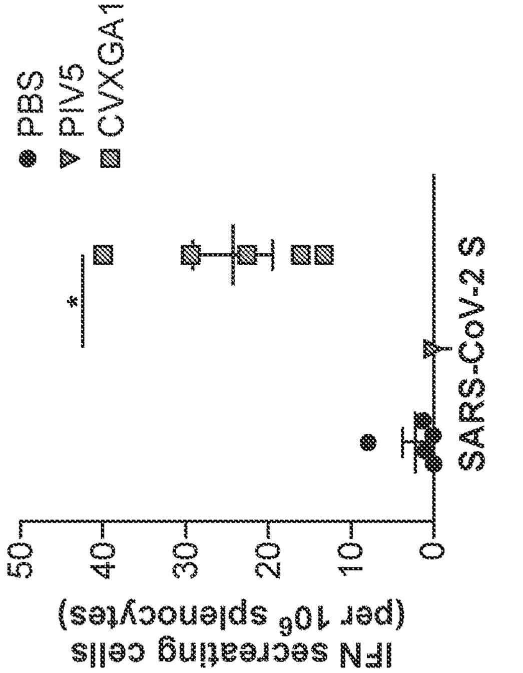

To investigate CVXGA1 antigenicity, mice were intranasally immunized with a range of CVXGA1 inocula. A dose-dependent increase in anti-S antibodies was detected in BALB/c mice after a single intranasal administration (FIG. 18D). Similarly, antibodies recognizing the receptor binding domain (RBD) of S were detected in a dose-dependent manner in BALB/c mice immunized with CVXGA1 (FIG. 18E). Furthermore, neutralizing antibodies against SARS-CoV-2 were detected in BALB/c mice immunized in a dose-dependent manner (FIG. 27). Significant antibody generation and cellular responses were observed in C57BL/6 mice after a single intranasal (IN) immunization with a dose as low as $6\times10^3$ plaque forming units (PFU) of CVXGA1 (FIG. 33). These results indicate that a single intranasal dose immunization with CVXGA1 generated robust immune responses in mice.

Figure 28A:
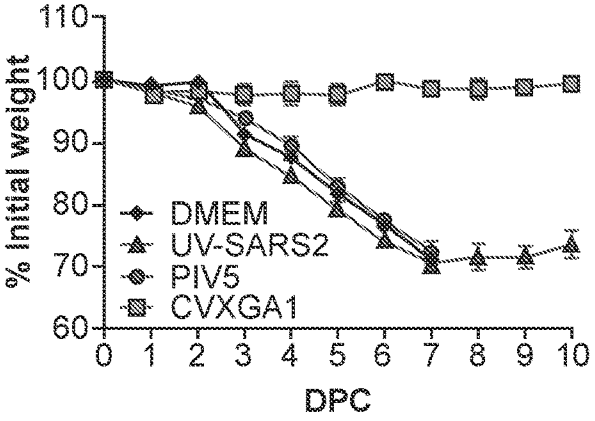
FIG. 28A-FIG. 28C show the results of intranasal vaccination with CVXGA1 protects K18-hACE2 transgenic mice against SARS-CoV-2 infection. Mice received DMEM intranasally; CVXGA1 immunization via intranasal (106 PFU, IN) route; UV-inactivated SARS-CoV-2 (UV-SARS2) administered via IM route with Alum adjuvant followed by a boost dose at 21 dpi; Wildtype PIV5 (106 PFU) via IN route. Five weeks following immunization, K18-hACE2 mice were intranasally infected with $4\times10^4$ PFU of SARS-CoV-2 in 50 μl of DMEM. Error bars represent the standard error of the mean.
Figure 28B:
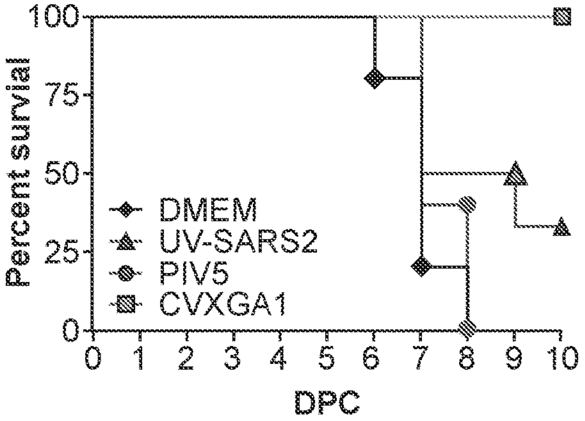

CVXGA1 Protected Mice with Human ACE2 Receptor Against SARS-CoV2 Lethal Challenge To determine CVXGA1 efficacy, two complementary animal models were used: a severe disease model using transgenic mice and an upper respiratory tract infection model using ferrets. Mice lack a functional ACE2 receptor for SARS-CoV-2, and thus are resistant to infection. To examine vaccine efficacy in a very stringent model human ACE2 (hACE2) transgenic mice were used. Mice expressing hACE2 under regulation of the cytokeratin 18 promoter (K18), originally developed to study SARS-CoV infection (McCray et al. *J Virol* 81, 813-821 (2007)), were recently demonstrated to develop severe lung disease in response to SARS-CoV-2 infection (Jiang et al. *Cell* 182, 50-58 e58 (2020); Zheng et al. *Nature*, (2020)). Inoculation K18-hACE2 mice with $10^5$ PFU of SARS-CoV-2 results in 100% mortality, lung disease with signs of diffuse alveolar damage, and variable spread to the CNS. The lethal dose, 50% (LD50) is estimated to be $10^4$ PFU (Jiang et al. *Cell* 182, 50-58 e58 (2020); Zheng et al. *Nature*, (2020)). K18-hACE2 mice were immunized intranasally with a single dose of CVXGA1 ($10^6$ PFU), and 4 weeks later challenged with $4\times10^4$ PFU of SARS-CoV-2. Another group of K18-ACE2 mice were immunized intramuscularly with UV-inactivated SARS-CoV-2, then boosted 2 weeks later. Non-vaccinated mice received intramuscular DMEM. A second control group was immunized intranasally with a single dose of PIV5 vector intranasally ($10^6$ PFU). In response to the SARS-CoV-2 challenge, the DMEM control group lost weight and succumbed to infection by 7 days post challenge (dpc) (FIG. 28A, 28B). Mice immunized with UV-inactivated SARS-CoV-2 or PIV5 lost as much weight as the DMEM group. All PIV5 immunized mice succumbed by 7 dpc, and 4 of 6 UV-inactivated SARS-CoV-2 immunized mice died (FIG. 28A, 28B). CVXGA1-immunized mice lost no weight and all survived (FIG. 28A, 28B).

Figure 28C:
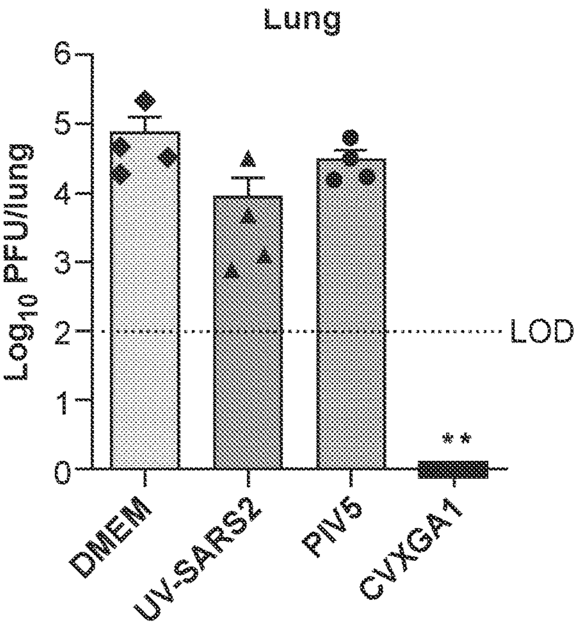
Figure 28D:
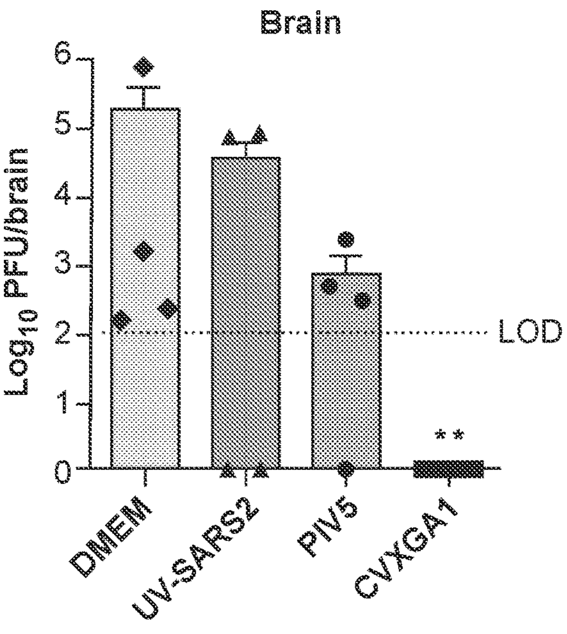

At 5 dpc, virus titers in the lung tissue of mice immunized with DMEM, UV inactivated SARS-CoV-2, or PIV5 were similar (FIG. 28C) and all three groups demonstrated evidence of brain infection (FIG. 28D). In contrast, CVXGA1 immunized mice had no detectable SARS-CoV-2 in lung tissue, demonstrating an ~5 log reduction in virus titer (FIG. 28C). Notably, 4 out of 4 CVXGA1 immunized mice had no virus detected in brain tissue (FIG. 28D) after SARS-CoV-2 challenge.

Figure 29A:
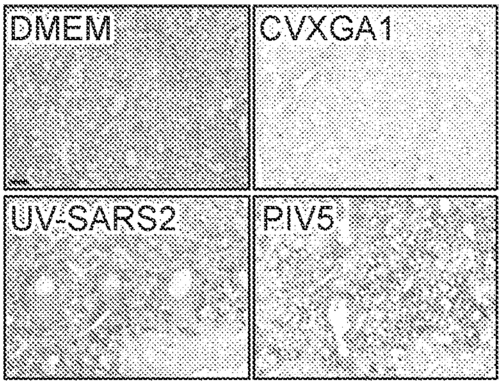
FIG. 29A-FIG. 29D show the histopathologic analysis of SARS-CoV-2 infection in K18-hACE2 transgenic mice immunized with CVXGA1.

Five days post SARS-CoV-2 challenge, virus antigen (N protein) in lung tissues was localized. Control DMEM treated animals had diffuse antigen staining throughout the airway and lung parenchymal epithelial cells (FIG. 29A). In contrast, CVXGA1 immunized mice exhibited only uncommon small foci of N protein positive cells, presumptively indicative of initial infection sites that did not progress (FIG. 29A). Lung tissues from UV-inactivated SARS-CoV-2 and PIV5 treatment groups both showed diffuse antigen positive cells (FIG. 29A)

Figure 29B:
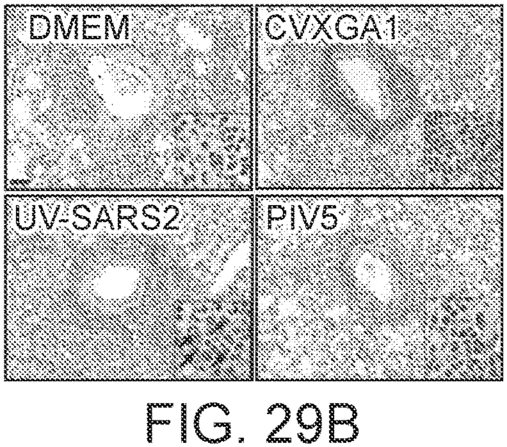

Lung tissue sections from animals infected with SARS-CoV-2 were examined and scored for the presence of perivascular eosinophilic infiltrates. At 5 days post infection an influx of eosinophils was clearly evident in the mice immunized with UV-inactivated SARS-CoV-2 and absent from the other groups (FIG. 29B, inset arrows). Lung tissues were also scored for the presence of perivascular inflammatory cell infiltrates. Perivascular pulmonary infiltrates, when comprised mostly of lymphoid cells, can be a favorable sign of previous antigenic exposure and effective vaccination. As shown in FIG. 29B, compared to the DMEM control group, CVXGA1 immunized mice had a significant increase in perivascular lymphoid cell infiltrates.

Figure 29C:
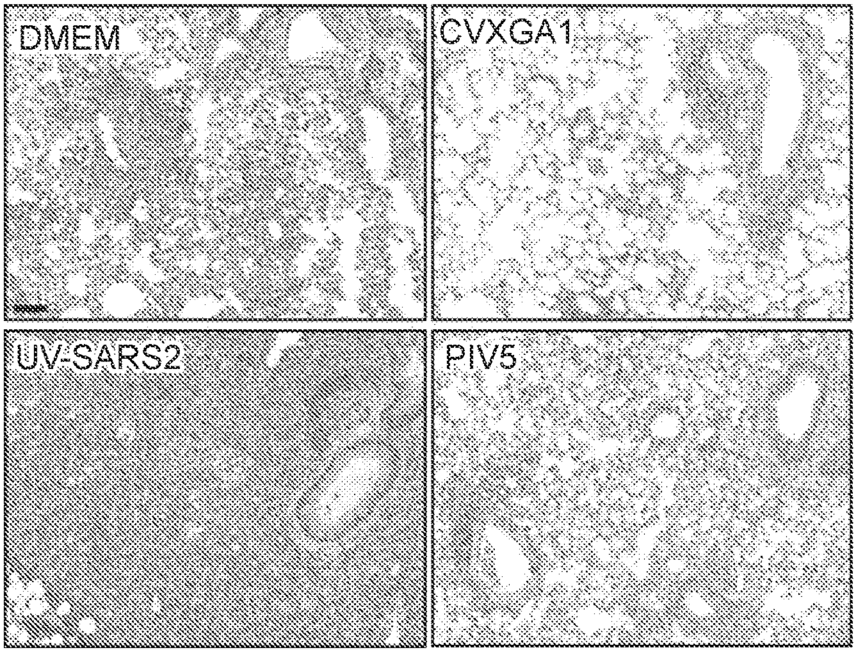
Figure 29D:
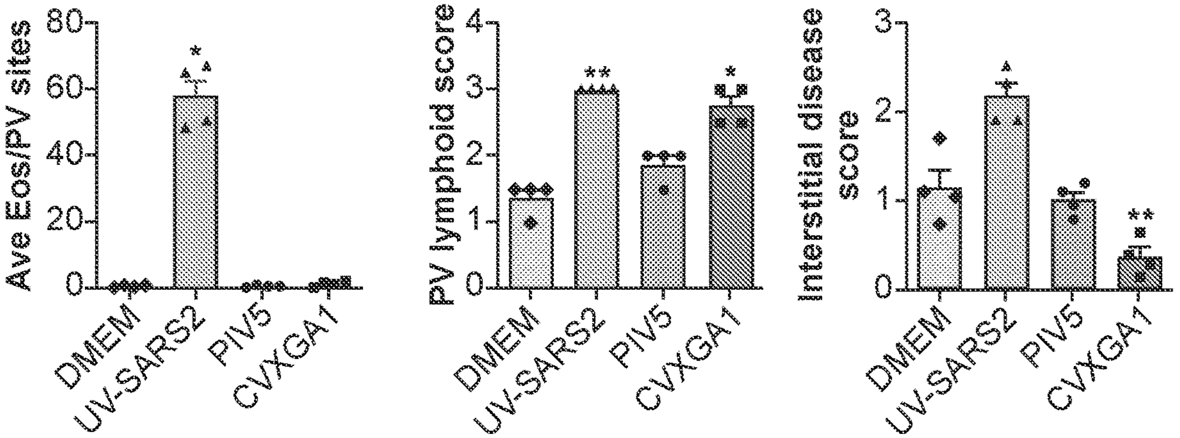

The presence of interstitial disease is often a hallmark of severe viral pneumonia. Lung tissues were examined and scored for the presence of interstitial disease (H-score), defined by the presence of alveolar septal infiltration, extension into the airspaces, and associated atelectasis and edema. Compared to the other treatment groups, CVXGA1 immunized mice had the least evidence of interstitial disease at 5 days post SARS-CoV-2 challenge (FIG. 29C). Histopathologic scores for eosinophilic infiltrates, perivascular infiltrates, and severity of interstitial lung disease are presented in FIG. 29D. Furthermore, efficacy of CVXGA1 immunization against a high challenge dose ($10^6$ PFU SARS-CoV-2 per mouse) and found CVXGA1 immunization protected 100% mice from this lethal challenge was examined (FIG. 34).

CVXGA1 Protected Ferrets From SARS-CoV 2 Infection

Figure 30A:
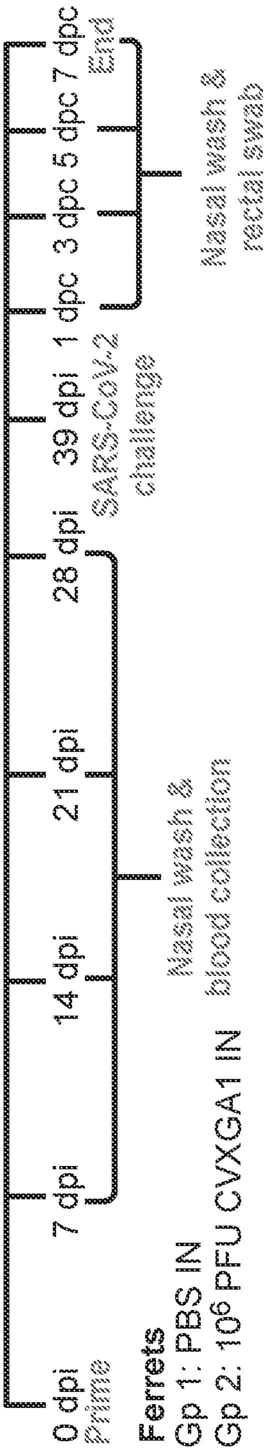
FIG. 30A-FIG. 30C show the immunogenicity of CVXGA1 in ferrets.
Figure 30B:
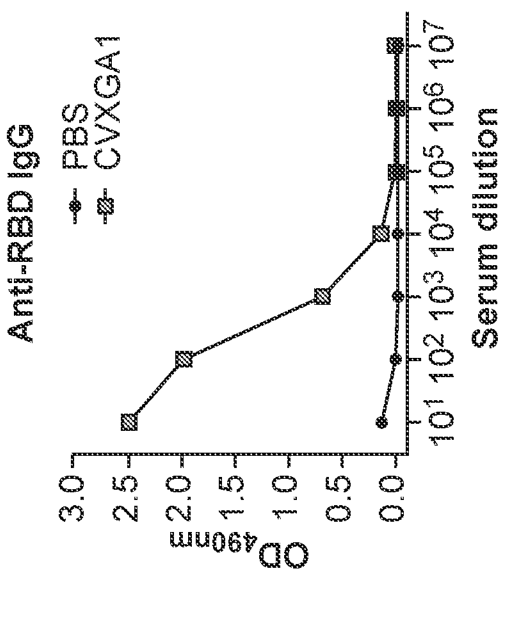
Figure 30C:
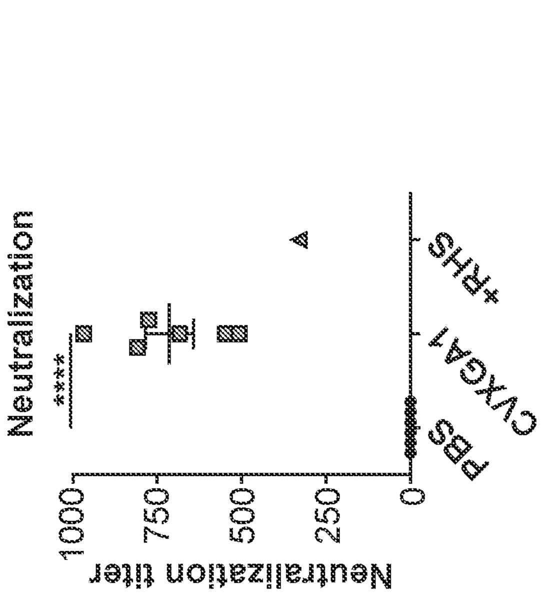
Figure 31B:
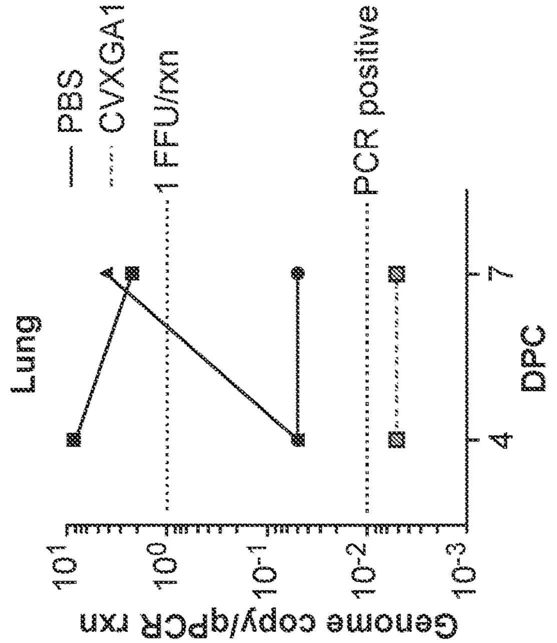
FIG. 31A-FIG. 31C show the efficacy of CVXGA1 in ferrets.
Figure 31A:
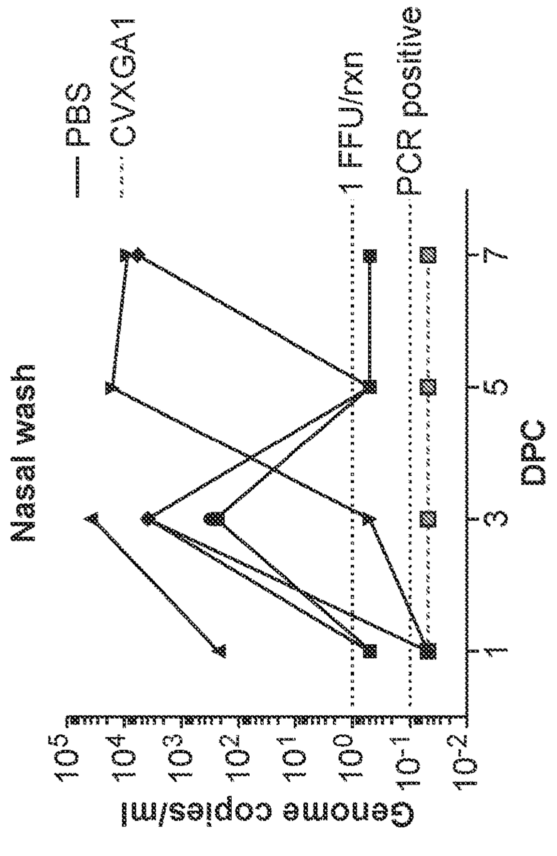
Figure 31C:
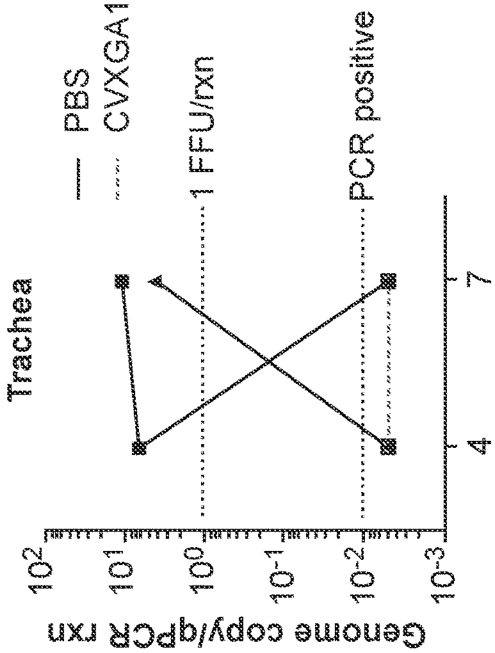
Figure 35A:
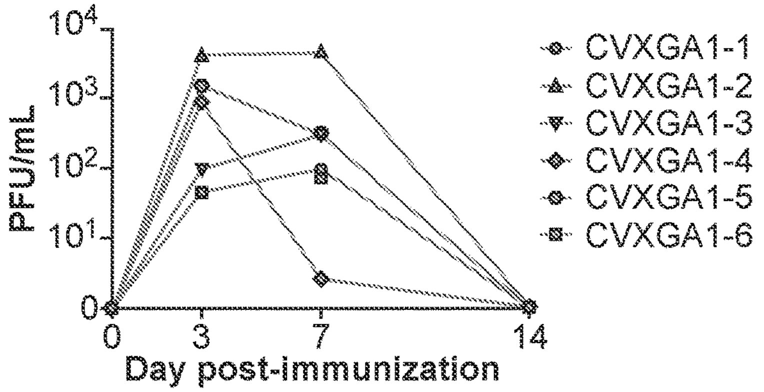
FIG. 35A-FIG. 35D show the immunogenicity and efficacy of CVXGA1 in ferrets.
Figure 35B:
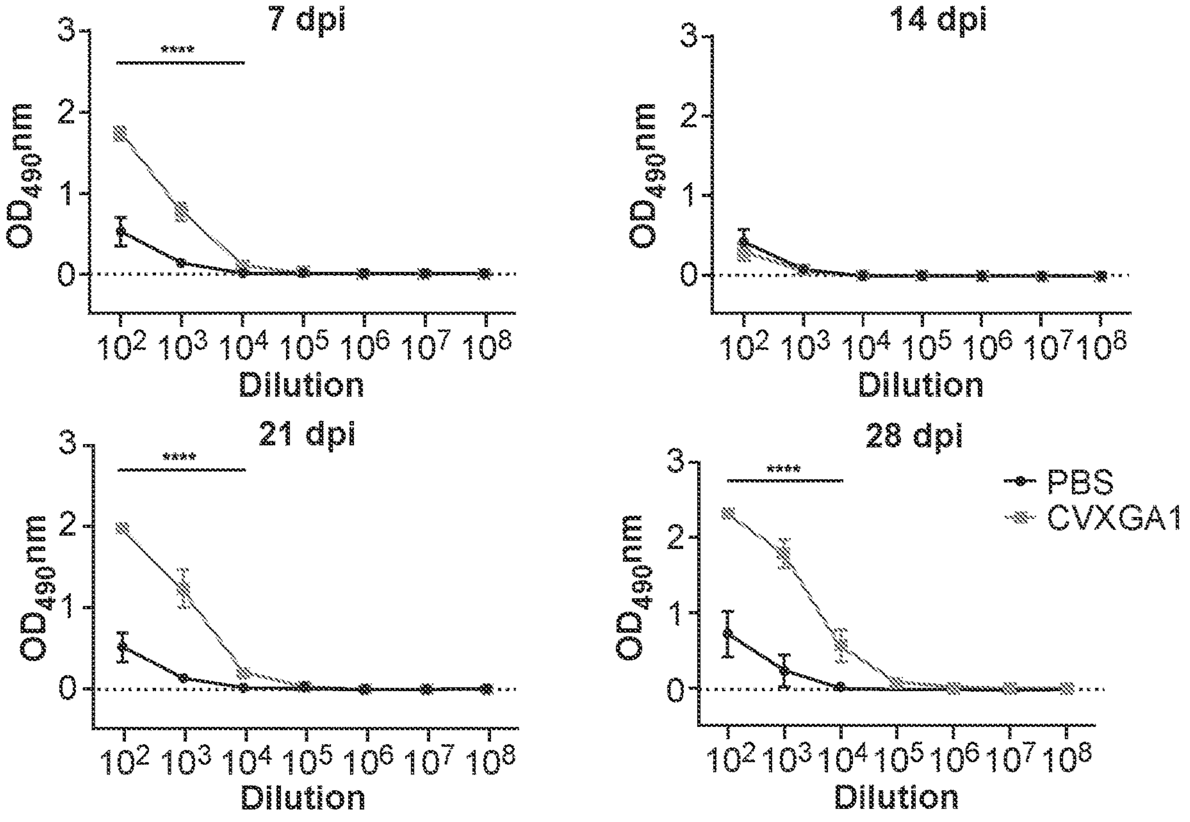
Figure 35C:
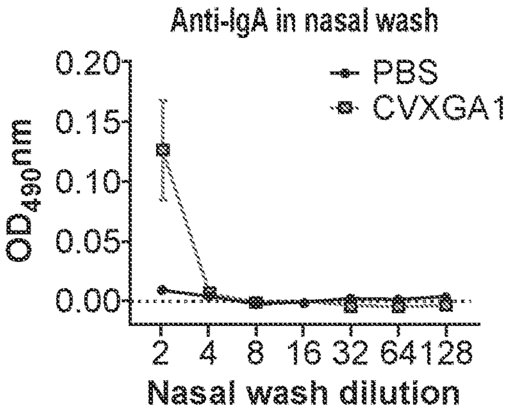
Figure 35D:
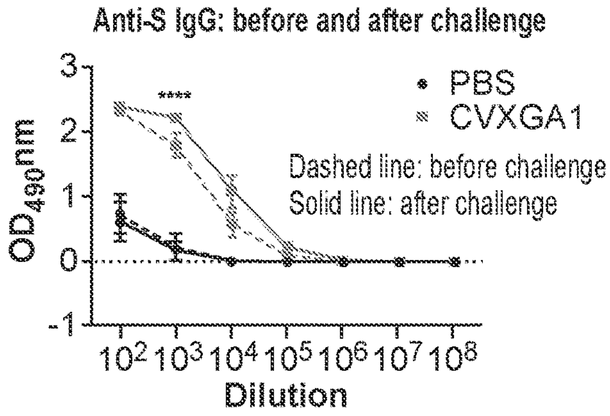

Ferrets are a widely used model of human respiratory infections, are susceptible to SARS-CoV-2 infection, and can transmit the virus to other animals via direct contact and aerosol (Kim et al. *Cell Host Microbe*, (2020); Shi et al. *Science*, (2020); Richard et al. *Nat Commun* 11, 3496 (2020)). To test CVXGA1 efficacy in ferrets, animals were immunized intranasally with PBS or CVXGA1 (FIG. 30A). CVXGA1 replicated in the nasal cavities of ferrets at day 3 and 7 post immunization with a peak titer greater than $10^4$ PFU/ml in nasal washes, and CVXGA1 was cleared by 14 days after immunization (FIG. 35A). CVXGA1 immunization generated robust antibody responses as evident by high titers of anti-S IgG (FIG. 35B), anti-RBD IgG (FIG. 30B), and neutralizing antibodies in FIG. 30C. Low levels of anti-S IgA were detected in nasal washes (FIG. 35C). When challenged with SARS-CoV-2 intranasally, no viral genome RNA was detected in nasal washes from CVXGA1 immunized ferrets (FIG. 31A). In contrast, viral RNA was detected in all mock-immunized ferrets over time (FIG. 31A). Viral RNA was also detected in the trachea and lungs of mock-immunized ferrets but not in trachea and lungs of CVXGA1 immunized ferrets (FIG. 31B, C). To assess SARS-CoV-2 exposure in ferrets, anti-S antibody levels were quantified at the time of experiment termination (7 dpc). Anti-S IgG levels in CVXGA1 immunized group increased after challenge (FIG. 35D), indicative of a memory response and exposure to the S antigen. These results indicate that CVXGA1 immunization markedly reduced SARS-CoV-2 replication in the upper respiratory tract, a site critical for SARS-CoV-2 onset.

Figures 32A, 32B:
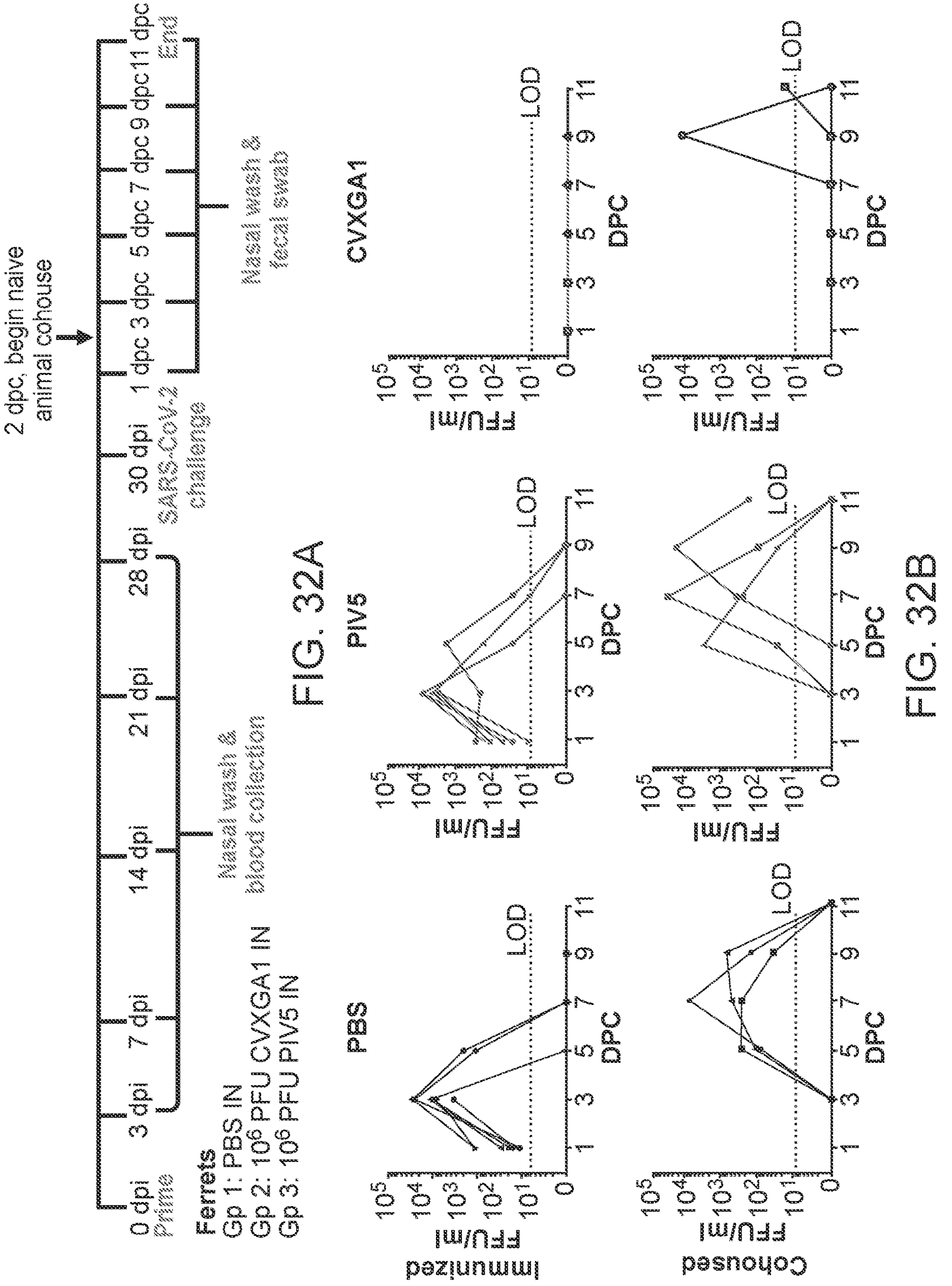
FIG. 32A-32B show the efficacy of transmission block by CVXGA1 immunization in ferrets.
Figure 36A:
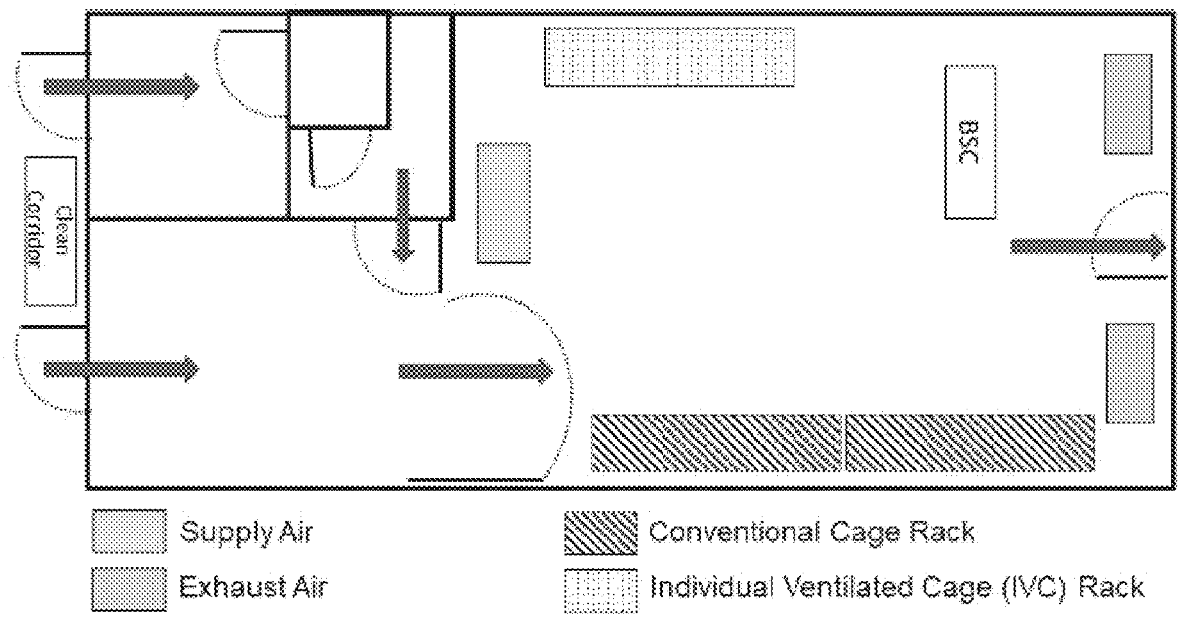
FIG. 36A-FIG. 36C show the ABSL3 facility for ferret SARS-CoV 2 infection.
Figure 36B:
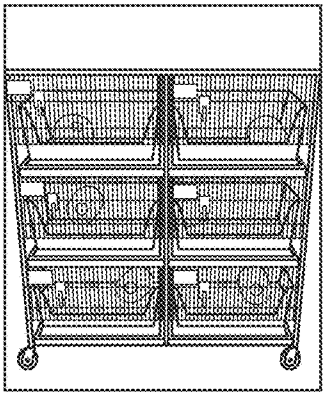
Figure 36C:
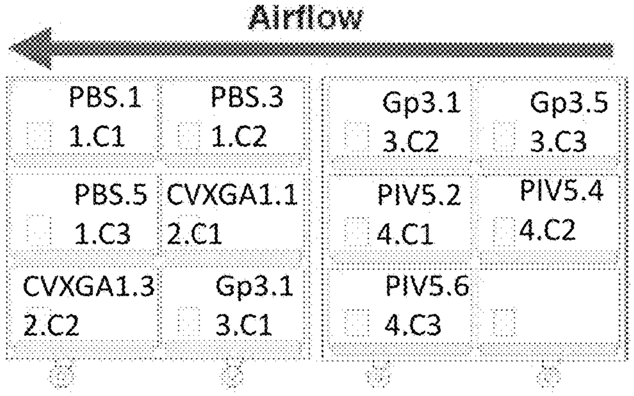

To determine if CVXGA1 immunization can block transmission, ferrets were immunized with a single dose of CVXGA1 as before. Control animals were immunized with PBS or empty PIV5 virus vector (FIG. 32A). 42 days after IN immunization, ferrets were challenged with SARS-CoV-2 and nasal washes collected at 1, 3, 5, 7, 9, and 11 dpc (FIG. 32A). Naïve ferrets were co-housed with the challenged ferrets at a ratio of 1 naïve: 1 infected beginning at 2 dpc (2 ferrets per cage). Due to animal welfare regulations, all ferrets were housed in open cages in the BSL3 facility (FIG. 36). All ferrets in the PBS and empty PIV5 vector groups became infected as indicated by detection of live SARS-CoV-2 in nasal secretions, peaking at 3 dpc (FIG. 32B). All naïve ferrets co-housed with the infected PBS and empty PIV5 vector groups contracted SARS-CoV-2, with peak titers detected around 5 days after co-housing. The titers in the exposed naïve animals reached similar levels as directly infected animals, consistent with 100% transmission (FIG. 32B). As before (FIG. 32B), no virus was detected in nasal cavities of CVXGA1 immunized ferrets after challenge. No virus was detected in the naïve ferrets co-housed with CVXGA1-immunized and SARS-CoV-2 challenged ferrets for first 5 days after co-housing (FIG. 32B), suggesting that direct contact with CVXGA1-immunized and challenged ferrets did not result in transmission of SARS-CoV-2 to naïve ferrets. Beginning 7 days after mixing, ferrets mixed with CVXGA1 immunized animals acquired infection, likely from the environment which included infected ferrets in neighboring cages (FIG. 36).

Figure 34A:
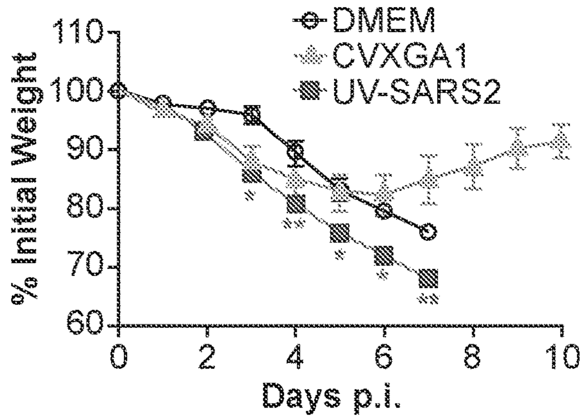
FIG. 34A-FIG. 34E show the intranasal vaccination with CVXGA1 protects K18-hACE2 transgenic mice against lethal SARS-CoV-2 infection. Mice received DMEM immunization via intramuscular (IM) route; CVXGA1 immunization via intranasal (IN) route; UV-inactivated SARS-CoV-2 (UV-SARS2) administered via IM route with Alum adjuvant followed by a second boost dose at 14 dpi. Four weeks following immunization, K18-hACE2 mice were intranasally infected with $10^6$ PFU of SARS-CoV-2 in 50 μl of DMEM.
Figure 34B:
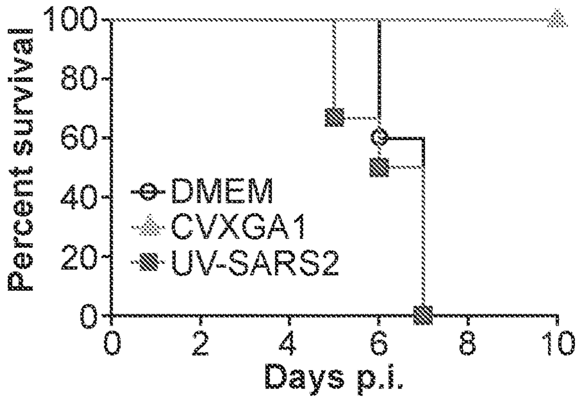
Figure 34C:
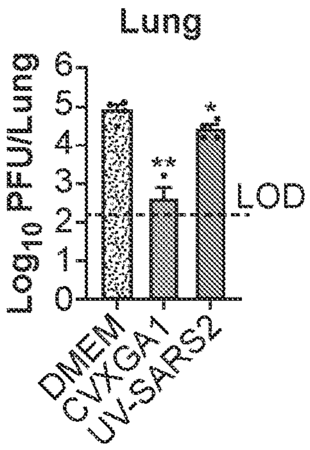
Figure 34D:
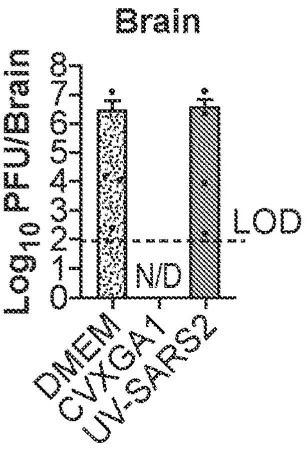
Figure 34E:
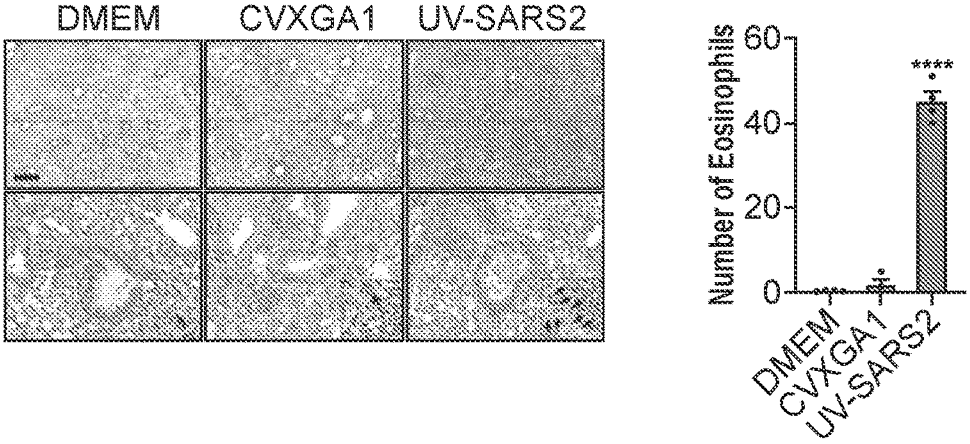

This work demonstrates that a PIV5-based mucosal COVID-19 vaccine can prevent lethal disease in a mouse model and markedly reduce upper respiratory tract virus replication and inhibit transmission in ferrets. While no animal model completely reproduces all features of severe SARS-CoV-2 infection in humans, K18-hACE2 mice support robust virus replication and develop dose-dependent severe disease, but to date transmission has not been studied in this model (Jiang et al. *Cell* 182, 50-58 e58 (2020); Zheng et al. *Nature*, (2020)). In K18-hACE2 mice, the lethal dose, 50% (LD50) is estimated to be $10^4$ PFU (Zheng et al. *Nature*, (2020); Winkler et al. *Nat Immunol*21, 1327-1335 (2020)). Prime-boost of K18-hACE2 mice with UV-inactivated SARS-CoV-2 failed to protect 100% of mice from a lethal challenge. Of note is that when an estimated 100 LD50 was used, challenge ($10^6$ PFU), mice immunized with inactivated virus lost more weight than the PBS control group (FIG. 34). Similar to previous observations with a UV-inactivated MERS-CoV vaccine, immunization with UV-inactivated SARS-CoV-2 followed with a $10^6$ PFU SARS-CoV-2 challenge triggered an influx of eosinophils, consistent with a hypersensitivity-type response (FIG. 34E). K18-hACE2 mice that received sublethal SARS-CoV-2 inocula survived subsequent lethal dose challenge, but virus was detected in lung tissue of surviving mice at 5 dpc (Jiang et al. *Cell* 182, 50-58 e58 (2020)). All mice immunized with a single dose of CVXGA1 survived an estimated 100 LD50 challenge ($10^6$ PFU) with no detectable virus in brain, and most importantly, 75% of the mice had no virus detected in lung tissue at 5 dpc, demonstrating the potent protective efficacy of CVXGA1.

Generating a native configuration of the viral glycoprotein as an antigen is desirable to maximize protective immune responses and may be challenging. Virus inactivation often results in undesirable changes in antigen conformation. To obtain optimal structure of purified viral glycoproteins, mutations are often introduced (Wrapp et al. *Science* 367, 1260-1263 (2020)). Previously, it was demonstrated that PIV5 is an excellent vector to display the RSV F protein. Cells expressing F following after infection with recombinant PIV5 containing F retains the same conformation as the native F protein in RSV-infected cells (Wang et al. *J Virol* 91, (2017)), demonstrating that a PIV5 live virus vector can appropriately express native viral glycoproteins. Expression of full-length SARS-CoV-2 S protein in CVXGA1-infected cells caused syncytia formation (FIG. 18C), consistent with display of a native, fusion competent S protein. PIV5 enters host cells via F and HN-mediated membrane fusion: HN binds to sialic acid residues on cell surface proteins and F promotes membrane fusion. Since sialic acid residues are ubiquitous, PIV5 is known to infect practically all mammalian cells. Thus, expressing a functional S of SARS-CoV 2 does not expand cell tropism of CVXGA1 since CVXGA1 expresses S as well as F and HN (FIG. 18A). Furthermore, the accelerated syncytia formation promoted by CVXGA1 (PIV5 also causes syncytia in Vero E6 cells, albeit at a slower rate) is unlikely to cause damage as syncytia are more commonly observed in cells grown in monolayer culture and rarely occur in primary epithelial cells that are typically well-differentiated and polarized.

Ferrets are very susceptible to SARS-CoV-2 infection, and readily transmit the virus by direct contact and aerosol (Kim et al. *Cell Host Microbe*, (2020); Shi et al. *Science*, (2020); Richard et al. *Nat Commun* 11, 3496 (2020)). Direct contact is a more efficient means of transmission than an indirect (aerosol) route. In published work, one infected ferret was co-housed with one or two naïve animals to study direct contact transmission (Kim et al. *Cell Host Microbe*, (2020); Richard et al. *Nat Commun* 11, 3496 (2020)). To test the vaccine in a robust transmission model, one naïve ferret was co-housed with one infected ferrets (FIG. 32A and FIG. 36). A single dose IN CVXGA1 immunization completely protected against SARS-CoV-2 infection: no viral RNA was detected in nasal cavities of immunized animals (FIG. 31A). Importantly, a single dose CVXGA1 immunization inhibited direct transmission of SARS-CoV-2 (FIG. 32). Because the ferrets were housed in open cages, animals co-housed with CVXGA1-immunized ferrets became infected at 7 and 9 days after mixing, likely through environmental transmission from other cages. It is also possible that the late infections of naïve ferrets co-housed with CVXGA1-immunized ferrets were a result of transmission by CVXGA1-immunized and SARS-CoV-2-challenged ferrets, thus, CVXGA1 just delayed transmission of SARS-CoV-2.

Figure 37A:
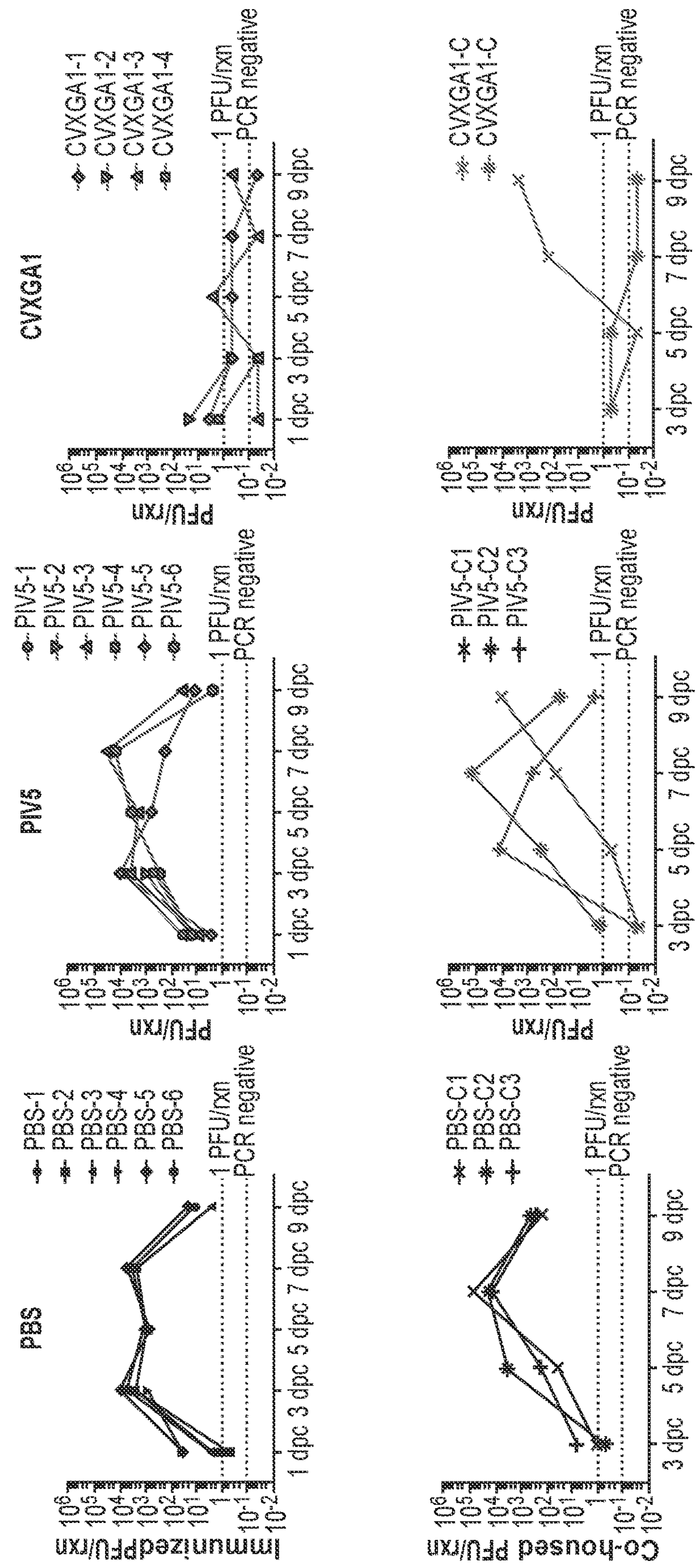
Figure 37B:
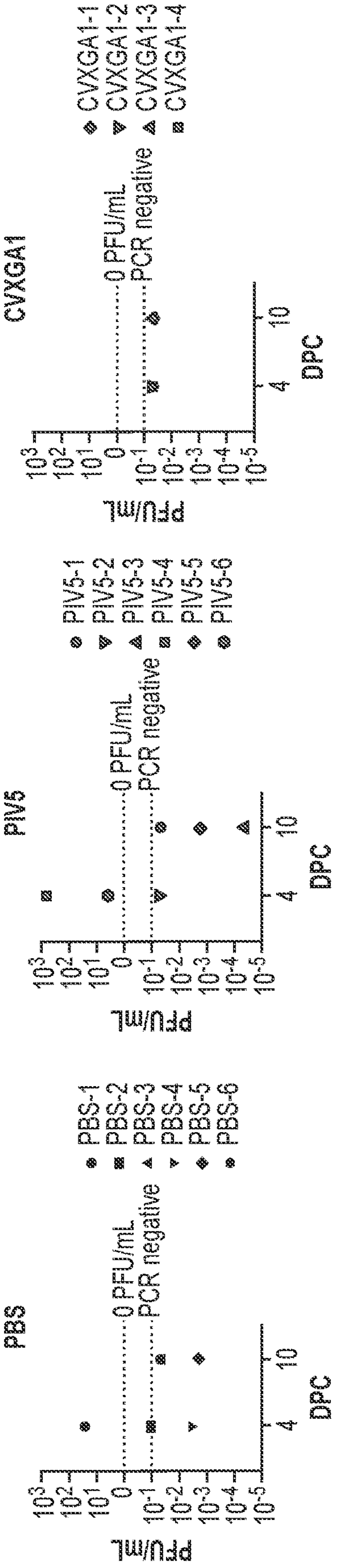
FIG. 37B shows the RNA levels in lungs of challenged ferrets. Lung samples were collected at days 4 and 10 dpc. Viral RNA was quantified via qRT-PCR, and PFU/mL was calculated with a standard curve. Each point represents a different animal, and 1 PFU/mL is marked to differentiate between infectious viral particles and un-infectious genomic remnants. The limit of detection (LOD) is indicated by the lowest dashed line.

However, no virus was detected in nasal washes or lungs of CVXGA1-immunized ferrets (FIG. 37), suggesting that the likely source of virus for the co-housed ferrets was from infected ferrets housed in neighboring open cages. The lack of viral RNA in CVXGA1-immunized ferrets after challenge supports that the late infection of ferrets co-housed with CVXGA1-immunized ferrets came from other infected ferrets (FIG. 37). There were two possible routes by which naïve ferrets co-housed with CVXGA1-immunized/SARS-CoV-2 challenged ferrets to become infected at later time points. One is that the ferrets acquired infection via aerosol transmission from infected ferrets in neighboring cages, as they were housed in open cages (FIG. 36). Another possibility was contamination from husbandry and equipment: the procedure mandated by our IACUC requires cage changes for the animals every 7 days. It is possible that the co-housed ferrets acquired infection through direct contact with contaminated equipment during these cage changes. A disconnect between the viral RNA level and live virus in the PBS group was observed (FIG. 32B and FIG. 37): live virus titers peaked at day 3 and were undetectable at day 7, while viral RNA first peaked at day 3 and had a high level at day 7. This delayed clearance of viral RNA may reflect methodologic differences, in which qRT-PCR can detect residual viral RNA. Intranasal CVXGA1 immunization generated robust serum antibody responses in mice and ferrets. Importantly, IN CVXGA1 immunization induced respiratory mucosal IgA in ferrets, consistent with previous report that PIV5 is a potent vector for vaccine development for respiratory infections, including influenza virus and respiratory syncytial virus (RSV) (Wang et al. *J Virol* 91, (2017); Mooney et al. *J Virol* 91, (2017)). Mucosal IgA was also detected in monkeys immunized intranasally with PIV5 expressing RSV F (Wang et al. *J Virol* 91, (2017)). As a live viral vector, it was hypothesized that CVXGA1 to generate robust cellular immune responses and, as observed in FIG. 33, cellular immune responses were detected in mice. Kennel cough vaccines have been produced inexpensively and safely used for many decades and the manufacturing capacity and vaccine delivery systems for PIV5 are well-established. Further development of a PIV5 vector-based vaccine may help block SARS-CoV-2 transmission and control the COVID-19 pandemic.

Materials and Methods

The virus and cells preparation, the immunoblotting method, the purification of S and RBD of S, the ELISA protocol and the focus forming units assay protocol are similar to those in Example 2.

Immunofluorescence

Immunofluorescent localization of SARS-CoV-2-S protein expression was performed in MDBK cells in 24-well plates that were infected with CVXGA1 or PIV5 at a MOI of 1. At 2 days after infection, the cells were washed with phosphate-buffered saline (PBS) and then fixed in 2% formaldehyde. The cells were permeabilized in 0.1% PBS-Saponin solution and incubated for 1 hr with anti-SARS-CoV-2 S (Sino Biological, catalog no.40150-R007) and anti-PIV5-V/P at 1:200 dilution, and then fluorescein isothiocyanate (FITC)-labeled goat anti-rabbit (KPL, catalog no. 02-15-16) and Cy3-labeled goat anti-mouse (KPL, catalog no. 072-01-18-06) secondary antibodies were added to the cells with 2 drops/ml of 4%6-diamidino-2-phenylindole (DAPI) (NucBlue Live Cell Stain ReadyProbes reagent, Life technologies Corporation, Eugene, Oregon, USA). The cells were incubated for 30 min and were examined and photographed using a Nikon Eclipse Ti confocal fluorescence microscope.

Immunization and Infection of Mice with SARS-CoV 2

Six to eight-week-old female mice (Envigo) or K18-hACE2 mice (B6.Cg.Tg (K18-hACE2)2Prlmn/J, Jackson Laboratory) were used in these studies. The mice were anesthetized by intraperitoneal injection of 250 μl 2,2,2-tribromoethanol in tert-amyl alcohol (Avertin) and intranasally inoculated with 50 μl of PBS (or DMEM) or $10^4$, 105, $10^6$ PFU CVXGA1 or $10^6$ PFU PIV5 vector. Twenty-eight days post-immunization, the mice were euthanized, serum was collected via cardiothoracic bleeds, and spleens were harvested. The mice were housed and immunized in enhanced biosafety level-2 facilities in HEPA-filtered isolators. All experiments were performed in accordance with protocols approved by the Institutional Animal Care and Use Committees at the University of Georgia and at the University of Iowa.

$10^6$ PFU UV-inactivated SARS-CoV-2 were 1:1 (vol/vol) mixed with Alum Adjuvant (Thermo, catalog no. 77161) in a volume of 200 μl and delivered to mice intramuscularly.

Infection of mice. Mice were lightly anesthetized with ketamine/xylazine and intranasally inoculated with the indicated amount of SARS-CoV-2 in a total volume of 50 μl DMEM. Animal weight and health were monitored daily. All experiments with SARS-CoV-2 were performed in a Biosafety Level-3 (BSL3) Laboratory.

Immunization and Infection of Ferrets With SARS-CoV-2

Twelve, eight to nine-month-old male and female (700-2000 g) fitch ferrets were received from Triple F Farms and acclimated in the UGA animal facilities. Prior to arrival, ferrets underwent sterilization and scent gland removal. Following an acclimation period of at least seven days, ferrets were anesthetized for subcutaneous placement of thermal transponders between the shoulder blades. Implantable Programmable Temperature Transponders (Bio Medic Data Systems, USA) were anchored securely to the tissue at the implantation site and allowed temperature readouts ranging from 90-110° F. Simultaneously, whole blood was collected for baseline serology and fecal swab performed for analysis of viral shedding.

Pre-challenge procedures were performed at the University of Georgia Biosciences Animal Facility. Animals were housed in pairs, with ad libitum access to food and water. Following vaccination, procedures, including nasal wash and blood collections, were performed on anesthetized animals using ketamine/xylazine (15-20 mg/kg/1-2 mg/kg xylazine) delivered IM. Ferrets were monitored daily for clinical signs. Weights and temperatures were recorded, at minimum, during each procedure under sedation.

Viral Challenge of Ferrets

For SARS-CoV-2 challenge, animals were transferred to the University of Georgia Animal Health Research Center Animal Biosafety Level-3 (ABSL3) facility. Procedures performed after viral challenge were done under short-term isoflurane gas anesthesia.

Groups of six ferrets were vaccinated intranasally (IN) with $1\times10^6$ PFU CVXGA1 in 1.0 ml sterile PBS distributed as 500 μl per nostril. Following vaccination, animals were monitored daily for clinical signs, including nasal discharge, sneezing, diarrhea, lethargy, increased respiratory rate and effort (congestion), cyanosis, neurological changes, and altered responses to external stimuli. Body temperature was tracked using the implanted temperature probes. Nasal washes and fecal swabs were collected 3, 7, 14, 21, and 28 days post immunization (dpi) to assess vaccine shedding. Whole blood was obtained weekly following immunization. Peripheral blood mononuclear cells (PBMCs) were isolated and cryopreserved for future analysis. For infectious challenge with SARS-CoV-2, $1\times10^6$ PFU were delivered via the IN route. Again, physical observations, weights, and temperatures were measured daily. A subset of six animals were humanely euthanized and necropsied on day 4 post-challenge, and the remaining animals (n=6) were humanely euthanized on day 7 post-challenge. All necropsies were performed under the guidance of a board-certified veterinary pathologist. Tissue samples (trachea and lung) were collected for pathology and viral load. Terminal blood collection was carried out for serum and PBMC isolation. For transmission study, at 2 days post challenge (dpc), two challenged ferrets were mixed with one naïve ferret.

Co-Housing of Ferrets

Two days post SARS-CoV-2 challenge a naïve ferret was paired with one challenged ferret. The second challenged ferret was transferred to isolation caging until necropsy 4 days post challenge.

All experiments were approved by the IACUC of the University of Georgia College of Veterinary Medicine.

Histology and Immunohistochemistry

Mice were anesthetized and perfused transcardially with PBS. Lung tissues were harvested, fixed in 10% neutral-buffered formalin, dehydrated through a series of alcohol and xylene baths, paraffin-embedded, sectioned at −4 μm, and stained with hematoxylin and eosin (HE) stains. Tissues were examined by a boarded pathologist in a masked manner and following principles for reproducible tissues scores (Meyerholz et al. *Lab Invest* 98, 844-855 (2018)). Perivascular eosinophil infiltration was assessed as previously described (Li et al. *mBio* 11, (2020)). Briefly, perivascular regions with cellular infiltration were randomly selected (n=20/lung), and the number of eosinophils was enumerated and averaged for a final score for each lung. Perivascular lymphoid aggregates were ordinally scored: 0—absent, 1—few solitary cells, 2—moderate small to medium aggregates, or 3—robust aggregates forming circumferential perivascular cuffs with compression of adjacent parenchyma. Interstitial disease was ordinally scored using a modified H—Score: 0—absent, 1—minor scattered cells in septa, 2—moderate infiltrates septa and extending into lumen, or 3—moderate to severe infiltrates in septa and lumen with associated consolidation/atelectasis and or edema. For each the tiers the % of lung affected was recorded. The final modified H-score for each lung was calculated by: % affected x each tier score, summed, and then divided by 100 to yield a score between 0 and 3.

Immunohistochemistry was performed as previously described (Zheng et al. *Nature* 589, 603-607 (2021)).

Briefly, primary anti-SARS-CoV-2 N protein antibody (1:20,000 dilution×60 min, 40143-R019, SinoBiological) was followed by Rabbit Envision (Dako) and diaminobenzidine (DAB, Dako) as chromogen with hematoxylin as counterstain. Ordinal scoring of immunostaining was performed in a distribution-based manner: 0—absent, 1-0 to 25%, 2-26-50%, 3-51-75% and 4—>75% of lung fields in tissue section.

SARS-CoV-2 S Neutralization

VSV pseudotyped with SARS-CoV-2 (VSV-S) described previously was used for neutralization assay (Havranek et al. Viruses 12, (2020)). VSV-S particles were titered by TCID50 in a 96-well plate in Vero cells to determine the optimal number of particles for neutralization. They were diluted in 2% FBS, 1% P/S in DMEM media. Titer was determined using Firefly luciferase detected Bio-Glo Luciferase Assay System by Promega. A particle control was used on each plate that consisted of a 1:1 ratio of diluted particles and sterile PBS (no serum). A negative control was also used on each plate consisting of sterile PBS and 2% FBS, 1% P/S in DMEM media to account for background.

Serum was heat inactivated at 56° C. for 45 minutes prior to neutralization assay. It was then serially diluted in sterile PBS using 1:2 dilutions starting at 1:100 (ferrets) in a 96-well untreated plate containing no cells. A recovered human serum sample (+RHS) was used as a positive control in each assay and was serially diluted 1:2 starting at 1:100. Samples and controls were done in quadruplicate.

50 µl of diluted VSV-S particles were added to the 96-well plate containing 50 µl of diluted serum and incubated for 1 hour at 5% $CO_2$ in 37° C. After 1 hour, the media was aspirated from a white 96-well plate containing Vero cells at 90-100% confluency, and the particle-serum mixture (100 l) was added to the cells. The plate was incubated at 5% C02 in 37° C. for 18-24 hours. The next day, the media was aspirated and 50 ul of Nano-glo reagent was added to each well. Plates were agitated and then read immediately using the Renilla-Luciferase Protocol on a GloMax Luminometer by Promega.

For neutralization with SARS-CoV-2, serum samples were heat inactivated at 56° C. for 30 minutes prior to neutralization assay. They were then serially diluted in sterile DMEM and mixed with an equal volume of DMEM containing ~20 PFU of SARS-CoV-2. After incubation at 37° C. for 1 hour, the aliquots were added into Vero E6 cells in 12-well plates and incubated at 37° C. in 5% $CO_2$ for 1 h. After removal of inocula, plates were overlaid with 1.2% agarose containing 4% FBS. After further incubation at 37° C. in 5% $CO_2$ for 2 days, overlays were removed, and plaques were visualized by staining with 0.1% crystal violet.

Sars-CoV-2 Nasal Shedding qPCR

For the SARS-CoV-2 RNA genome standard curve, 1.1×$10^6$ PFU/ml or 1.44×$10^7$ PFU/ml for ferret and feline standards, respectively, were inactivated by dilution 1:1 (vol/vol) with TRIzol Reagent (ThermoFisher Scientific) according to inactivation protocols. RNA was extracted from 600 µl of the diluted virus using a Direct-zol RNA Miniprep Plus kit (Zymo Research) and eluted in 50 µl DNA/RNA-free water according to protocol. RNA purity ($A_{260}/A_{280}$) and concentration were assessed using a DeNovix DS-11 FX+ Spectrophotometer/Fluorometer (DeNovix). RNA was stored at −80° C. For the standard curve, RNA was diluted 10-fold, and 10 µl of each RNA dilution was used in a 40 µl qPCR reaction with 10 L TaqPath 1-Step RT-qPCR Master Mix (ThermoFisher Scientific) and 3 µl nCov N1 primer/probe from EUA CDC SARS-2 kit (Integrated DNA Technologies). For nasal wash samples, 500 µl of recovered nasal wash or rectal swab sample was inactivated by dilution 1:1 with 2×DNA/RNA Shield (Zymo Research) and stored at −20° C. until extraction. RNA was extracted from 600 µl of the diluted sample using a Quick RNA Viral Kit (Zymo Research) and eluted in 15 µl DNA/RNA-free water according to protocol. RNA purity ($A260/A_{280}$) and concentration were assessed using a DeNovix DS-11 FX+ Spectrophotometer/Fluorometer. RNA was stored at −80° C. All qPCR reactions were analyzed using an Agilent Mx3000P.

Ferret nasal wash qPCR. qPCR was performed using TaqPath 1-Step RT-qPCR Master Mix (ThermoFisher Scientific) on an Agilent Mx3000P qPCR System. Each nasal wash reaction consisted of 10 µl of TaqPath, 3 µl of primer/probe mix, 17 µl of water, and 10 µl of sample diluted to 2 ng for a final reaction volume of 40 µl per well. The nCoV N gene specific primers were as follows:

forward, 5'-GACCCCAAAATCAGCGAAAT-3' (SEQ ID NO: 14);

reverse, 5'-TCTGGTTACTGCCAGTTGAATCTG-3' (SEQ ID NO: 15) and probe (5'-(FAM)ACCCCGCATTACGTTTGGTGGACC (BHQ1)-3' (SEQ ID NO: 16) and were purchased from Integrated DNA Technologies as part of the RUO CDC SARS-2 kit. The thermal profile consisted of 1 cycle for 2 minutes at 25° C., 1 cycle for 15 minutes at 50° C., 1 cycle for 2 minutes at 95° C., and 50 cycles of 3 seconds at 95° C., then 30 seconds at 55° C. qPCR runs for each plate included RNA standards (10-fold dilutions, 10 µl per reaction, in duplicate), no template control, no polymerase control, and a sample spiked with viral RNA for a positive control. PFU/ml concentration of each sample was determined using the original PFU/ml concentration of the viral stock used for the RNA standard curve. The ratio of RNA used in the qPCR reaction was calculated by dividing 2 ng by the total RNA concentration per sample. The PFU/ml output from the standard curve was multiplied by the ratio of RNA used in the reaction, and the total PFU/ml content of the sample was determined through back-calculation using the dilution and extraction volumes described. Samples with Ct values greater than 37 were considered PCR-negative. For each qPCR plate the 1 PFU/PCR reaction (rxn) Ct value was established from the standard curve and set as y=0, the limit of detection was set at the standard curve concentration at the Ct value of 37, and the challenge dose was included for reference. All samples between 1 PFU/rxn and the limit of detection are considered PCR-positive but having non-infectious genomic material.

Ferret Tissue qPCR.

Tissue samples were inactivated with 1× DNA/RNA Shield at a ratio of 1 ml of Shield per 100 mg tissue. The tissue was bead-homogenized (TissueLyser II, Qiagen) at a frequency of for 1.5 minutes and homogenate was stored at −20° C. until extraction. The extraction process was the same as for nasal washes. Ferret tissues were assayed using the above protocol with the following exceptions. Each reaction consisted of 6.66 µl of TaqPath, 2 µl of primer/probe mix, 20.34 µl of water, and 1 µl of sample for a final reaction volume of 30 µl per well. HPRT was used as a housekeeping gene to ensure the presence of tissue RNA in the absence of viral RNA.

The HPRT gene specific primers (forward, 5'-CACTGGGAAAACAATGCAGA-3' (SEQ ID NO: 17); and reverse, 5'-ACAAAGTCAGGTTTATAGCCAACA-3' (SEQ ID NO: 18)) were synthesized by Integrated DNA Technologies. The gene specific TaqMan MGB probe 5'-NED-TGCTGGT- GAAgAGGACCCCTCG-MGBNFQ-3' (SEQ ID NO:19) was synthesized by Applied Biosystems. HPRT fluorescence was read using the HEX absorption and emission spectra. PFU/ml concentration of each sample was determined using the original PFU/ml concentration of the viral stock used for the RNA standard curve. The total PFU/ml content of the sample was determined through back-calculation using the dilution and extraction volumes described to PFU/ml of homogenate. Samples with Ct values greater than 37 were considered PCR-negative. For each qPCR plate, the 1 PFU/ml Ct value was established from the standard curve and set as y=0, the limit of detection was set at the standard curve concentration at the Ct value of 37. All samples between 1 PFU/ml and the limit of detection are considered PCR-positive but having non-infectious genomic material. For graphing purpose CT values under 37, but over the 1 PFU/rxn cutoff, were assigned a genome copy/mL value of 0.5.

Example 4

Mutations at Amino Acid Residue W886 and/or F888

Following procedures detailed in the previous examples, a construct in which the coronavirus S protein further contains mutations at amino acid residue W886 and/or F888 was produced. A schematic of this construct is shown in FIG. 38. For example, the amino acid substitution at amino acid residue W886 can be a substitution of tryptophan (W) to arginine (R) and/or the amino acid substitution at amino acid residue W888 can be a substitution of phenylalanine (F) to arginine(R).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Sequence Listing Free Text

SEQ ID NO: 1 Sequence of the pDA27 (CVX-UGA1) plasmid

SEQ ID NOs: 2-19 Artificial Oligonucleotide Primers

What is claimed is:

1. A viral expression vector comprising a parainfluenza virus 5 (PIV5) genome comprising a heterologous nucleotide sequence expressing a heterologous polypeptide, wherein the heterologous polypeptide comprises a coronavirus spike (S) protein;

wherein the coronavirus S protein comprises the coronavirus S protein of the severe acute respiratory syndrome coronavirus 2 (SARS-CoV-2);

wherein the cytoplasmic tail of the coronavirus S protein has been replaced with the cytoplasmic tail of the fusion (F) protein of PIV5; and wherein the heterologous nucleotide sequence is inserted between the small hydrophobic protein (SH) gene and the hemagglutinin-neuraminidase (HN) gene of the PIV5 genome; replaces the SH gene nucleotide sequence; is inserted between the hemagglutinin-neuraminidase (HN) gene and the large RNA polymerase protein (L) gene of the PIV5 genome; is inserted closer to the leader than between the hemagglutinin-neuraminidase (HN) gene and the large RNA polymerase protein (L) gene of the PIV5 genome; is inserted upstream of the nucleocapsid protein (NP) gene of the PIV5 genome; is inserted immediately downstream of the leader sequence of the PIV5 genome; is inserted between the fusion (F) protein gene and the SH gene of the PIV5 genome; is inserted between the VP gene and the matrix protein (M) gene of the PIV5 genome; is inserted between the M gene and the F gene of the PIV5 genome; is inserted between the nucleocapsid protein (NP) gene and the V/P gene of the PIV5 genome; is inserted between the leader sequence and the nucleocapsid protein (NP) gene of the PIV5 genome; is inserted wherein a portion of the F or HN gene of PIV5 has been replaced with the heterologous nucleotide sequence; is inserted within the SH gene nucleotide sequence, is inserted within the NP gene nucleotide sequence, is inserted within the V/P gene nucleotide sequence, is inserted within the M gene nucleotide sequence, is inserted within the F gene nucleotide sequence, is inserted within the HN gene nucleotide sequence, and/or is inserted within the L gene nucleotide sequence.

2. A viral expression vector comprising a parainfluenza virus 5 (PIV5) genome comprising a heterologous nucleotide sequence expressing a heterologous polypeptide, wherein the heterologous polypeptide comprises a coronavirus spike(S) protein, and wherein the cytoplasmic tail of the coronavirus S protein has been replaced with the cytoplasmic tail of the fusion (F) protein of PIV5.

3. The viral expression vector of claim 2, wherein the heterologous polypeptide comprises a coronavirus spike(S) protein that contains mutations at amino acid residue W886 and/or F888.

4. The viral expression vector of claim 3, wherein the amino acid substitution at amino acid residue W886 comprises a substitution of tryptophan (W) to arginine (R) and/or the amino acid substitution at amino acid residue F888 comprises a substitution of phenylalanine (F) to arginine (R).

5. The viral expression vector of claim 1, wherein the PIV5 genome further comprises one or more mutations.

6. The viral expression vector of claim 5, wherein the one or more mutations comprise a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, or a combination thereof.

7. The viral expression vector of claim 5, wherein the one or more mutations comprise PIV5VΔC, PIV5ΔSH, PIV5-P-S308G, or a combination thereof.

8. A viral particle comprising the viral expression vector of claim 1.

9. A composition comprising the viral expression vector of claim 1.

10. A method of expressing a heterologous coronavirus spike(S) glycoprotein in a cell, the method comprising contacting the cell with a viral expression vector of claim 2.

11. A method of inducing an immune response in a subject to a coronavirus spike(S) glycoprotein, the method comprising administering the viral expression vector of claim 1 to the subject.

12. The method of claim 11 wherein the immune response comprises a humoral immune response and/or a cellular immune response.

13. A method of vaccinating a subject against coronavirus disease 2019 (COVID-19), the method comprising administering the viral expression vector of claim 1 to the subject.

14. The method of claim 11, wherein the viral expression vector, viral particle, or composition is administered intranasally, intramuscularly, topically, or orally.

15. A method of expressing a heterologous coronavirus spike(S) glycoprotein in a cell, the method comprising contacting the cell with the viral expression vector of claim 1.

16. The viral expression vector of claim 1, wherein the heterologous polypeptide comprises a coronavirus spike(S) protein that contains mutations at amino acid residue W886 and/or F888.

17. The viral expression vector of claim 16, wherein the amino acid substitution at amino acid residue W886 comprises a substitution of tryptophan (W) to arginine (R) and/or the amino acid substitution at amino acid residue F888 comprises a substitution of phenylalanine (F) to arginine (R).

18. The viral expression vector of claim 2, wherein the coronavirus S protein comprises the coronavirus S protein of the severe acute respiratory syndrome coronavirus 2 (SARS-COV-2).

19. The viral expression vector of claim 2, wherein the heterologous nucleotide sequence is inserted between the small hydrophobic protein (SH) gene and the hemagglutinin-neuraminidase (HN) gene of the PIV5 genome; replaces the SH gene nucleotide sequence; is inserted between the hemagglutinin-neuraminidase (HN) gene and the large RNA polymerase protein (L) gene of the PIV5 genome; is inserted closer to the leader than between the hemagglutinin-neuraminidase (HN) gene and the large RNA polymerase protein (L) gene of the PIV5 genome; is inserted upstream of the nucleocapsid protein (NP) gene of the PIV5 genome; is inserted immediately downstream of the leader sequence of the PIV5 genome; is inserted between the fusion (F) protein gene and the SH gene of the PIV5 genome; is inserted between the VP gene and the matrix protein (M) gene of the PIV5 genome; is inserted between the M gene and the F gene of the PIV5 genome; is inserted between the nucleocapsid protein (NP) gene and the V/P gene of the PIV5 genome; is inserted between the leader sequence and the nucleocapsid protein (NP) gene of the PIV5 genome; is inserted wherein a portion of the F or HN gene of PIV5 has been replaced with the heterologous nucleotide sequence; is inserted within the SH gene nucleotide sequence, is inserted within the NP gene nucleotide sequence, is inserted within the V/P gene nucleotide sequence, is inserted within the M gene nucleotide sequence, is inserted within the F gene nucleotide sequence, is inserted within the HN gene nucleotide sequence, and/or is inserted within the L gene nucleotide sequence.

20. A method of inducing an immune response in a subject to a coronavirus spike(S) glycoprotein, the method comprising administering the viral expression vector of claim 2 to the subject.

21. The method of claim 20, wherein the viral expression vector, viral particle, or composition is administered intranasally, intramuscularly, topically, or orally.

22. A viral particle comprising the viral expression vector of claim 2.

23. A composition comprising the viral expression vector of claim 2.

24. The viral expression vector of claim 2, wherein the PIV5 genome further comprises one or more mutations.

25. The viral expression vector of claim 24, wherein the one or more mutations comprise a mutation of the V/P gene, a mutation of the shared N-terminus of the V and P proteins, a mutation of residues 26, 32, 33, 50, 102, and/or 157 of the shared N-terminus of the V and P proteins, a mutation lacking the C-terminus of the V protein, a mutation lacking the small hydrophobic (SH) protein, a mutation of the fusion (F) protein, a mutation of the phosphoprotein (P), a mutation of the large RNA polymerase (L) protein, a mutation incorporating residues from canine parainfluenza virus, a mutation inducing apoptosis, PIV5VΔC, PIV5ΔSH, PIV5-P-S308G, or a combination thereof.

* * * * *

SEQUENCE LISTING

```
<160> NUMBER OF SEQ ID NOS: 19

<210> SEQ ID NO 1
<211> LENGTH: 25935
<212> TYPE: DNA
<213> ORGANISM: Artificial
<220> FEATURE:
<223> OTHER INFORMATION: pDA27 (CVX-UGA1) plasmid

<400> SEQUENCE: 1

gatctgacgt cgaattctaa tacgactcac tatagggacc agggggaaaa cgaagtggtg     60

actcaaatca tcgaagaccc tcgagattac ataggtccgg aacctatggc cttcgtgacc    120

gacctcgagt cagagtagtt caataaggac ctatcaagtt tgggcaattt ttcgtccccg    180

acacaaaaat gtcatccgtg cttaaagcat atgagcgatt cacactcact caagaactgc    240

aagatcagag tgaggaaggt acaatcccac ctacaacact aaaaccggta atcagggtat    300

ttatactaac ctctaataac ccagagctaa gatcccggct tcttctattc tgcctacgga    360

ttgttctcag taatggtgca agggattccc atcgctttgg agcattactt acaatgtttt    420

cgctaccatc agccacaatg ctcaatcatg tcaaattagc tgaccagtca ccagaagctg    480

atatcgaaag ggtagagatc gatggctttg aggagggatc attccgctta atccccaatg    540

ctcgttcagg tatgagccgt ggagagatca atgcctatgc tgcacttgca gaagatctac    600

ctgacacact aaaccatgca acaccttttg ttgattccga agtcgaggga actgcatggg    660

atgagattga gactttctta gatatgtgtt acagtgtcct aatgcaggca tggatagtga    720

cttgcaagtg catgactgcg ccagaccaac ctgctgcttc tattgagaaa cgcctgcaaa    780

aatatcgtca gcaaggcagg atcaacccga gatatctcct gcaaccggag gctcgaagaa    840

taatccagaa tgtaatccga aagggaatgg tggtcagaca tttcctcacc tttgaactgc    900

agcttgcccg agcacaaagc cttgtatcaa ataggtatta tgctatggta ggggatgttg    960

gaaagtatat agagaattgt ggaatgggag gcttcttttt gacactaaaa tatgcattag   1020
```

```
gaaccagatg gcccacactt gctttagctg cattttcagg agagctaaca aagctaaagt   1080
ccctcatggc attataccag acccttggtg agcaggcccg atatttggcc ctattggagt   1140
caccacattt gatggatttt gctgcagcaa actacccact gctatatagc tatgctatgg   1200
gaataggcta tgtgttagat gtcaacatga ggaactacgc tttctccaga tcatacatga   1260
ataagacata tttccaattg ggaatggaaa ctgcaagaaa acaacagggt gcagttgaca   1320
tgaggatggc agaagatctc ggtctaactc aagccgaacg caccgagatg gcaaatacac   1380
ttgccaaatt gaccacagca aatcgagggg cagacaccag gggaggagtc aacccgttct   1440
catctatcac tgggacaact caggtgcccg ctgcagcaac aggtgacaca ttcgagagtt   1500
acatggcagc ggatcgactg aggcagagat atgctgatgc aggcacccac gatgatgaga   1560
tgccaccatt ggaagaggag gaagaggacg acacatctgc aggtccacgc actggactaa   1620
ctcttgaaca agtggccttg gacatccaga acgcagcagt tggagctccc atccatacag   1680
atgacctgaa tgccgcactg ggtgatcttg acatctagac aattcagatc ccaatcttaa   1740
atcgacacac ctaattgacc agttagatgg aactacagtg gattccataa ggttcctgcc   1800
taccatcggc ttttaagaaa aaaataggcc cggacgggtt agcaacaagc gactgccgat   1860
gccaataaca caatccacaa tctacaatgg atcccactga tctgagcttc tccccagatg   1920
agatcaataa gctcatagag acaggcctga atactgtgga gtattttact tcccaacaag   1980
tcacaggaac atcctctctt ggaaagaata caataccacc aggggtcaca ggactactaa   2040
ccaatgctgc agaggcaaag atccaagagt caaccaacca tcagaagggt tcagttggtg   2100
ggggcgcaaa accaaagaaa ccgcgaccaa aaattgccat tgtgccagca gatgacaaaa   2160
cggtgcccgg aaagccgatc ccaaaccctc tattaggtct ggactccacc ccgagcaccc   2220
aaactgtgct tgatctaagt gggaaaacat taccatcagg atcctataag gggggttaaac   2280
ttgcgaaatt tggaaaagaa aatctgatga cacggttcat cgaggaaccc agagagaatc   2340
ctatcgcaac caattccccc atcgatttta agaggggcag ggataccggc gggttccata   2400
gaagggagta ctcaatcgga tgggtgggag atgaagtcaa ggtcactgag tggtgcaatc   2460
catcctgttc tccaatcacc gctgcagcaa ggcgatttga atgcacttgt caccagtgtc   2520
cagtcacttg ctctgaatgt gaacgagata cttaatacag tgagaaattt ggactctcgg   2580
atgaatcaac tggagacaaa agtagatcgc attctctcat ctcagtctct aatccagacc   2640
atcaagaatg acatagttgg acttaaagca gggatggcta ctttagaagg aatgattaca   2700
actgtgaaaa tcatggaccc gggagttccc agtaatgtta ctgtggaaga tgtacgcaag   2760
aaactaagta accatgctgt tgttgtgcca gaatcattca atgatagttt cttgactcaa   2820
tctgaagatg taatttcact tgatgagttg gctcgaccaa ctgcaacaag tgttaagaag   2880
attgtcagga aggttcctcc tcagaaggat ctgactggat tgaagatcac actagagcaa   2940
ttggcaaagg attgcatcag caaaccgaag atgagggaag agtatctcct caaaatcaac   3000
caggcttcca gtgaggctca gctaattgac ctcaagaaag caatcatccg cagtgcaatt   3060
tgatcaagaa acacccaatt acactacact ggtatgacac tgtactaacc ctgagggttt   3120
tagaaaaaac gattaacgat aaataagccc gaacactaca caccacccga ggcagccatg   3180
ccatccatca gcatccccgc agaccccacc aatccacgtc aatcaataaa agcgttccca   3240
attgtgatca accgtgatgg gggtgagaaa ggtcgcttgg ttaaacaact acgcacaacc   3300
tacttgaatg acctagatac tcatgagcca ctggtgacat tcgtaaatac ttatggattc   3360
atctacgaac aggatcgggg aaataccatt gtcggagagg atcaacatgg gaagaaaaga   3420
```

```
gaggctgtga ctgctgcaat ggttaccctt ggatgtgggc ctaatctacc atcattaggg   3480
aatgtcctgg gacaactgag tgaattccag gtcattgtta ggaagacatc cagcaaagcg   3540
gaagagatgg tctttgaaat tgttaagtat ccgagaatat ttcggggtca tacattaatc   3600
cagaaaggac tagtctgtgt ctccgcagaa aaatttgtta agtcaccagg gaaagtacaa   3660
tctggaatgg actatctctt cattccgaca tttctgtcag tgacttactg tccagctgca   3720
atcaaatttc aggtacctgg ccccatgttg aaaatgagat caagatacac tcagagctta   3780
caacttgaac taatgataag aatcctgtgt aagcccgatt cgccacttat gaaggtccat   3840
atccctgaca aggaaggaag aggatgtctt gtatcagtat ggttgcatgt atgcaatatc   3900
ttcaaatcag gaaacaagaa tggcagtgag tggcaggaat actggatgag aaagtgtgct   3960
aacatgcaac ttgaagtgtc gattgcagat atgtggggac caactatcat aattcatgcc   4020
agaggtcaca ttcccaaaag tgctaagttg tttttggaa agggtggatg gagctgccat   4080
ccacttcacg aagttgttcc aagtgtcact aaaacactat ggtccgtggg ctgtgagatt   4140
acaaaggcga aggcaataat acaagagagt agcatctctc ttctcgtgga gactactgac   4200
atcataagtc caaaagtcaa aatttcatct aagcatcgcc gctttgggaa atcaaattgg   4260
ggtctgttca agaaaaccaa atcactgccc aacctgacgg agctggaatg actgaccccc   4320
aatcgagact acaccacctc aaactatagg tgggtggtac ctcagtgatt aatctcgtaa   4380
gcactgatcg taggctacaa cacactaata ttatccagat tagagagctt aattagctct   4440
gtattaataa taacactact attccaataa ctggaatcac cagcttgatt tatctccaaa   4500
atgattcaaa gaaaacaaat catattaaga ctatcctaag cacgaaccca tatcgtcctt   4560
caaatcatgg gtactataat tcaatttctg gtggtctcct gtctattggc aggagcaggc   4620
agtcttgatc cagcagccct catgcaaatc ggtgtcattc caacaaatgt ccggcaactt   4680
atgtattata ctgaggcctc atcagcattc attgttgtga agttaatgcc tacaattgac   4740
tcgccgatta gtggatgtaa tataacatca atttcaagct ataatgcaac agtgacaaaa   4800
ctcctacagc cgatcggtga gaatttggag acgattagga accagttgat tccaactcgg   4860
aggagacgcc ggtttgcagg ggtggtgatt ggattagctg cattaggagt agctactgcc   4920
gcacaggtca ctgccgcagt agcactagta aaggcaaatg aaaatgctgc ggctatactc   4980
aatctcaaaa atgcaatcca aaaaacaaat gcagcagttg cagatgtggt ccaggccaca   5040
caatcactag gaacagcagt tcaagcagtt caagatcaca taaacagtgt ggtaagtcca   5100
gcaattacag cagccaattg taaagcccaa gatgctatca ttggctcaat cctcaatctc   5160
tatttgaccg agttgacaac tatcttccac aatcaaatta caaaccctgc attgagtcct   5220
attacaattc aagctttaag gatcctacta gggagtacct tgccgactgt ggtcgaaaaa   5280
tctttcaata cccagataag tgcggctgag cttctctcat cagggttatt gacaggccag   5340
attgtgggat tagatttgac ctatatgcag atggtcataa aaattgagct gccaacttta   5400
actgtacaac ctgcaaccca gatcatagat ctggccacca tttctgcatt cattaacaat   5460
caagaagtca tggcccaatt accaacacgt gttattgtga ctggcagctt gatccaagcc   5520
tatcccgcat cgcaatgcac tattacaccc aacactgtgt actgtaggta taatgatgcc   5580
caagtactct cagatgatac gatggcttgc ctccaaggta acttgacaag atgcaccttc   5640
tctccagtgg ttgggagctt tctcactcga ttcgtgctgt tcgatggaat agtttatgca   5700
aattgcaggt cgatgttgtg caagtgcatg cagcctgctg ctgtgatcct acagccgagt   5760
```

```
tcatcccctg taactgtcat tgacatgtac aaatgtgtga gtctgcagct tgacaatctc   5820
agattcacca tcactcaatt ggccaatgta acctacaata gcaccatcaa gcttgaaaca   5880
tcccagatct tgcctattga tccgttggat atatcccaga atctagctgc ggtgaataag   5940
agtctaagtg atgcactaca acacttagca caaagtgaca catacctttc tgcaatcaca   6000
tcagctacga ctacaagtgt attatccata atagcaatct gtcttggatc gttaggttta   6060
atattaataa tcttgctcag tgtagttgtg tggaagttat tgaccattgt cgctgctaat   6120
cgaaatagaa tggagaattt tgtttatcat aattcagcat tccaccactc acgatctgat   6180
ctcagtgaga aaaatcaacc tgcaactctt ggaacaagat aagacagtca tccattagta   6240
atttttaaga aaaaaacgat aggaccgaaa ctagtattga aagaaccgtc tcggtcaatc   6300
taggtaatcg agctgctacc gtctcggaaa gctcaaatca tgctgcctga tccggaagat   6360
ccggaaagca aaaaagctac aaggagaaca ggaaacctaa ttatctgctt cctattcatc   6420
ttctttccgt ttgtaaactt cattgttcca actctaagac acttgctgtc ctaacacctg   6480
ctataggcta tccactgcat catctctttt taagaaaaaa ataggcccgg acgggttagc   6540
aacaagcgac tgccggtgcc aacaacacaa tccacaatct acagtcgacg cggccgccat   6600
gttcgtcttc ctggtcctgc tgcctctggt ctcctcacag tgcgtcaatc tgacaactcg   6660
gactcagctg ccacctgctt atactaatag cttcaccaga ggcgtgtact atcctgacaa   6720
ggtgtttaga agctccgtgc tgcactctac acaggatctg tttctgccat tctttagcaa   6780
cgtgacctgg ttccacgcca tccacgtgag cggcaccaat ggcacaaagc ggttcgacaa   6840
tcccgtgctg ccttttaacg atggcgtgta cttcgcctct accgagaaga gcaacatcat   6900
cagaggctgg atctttggca ccacactgga ctccaagaca cagtctctgc tgatcgtgaa   6960
caatgccacc aacgtggtca tcaaggtgtg cgagttccag ttttgtaatg atcccttcct   7020
gggcgtgtac tatcacaaga acaataagag ctggatggag tccgagttta gagtgtattc   7080
tagcgccaac aactgcacat ttgagtacgt gagccagcct ttcctgatgg acctggaggg   7140
caagcagggc aatttcaaga acctgaggga gttcgtgttt aagaatatcg acggctactt   7200
caaaatctac tctaagcaca cccccatcaa cctggtgcgc gacctgcctc agggcttcag   7260
cgccctggag cccctggtgg atctgcctat cggcatcaac atcacccggt ttcagacact   7320
gctggccctg cacagaagct acctgacacc cggcgactcc tctagcggat ggaccgccgg   7380
cgctgccgcc tactatgtgg gctacctcca gccccggacc ttcctgctga agtacaacga   7440
gaatggcacc atcacagacg cagtggattg cgccctggac cccctgagcg agacaaagtg   7500
tacactgaag tcctttaccg tggagaaggg catctatcag acatccaatt tcagggtgca   7560
gccaaccgag tctatcgtgc gctttcctaa tatcacaaac ctgtgcccat ttggcgaggt   7620
gttcaacgca acccgcttcg ccagcgtgta cgcctggaat aggaagcgga tcagcaactg   7680
cgtggccgac tatagcgtgc tgtacaactc cgcctctttc agcaccttta agtgctatgg   7740
cgtgtccccc acaaagctga atgacctgtg ctttaccaac gtctacgccg attctttcgt   7800
gatcaggggc gacgaggtgc gccagatcgc ccccggccag acaggcaaga tcgcagacta   7860
caattataag ctgccagacg atttcaccgg ctgcgtgatc gcctggaaca gcaacaatct   7920
ggattccaaa gtgggcggca actacaatta tctgtaccgg ctgtttagaa agagcaatct   7980
gaagcccttc gagagggaca tctctacaga aatctaccag gccggcagca ccccttgcaa   8040
tggcgtggag ggctttaact gttatttccc actccagtcc tacggcttcc agcccacaaa   8100
cggcgtgggc tatcagcctt accgcgtggt ggtgctgagc tttgagctgc tgcacgcccc   8160
```

```
agcaacagtg tgcggcccca agaagtccac caatctggtg aagaacaagt gcgtgaactt   8220
caacttcaac ggcctgaccg gcacaggcgt gctgaccgag tccaacaaga agttcctgcc   8280
atttcagcag ttcggcaggg acatcgcaga taccacagac gccgtgcgcg acccacagac   8340
cctggagatc ctggacatca caccctgctc tttcggcggc gtgagcgtga tcacacccgg   8400
caccaataca agcaaccagg tggccgtgct gtatcaggac gtgaattgta ccgaggtgcc   8460
cgtggctatc cacgccgatc agctgacccc aacatggcgg gtgtacagca ccggctccaa   8520
cgtcttccag acaagagccg gatgcctgat cggagcagag cacgtgaaca attcctatga   8580
gtgcgacatc ccaatcggcg ccggcatctg tgcctcttac cagacccaga caaactctcc   8640
cagaagagcc cggagcgtgg cctcccagtc tatcatcgcc tataccatgt ccctgggcgc   8700
cgagaacagc gtggcctact ctaacaatag catcgccatc ccaaccaact tcacaatctc   8760
tgtgaccaca gagatcctgc ccgtgtccat gaccaagaca tctgtggact gcacaatgta   8820
tatctgtggc gattctaccg agtgcagcaa cctgctgctc cagtacggca gcttttgtac   8880
ccagctgaat agagccctga caggcatcgc cgtggagcag gataagaaca cacaggaggt   8940
gttcgcccag gtgaagcaaa tctacaagac ccccccctatc aaggactttg gcggcttcaa   9000
tttttcccag atcctgcctg atccatccaa gccttctaag cggagcttta tcgaggacct   9060
gctgttcaac aaggtgaccc tggccgatgc cggcttcatc aagcagtatg gcgattgcct   9120
gggcgacatc gcagccaggg acctgatctg cgcccagaag tttaatggcc tgaccgtgct   9180
gccacccctg ctgacagatg agatgatcgc acagtacaca agcgccctgc tggccggcac   9240
catcacatcc ggatggacct tcggcgcagg agccgccctc cagatcccct ttgccatgca   9300
gatggcctat aggttcaacg gcatcggcgt gacccagaat gtgctgtacg agaaccagaa   9360
gctgatcgcc aatcagttta actccgccat cggcaagatc caggacagcc tgtcctctac   9420
agccagcgcc ctgggcaagc tccaggatgt ggtgaatcag aacgcccagg ccctgaatac   9480
cctggtgaag cagctgagca gcaacttcgg cgccatctct agcgtgctga atgacatcct   9540
gagccggctg gacaaggtgg aggcagaggt gcagatcgac cggctgatca ccggccggct   9600
ccagagcctc cagacctatg tgacacagca gctgatcagg gccgccgaga tcagggccag   9660
cgccaatctg gcagcaacca agatgtccga gtgcgtgctg ggccagtcta agagagtgga   9720
cttttgtggc aagggctatc acctgatgtc cttccctcag tctgccccac acggcgtggt   9780
gtttctgcac gtgacctacg tgcccgccca ggagaagaac ttcaccacag cccctgccat   9840
ctgccacgat ggcaaggccc actttccaag ggagggcgtg ttcgtgtcca acggcaccca   9900
ctggtttgtg acacagcgca atttctacga gccccagatc atcaccacag acaacacctt   9960
cgtgagcggc aactgtgacg tggtcatcgg catcgtgaac aataccgtgt atgatccact  10020
ccagcccgag ctggacagct ttaaggagga gctggataag tatttcaaga atcacacctc  10080
ccctgacgtg gatctgggcg acatcagcgg catcaatgcc tccgtggtga acatccagaa  10140
ggagatcgac cgcctgaacg aggtggctaa gaatctgaac gagagcctga tcgacctcca  10200
ggagctgggc aagtatgagc agtacatcaa gtggccctgg tacatctggc tgggcttcat  10260
cgccggcctg atcgccatcg tgatggtgac catcatgctg tgctgtatga catcctgctg  10320
ttcttgcctg aagggctgct gtagctgtgg ctcctgctgt aagttattga ccattgtcgt  10380
tgctaatcga aatagaatgg agaattttgt ttatcataaa tgaacgcgtg ctagcctcct  10440
gccatacttc ctactcacat catatctatt ttaaagaaaa aataggcccg aacactaatc  10500
```

-continued

```
gtgccggcag tgccactgca cacacaacac tacacataca atacactaca atggttgcag  10560
aagatgcccc tgttaggggc acttgccgag tattatttcg aacaacaact ttaatttttc  10620
tatgcacact attagcatta agcatctcta tcctttatga gagtttaata acccaaaagc  10680
aaatcatgag ccaagcaggc tcaactggat ctaattctag attaggaagt atcactgatc  10740
ttcttaataa tattctctct gtcgcaaatc agattatata taactctgca gtcgctctac  10800
ctctacaatt ggacactctt gaatcaacac tccttacagc cattaagtct cttcaaacaa  10860
gtgacaagct agaacagaac tgctcgtggg gtgctgcact gattaatgat aatagataca  10920
ttaatggcat caatcagttc tatttctcaa ttgctgaggg tcgcaagctg acacttggcc  10980
cacttcttaa tatacctagt ttcattccaa ctgccacgac accagagggc tgcaccagga  11040
tcccatcatt ctcgctcacc aagacacact ggtgttatac acacaatgtt atcctgaatg  11100
gatgccagga tcatgtatcc tcaaatcaat ttgtttccat gggaatcatt gaacccactt  11160
ctgccgggtt tccatccttt cgaaccctaa agactctata tctcagcgat ggggtcaatc  11220
gtaagagctg ctctatcagt acagttccgg ggggttgtat gatgtactgt ttcgtctcta  11280
ctcaaccaga gagggatgac tacttttcta ccgctcctcc agaacaacga attattataa  11340
tgtactataa tgatacaatc gtggagcgca taattaatcc acccggggta ctagatgtat  11400
gggcaacatt gaacccagga acaggaagcg ggtatattta tttaggttgg gtactctttc  11460
caatatatgg cggcgtgatt aaagatacga gtttatggaa taatcaagca aataaatact  11520
ttatccccca gatggttgct gctctctgct cacaaaacca ggcaactcaa gtccaaaatg  11580
ctaagtcatc atactatagc agctggtttg gcaatcgaat gattcagtct gggatcctgg  11640
catgtcctct tcaacaggat ctaaccaatg agtgtttagt tctgcccttt tctaatgatc  11700
aggtgcttat gggtgctgaa gggagattat acatgtatgg tgactcggtg tattactacc  11760
aaagaagcaa tagttggtgg cctatgacca tgctgtataa ggtaaccata acattcacta  11820
atggtcagcc atctgctata tcagctcaga atgtgcccac acagcaggtc cctagacctg  11880
ggacaggaag ctgctctgca acaaatagat gtcccggttt ttgcttgaaa ggagtgtatg  11940
ctgatgcctg gttactgacc aacccttcgt ctaccagtac atttggatca gaagcaacct  12000
tcactggttc ttatctcaac gcagcaactc agcgtatcaa tccgacgatg tatatcgcga  12060
acaacacaca gatcataagc tcacagcaat ttggatcaag cggtcaagaa gcagcatatg  12120
gccacacaac ttgttttagg gacacaggct ctgttatggt atactgtatc tatattattg  12180
aattgtcctc atctctctta ggacaatttc agattgtccc atttatccgt caggtgacac  12240
tatcctaaag gcagaagcct ccaggtctga cccagccaat caaagcatta taccagacca  12300
tggaatgcat accaaacatt attgacacta atgacacaca aaattggttt taagaaaaac  12360
caagagaaca ataggccaga atggctgggt ctcgggagat attactccct gaagtccatc  12420
tcaattcacc aattgtaaag cataagctat actattacat tctacttgga aacctcccaa  12480
atgagatcga cattgacgat ttaggtccat tacataatca aaattggaat caaatagcac  12540
atgaagagtc taacttagcc caacgcttgg taaatgtaag aaattttcta attacccaca  12600
tccctgatct tagaaagggc cattggcaag agtatgtcaa tgtaatactg tggccgcgaa  12660
ttcttccctt gatcccggat tttaaaatca atgaccaatt gcctctactc aaaaattggg  12720
acaagttagt taaagaatca tgttcagtaa tcaatgcggg tacttcccag tgcattcaga  12780
atctcagcta tggactgaca ggtcgtggga acctctttac acgatcacgt gaactctctg  12840
gtgaccgcag ggatattgat cttaagacgg ttgtggcagc atggcatgac tcagactgga  12900
```

```
aaagaataag tgatttttgg attatgatca aattccagat gagacaatta attgttaggc  12960
aaacagatca taatgatcct gatttaatca cgtatatcga aaatagagaa ggcataatca  13020
tcataacccc tgaactggta gcattattta acactgagaa tcatacacta acatacatga  13080
cctttgaaat tgtactgatg gtttcagata tgtacgaagg tcgtcacaac attttatcac  13140
tatgcacagt tagcacttac ctgaatcctc tgaagaaaag aataacatat ttattgagcc  13200
ttgtagataa cttagctttt cagataggtg atgctgtata taacataatt gctttgctag  13260
aatcctttgt atatgcacag ttgcaaatgt cagatcccat cccagaactc agaggacaat  13320
tccatgcatt cgtatgttct gagattcttg atgcactaag ggaactaat agtttcaccc   13380
aggatgaatc aagaactgtg acaaccaatt tgatatcccc attccaagat ctgaccccag  13440
atcttacggc tgaattgctc tgtataatga ggctttgggg acaccccatg ctcaccgcca  13500
gtcaagctgc gggaaaggta cgcgagtcca tgtgtgctgg aaaagtatta gactttccca  13560
ccattatgaa aacactagcc tttttccata ctattctgat caatggatac aggaggaagc  13620
atcatggagt atggccaccc ttaaacttac cgggtaatgc ttcaaagggt ctcacggaac  13680
ttatgaatga caatactgag ataagctatg aattcacact taagcattgg aaggaaatct  13740
ctcttataaa attcaagaaa tgttttgatg cagacgcagg tgaggaactc agtatattta  13800
tgaaagataa agcaattagt gccccaaaac aagattggat gagtgtgttt agaagaagcc  13860
taatcaaaca gcgccatcag catcatcagg tcccctacc aaatccattc aatcgacggc   13920
tattgctaaa ctttctcgga gatgacaaat tcgacccgaa tgtggagcta cagtatgtaa  13980
catcaggtga gtatctacat gatgacacgt tttgtgcatc atattcacta aaagagaagg  14040
aaattaaacc tgatggtcga atttttgcaa agttgactaa gagaatgaga tcatgtcaag  14100
ttatagcaga atctctttta gcgaaccatg ctgggaagtt aatgaaagag aatggtgttg  14160
tgatgaatca gctatcatta acaaaatcac tattaacaat gagtcagatt ggaataatat  14220
ccgagaaagc tagaaaatcg actcgagata acataaatca acctggtttc cagaatatcc  14280
agagaaataa atcacatcac tccaagcaag tcaatcagcg agatccaagt gatgactttg  14340
aattggcagc atcttttta actactgatc tcaaaaaata ttgtttacaa tggaggtacc   14400
agacaattat cccatttgct caatcattaa acagaatgta tggttatcct catctctttg  14460
agtggattca cttacggcta atgcgtagta cactttacgt gggggatccc ttcaacccac  14520
cagcagatac cagtcaattt gatctagata aagtaattaa tggagatatc ttcattgtat  14580
cacccagagg tggaattgaa gggctatgtc aaaaggcttg gacaatgata tctatctctg  14640
tgataattct atctgccaca gagtctggca cacgagtaat gagtatggtg cagggagata  14700
atcaagcaat tgctgtcacc acacgagtac caaggagcct gccgactctt gagaaaaaga  14760
ctattgcttt tagatcttgt aatctattct ttgagaggtt aaaatgtaat aattttggat  14820
taggtcacca tttgaaagaa caagagacta tcattagttc tcacttcttt gtttatagca  14880
agagaatatt ctatcagggg aggattctaa cgcaagcctt aaaaaatgct agtaagctct  14940
gcttgacagc tgatgtccta ggagaatgta cccaatcatc atgttctaat cttgcaacta  15000
ctgtcatgag gttaactgag aatggtgttg aaaaagatat ctgtttctac ttgaatatct  15060
atatgaccat caaacagctc tcctatgata tcatcttccc tcaagtgtca attcctggag  15120
atcagatcac attagaatac ataaataatc cacacctggt atcacgattg gctcttctgc  15180
catcccagct aggaggtcta aactacctgt catgcagtag gctgttcaat cgaaacatag  15240
```

```
gcgacccggt ggtttccgca gttgcagatc ttaagagatt aattaaatca ggatgtatgg  15300
attactggat cctttataac ttattaggga gaaaaccggg aaacggctca tgggctactt  15360
tagcagctga cccgtactca atcaatatag agtatcaata ccccccaact acagctctta  15420
agaggcacac ccaacaagct ctgatggaac tcagtacgaa tccaatgtta cgtggcatat  15480
tctctgacaa tgcacaggca gaagaaaata atcttgctag atttctcctg gatagggagg  15540
tgatctttcc gcgtgtagct cacatcatca ttgagcaaac cagtgtcggg aggagaaaac  15600
agattcaagg atatttggat tcaactagat cgataatgag taaatcacta gaaattaagc  15660
ccttgtccaa taggaagctt aatgaaatac tggattacaa catcaattac ctagcttaca  15720
atttggcatt actcaagaat gctattgaac ctccgactta tttgaaagca atgactcttg  15780
aaacatgtag catcgacatt gcaaggagcc tccggaagct ctcctgggcc ccactcttgg  15840
gtgggagaaa tcttgaagga ttagagacgc cagatcccat tgaaattact gcaggagcat  15900
taattgttgg atcgggctac tgtgaacagt gtgctgcagg agacaatcga ttcacatggt  15960
ttttcttgcc atctggtatc gagataggag gggatccccg tgataatcct cctatccgtg  16020
taccgtacat tggctccagg actgatgaga ggagggtagc ctcaatggca tacatcaggg  16080
gtgcctcgag tagcctaaaa gcagttctta gactggcggg agtgtacatc tgggcattcg  16140
gagatactct ggagaattgg atagatgcac tggatttgtc tcacactaga gttaacatca  16200
cacttgaaca gctgcaatcc ctcaccccac ttccaacctc tgccaatcta acccatcggt  16260
tggatgatgg cacaactacc ctaaagttta ctcctgcgag ctcttacacc ttttcaagtt  16320
tcactcatat atcaaatgat gagcaatacc tgacaattaa tgacaaaact gcagattcaa  16380
atataatcta ccaacagtta atgatcactg gactcggaat tttagaaaca tggaataatc  16440
ccccaatcaa tagaacattc gaagaatcta ccctacattt gcacactggt gcatcatgtt  16500
gtgtccgacc tgtggactcc tgcatcatct cagaagcatt aacagtcaag ccacatatta  16560
cagtaccgta cagcaataaa tttgtatttg atgaagaccc gctatctgaa tatgagactg  16620
caaaactgga atcgttatca tttcaagccc aattaggcaa cattgatgct gtagatatga  16680
caggtaaatt aacattattg tcccaattca ctgcaaggca gattattaat gcaatcactg  16740
gactcgatga gtctgtctct cttactaatg atgccattgt tgcatcagac tatgtctcca  16800
attggattag tgaatgcatg tataccaaat tagatgaatt atttatgtat tgtgggtggg  16860
aactactatt ggaactatcc tatcaaatgt attatctgag ggtagttggg tggagtaata  16920
tagtggatta ttcttacatg atcttgagaa gaatcccggg tgcagcatta aacaatctgg  16980
catctacatt aagtcatcca aaacttttcc gacgagctat caacctagat atagttgccc  17040
ccttaaatgc tcctcatttt gcatctctgg actacatcaa gatgagtgtg gatgcaatac  17100
tctggggctg taaaagagtc atcaatgtgc tctccaatgg aggggactta gaattagttg  17160
tgacatctga agatagcctt attctcagtg accgatccat gaatctcatt gcaaggaaat  17220
taactttatt atcactgatt caccataatg gtttggaact accaaagatt aaggggttct  17280
ctcctgatga gaagtgtttc gctttgacag aatttttgag gaaagtggtg aactcagggt  17340
tgagttcaat agagaaccta tcaaatttta tgtacaatgt ggagaaccca cggcttgcag  17400
cattcgccag caacaattac tacctgacca gaaaattatt gaattcaata cgagatactg  17460
agtcgggtca agtagcagtc acctcatatt atgaatcatt agaatatatt gatagtctta  17520
agctaacccc acatgtgcct ggtacctcat gcattgagga tgatagtcta tgtacaaatg  17580
attacataat ctggatcata gagtctaatg caaacttgga gaagtatcca attccaaata  17640
```

gccctgagga tgattccaat ttccataact ttaagttgaa tgctccatcg caccatacct 17700
tacgcccatt agggttgtca tcaactgctt ggtataaggg tataagctgt tgcaggtacc 17760
ttgagcgatt aaagctacca caaggtgatc atttatatat tgcagaaggt agtggtgcca 17820
gtatgacaat catagaatac ctattcccag gaagaaagat atattacaat tctttattta 17880
gtagtggtga caatccccca caaagaaatt atgcaccaat gcctactcag ttcattgaga 17940
gtgtcccata caagctctgg caagcacaca cagatcaata tcccgagatt tttgaggact 18000
tcatccctct atggaacgga aatgccgcca tgactgacat aggaatgaca gcttgtgtag 18060
aattcatcat caatcgagtc ggcccaagga cttgcagttt agtacatgta gatttggaat 18120
caagtgcaag cttaaatcaa caatgcctgt caaagccgat aattaatgct atcatcactg 18180
ctacaactgt tttgtgccct catggggtgc ttattctgaa atatagttgg ttgccattta 18240
ctagatttag tactttgatc actttcttat ggtgctactt tgagagaatc actgttctta 18300
ggagcacata ttctggtcca gctaatcatg aggtttattt aatttgtatc cttgccaaca 18360
actttgcatt ccagactgtc tcgcaggcaa caggaatggc gatgacttta accgatcaag 18420
ggtttacttt gatatcacct gaaagaataa atcagtattg ggatggtcac ttgaagcaag 18480
aacgtatcgt agcagaagca attgataagg tggttctagg agaagatgct ctattcaatt 18540
cgagtgataa tgaattaatt ctcaaatgtg gagggacacc aaatgcacgg aatcttatcg 18600
atatcgagcc agtcgcaact ttcatagaat ttgaacaact gatctgcaca atgttgacaa 18660
cccacttgaa ggaaataatt gatataacaa ggtctggaac ccaggattat gaaagtttat 18720
tactcactcc ttacaattta ggtcttcttg gtaaaatcag tacgatagtg agattattaa 18780
cagaaaggat tctaaatcat actatcagga attggttgat cctcccacct tcgctccgga 18840
tgatcgtgaa gcaggacttg gaattcggca tattcaggat tacttccatc ctcaattctg 18900
atcggttcct gaagctttct ccaaatagga aatacttgat tacacaatta actgcaggct 18960
acattaggaa attgattgag gggattgta atatcgatct aaccagacct atccaaaaac 19020
aaatctggaa agcattaggt tgtgtagtct attgtcacga tccagtagat caaagggaat 19080
caacagagtt tattgatata aatattaatg aagaaataga ccgcgggatc gatggcgagg 19140
aaatctaaat atatcaagaa tcagaattag tttaagaaaa aagaagagga ttaatcttgg 19200
ttttcccctt ggtgggtcgg catggcatct ccacctcctc gcggtccgac ctgggcatcc 19260
gaaggaggac gcacgtccac tcggatggct aagggagcgg ccggggatcc ggctgctaac 19320
aaagcccgaa aggaagctga gttggctgct gccaccgctg agcaataact agcataaccc 19380
cttggggcct ctaaacgggt cttgaggggt tttttgctga aaggaggaac tatatccgga 19440
tcatgtgagc aaaaggccag caaaaggcca ggaaccgtaa aaaggccgcg ttgctggcgt 19500
ttttccatag gctccgcccc cctgacgagc aaagcttctc gaccaattct catgtttgac 19560
agcttatcat cgaatttctg ccattcatcc gcttattatc acttattcag gcgtagcaac 19620
caggcgttta agggcaccaa taactgcctt aaaaaaatta cgccccgccc tgccactcat 19680
cgcagtactg ttgtaattca ttaagcattc tgccgacatg gaagccatca caaacggcat 19740
gatgaacctg aatcgccagc ggcatcagca ccttgtcgcc ttgcgtataa tatttgccca 19800
tggtgaaaac gggggcgaag aagttgtcca tattggccac gtttaaatca aaactggtga 19860
aactcaccca gggattggct gagacgaaaa acatattctc aataaaccct ttagggaaat 19920
aggccaggtt ttcaccgtaa cacgccacat cttgcgaata tatgtgtaga aactgccgga 19980

```
aatcgtcgtg gtattcactc cagagcgatg aaaacgtttc agtttgctca tggaaaacgg  20040
tgtaacaagg gtgaacacta tcccatatca ccagctcacc gtctttcatt gccatacgga  20100
attccggatg agcattcatc aggcgggcaa gaatgtgaat aaaggccgga taaaacttgt  20160
gcttattttt ctttacggtc tttaaaaagg ccgtaatatc cagctgaacg gtctggttat  20220
aggtacattg agcaactgac tgaaatgcct caaaatgttc tttacgatgc cattgggata  20280
tatcaacggt ggtatatcca gtgatttttt tctccatttt agcttcctta gctcctgaaa  20340
atctcgataa ctcaaaaaat acgcccggta gtgatcttat ttcattatgg tgaaagttgg  20400
aacctcttac gtgccgatca acgtctcatt ttcgccaaaa gttggcccag ggcttcccgg  20460
tatcaacagg gacaccagga tttatttatt ctgcgaagtg atcttccgtc acaggtattt  20520
attcgcgata agctcatgga gcggcgtaac cgtcgcacag gaaggacaga gaaagcgcgg  20580
atctgggaag tgacggacag aacggtcagg acctggattg gggaggcggt tgccgccgct  20640
gctgctgacg gtgtgacgtt ctctgttccg gtcacaccac atacgttccg ccattcctat  20700
gcgatgcaca tgctgtatgc cggtataccg ctgaaagttc tgcaaagcct gatgggacat  20760
aagtccatca gttcaacgga agtctacacg aaggtttttg cgctggatgt ggctgcccgg  20820
caccgggtgc agtttgcgat gccggagtct gatgcggttg cgatgctgaa acaattatcc  20880
tgagaataaa tgccttggcc tttatatgga aatgtggaac tgagtggata tgctgttttt  20940
gtctgttaaa cagagaagct ggctgttatc cactgagaag cgaacgaaac agtcgggaaa  21000
atctcccatt atcgtagaga tccgcattat taatctcagg agcctgtgta gcgtttatag  21060
gaagtagtgt tctgtcatga tgcctgcaag cggtaacgaa aacgatttga atatgccttc  21120
aggaacaata gaaatcttcg tgcggtgtta cgttgaagtg gagcggatta tgtcagcaat  21180
ggacagaaca acctaatgaa cacagaacca tgatgtggtc tgtcctttta cagccagtag  21240
tgctcgccgc agtcgagcga cagggcgaag ccctcgagtg agcgaggaag caccagggaa  21300
cagcacttat atattctgct tacacacgat gcctgaaaaa acttcccttg gggttatcca  21360
cttatccacg gggatatttt tataattatt ttttttatag tttttagatc ttcttttttta  21420
gagcgccttg taggccttta tccatgctgg ttctagagaa ggtgttgtga caaattgccc  21480
tttcagtgtg acaaatcacc ctcaaatgac agtcctgtct gtgacaaatt gcccttaacc  21540
ctgtgacaaa ttgccctcag aagaagctgt tttttcacaa agttatccct gcttattgac  21600
tctttttttat ttagtgtgac aatctaaaaa cttgtcacac ttcacatgga tctgtcatgg  21660
cggaaacagc ggttatcaat cacaagaaac gtaaaaatag cccgcgaatc gtccagtcaa  21720
acgacctcac tgaggcggca tatagtctct cccgggatca aaaacgtatg ctgtatctgt  21780
tcgttgacca gatcagaaaa tctgatggca ccctacagga acatgacggt atctgcgaga  21840
tccatgttgc taaatatgct gaaatattcg gattgacctc tgcggaagcc agtaaggata  21900
tacggcaggc attgaagagt ttcgcgggga aggaagtggt tttttatcgc cctgaagagg  21960
atgccggcga tgaaaaaggc tatgaatctt ttccttggtt tatcaaacgt gcgcacagtc  22020
catccagagg gctttacagt gtacatatca acccatatct cattcccttc tttatcgggt  22080
tacagaaccg gtttacgcag tttcggctta gtgaaacaaa agaaatcacc aatccgtatg  22140
ccatgcgttt atacgaatcc ctgtgtcagt atcgtaagcc ggatggctca ggcatcgtct  22200
ctctgaaaat cgactggatc atagagcgtt accagctgcc tcaaagttac cagcgtatgc  22260
ctgacttccg ccgccgcttc ctgcaggtct gtgttaatga gatcaacagc agaactccaa  22320
tgcgcctctc atacattgag aaaaagaaag gccgccagac gactcatatc gtattttcct  22380
```

```
tccgcgatat cacttccatg acgacaggat agtctgaggg ttatctgtca cagatttgag  22440
ggtggttcgt cacatttgtt ctgacctact gagggtaatt tgtcacagtt ttgctgtttc  22500
cttcagcctg catggatttt ctcatacttt ttgaactgta atttttaagg aagccaaatt  22560
tgagggcagt ttgtcacagt tgatttcctt ctctttccct tcgtcatgtg acctgatatc  22620
gggggttagt tcgtcatcat tgatgagggt tgattatcac agtttattac tctgaattgg  22680
ctatccgcgt gtgtacctct acctggagtt tttcccacgg tggatatttc ttcttgcgct  22740
gagcgtaaga gctatctgac agaacagttc ttctttgctt cctcgccagt tcgctcgcta  22800
tgctcggtta cacggctgcg gcgagcgcta gtgataataa gtgactgagg tatgtgctct  22860
tcttatctcc ttttgtagtg ttgctcttat tttaaacaac tttgcggttt tttgatgact  22920
ttgcgatttt gttgttgctt tgcagtaaat tgcaagattt aataaaaaaa cgcaaagcaa  22980
tgattaaagg atgttcagaa tgaaactcat ggaaacactt aaccagtgca taaacgctgg  23040
tcatgaaatg acgaaggcta tcgccattgc acagtttaat gatgacagcc cggaagcgag  23100
gaaaataacc cggcgctgga gaataggtga agcagcggat ttagttgggg tttcttctca  23160
ggctatcaga gatgccgaga aagcagggcg actaccgcac ccggatatgg aaattcgagg  23220
acgggttgag caacgtgttg gttatacaat tgaacaaatt aatcatatgc gtgatgtgtt  23280
tggtacgcga ttgcgacgtg ctgaagacgt atttccaccg gtgatcgggg ttgctgccca  23340
taaaggtggc gtttacaaaa cctcagtttc tgttcatctt gctcaggatc tggctctgaa  23400
ggggctacgt gttttgctcg tggaaggtaa cgacccccag ggaacagcct caatgtatca  23460
cggatgggta ccagatcttc atattcatgc agaagacact ctcctgcctt tctatcttgg  23520
ggaaaaggac gatgtcactt atgcaataaa gcccacttgc tggccggggc ttgacattat  23580
tccttcctgt ctggctctgc accgtattga aactgagtta atgggcaaat ttgatgaagg  23640
taaactgccc accgatccac acctgatgct ccgactggcc attgaaactg ttgctcatga  23700
ctatgatgtc atagttattg acagcgcgcc taacctgggt atcggcacga ttaatgtcgt  23760
atgtgctgct gatgtgctga ttgttcccac gcctgctgag ttgtttgact acacctccgc  23820
actgcagttt ttcgatatgc ttcgtgatct gctcaagaac gttgatctta aagggttcga  23880
gcctgatgta cgtattttgc ttaccaaata cagcaatagt aatggctctc agtccccgtg  23940
gatggaggag caaattcggg atgcctgggg aagcatggtt ctaaaaaatg ttgtacgtga  24000
aacggatgaa gttggtaaag gtcagatccg gatgagaact gtttttgaac aggccattga  24060
tcaacgctct tcaactggtg cctggagaaa tgctctttct atttgggaac ctgtctgcaa  24120
tgaaattttc gatcgtctga ttaaaccacg ctgggagatt agataatgaa gcgtgcgcct  24180
gttattccaa aacatacgct caatactcaa ccggttgaag atacttcgtt atcgacacca  24240
gctgccccga tggtggattc gttaattgcg cgcgtaggag taatggctcg cggtaatgcc  24300
attactttgc ctgtatgtgg tcgggatgtg aagtttactc ttgaagtgct ccggggtgat  24360
agtgttgaga agacctctcg ggtatggtca ggtaatgaac gtgaccagga gctgcttact  24420
gaggacgcac tggatgatct catcccttct tttctactga ctggtcaaca gacaccggcg  24480
ttcggtcgaa gagtatctgg tgtcatagaa attgccgatg ggagtcgccg tcgtaaagct  24540
gctgcactta ccgaaagtga ttatcgtgtt ctggttggcg agctggatga tgagcagatg  24600
gctgcattat ccagattggg taacgattat cgcccaacaa gtgcttatga acgtggtcag  24660
cgttatgcaa gccgattgca gaatgaattt gctggaaata tttctgcgct ggctgatgcg  24720
```

gaaaatattt cacgtaagat tattacccgc tgtatcaaca ccgccaaatt gcctaaatca 24780
gttgttgctc ttttttctca ccccggtgaa ctatctgccc ggtcaggtga tgcacttcaa 24840
aaagccttta cagataaaga ggaattactt aagcagcagg catctaacct tcatgagcag 24900
aaaaaagctg ggtgatattt tgaagctgaa gaagttatca ctcttttaac ttctgtgctt 24960
aaaacgtcat ctgcatcaag aactagttta agctcacgac atcagtttgc tcctggagcg 25020
acagtattgt ataagggcga taaaatggtg cttaacctgg acaggtctcg tgttccaact 25080
gagtgtatag agaaaattga ggccattctt aaggaacttg aaaagccagc accctgatgc 25140
gaccacgttt tagtctacgt ttatctgtct ttacttaatg tcctttgtta caggccagaa 25200
agcataactg gcctgaatat tctctctggg cccactgttc cacttgtatc gtcggtctga 25260
taatcagact gggaccacgg tcccactcgt atcgtcggtc tgattattag tctgggacca 25320
cggtcccact cgtatcgtcg gtctgattat tagtctggga ccacggtccc actcgtatcg 25380
tcggtctgat aatcagactg ggaccacggt cccactcgta tcgtcggtct gattattagt 25440
ctgggaccat ggtcccactc gtatcgtcgg tctgattatt agtctgggac cacggtccca 25500
ctcgtatcgt cggtctgatt attagtctgg aaccacggtc ccactcgtat cgtcggtctg 25560
attattagtc tgggaccacg gtcccactcg tatcgtcggt ctgattatta gtctgggacc 25620
acgatcccac tcgtgttgtc ggtctgatta tcggtctggg accacggtcc cacttgtatt 25680
gtcgatcaga ctatcagcgt gagactacga ttccatcaat gcctgtcaag ggcaagtatt 25740
gacatgtcgt cgtaacctgt agaacggagt aacctcggtg tgcggttgta tgcctgctgt 25800
ggattgctgc tgtgtcctgc ttatccacaa cattttgcgc acggttatgt ggacaaaata 25860
cctggttacc caggccgtgc cggcacgtta accgggctgc atccgatgca agtgtgtcgc 25920
tgtcgagttt aaacg 25935

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2
accaagggga aaatgaagtg gtgac 25

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
tccaggtcac tgttaggaag acatc 25

<210> SEQ ID NO 4
<211> LENGTH: 25
<212> TYPE: DNA
<213> ORGANISM: Artificial
<220> FEATURE:
<223> OTHER INFORMATION: Primer

<400> SEQUENCE: 4
agtgtgttgt agcctacgat cagtg 25

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
caagatgcac cttctctcca gtg 23

<210> SEQ ID NO 6
<211> LENGTH: 26
<212> TYPE: DNA
<213> ORGANISM: Artificial
<220> FEATURE:
<223> OTHER INFORMATION: Primer

<400> SEQUENCE: 6
gctcgattac ctagattgac cgagac 26

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
taactctgca gtcgctctac ctc 23

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
acatgatcct ggcatccatt cag 23

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
tcaacccacc agcagatacc ag 22

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
tcaatgatga tgtgagctac acgc 24

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
accaagggga aaaccaagat taatcc 26

<210> SEQ ID NO 12
<211> LENGTH: 49
<212> TYPE: DNA
<213> ORGANISM: Artificial
<220> FEATURE:
<223> OTHER INFORMATION: Primer

<400> SEQUENCE: 12
atccacaatc tacagtcgac gcggccgcca tgttcgtctt cctggtcct 49

<210> SEQ ID NO 13
<211> LENGTH: 104
<212> TYPE: DNA
<213> ORGANISM: Artificial
<220> FEATURE:
<223> OTHER INFORMATION: Primer

<400> SEQUENCE: 13
gtatggcagg aggctagcac gcgttcattt atgataaaca aaattctcca ttctatttcg 60
attagcaacg acaatggtca ataacttaca gcaggagcca cagc 104

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gaccccaaaa tcagcgaaat 20

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
tctggttact gccagttgaa tctg 24

<210> SEQ ID NO 16
<211> LENGTH: 29
<212> TYPE: DNA
<213> ORGANISM: Artificial
<220> FEATURE:
<223> OTHER INFORMATION: Primer

<400> SEQUENCE: 16
tttccccgca ttacgtttgg tggaccggg 29

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
cactgggaaa acaatgcaga 20

-continued

```
<210> SEQ ID NO 18
<211> LENGTH: 24
<212> TYPE: DNA
<213> ORGANISM: Artificial
<220> FEATURE:
<223> OTHER INFORMATION: Primer

<400> SEQUENCE: 18

acaaagtcag gtttatagcc aaca                                        24


<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19

ttttgctggt gaagaggacc cctcg                                       25
```